United States Patent
Zharov

(10) Patent No.: US 10,945,610 B2
(45) Date of Patent: Mar. 16, 2021

(54) DEVICES AND METHODS FOR FRACTIONATED PHOTOACOUSTIC FLOW CYTOMETRY

(71) Applicant: BioVentures, LLC, Little Rock, AR (US)

(72) Inventor: Vladimir Pavlovich Zharov, Little Rock, AR (US)

(73) Assignee: BioVentures, LLC

( * ) Notice: Subject to any disclaimer, the term of this patent is extended or adjusted under 35 U.S.C. 154(b) by 552 days.

(21) Appl. No.: 15/541,264

(22) PCT Filed: Dec. 31, 2015

(86) PCT No.: PCT/US2015/068341
§ 371 (c)(1),
(2) Date: Jun. 30, 2017

(87) PCT Pub. No.: WO2016/109831
PCT Pub. Date: Jul. 7, 2016

(65) Prior Publication Data
US 2018/0000351 A1    Jan. 4, 2018

Related U.S. Application Data

(60) Provisional application No. 62/098,893, filed on Dec. 31, 2014.

(51) Int. Cl.
*A61B 5/00* (2006.01)
*A61B 8/00* (2006.01)
(Continued)

(52) U.S. Cl.
CPC .......... *A61B 5/0095* (2013.01); *A61B 8/4461* (2013.01); *A61B 8/4477* (2013.01);
(Continued)

(58) Field of Classification Search
CPC ........ A61B 2560/04; A61B 2562/0204; A61B 5/0095; A61B 8/4461; A61B 8/4477;
(Continued)

(56) References Cited

U.S. PATENT DOCUMENTS

| 4,333,474 A | 6/1982 | Nigam |
| 5,972,721 A | 10/1999 | Bruno et al. |

(Continued)

FOREIGN PATENT DOCUMENTS

| DE | 10343442 A1 | 4/2005 |
| WO | 2006049570 A2 | 5/2006 |

(Continued)

OTHER PUBLICATIONS

Office Action dated Oct. 6, 2014 from related U.S. Appl. No. 13/253,767; 18 pgs.

(Continued)

*Primary Examiner* — Michael T Rozanski
(74) *Attorney, Agent, or Firm* — Polsinelli PC

(57) ABSTRACT

A fractionated photoacoustic flow cytometry (PAFC) system and methods for the in vivo detection of target objects in biofluidic systems (e.g., blood, lymph, urine, or cerebrospinal fluid) of a living organism is described. The fractionated system includes a fractionated laser system, a fractionated optical system, a fractionated acoustic system, and combinations thereof. The fractionated laser system includes at least one laser or laser array for pulsing a target object within the circulatory vessel with fractionated focused laser beams. The fractionated optical system separates one or several laser beams into multiple beams in a spatial configuration on the skin above the circulatory vessel of the living organism. The fractionated acoustic system includes multiple focused (Continued)

ultrasound transducers for receiving photoacoustic signals emitted by the target object in response to the fractionated laser beams.

18 Claims, 68 Drawing Sheets
(51 of 68 Drawing Sheet(s) Filed in Color)

(51) Int. Cl.
    *G01N 15/10*     (2006.01)
    *G01N 15/14*     (2006.01)

(52) U.S. Cl.
    CPC ..... *G01N 15/1056* (2013.01); *G01N 15/1434* (2013.01); *G01N 15/1459* (2013.01); *G01N 15/1463* (2013.01); *G01N 15/1475* (2013.01); *A61B 2560/04* (2013.01); *A61B 2562/0204* (2013.01); *G01N 2015/1006* (2013.01); *G01N 2015/1062* (2013.01); *G01N 2015/1075* (2013.01); *G01N 2015/1438* (2013.01); *G01N 2015/1477* (2013.01)

(58) Field of Classification Search
CPC ........... G01N 15/1056; G01N 15/1434; G01N 15/1459; G01N 15/1463; G01N 15/1475; G01N 2015/1006; G01N 2015/1062; G01N 2015/1075; G01N 2015/1438; G01N 2015/1477
See application file for complete search history.

(56) References Cited

U.S. PATENT DOCUMENTS

| | | | |
|---|---|---|---|
| 6,368,318 | B1 | 4/2002 | Visuri et al. |
| 6,428,531 | B1 | 8/2002 | Visuri et al. |
| 6,446,806 | B1 | 9/2002 | Ohori et al. |
| 6,514,203 | B2 | 2/2003 | Bukshpan |
| 6,530,944 | B2 | 3/2003 | West et al. |
| 6,710,871 | B1 | 3/2004 | Goix |
| 6,833,540 | B2 | 12/2004 | MacKenzie et al. |
| 6,846,288 | B2 | 1/2005 | Nagar et al. |
| 7,220,385 | B2 | 5/2007 | Blecka et al. |
| 7,500,953 | B2 | 3/2009 | Oraevsky et al. |
| 9,144,383 | B2 | 9/2015 | Zharov |
| 9,217,703 | B2 | 12/2015 | Zharov |
| 9,451,884 | B2 | 9/2016 | Zharov et al. |
| 10,342,430 | B2 | 7/2019 | Zharov |
| 2002/0099283 | A1 | 7/2002 | Christ et al. |
| 2003/0216663 | A1 | 11/2003 | Jersey-Willuhn et al. |
| 2004/0039379 | A1 | 2/2004 | Viator et al. |
| 2004/0188602 | A1 | 9/2004 | Chinn et al. |
| 2005/0004458 | A1 | 1/2005 | Kanayama et al. |
| 2005/0124869 | A1 | 6/2005 | Hefti et al. |
| 2005/0175540 | A1 | 8/2005 | Oraevsky et al. |
| 2006/0078949 | A1 | 4/2006 | Offer et al. |
| 2006/0122583 | A1 | 6/2006 | Pesach et al. |
| 2007/0015978 | A1 | 1/2007 | Kanayama et al. |
| 2007/0015992 | A1 | 1/2007 | Filkins et al. |
| 2007/0121697 | A1 | 5/2007 | Burgholzer et al. |
| 2007/0213613 | A1 | 9/2007 | Ishida et al. |
| 2007/0232940 | A1 | 10/2007 | Fine et al. |
| 2007/0269345 | A1 | 11/2007 | Schilffarth et al. |
| 2007/0292495 | A1 | 12/2007 | Ludwig et al. |
| 2008/0149566 | A1 | 6/2008 | Messersmith et al. |
| 2008/0160090 | A1 | 7/2008 | Oraevsky et al. |
| 2008/0269847 | A1 | 10/2008 | Nemenov |
| 2008/0269849 | A1 | 10/2008 | Lewis |
| 2009/0093713 | A1 | 4/2009 | Hyde et al. |
| 2009/0156932 | A1 | 6/2009 | Zharov |
| 2009/0227997 | A1 | 9/2009 | Wang et al. |
| 2009/0292195 | A1 | 11/2009 | Boyden et al. |
| 2009/0326614 | A1 | 12/2009 | El-Sayed et al. |
| 2010/0278923 | A1 | 11/2010 | Chen et al. |
| 2011/0105867 | A1 | 5/2011 | Schultz et al. |
| 2011/0117028 | A1 | 5/2011 | Zharov |
| 2011/0134426 | A1 | 6/2011 | Kaduchak et al. |
| 2011/0218140 | A1 | 9/2011 | Gonsalves et al. |
| 2011/0306865 | A1 | 12/2011 | Thornton et al. |
| 2012/0022360 | A1 | 1/2012 | Kemp |
| 2012/0065490 | A1 | 3/2012 | Zharov et al. |
| 2012/0179227 | A1 | 7/2012 | Schomacker et al. |
| 2012/0202278 | A1 | 8/2012 | Wagner et al. |
| 2012/0237605 | A1 | 9/2012 | Messersmith et al. |
| 2013/0030307 | A1 | 1/2013 | Rajan et al. |
| 2013/0060122 | A1 | 3/2013 | Zharov |
| 2013/0123604 | A1 | 5/2013 | Oyama |
| 2015/0065685 | A1 | 3/2015 | Arany et al. |
| 2015/0150463 | A1 | 6/2015 | Smeltzer et al. |
| 2015/0282716 | A1 | 10/2015 | Smeltzer et al. |
| 2015/0335741 | A1 | 11/2015 | Smeltzer et al. |
| 2015/0351640 | A1 | 12/2015 | Zharov |
| 2016/0058297 | A1 | 3/2016 | Zharov |
| 2016/0354150 | A1 | 12/2016 | Zharov |

FOREIGN PATENT DOCUMENTS

| | | |
|---|---|---|
| WO | 2013067419 A1 | 5/2013 |
| WO | 2014052449 A1 | 4/2014 |
| WO | 2016109831 A1 | 7/2016 |
| WO | 2016196791 A1 | 12/2016 |

OTHER PUBLICATIONS

Office Action dated Apr. 16, 2015 from related U.S. Appl. No. 13/253,767; 17 pgs.
Office Action dated Jul. 30, 2015 from related U.S. Appl. No. 13/253,767; 16 pgs.
Office Action dated Feb. 22, 2016 from related U.S. Appl. No. 13/253,767; 7 pgs.
Office Action dated Feb. 13, 2014 from related U.S. Appl. No. 13/661,551; 11 pgs.
Office Action dated Oct. 7, 2014 from related U.S. Appl. No. 13/661,551; 10 pgs.
Office Action dated Apr. 3, 2015 from related U.S. Appl. No. 13/661,551; 11 pgs.
Office Action dated Jan. 30, 2017 from related U.S. Appl. No. 14/552,143; 14 pgs.
Office Action dated Oct. 26, 2016 from related U.S. Appl. No. 14/668,418; 11 pgs.
Office Action dated May 24, 2017 from related U.S. Appl. No. 14/668,418; 12 pgs.
Office Action dated Nov. 27, 2017 from related U.S. Appl. No. 14/728,849; 9 pgs.
Office Action dated Dec. 8, 2017 from related U.S. Appl. No. 14/668,418; 29 pgs.
Office Action dated Dec. 14, 2017 from related U.S. Appl. No. 14/552,143; 9 pgs.
Ozkumur, E. et al., "Inertial Focusing for Tumor Antigen-Dependent and -Independent Sorting of Rare Circulating Tumor Cells," NIH Public Access Author Manuscript, available in PMC Oct. 3, 2013, pp. 1-20, Published in final edited form as: Sci. Transl. Med., Apr. 3, 2013, pp. 179ra47, vol. 5, No. 179.
Pantel, K. et al., "Detection, clinical relevance and specific biological properties of disseminating tumour cells, "Nat. Rev. Cancer, May 2008, pp. 329-340, vol. 8, Nature Publishing Group.
Pelan-Mattocks, L. et al., "Flow cytometric analysis of intracellular complexity and CD45 expression for use in rapid differentiation of leukocytes in bovine blood samples," Am. J. Vet Res., Nov. 2001, pp. 1740-1744, vol. 62, No. 11.
Perez-Gutierrez, F. et al., "Plasma Membrane Integrity and Survival of Melanoma Cells After Nanosecond Laser Pulses," Ann. Biomed. Eng., Nov. 2010, pp. 3521-3531, vol. 38, No. 11.
Piyasena, M. et al., "Multinode acoustic focusing for parallel flow cytometry," NIH Public Access Author Manuscript, available in PMC Feb. 21, 2013, pp. 1-18, Published in final edited form as: Anal. Chem., Feb. 21, 2012, pp. 1831-1839, vol. 84, No. 4.

(56) References Cited

OTHER PUBLICATIONS

Prahl, S., "Optical Absorption of Hemoglobin," available at http://omlc.ogi.edu/spectra/hemoglobin, Dec. 15, 1999, 4 pgs.
Proskurnin, M. et al., "In Vivo Multispectral Photoacoustic and Photothermal Flow Cytometry with Multicolor Dyes: A Potential for Real-Time Assessment of Circulation, Dye-Cell Interaction, and Blood Volume," Cytometry Part A, 2011, pp. 834-847, vol. 79A.
Rai, R. et al., "Nanoparticles and their potential application as antimicrobials," Formatex Microbiology Series No. 3, Dec. 31, 2011, pp. 197-209, vol. 1.
Rao, C. et al., "Circulating melanoma cells and survival in metastatic melanoma," Int. J. Oncol., 2011, pp. 755-760, vol. 38.
Reggiori, G. et al., "Early alterations of red blood cell rheology in critically ill patients," Crit. Care Med., 2009, pp. 3041-3046, vol. 37, No. 12.
Riethdorf, S. et al., "Detection of Circulating Tumor Cells in Peripheral Blood of Patients with Metastatic Breast Cancer: A Validation Study of the CellSearch System," Clin. Cancer Res., Feb. 1, 2007, pp. 920-928, vol. 13, No. 3.
Sarimollaoglu, M. et al., "In vivo photoacoustic time-of-flight velocity measurement of single cells and nanoparticles," NIH Public Access Author Manuscript, available in PMC Oct. 15, 2012, pp. 1-8, Published in final edited form as: Opt. Lett., Oct. 15, 2011, pp. 4086-4088, vol. 36, No. 20.
Sarimollaoglu, M. et al., "Nonlinear photoacoustic signal amplification from single targets in absorption background," Photoacoustics, Article in Press, 2013, pp. 1-11, vol. 12, Elsevier.
Schmid, T. et al., "Process analysis of biofilms by photoacoustic spectroscopy," Anal. Bioanal. Chem., 2003, pp. 1124-1129, vol. 375.
Schmid, T. et al., "Photoacoustic absorption spectra of biofilms," Review of Scientific Instruments, Jan. 2003, pp. 755-757, vol. 74, No. 1.
Schmidt-Kittler, O. et al., "From latent disseminated cells to overt metastasis: Genetic analysis of systemic cancel progression," PNAS, Jun. 24, 2003, pp. 7737-7742, vol. 100. No. 13.
Setia, N. et al., "Profiling of ABC transporters ABCB5, ABCF2, and nestin-positive stem cells in nevi, in situ and invasive melanoma," Mod. Pathol., 2012, pp. 1169-1175, vol. 25.
Shao, J. et al., "Photothermal nanodrugs: potential of TNF-gold nanospheres for cancer theranostics," Nature Scientific Reports, 2013, pp. 1-9, vol. 3, No. 1293, Nature Publishing Group.
Shashkov, E. et al., "Quantum dots as multimodal photoacoustic and photothermal contrast agents," NIH Public Access Author Manuscript, available in PMC Nov. 1, 2009, pp. 1-13, Published in final edited form as: Nano Lett., Nov. 2008, pp. 3953-3958, vol. 8, No. 11.
Shashkov, E. et al., "Photothermal and photoacoustic Raman cytometry in vitro and in vivo," Opt. Exp., Mar. 29, 2010, pp. 6929-6944, vol. 18, No. 7.
Shibue, T. et al., "Metastatic colonization: Settlement, adaptation and propagation of tumor cells in a foreign tissue environment," Semin. Cancer Biol., 2011, pp. 99-106, vol. 21, Elsevier Ltd.
Sieuwerts, A. et al., "Anti-Epithelial Cell Adhesion Molecule Antibodies and the Detection of Circulating Normal-Like Breast Tumor Cells," J. Natl. Cancer Inst., Jan. 7, 2009, pp. 61-66, vol. 101, No. 1.
Sleeman, J. et al., "Do all roads lead to Rome? Routes to metastasis development," Int. J. Cancer, 2011, pp. 2511-2526, vol. 128.
Stott, S. et al., "Isolation of circulating tumor cells using a microvertex-generating herringbone-chip," PNAS, Oct. 26, 2010, pp. 18392-18397, vol. 107, No. 43.
Tamaki, E. et al., "Single-Cell Analysis by a Scanning Thermal Lens Microscope with a Microchip: Direct Monitoring of Cytochrome c Distribution during Apoptosis Process," Anal. Chem., Apr. 1, 2002, pp. 1560-1564, vol. 74, No. 7.
Tanev, S. et al., "Flow Cytometry with Gold Nanoparticles and their Clusters as scattering Contrast Agents: FDTD Simulation of Light-Cell Interaction," NIH Public Access Author Manuscript, available in PMC Sep. 1, 2010, pp. 1-24, Published in final edited form as: J. Biophotonics, Sep. 2009, pp. 505-520, vol. 2, Nos. 8-9.
Tibbe, A. et al., "Statistical Considerations for Enumeration of Circulating Tumor Cells," Cytometry Part A, 2007, pp. 154-162, vol. 71A.
Tokeshi, M. et al., "Determination of Subyoctomole Amounts of Nonfluorescent Molecules Using a Thermal Lens Microscope: Subsingle-Molecule Determination," Anal. Chem., May 1, 2001, pp. 2112-2116, vol. 73, No. 9.
Tuchin, V. et al., "Towards in vivo flow cytometry," HHS Publi Access Author Manuscript, available in PMC Mar. 2, 2016, pp. 1-4, Published in final edited form as: J. Biophotonics, Sep. 2009, pp. 457-458, vol. 2, No. 0.
Tuchin, V. et al., "In Vivo Flow Cytometry: A Horizon of Opportunities," Cytometry Part A, 2011, pp. 737-745, vol. 79A.
Ulmer, A. et al., "Detecting Circulating Melanoma Cells," J. Invest. Dermatol., 2011, pp. 1774-1775, vol. 131.
Van Dijk, M. et al., "Absorption and scattering microscopy of single metal nanoparticles," Phys. Chem. Chem. Phys., 2006, pp. 3486-3495, vol. 8.
Wang, L., "Multiscale photoacoustic microscopy and computed tomography," NIH Public Access Author Manuscript, available in PMC Aug. 29, 2010, pp. 1-16, Published in final edited form as: Nat. Photonics, Aug. 29, 2009, pp. 503-509, vol. 3, No. 9.
Wang, Y. et al., "Fiber-laser-based photoacoustic microscopy and melanoma cell detection," J. Biomed. Opt., Jan. 2011, pp. 011014-1 to 011014-4, vol. 16, No. 1.
Wang, L. et al., "Photoacoustic Tomography: In Vivo Imaging from Organelles to Organs," Sci., Mar. 23, 2012, pp. 1458-1462, vol. 335.
Wang, Z. et al., "CD146, a multi-functional molecule beyond adhesion," Cancer Lett., 2013, pp. 150-162, vol. 330.
Wei, X. et al., "Selective Uptake of Indocyanine Green by Reticulocytes in Circulation," Invest. Ophthalmol. Vis. Sci., Oct. 2003, pp. 4489-4496, vol. 44, No. 10.
Office Action dated Jul. 13, 2018 from related U.S. Appl. No. 14/728,849; 12 pgs.
Office Action dated Jul. 13, 2018 from related U.S. Appl. No. 14/552,143; 9 pgs.
Haruna, M. et al., "Blood Volume Measurement at the Bedside Using ICG Pulse Spectrophotometry," Anesthesiology, 1998, pp. 1322-1328, vol. 89.
Ilda, J. et al., "Cell surface chondroitin sulfate glycosaminoglycan in melanoma: role in the activation of pro-MMP-2 (progelatinase A)," Biochem. J., May 1, 2007, pp. 553-563, vol. 403, No. 3, Biochemical Society, Great Britain.
International Search Report and Written Opinion dated Dec. 16, 2013 from related International Patent Application No. PCT/US2013/061673; 8 pgs.
International Search Report and Written Opinion dated Mar. 17, 2016 from related International Patent Application No. PCT/US2015/068341; 8 pgs.
International Search Report and Written Opinion dated Oct. 6, 2016 from related International Patent Application No. PCT/US2016/035512; 12 pgs.
Ion, R-M. et al., "The incorporation of various porphyrins into blood cells measured via flow cytometry, absorption and emission spectroscopy," Acta Biochim. Pol., 1998, pp. 833-845, vol. 45, No. 3.
Joosse, S. et al., "Biologic Challenges in the Detection of Circulating Tumor Cells," Cancer Res., Jan. 1, 2013, pp. 8-11, vol. 73, No. 1.
Kaiser, J., "Cancer's Circulation Problem," Sci., Feb. 26, 2010, pp. 1072-1074, vol. 327.
Khlebtsov, B. et al., "Optical amplification of photothermal therapy with gold nanoparticles and nanoclusters," Nanotechnol., 2006, pp. 5167-5179, vol. 17, Institute of Physics Publishing.
Khoja, L. et al., "Biomarker utility of circulating tumor cells in metastatic cutaneous melanoma," J. Invest. Dermatol., Jun. 2013, pp. 1582-1590, vol. 133, No. 6.
Kim, Y. et al., "Subtyping Lymphocytes in Peripheral Blood by Immunoperoxidase Labeling and Light Scatter/Absorption Flow Cytometry," Clin. Chem., 1985, pp. 1481-1486, vol. 31, No. 9.
Kim, J-W. et al., "In situ fluorescence microscopy visualization and characterization of nanometer-scale carbon nanotubes labeled with

(56) References Cited

OTHER PUBLICATIONS 1-pyrenebutanoic acid, succinimdyl ester," Appl. Phys. Lett., 2006, pp. 213110-1 to 213110-3, vol. 88.
Kim, M. et al., "Tumor Self-Seeding by Circulating Cancer Cells," Cell, Dec. 24, 2009, pp. 1315-1326, vol. 139, Elsevier Inc.
Kim, J-W. et al., "Golden carbon nanotubes as multimodal photoacoustic and photothermal high-contrast molecular agents," NIH Public Access Author Manuscript, available in PMC May 24, 2013, pp. 1-15, Published in final edited form as: Nat. Nanotechnol., Oct. 2009, pp. 688-694, vol. 4, No. 10.
Kim, J-W. et al., "Nanotheranostics of Circulating Tumor Cells, Infections and Other Pathological Factors In Vivo," NIH Public Access Author Manuscript, available in PMC Mar. 4, 2014, pp. 1-37, Published in final edited form as: Mol. Pharm., Mar. 4, 2013, pp. 813-830, vol. 10, No. 3.
Krishnamurthy, S., "The Emerging Role of Circulating Tumor Cells in Breast Cancer," Cancer Cytopathol., Jun. 25, 2012, pp. 161-166, vol. 120.
Lai, C et al., "CD133+ Melanoma Subpopulations Contribute to Perivascular Niche Morphogenesis and Tumorigenicity Through Vasculogenic Mimicry," Cancer Res., 2012, pp. 5111-5118, vol. 72, No. 19.
Langley, R. et al., "Tumor Cell-Organ Microenvironment Interactions in the Pathogenesis of Cancer Metastasis," Endocr. Rev., 2007, pp. 297-321, vol. 28, No. 3.
Lapotko, D. et al., "Photothermal image cytometry of human neutrophils," Cytometry, 1996, pp. 198-203, vol. 24, Wiley-Liss, Inc.
Lapotko, D. et al., "Spectral Evaluation of Laser-Induced Cell Damage With Photothermal Microscopy," Lasers in Surgery and Medicine, 2005, pp. 22-30, vol. 36, No. 1, Wiley-Liss, Inc.
Lasne, D. et al., "Label-free optical imaging of mitochondria in live cells," Opt. Exp., Oct. 17, 2007, pp. 14184-14193, vol. 15, No. 21.
Letfullin, R. et al., "Laser-induced explosion of gold nanoparticles: potential role for nanophotothermolysis of cancer," Nanomed., 2006, pp. 473-480, vol. 1, No. 4, Future Medicine Ltd.
Leung, C. et al., "Tumor Self-Seeding: Bidirectional Flow of Tumor Cells," Cell, Dec. 24, 2009, pp. 1226-1228, vol. 139, Elsevier Inc.
Li, C. et al., "Preparation and characterization of flexible nanoliposomes loaded with daptomycin, a novel antibiotic, for topical skin therapy," International Journal of Nanomedicine, Mar. 24, 2013, pp. 1285-1292, vol. 8.
Lianidou, E., "Circulating Tumor Cells—New Challenges Ahead," Clin. Chem., 2012, pp. 805-807, vol. 58, No. 5.
Liao, H. et al., "Gold Nanorod Bioconjugates," Chem. Mater., 2005, pp. 4636-4641, vol. 17, No. 18, American Chemical Society.
Liu, Z. et al., "Negative enrichment by immunomagnetic nanobeads for unbiased characterization of circulating tumor cells from peripheral blood of cancer patients," J. Transl. Med., 2011, pp. 1-8, vol. 9, No. 70.
Ma, J. et al., "Isolation of tumorigenic circulating melanoma cells," Biochem. Biophys. Res. Commun., 2010, pp. 711-717, vol. 402, No. 4, Elsevier Inc.
Maheswaran, S. et al., "Circulating Tumor Cells: a window into cancer biology and metastasis," HHMI Author Manuscript, pp. 1-6, Published as: Curr. Opin. Genet. Dev., Feb. 2010, pp. 96-99, vol. 20, No. 1.
Menyaev, Y. et al., "Resolution of photoacoustic flow cytometry," Optical Society of America, 2013, 16 pgs.
Molino, A. et al., "A Comparative Analysis of Three Different Techniques for the Detection of Cancer Cells in Bone Marrow;" Cancer, Feb. 15, 1991, pp. 1033-1036, vol. 67.
Nagrath, S. et al., "Isolation of rare circulating tumour cells in cancer patients by microchip technology," NIH Public Access Author Manuscript, available in PMC May 10, 2011, pp. 1-11, Published in final edited form as: Nat., Dec. 20, 2007, pp. 1235-1239, vol. 450, No. 7173.

Nedosekin, D. et al., "Photothermal Multispectral Image Cytometry for Quantitative Histology of Nanoparticles and Micrometastasis in Intact, Stained and Selectively Burned Tissue," Cytometry Part A, 2010, pp. 1049-1058, vol. 77A.
Nedosekin, D. et al., "Ultra-fast photoacoustic flow cytometry with a 0.5 MHz pulse repetition rate nanosecond laser," Opt. Exp., 2010, pp. 8605-8620, vol. 18.
Nedosekin, D. et al., "In Vivo Ultra-Fast Photoacoustic Flow Cytometry of Circulating Human Melanoma Cells Using Near-Infrared High-Pulse Rate Lasers," Cytometry Part A, 2011, pp. 825-833, vol. 79A.
Nedosekin, D. et al., "In Vivo Plant Flow Cytometry: A First Proof-of-Concept," Cytometry Part A, 2011, pp. 855-865, vol. 79A.
Nedosekin, D. et al., "Photothermal Confocal Spectromicroscopy of Multiple Cellular Chromophores and Fluorophores," Biophys. J., Feb. 2012, pp. 672-681, vol. 102.
Nedosekin, D. et al., "Synergy of photoacoustic and fluorescence flow cytometry of circulating cells with negative and positive contrasts," J. Biophotonics, 2013, pp. 425-434, vol. 6, No. 5, Wiley-VCH Verlag GmbH & Co. KGaA, Weinheim, Germany.
Nedosekin, D. et al., "Photoacoustic and photothermal detection of circulating tumor cells, bacteria and nanoparticles in cerebrospinal fluid in vivo and ex vivo," J. Biophotonics, 2013, pp. 523-533, vol. 6, No. 6-7, Wiley-VCH Verlag GmbH & Co. KGaA, Weinheim, Germany.
Nedosekin, D. et al., "Photoacoustic-fluorescence in vitro flow cytometry for quantification of absorption, scattering and fluorescence properties of the cells," Proc. SPIE, 2013, pp. 858141-1 to 858141-6, vol. 8581.
Neeves, K. et al., "Catch Me if You Can: Isolating Circulating Tumor Cells from Flowing Blood," Clin. Chem., 2012, pp. 803-804, vol. 58, No. 5.
Nguyen, D. et al., "Metastasis: from dissemination to organ-specific colonization," Nat. Rev. Cancer, Apr. 2009, pp. 274-284, vol. 9, Macmillan Publishers Limited.
Novak, J. et al., "In vivo flow cytometer for real-time detection and quantification of circulating cells," NIH Public Access Author Manuscript, available in PMC Jan. 4, 2010, pp. 1-8, Published in final edited form as: Opt. Lett., Jan. 1, 2004, pp. 77-79, vol. 29, No. 1.
Notice of Allowance dated May 19, 2015 from related U.S. Appl. No. 12/945,576; 11 pgs.
Notice of Allowance dated Jun. 28, 2016 from related U.S. Appl. No. 13/253,767; 9 pgs.
Notice of Allowance dated Aug. 14, 2015 from related U.S. Appl. No. 13/661,551; 9 pgs.
O'Brien, C. et al., "Detection and Isolation of Circulating Melanoma Cells using Photoacoustic Flowmetry," J. Vis. Exp., Nov. 2011, pp. 1-5, vol. 57, e3559.
O'Brien, C. et al., "Capture of circulating tumor cells using photoacoustic flowmetry and two phase flow," J. Biomed. Opt., Jun. 2012, pp. 061221-1 to 061221-9, vol. 17, No. 6.
Office Action dated Nov. 30, 2011 from related U.S. Appl. No. 12/334,217; 12 pgs.
Office Action dated Apr. 26, 2012 from related U.S. Appl. No. 12/334,217; 10 pgs.
Beard, P., "Biomedical photoacoustic imaging," Interface Focus, 2011, pp. 602-631, vol. 1.
Mallidi, S. et al., "Photoacoustic imaging in cancer detection, diagnosis, and treatment guidance," Trends Biotechnol., May 2011, pp. 213-221, vol. 29, No. 5.
Tuchin, V. et al., "In vivo Image Flow Cytometry," In: Advanced Optical Flow Cytometry: Methods and Disease Diagnoses, V. Tuchin, ed., 2011, pp. 387-431, Chapter 14, Wiley-VCH Verlag GmbH & Co. KGaA, Weinheim, Germany.
Tuchin, V. et al., "In vivo photothermal and photoacoustic flow cytometry," In: Advanced Optical Flow Cytometry: Methods and Disease Diagnoses, V. Tuchin, ed., 2011, pp. 501-571, Chapter 17, Wiley-VCH Verlag GmbH & Co. KGaA, Weinheim, Germany.
Zhe, X. et al., "Circulating tumor cells: finding the needle in the haystack," Am. J. Cancer Res., 2011, pp. 740-751, vol. 1, No. 6.

(56) References Cited

OTHER PUBLICATIONS

Zheng, H. et al., "Detection of the Cancer Marker CD146 Expression in Melanoma Cells with Semiconductor Quantum Dot Label," J. Biomed. Nanotechnol., Aug. 2010, pp. 303-311, vol. 6, No. 4.

Aguirre-Ghiso, J., "On the theory of self-seeding: implications for metastasis progression in humans," Breast Cancer Res., 2010, pp. 1-2, vol. 12, No. 304.

Al-Hajj, M. et al., "Prospective identification of tumorigenic breast cancer cells," PNAS, Apr. 1, 2003, pp. 3983-3988, vol. 100, No. 7, with Correction, PNAS, May 27, 2003, pp. 6890-6891, vol. 100, No. 11.

Alexander, J., "The Normal Blood Clotting Time in the Light of Experience with the 'Two-syringe' Technique," J. Clin. Pathol., 1955, pp. 227-228, vol. 8.

Alix-Panabieres, C. et al., "Circulating Tumor Cells and Circulating Tumor DNA," Annu. Rev. Med., 2012, pp. 199-215, vol. 63.

Alix-Panabieres, C. et al., "Circulating Tumor Cells: Liquid Biopsy of Cancer," Clin. Chem., 2013, pp. 110-118, vol. 59, No. 1.

Allan, A. et al., "Detection and Quantification of Circulating Tumor Cells in Mouse Models of Human Breast Cancer Using Immunomagnetic Enrichment and Multiparameter Flow Cytometry," Cytometry Part A, May 2005, pp. 4-14, vol. 55A, No. 1, Wiley-Liss, Inc.

Alunni-Fabbroni, M. et al., "Circulating tumour cells in clinical practice: Methods of detection and possible characterization," Methods, 2010, pp. 289-297, vol. 50, Elsevier Inc.

Ara, G. et al., "Irradiation of Pigmented Melanoma Cells With High Intensity Pulsed Radiation Generates Acoustic Naves and Kills Cell," Lasers in Surgery and Medicine, 1990, pp. 52-59, vol. 10, No. 1.

Autebert, J. et al., "Microfluidic: an innovative tool for efficient cell sorting," Methods, 2012, pp. 297-307, vol. 57, No. 3, Elsevier.

Baeuerle, P. et al., "EpCAM (CD326) finding its own role in cancer," Br. J. Cancer, Feb. 12, 2007, pp. 417-423, vol. 96.

Berciaud, S. et al., "Photothermal Heterodyne Imaging of Individual Nonfluorescent Nanoclusters and Nanocrystals," Phys. Rev. Lett., Dec. 17, 2004, pp. 257402-1 to 257402-4, vol. 93.

Bhattacharyya, B. et al., "Gold nanoparticle-mediated detection of circulating cancer cells," NIH Public Access Author Manuscript, available in PMC Mar. 1, 2013, pp. 1-18, Published in final form as: Clin. Lab. Med., Mar. 2012, pp. 89-101, vol. 32, No. 1.

Bhattacharyya, K. et al., "Detection, isolation, and capture of circulating breast cancer cells with photoacoustic flow cytometry," Proc. SPIE, 2013, 9 pgs., vol. 8570A.

Biris, A. et al., "In vivo Raman flow cytometry for real-time detection of carbon nanotube kinetics in lymph, blood, and tissues," J. Biomed. Opt., Mar./Apr. 2009, pp. 021006-1-021006-10, vol. 14, No. 2.

Blab, G. et al., "Optical readout of gold nanoparticle-based DNA microarrays without silver enhancement," Biophys. J. Biophys. Lett., 2006, pp. L13-L15, vol. 90, No. 1.

Bland, J. et al., "Statistical methods for assessing agreement between two methods of clinical measurement," Lancet, Feb. 8, 1986, pp. 307-310, vol. 1.

Boutrus, S. et al., "Portable two-color in vivo flow cytometer for real-time detection of fluorescently-labeled circulating cells," NIH Public Access, Author Manuscript, available in PMC Dec. 28, 2009, pp. 1-8, published in final edited form as: J. Biomed. Opt., 2007, p. 020507, vol. 12, No. 2.

Brusnichkin, A. et al., "Ultrasensitive label-free photothermal imaging, spectral identification, and quantification of cytochrome c in mitochondria, live cells, and solutions," NIH Public Access Author Manuscript, available in PMC May 11, 2012 pp. 1-28, Published in final edited form as: J. Biophotonics, Dec. 2010, pp. 791-806, vol. 3, No. 12.

Budd, G. et al., "Circulating Tumor Cells versus Imaging-Predicting Overall Survival in Metastatic Breast Cancer," Clin. Cancer Res., Nov. 1, 2006, pp. 6403-6409, vol. 12, No. 21.

Chaffer, C. et al., "A Perspective on Cancer Cell Metastasis," Sci., Mar. 25, 2011, pp. 1559-1564, vol. 25, No. 331.

Chen, Y. et al., "Platelet CD62P Expression and Microparticle in Murine Acquired Immune Deficiency Syndrome and Chronic Ethanol Consumption," Alcohol Alcoholism, Jan. 1, 2003, pp. 25-30, vol. 38, No. 1.

Chu, J. et al., "The Role of Cancer Stem Cells in the Organ Tropism of Breast Cancer Metastasis: A Mechanistic Balance between the "Seed" and the "Soil"?," Int. J. Breast Cancer, 2012, pp. 1-12, vol. 2012, Article ID 209748, Hindawi Publishing Corporation.

Cristofanilli, M. et al., "Circulating tumor cells, disease progression, and survival in metastatic breast cancer," N. Engl. J. Med., 2004, pp. 781-791, vol. 351.

Cristofanilli, M. et al., "Circulating Tumor Cells: A Novel Prognostic Factor for Newly Diagnosed Metastatic Breast Cancer," J. Clin. Oncol., Mar. 1, 2005, pp. 1420-1430, vol. 23, No. 7.

De Bruyn, M. et al., "Melanoma-associated Chondroitin Sulfate Proteoglycan (MCSP)-targeted delivery of soluble TRAIL potently inhibits melanoma outgrowth in vitro and in vivo," Mol. Cancer, 2010, pp. 1-14, vol. 9, No. 301.

De Giorgi, V. et al., "Application of a Filtration- and Isolation-by-Size Technique for the Detection of Circulating Tumor Cells in Cutaneous Melanoma," J. Invest. Dermatol., 2010, pp. 2440-2447, vol. 130.

De La Zerda, A. et al., "Advanced contrast nanoagents for photoacoustic molecular imaging, cytometry, blood test and photothermal theranostics," Contrast Media Mol. Imaging, 2011, pp. 346-369, vol. 6, John Wiley & Sons, Ltd.

Dick, J., "Breast cancer stem cells revealed," PNAS, Apr. 1, 2003, pp. 3547-3549, vol. 100, No. 7.

Freeman, J. et al., "Evaluation of a multi-marker immunomagnetic enrichment assay for the quantification of circulating melanoma cells," J. Transl. Med., 2012, pp. 1-9, vol. 10, No. 192.

Fukunaga-Kalabis, M. et al., "Beyond ABC: Another Mechanism of Drug Resistance in Melanoma Side Population," J. Invest. Dermatol., 2012, pp. 2317-2319, vol. 132.

Gaiduk, A. et al., "Room-Temperature Detection of a Single Molecule's Absorption by Photothermal Contrast," Sci., Oct. 15, 2010, pp. 353-356, vol. 330.

Galanzha, E. et al., "In vivo integrated flow image cytometry and lymph/blood vessels dynamic microscopy," J. Biomed. Opt., Sep./Oct. 2005, pp. 054018-1-054018-8, vol. 10, No. 5.

Galanzha, E. et al., "Advances in small animal mesentery models for in vivo flow cytometry, dynamic microscopy, and drug screening," World J. Gastroenterol., Jan. 14, 2007, pp. 192-218, vol. 13, No. 2, The WJG Press.

Galanzha, E. et al., "In vivo multispectral, multiparameter, photoacoustic lymph flow cytometry with natural cell focusing, label-free detection and multicolor nanoparticle probes," Cytometry A, 2008, pp. 884-894, vol. 73A, No. 10, with NIH Public Access Author Manuscript, available in PMC Oct. 1, 2009, pp. 1-19.

Galanzha, E. et al., "In vivo, Noninvasive, Label-Free Detection and Eradication of Circulating Metastatic Melanoma Cells Using Two-Color Photoacoustic Flow Cytometry with a Diode Laser," Cancer Res., 2009, pp. 7926-7934, vol. 69, No. 20.

Galanzha, E. et al., "In vivo fiber-based multicolor photoacoustic detection and photothermal purging of metastasis in sentinel lymph nodes targeted by nanoparticles," NIH Public Access Author Manuscript, available in PMC May 24, 2013, pp. 1-17, Published in final edited form as: J. Biophoton., Sep. 2009, pp. 528-539, vol. 2.

Galanzha, E. et al., "Nanotechnology-based molecular photoacoustic and photothermal flow cytometry platform for in-vivo detection and killing of circulating cancer stem cells," J. Biophoton., 2009, pp. 725-735, vol. 2, No. 12.

Galanzha, E. et al., "In vivo magnetic enrichment and multiplex photoacoustic detection of circulating tumour cells," NIH Public Access Author Manuscript, available in PMC May 24, 2013, pp. 1-13, Published in final edited form as: Nat. Nanotechnol., Dec. 2009, pp. 855-860, vol. 4, No. 12.

Galanzha, E. et al., "In Vivo Photoacoustic and Photothermal Cytometry for Monitoring Multiple Blood Rheology Parameters," Cytometry Part A, Oct. 2011, pp. 746-757, vol. 79, No. 10.

Galanzha, E. et al., "In Vivo Flow Cytometry of Circulating Clots Using Negative Photothermal and Photoacoustic Contrasts," Cytometry

(56) References Cited

OTHER PUBLICATIONS

Part A, Oct. 2011, pp. 814-824, vol. 79A, No. 10, with Corrigendum, Cytometry Part A, 2011, pp. 1024, vol. 79A, No. 12.
Galanzha, E. et al., "Photoacoustic flow cytometry," Methods, Jul. 2012, pp. 280-296, vol. 57, No. 3, with HHS Public Access Author Manuscript, Mar. 19, 2016, pp. 1-44.
Galanzha, E. et al., "In vivo Magnetic Enrichment, Photoacoustic Diagnosis, and Photothermal Purging of Infected Blood Using Multifunctional Gold and Magnetic Nanoparticles," PLoS One, Sep. 2012, pp. 1-14, vol. 7, No. 9, e45557.
Galanzha, E. et al., "Circulating tumor cell detection and capturing using photoacoustic flow cytometry in vivo and ex vivo," Cancers, Manuscript, 2013, pp. 1-45, vol. 5.
Garrett, T et al., "Bacterial adhesion and biofilms on surfaces," Progress in Natural Science, 2008, pp. 1049-1056, vol. 18, Elsevier.
Givan, A., "Flow Cytometry. An Introduction," Methods in Molecular Biology, Flow Cytometry Protocols, Second Edition, 2004, pp. 1-31, vol. 263, Humana Press.
Goddard, G. et al., "Ultrasonic Particle-Concentration for Sheathless Focusing of Particles for Analysis in a Flow Cytometer," Cytometry Part A, 2006, pp. 66-74, vol. 69A.
Gutierrez-Juarez, G. et al., "Optical Photoacoustic Detection of Circulating Melanoma Cells In Vitro," Int. J. Thermophys., 2010, pp. 784-792, vol. 31, Springer Science+Business Media, LLC.
Gutierrez-Juarez, G. et al., "Detection of Melanoma Cells In Vitro Using an Optical Detector of Photoacoustic Waves," Lasers Surg. Med., 2010, pp. 274-281, vol. 42.
Weight, R. et al., "Photoacoustic detection of metastatic melanoma cells in the human circulatory system," Opt. Lett., Oct. 15, 2006, pp. 2998-3000, vol. 31, No. 20, Optical Society of America.
Wicha, M. et al., "Circulating Tumor Cells: Not All Detected Cells are Bad and Not All Bad Cells are Detected," J. Clin. Oncol., 2011, pp. 1508-1511, vol. 29.
Williams, S., "Circulating Tumor Cells," PNAS, Mar. 26, 2013, p. 4861, vol. 110, No. 13.
Witzig, T. et al., "Detection of Circulating Cytokeratin-positive Cells in the Blood of Breast Cancer Patients Using Immunomagnetic Enrichment and Digital Microscopy," Clin. Cancer Res., May 2002, pp. 1085-1091, vol. 8.
Xu, M. et al., "Photoacoustic imaging in biomedicine," Rev. Sci. Instrum., 2006, pp. 041101-1 to 041101-22, vol. 77.
Xu, X. et al., "Circulating Tumor Cells and Melanoma Progression," J. Invest. Dermatol., 2010, pp. 2349-2351, vol. 130.
Yang, J. et al., "Melanoma Proteoglycan Modifies Gene Expression to Stimulate Tumor Cell Motility, Growth, and Epithelial-to-Mesenchymal Transition," Cancer Res., 2009, pp. 7538-7547, vol. 69, No. 19.
Yu, M. et al., "Circulating tumor cells: approaches to isolation and characterization," J. Cell Biol., 2011, pp. 373-382, vol. 192, No. 3.
Yu, M. et al., "Circulating Breast Tumor Cells Exhibit Dynamic Changes in Epithelial and Mesenchymal Composition," Sci., Feb. 1, 2013, pp. 580-584, vol. 339.
Zharov, V. et al., "Photothermal detection of local thermal effects during selective nanophotothermolysis," Appl. Phys. Lett., Dec. 15, 2003, pp. 1-3, vol. 83, No. 24.
Zharov, V. et al., "Infrared imaging of subcutaneous veins," Lasers Surg. Med., Jan. 2004, pp. 56-61, vol. 34, No. 1, Wiley-Liss, Inc.
Zharov, V. et al., "Photothermal Imaging of Nanoparticles and Cells," IEEE Journal of Selected Topics in Quantum Electronics, Jul./Aug. 2005, pp. 733-751, vol. 11, No. 4.
Zharov, V. et al., "Microbubbles-overlapping mode for laser killing of cancer cells with absorbing nanoparticle clusters," J. Physics D: Appl. Phys., 2005, pp. 2571-2581, vol. 38.
Zharov, V. et al., "Photoacoustic tweezers with a pulsed laser source: theory and experiments," J. Physics D: Appl. Phys., 2005, pp. 1-13, vol. 38, IOP Publishing Ltd, United Kingdom.
Zharov, V. et al., "Photothermal image flow cytometry in vivo," Opt. Lett., Mar. 15, 2005, pp. 628-630, vol. 30, No. 6.
Zharov, V. et al., "In Vivo Photothermal Flow Cytometry: Imaging and Detection of Individual Cells in Blood and Lymph Flow," J. Cellular Biochem., 2006, pp. 916-932, vol. 97, No. 5.
Zharov, V. et al., "In vivo photoacoustic flow cytometry for monitoring of circulating single cancer cells and contrast agents," Opt. Lett., Dec. 15, 2006, pp. 3623-3625, vol. 31, No. 24.
Zharov, V. et al., "Photothermal Flow Cytometry In Vitro for Detection and Imaging of Individual Moving Cells," Cytometry Part A, 2007, pp. 191-206, vol. 71A.
Zharov, V. et al., "Confocal photothermal flow cytometry in vivo," Proc. SPIE, Apr. 2005, pp. 15-26, vol. 5697.
Zharov, V. et al., "Integrated photothermal flow cytometry in vivo," J. Biomed. Opt., Sep./Oct. 2005, pp. 051502-1-051502-13, vol. 10, No. 5.
Zharov, V. et al., "Nanocluster model of photothermal assay: application for high-sensitive monitoring of nicotine-induced changes in metabolism, apoptosis, and necrosis at a cellular level," J. Biomed. Opt., Jul./Aug. 2005, pp. 044011-1-044011-15, vol. 10, No. 4.
Zharov, V. et al., "Self-assembling nanoclusters in living systems: application for integrated photothermal nanodiagnostics and nanotherapy," J. Nanomed., Dec. 2005, pp. 326-345, vol. 1, No. 4.
Zharov, V. et al., "Synergistic enhancement of selective nanophotothermolysis with gold nanoclusters: Potential for cancer therapy," Laser Surg. Med., 2005, pp. 219-226, vol. 37, No. 3.
Zharov, V. et al., "In vivo high-speed imaging of individual cells in fast blood flow," J. Biomed. Opt., Sep./Oct. 2006, pp. 054034-1-054034-4, vol. 11, No. 5.
Zharov, V. et al., "Photothermal Nanotherapeutics and Nanodiagnostics for Selective Killing of Bacteria Targeted with Gold Nanoparticles," Biophys. J., Jan. 2006, pp. 619-627, vol. 90, Biophysical Society.
Zharov, V. et al., "Photoacoustic flow cytometry: principle and application for real-time detection of circulating nanoparticles, pathogens, and contrast dyes in vivo," J. Biomed. Opt., Sep. 1, 2007, pp. 051503-1-051503-14, vol. 12, No. 5.
Zharov, V. et al., "Ultrasharp nonlinear photothermal and photoacoustic resonances and holes beyond the spectral limit," HHS Public Access Author Manuscript, available in PMC Jan. 2, 2015, pp. 1-16, Published in final edited form as: Nat. Photonics, Feb. 2011, pp. 110-116, vol. 5, No. 2.
Office Action dated Oct. 11, 2019 from related U.S. Appl. No. 14/939,039; 9 pgs.
Birtill, D. et al., "Photoacoustic Spectroscopy," Central Laser Facility Annual Report, 2010-2011, Laser for Science Facility-Biology, 25 pgs.
Chitnis, P. et al., "Feasibility of optoacoustic visualization of high-intensity focused ultrasound-induced thermal lesions in live tissue," J. Biomed. Opt., Mar./Apr. 2010, pp. 021313-1 to 021313-5, vol. 15, No. 2.
Karpiouk, A. et al., "Combined ultrasound and photoacoustic imaging to detect and stage deep vein thrombosis: phantom and ex vivo studies," J. Biomed. Opt., Sep./Oct. 2008, pp. 054061-1 to 054061-8, vol. 13, No. 5.
Notice of Allowance dated Feb. 26, 2019 from related U.S. Appl. No. 14/754,034; 7 pgs.
Office Action dated Feb. 8, 2019 from related U.S. Appl. No. 15/240,712; 37 pgs.
European Extended Search Report dated Aug. 10, 2018 from related European Patent Application No. 15876378.9; 13 pgs.
Galanzha, E. et al., "Photoacoustic and photothermal cytometry using photoswitchable proteins and nanoparticles with ultrasharp resonances" J. Biophoton., Jan. 2015, pp. 81-93, vol. 8, No. 1-2, Wiley-VCH Verlag GmbH & Co. KGaA, Weinheim.
Office Action dated Aug. 10, 2018 from related U.S. Appl. No. 14/668,418; 16 pgs.
Office Action dated Sep. 26, 2018 from related U.S. Appl. No. 14/754,034; 7 pgs.
Office Action dated Aug. 22, 2019 from related U.S. Appl. No. 15/240,712; 13 pgs.
Karpiouk, A. et al., "Combined Ultrasound and Photoacoustic Imaging to Age Deep Vein Thrombosis: Preliminary Studies," IEEE Ultrasonics Symposium, 2005, pp. 399-402, vol. 1.

(56) References Cited

OTHER PUBLICATIONS

Office Action dated Jun. 25, 2020 from related U.S. Appl. No. 15/240,712; 18 pgs.
Office Action dated Dec. 16, 2020 from related U.S. Appl. No. 14/939,039; 9 pgs.

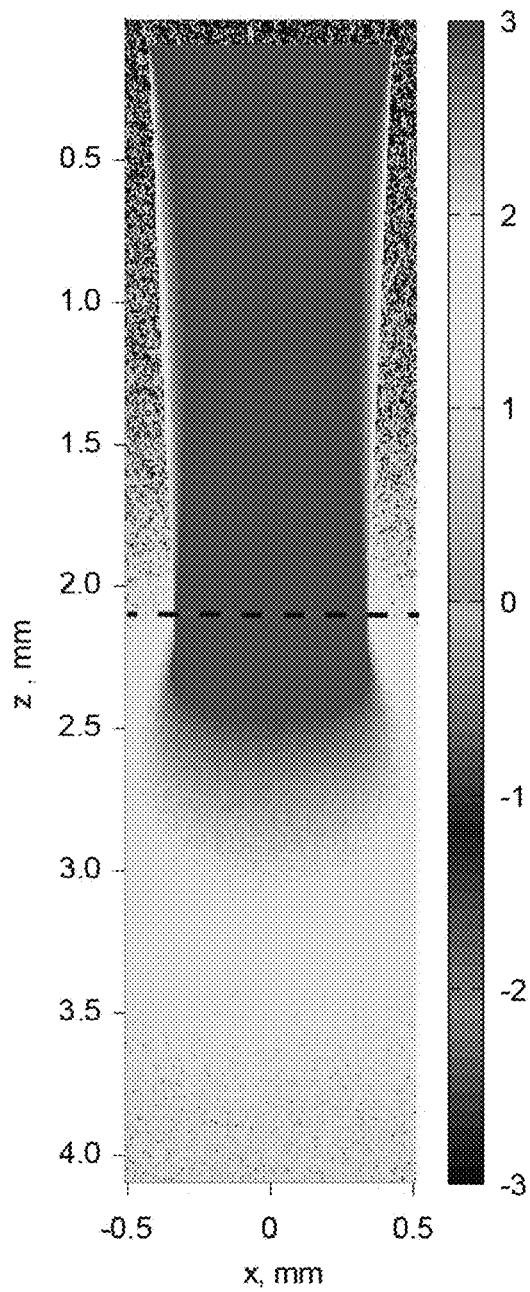 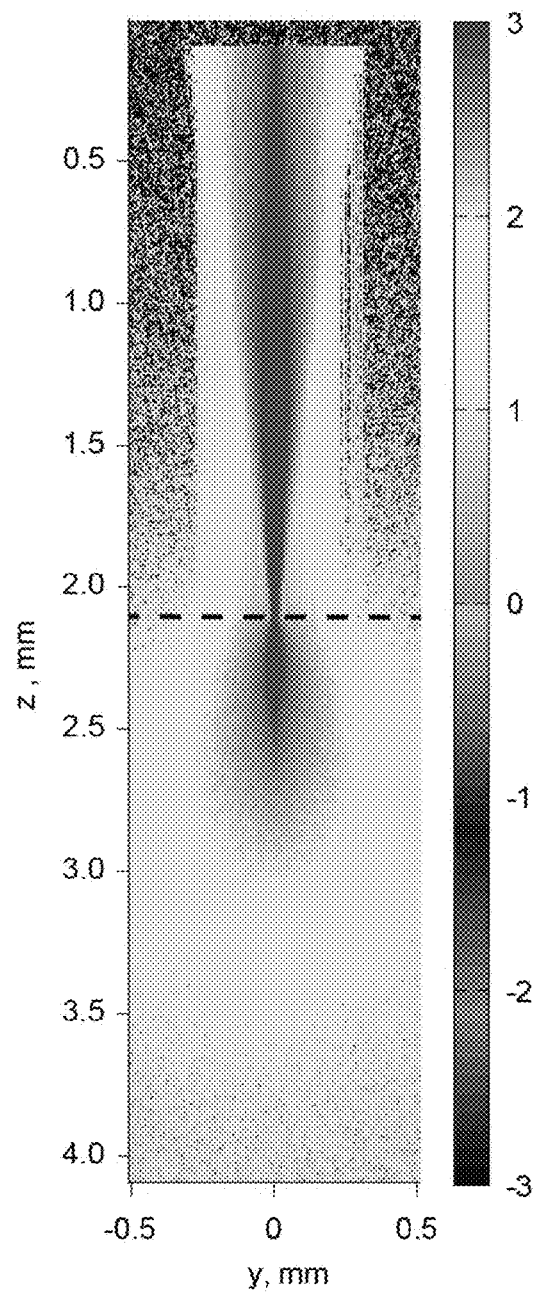
FIG. 2D  FIG. 2E

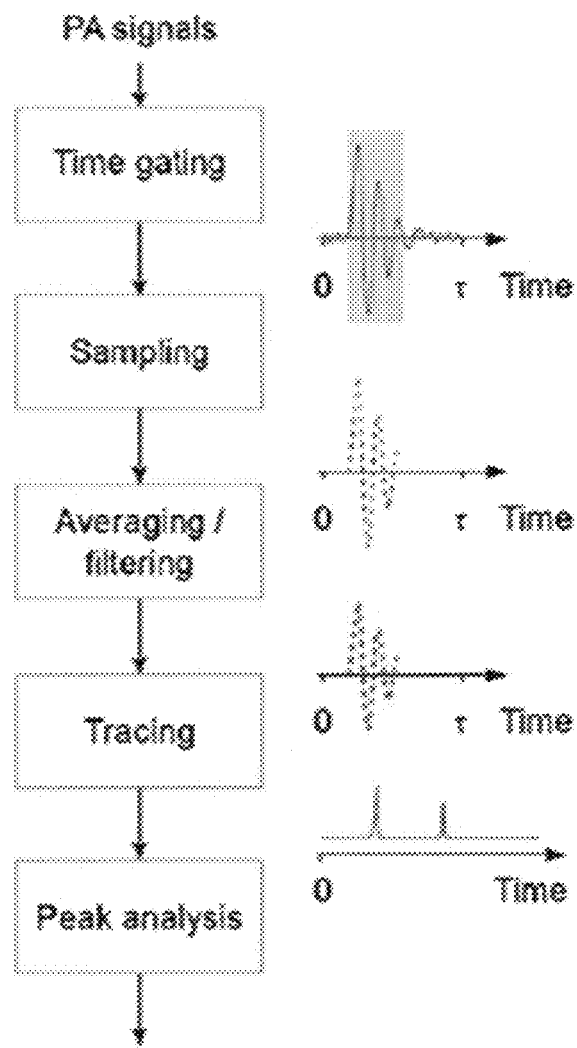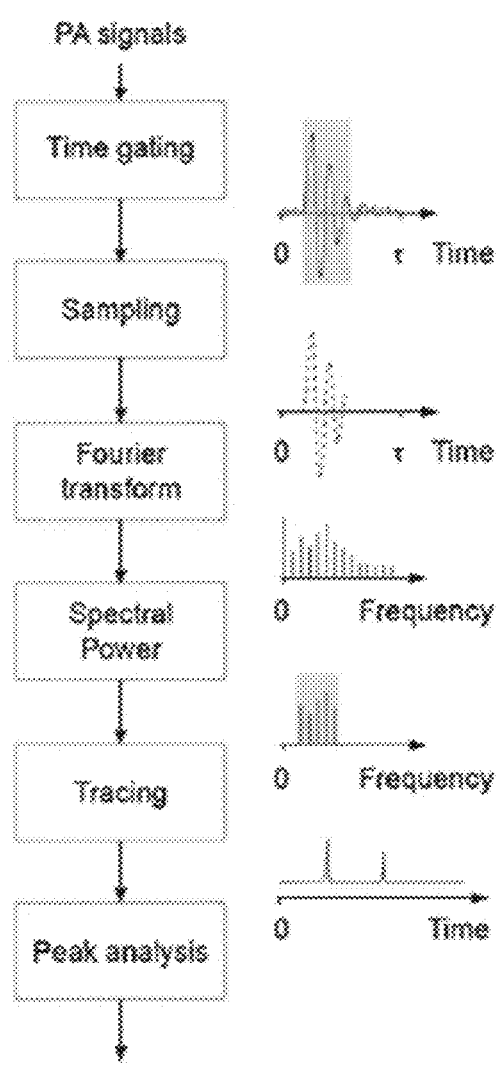
FIG. 25A  FIG. 25B

DEVICES AND METHODS FOR FRACTIONATED PHOTOACOUSTIC FLOW CYTOMETRY

CROSS REFERENCE TO RELATED APPLICATIONS

This application claims the priority of PCT Application PCT/US2015/068341 entitled "DEVICES AND METHODS FOR FRACTIONATED PHOTOACOUSTIC FLOW CYTOMETRY" filed Dec. 31, 2015, which claims priority from U.S. provisional patent application Ser. No. 62/098,893 entitled "IN VIVO PHOTOACOUSTIC BIO-BARCODING DEVICES AND METHODS" filed on Dec. 31, 2014, each of which is hereby incorporated by reference herein in its entirety.

GOVERNMENTAL RIGHTS

The invention was made with government support under R01CA131164 and R01EB017217 awarded by the National Institutes of Health. The government has certain rights in the invention.

FIELD OF THE INVENTION

This application relates to systems and methods of non-invasively detecting and imaging individual target objects in vivo using a fractionated photoacoustic flow cytometry system and using a fractionated optical system with photoacoustic, photothermal, fluorescence, Raman, scattering, and other analytical techniques. In particular, this application relates to a fractionated in vivo photoacoustic (PA) flow cytometer device and methods for detecting individual circulating target objects in deep vessels by increased laser energy in the vessels while simultaneously keeping safe laser fluence without side effects (e.g., overheating, skin burning, and pain) in the superficial skin layer.

BACKGROUND

Despite significant progress in diagnostic techniques (e.g., magnetic resonance imaging (MRI), positron emission tomography (PET), optical and bio-assays), no clinically relevant method has yet been developed for in vivo real-time counting of individual normal and abnormal cells in blood circulation. In particular, despite in vivo clinical use of pulse oximetry and optical coherence tomography, none of these biophotonic instruments is able to count individual, fast-flowing blood cells due to limited spatial and temporal resolution. Although fluorescent labeling in vivo shows promise for detecting flowing cells in animal models as a research tool, translation of this technology to humans is problematic due to 1) the necessity to use fluorophores, most of which are currently toxic, 2) undesirable immune responses to tags, and 3) the small volume of blood (10-100 µL) that is sampled, because the technology assesses only superficial microvessels with slow flow rates.

Laser-based PA spectroscopy and imaging currently are the fastest-growing area of biomedical optics, providing higher sensitivity and resolution in deeper tissues compared to other optical modalities. The tremendous clinical potential of the viable PA-based techniques have been successfully demonstrated in several trials in humans including diagnosing breast tumors at a depth of 3 cm, and imaging blood vessels in deep tissue up to 7 cm. Nevertheless, PA-based techniques have not yet proven to be suitable for highly sensitive, rapid in vivo blood testing at the single-cell level. Counting individual rare normal and abnormal cells, aggregates, and many other objects noninvasively in the blood vessels of a living organism with native cell flow is an exciting challenge that may enable revolutionary breakthroughs in early disease diagnosis including cancer, infection, and cardiovascular disorders by analysis of almost the entire blood volume.

A primary clinical goal is real-time multiparameter monitoring of blood composition at single cell or cell aggregate levels in 1-3-mm blood vessels at a depth of 1-10 mm, which is well within the documented capabilities of PA-based methods that are capable of assessing deep (at least 1-2 cm, if not 3-7 cm) and large (10-15 mm) human blood vessels. A need exists for a highly sensitive and high-speed in vivo PA flow cytometry (PAFC) platform to assess deep vessels.

The sensitivity of PAFC can be significantly improved by increasing laser energy which, however, can damage the superficial skin layer where energy is much higher (10-50 times) than in deeper tissues. Therefore, there is a need for a system and method for analyzing a large portion of the blood volume in vivo for rare target objects. A new PA schematic may decrease the laser beam sizes leading to a decrease in the thermal relaxation time with a simultaneous increase in the number of beams with a certain spatial configuration.

SUMMARY

Disclosed herein is a fractionated photoacoustic flow cytometry (PAFC) system for the in vivo detection of target objects in a biofluid system of a living organism. The fractionated PAFC system may include a laser system including at least one laser for providing at least one laser beam to at least one target object within the biofluid system; a fractionated optical system configured to separate the at least one laser beam into fractionated laser beams having a spatial configuration on the skin above the biofluid system of the living organism; and an acoustic system comprising at least one focused ultrasound transducer for receiving more than one photoacoustic signal emitted by the at least one target object in response to the fractionated laser beams.

The acoustic system may be a fractionated acoustic system including more than one focused ultrasound transducer. Each focused ultrasound transducer may be an independent amplifier for sending the photoacoustic signal received by each focused ultrasound transducer to a multichannel data acquisition board. The multichannel data acquisition board may create traces of signals from the target object passing non-overlapped acoustic focal volumes together covering the whole cross-section of the biofluid system. The at least one laser may be capable of providing more than one laser beam as fractionated laser beams having a spatial configuration. The fractionated optical system may include an optical component selected from a non-transparent mask, a beam splitter, an optical fiber array, a lens array, a microlens array, a mirror array, a diffraction element, a diffuser, a pinhole, and combinations thereof. The fractionated laser beams from the fractionated optical system may not overlap at a location in the living organism with first temperature, pressure, or pain receptors and wherein the fractionated laser beams spatially overlap at the biofluid system. The spatial configuration of the fractionated laser beams may include gaps of about 5 µm to about 1 cm between the individual laser beams on the skin of the living organism. The spatial configuration of the fractionated laser beams may be one-dimensional or two-dimensional. The fractionated laser beams may have a shape selected from circular, linear, strip, elliptical, square, and combinations thereof. The fractionated optical system may be configured to scan the more than one laser beams across the biofluid system. Each focused ultrasound transducer may include an acoustic focal volume and the fractionated acoustic system may be configured to scan the acoustic focal volumes across the biofluid system. The focused ultrasound transducers may be focused spherical ultrasound transducers. The laser system may include more than one laser in a laser array. The more than one laser may be assembled in the laser array as independent lasers or as microchip with individual emitters and a triggering system for controlling the more than one pulsed lasers. The laser system may include more than one laser providing laser pulses with different wavelengths. The fractionated PAFC system may further include a triggering system for providing time delays between the laser pulses with different wavelengths.

Further provided herein is a fractionated PAFC system which may include a fractionated laser system including an array of more than one laser for providing more than one laser beam in a spatial configuration to at least one target object within the biofluid system; an optical system configured to deliver the more than one laser beam in a spatial configuration on the skin above the biofluid system of the living organism; and an acoustic system comprising more than one focused ultrasound transducer for receiving more than one photoacoustic signal emitted by the at least one target object in response to the more than one laser beam. In an aspect, the optical system may be non-scanning or scanning.

This system may further include a triggering system for controlling the more than one pulsed lasers and providing time delays between laser pulses with different wavelengths. The system may further include a time-resolved acoustic detection system. The acoustic system may be a fractionated acoustic system including more than one focused ultrasound transducer. Each focused ultrasound transducer may be an independent amplifier for sending the photoacoustic signal received by each focused ultrasound transducer to a multichannel data acquisition board. The focused ultrasound transducers may be spherical or cylindrical and non-scanning or scanning. The laser array may provide more than one laser beam as fractionated laser beams having a spatial configuration. Each laser in the array may have a different wavelength. The optical system may be a fractionated optical system configured to separate the more than one laser beam into fractionated laser beams. The fractionated optical system may include an optical component selected from a non-transparent mask, a beam splitter, an optical fiber array, a lens array, a microlens array, a mirror array, a diffraction element, a diffuser, a pinhole, and combinations thereof. The fractionated laser beams may not overlap at a location in the living organism with first pain receptors and wherein the fractionated laser beams spatially overlap at the biofluid system. The spatial configuration of the fractionated laser beams may include gaps of about 5 µm to about 1 cm between the individual laser beams on the skin of the living organism. The spatial configuration of the fractionated laser beams may be one-dimensional or two-dimensional. The fractionated laser beams may have a shape selected from circular, linear, strip, elliptical, square, and combinations thereof. The optical system may be configured to scan the more than one laser beams across the biofluid system. Each focused ultrasound transducer may include an acoustic focal volume and the fractionated acoustic system may be configured to scan the acoustic focal volumes across the biofluid system.

Provided herein is a fractionated PAFC method for detecting circulating target objects in a biofluid system of a living organism in vivo. The method may include providing the target object with a laser beam from a laser in a laser system at a first wavelength; separating the laser beam into fractionated laser beams in a fractionated optical system to form a spatial configuration on the skin above the biofluid system of the living organism; obtaining in a fractionated acoustic system more than one photoacoustic signal emitted by the circulating target objects induced by the fractionated laser beams; and analyzing the photoacoustic signals to calculate the combination of photoacoustic signals emitted by the circulating target objects. The combination of photoacoustic signals is characteristic of each circulating target object. The method may further include providing the target object with a second laser beam from a second laser in the laser system at a second wavelength. The method may further include introducing time delay between laser pulses using a triggering system. The method may further include color decoding by time-resolved detection of color-coded photoacoustic signals. The method may further include generating microbubbles or nanobubbles by the fractionated laser beams to detect the circulating target objects with intrinsic photoacoustic contrast or the circulating target object labeled with a non-photoswitchable or photoswitchable photoacoustic probe. The method may further include cooling the skin by placing clearing or cooling agents on the skin.

Provided herein is a fractionated PAFC method which may include providing the target object with multiple laser beams from more than one laser in a laser array, each having a first wavelength; delivering the laser beams through an optical system and forming a spatial configuration of laser beams on the skin above the biofluid system of the living organism; obtaining in a fractionated acoustic system more than one photoacoustic signal emitted by the circulating target object induced by the fractionated laser beams; and analyzing the photoacoustic signals to calculate the combination of photoacoustic signals emitted by the circulating target object. The combination of photoacoustic signals is characteristic of the circulating target object. The method may further include separating the laser beams into fractionated laser beams in a fractionated optical system. The method may further include generating microbubbles or nanobubbles when providing the circulating target object with the fractionated laser beams.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The patent or application file contains at least one drawing executed in color. Copies of this patent or patent application with color drawing(s) will be provided by the Office by request and payment of the necessary fee.

The following figures illustrate various aspects of the disclosure.

FIG. 2A, FIG. 2B, FIG. 2C, FIG. 2D, and FIG. 2E provide phenomenological schematics of conventional optical diagnostics using relatively broad laser beams and new diagnostics in fractionated PAFC using strongly focused beams with a small diameter.

FIG. 16A shows the light distribution on the focal plane. FIG. 16B shows the light distribution about 3 mm above the focal plane. FIG. 16C shows the light distribution in a chess-board-like light distribution after rotation of the lens array.

FIG. 25A is a flow chart illustrating signal processing in four-color fractionated PAFC system in the time domain. FIG. 25B is a flow chart illustrating signal processing in the frequency domain. As an alternative method, a PA trace may be constructed using the spectral power of the PA waveforms as illustrated in FIG. 25B instead of their peak-to-peak amplitudes as illustrated in FIG. 25A. This approach has advantages in certain cases. If the Fourier transform is performed on the digitizer firmware and few representative coefficients are transferred to the computer memory, the throughput is significantly reduced. It can also improve signal-to-noise ratio (SNR), especially when there exist oscillating PA tails.

FIG. 26A illustrates bio-barcoding using multicolor probes (nanoparticles) with ultrasharp PA resonances. FIG. 26B illustrates multi-color laser excitation with temporal separation of laser pulses (i.e., time delay) with the different wavelengths. FIG. 26C illustrates the time-resolved reading (decoding) of bio-color-coded PA signals associated with the different markers.

FIG. 32C illustrates a typical PA signal trace from melanoma CTCs in WBC-rich samples without RBCs (lysed).

FIG. 44B shows a principal optical schematic of malaria parasites detection by PA and fluorescence flow cytometry (PAFFC) in linear mode. FIG. 44C presents detection of infected RBCs and parasite expressing GFP in mice. FIG. 44D illustrates light absorbance of hemozoin crystals. For GFP: EX-Absorption, Em-Emission. Blood curve for approximately 70% of oxygenation (modified by http://omlc.org). FIG. 44E demonstrates spectral identification of in vivo linear PA signals from hemozoins in infected with malaria parasites RBCs at three color PAFC (532 nm, 671 nm, and 820 nm) above blood background.

Corresponding reference characters indicate corresponding elements among the views of the drawings. The headings used in the figures should not be interpreted to limit the scope of the claims.

DETAILED DESCRIPTION

Figure 1:
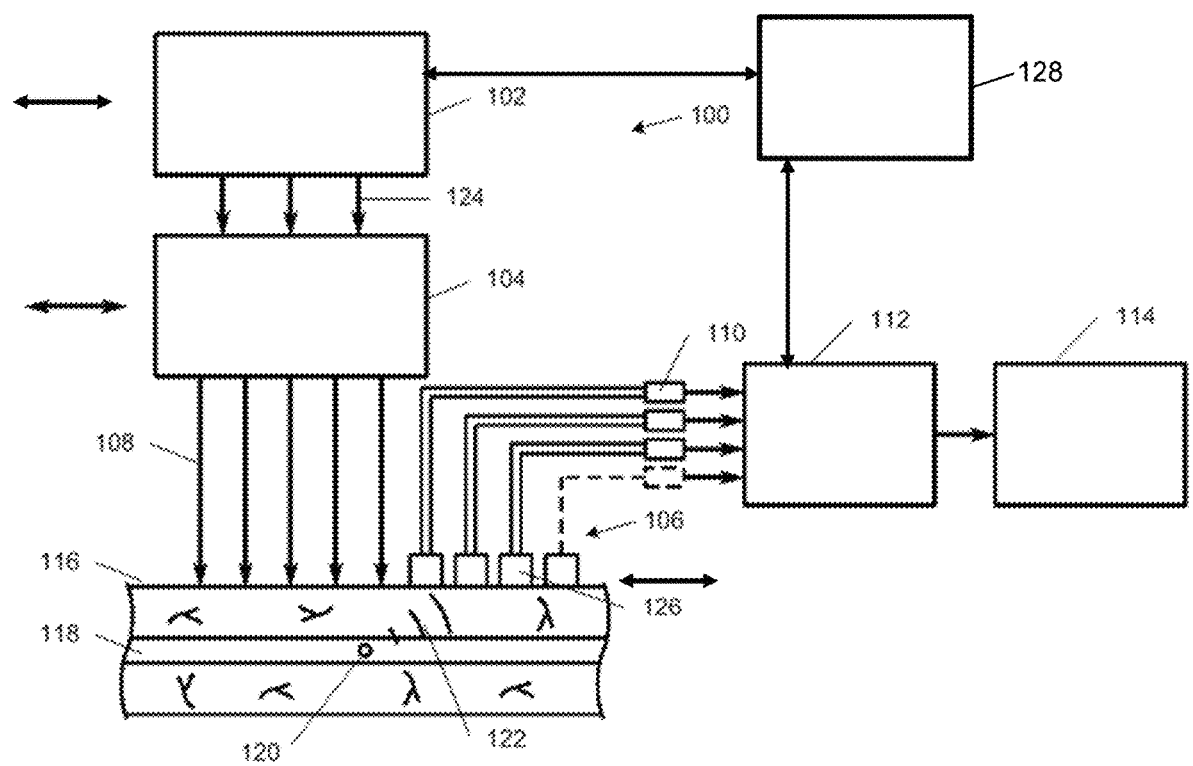
FIG. 1 illustrates a fractionated photoacoustic (PA) flow cytometry (PAFC) system that includes either a fractionated laser or laser array generating multiple beams of certain spatial profiles, or/and a fractionated optical system splitting of one or several laser beams from one or several lasers into multiple beams, and a fractionated acoustic detection system using one or multiple focused ultrasound transducers arrays with individual amplifiers connecting to a recording system.

Provided herein are systems and methods for the improvement of blood tests for early diagnosis and prevention of cardiovascular disorders (e.g., stroke and heart attack), cancers, and infections (e.g., antibiotic resistant bacteria or malaria) and which remain the main causes of death in the world with annual mortality particularly in the U.S of approximately 720,000, 580,000, and 140,000 people, respectively. The diagnosis of these and many other diseases begins with a common medical procedure: examination of extracted blood samples. The sensitivity of current blood testing is limited by the small volume of blood collected, in which no less than one disease-specific marker (e.g., tumor cell and bacterium) can be detected. It can miss many thousands of abnormal cells in the whole blood volume (~5 L in adults), which can be sufficient for disease progression. As a result, barely treatable or incurable disease complications may already be established by the time of the initial diagnosis. For example, despite enormous efforts to detect circulating tumor cells (CTCs) that lead to 90% of all cancer deaths as a result of the development of deadly metastases, the mortality rates for metastatic cancer have still been significant. This failure is explained by the low sensitivity of existing CTC assays ex vivo, which, with a sensitivity of 1-10 CTCs/mL, miss up to 99.9% of CTCs in circulation. Likewise, in the case of cardiovascular disorders, one-third of people who die from heart attacks or stroke do not have the usual risk factors such as family history, high blood pressure, or high cholesterol. This situation emphasizes the importance of the early detection of circulating blood clots (CBCs) called also emboli as precursors of large CBCs that cause the final fatal events.

The present application describes a clinically relevant, noninvasive, universal platform for realizing the concept of in vivo reading of what is written in blood to improve the early diagnosis of, and potentially prevent, life-threatening diseases. Unlike typical blood sampling involving extraction of a volume of blood ranging from 10 µL (drop) to a few milliliters (CTC assays), in vivo examination involves nearly the entire volume of blood passing through 1-2-mm-diameter peripheral vessels over 0.5-1 h (a few minutes in larger vessels) and thus will enable a dramatic increase in diagnostic sensitivity, ultimately up to $10^3$-$10^5$ times, reflecting the ratio of the volume of blood sampled in vivo to that in vitro. In addition, the integration of simultaneous diagnosis and well-timed therapy—theranostics—can optimize therapy and control its efficacy.

The described diagnostic platform is relatively universal and, by either in label-free mode using intrinsic positive and negative contrast agents (e.g., melanin, hemozoin or platelet/fibrins/white blood cells [WBCs] for melanoma, malaria or clot-related pulmonary embolism and stroke) or by targeting of disease-specific markers with functionalized probes can be applied to the early diagnosis, prognosis, and prevention of many major diseases and conditions, including stroke, heart attack, thrombosis, infections (e.g., S. aureus, E. coli, HIV, and malaria parasites producing hemozoin pigment), cancer, Alzheimer's (through particle and exosome detection), sickle cell anemia, or immune system dysfunction, as well as to the evaluation of blood chemistry. This will yield insights into blood epigenetics, hemodynamics, rheology, and red blood cell (RBC) aggregation.

The development of laser methods such as PA imaging, optical coherent tomography (OCT), fluorescence spectroscopy and many others has already revolutionized noninvasive optical disease diagnosis with focus on superficial targets in dermatology, dentistry and ophthalmology. The assessing of targets deeper tissue, vessels and organs (e.g., brain, lung, or liver) is challenging due to light scattering and absorption effects leading to attenuation laser energy and beam blurring. As a result, difficult to treat if not already incurable disease complications (e.g., metastasis, sepsis, stroke) may be developed at the time of initial diagnosis with the existing methods. Further increasing the sensitivity of laser methods to assess deep tissue is needed to provide diagnosis of fatal diseases at early stage when well-time therapy is more effective. As the optical signals from targets in many methods increase with increasing laser energy, one of potential ways to increase the sensitivity of these methods is to improve delivery of high energy in deep tissue. It is believed that this approach is limited by possible photodamage of skin where laser energy is much higher. Is also commonly accepted that maximum laser energy is regulated by the laser safety standard establishing maximum permissible exposure (MPE). In the spectral range of 500-1,100 nm, for nanosecond laser pulses, the MPE is 20-100 mJ/cm$^2$, respectively, at a pulse rate f≤10 Hz and drops at higher pulse rates due to accumulative effects, for example to 0.1 mJ/cm$^2$ at f=10 kHz at 1064 nm.

This safety standard establishes maximal laser power or energy for safe laser applications in many areas from the public use (e.g., pointers and laser barcode scanners, laser shows, art holography), to science, industry, and consumer electronic products. It is assumed that this standard can be applied for laser medical diagnosis. This is a reasonable requirement in laser imaging, eye's examination, or use pilot laser for scheme alignment in optical medical instruments. Provided herein is a new concept of optical diagnostics with dramatically increased (up to 100-1000-times) sensitivity without violation of a current laser safety standard. It is achieved by replacing a conventional one pulsed broad beam on many (up to $10^3$-$10^4$) small laser beams of certain spatial profiles allowing delivery much higher laser energy ($10^3$-fold and in same case up to $10^5$-fold) in deep tissue. Moreover, without being limited to a particular theory, early laser diagnosis of fatal diseases such as cancer, infections, and cardiovascular disorder can be accompanied by nonessential skin alteration only without any the risk for humans. In the described methods and devices herein, the energy fluences are still lower than those employed in many FDA-approved laser cosmetic and therapeutic systems (up to 10 $J/cm^2$) that have been broadly used to treat blood vessel abnormalities (e.g., port-wine stains), skin resurfacing (e.g., wrinkle removal) or hair removal with no evidence of significant risk that that was confirmed during long (at least 30 years) application of laser medical devices.

A fractionated photoacoustic (PA) flow cytometry (PAFC) system and methods for the in vivo detection of target objects in biofluidic systems (e.g., blood, lymph, urine, serum, tear, or cerebrospinal fluid) of a living organism is described. The fractionated PAFC system may include a fractionated laser system, a fractionated optical system, a fractionated acoustic system, and combinations thereof. The fractionated laser system includes at least one of a laser or laser array for pulsing a target object within the circulatory vessel with fractionated focused laser beams. The fractionated optical system separates one or several laser beams into multiple beams in a spatial configuration on the skin above the circulatory vessel of the living organism. The fractionated acoustic system includes multiple focused ultrasound transducers for receiving photoacoustic signals emitted by the target object in response to the fractionated laser beams. The target objects have intrinsic photoacoustic contrast or may be labeled with photoswitchable or spaser-based probes. Fractioned beams may also be used for diagnostics with other spectroscopic methods (e.g., fluorescence, Raman or scattering) and energy sources both coherent and conventional such as lamp and LED in the broad spectral range from 10 Å to 1 cm (e.g., X-ray, UV, visible, NIR or microwaves) in continuous wave and pulse modes in the broad range of pulse duration from 10 ps to 1 ms.

Provided herein are various aspects of devices and methods for fractionated PAFC with delivery of multiple (fractionated) laser beams with a specific shape and gaps between the individual beams with high pulse rates and different wavelengths to deep in vivo biotissue, in particular blood vessels, for early diagnosis of many diseases with focus on cancer, infections and cardiovascular disorders by ultrasensitive detection using fractionated acoustic system of a single specific target object or marker or multiple markers in vivo using either intrinsic PA contrast agents or targeting of markers by artificial PA probes. The markers may be associated with normal cells and physiological processes or may be associated with disease processes. In various aspects, devices and methods for in vivo detection of individual cells using bio-barcoding and multi-color time-resolved detection of individual normal and abnormal cells in circulation in a subject in vivo are disclosed. In one aspect, the in vivo detection of the individual cells may be enabled using an in vivo fractionated PAFC device that may include multiple laser sources, optical systems for the delivery of laser radiation, PA probes, and a detection system.

The fractionated PAFC system provides for multiple beams with a small diameter for a circular shape or width for a linear shape. In an aspect, the individual laser beams may have one dimension of about 0.2 µm to about 1 cm, in a preferred aspect, the beams may have one dimension of about 0.2 µm to about 200 µm. The small size of the beams may reduce thermal relaxation time and heat spatial and temporal accumulation. It allows for preventing overheating of superficial skin layers and accompanied pain while simultaneously increasing laser energy in deep vessels to increase the sensitivity of PAFC and other optical methods (e.g. fluorescence, Raman, CARS, second and third harmonic generation, multiphoton and others). Thus, the fractionated PAFC and other methods may use specific beam shapes and spatial configurations with specific the gaps between laser beams. Novel aspects of the devices and methods disclosed herein may include: fractionated delivery of laser radiation with multiple beams in PAFC; PAFC with a fractionated acoustic detection system; integration of optical resolution (OR) and acoustic resolution (AR) in fractionated PAFC (OR-PAFC and AR-PAFC, respectively); multicolor fractionated PAFC; bio-barcoding of multiple markers using narrow spectral resonances followed by time-spectral reading (decoding); fractionated PAFC with photoswitchable PA probes; fractionated PAFC integrated with fluorescence flow cytometry (FFC) using spaser as new super contrast multimodal multifunctional probes and spasers; time-of-flight fractionated PAFC using two-beam and/or multiple beams; and PA signal processing algorithms in multicolor and time-of flight fractionated PAFC.

Physical and technical principles of fractionated PAFC are based on irradiation of blood vessels with pulsed multiple beams followed by the detection of laser-induced acoustic waves (referred to as PA signals) from individual target objects with a fractionated acoustic system using an acoustic focused ultrasound transducer array attached to the skin through a thin layer of water or ultrasound gel (for acoustic matching of the skin and transducer and simultaneous skin cooling). In various aspects, the target object may be circulating tumor cells (CTCs), such as melanoma, infections such as a virus (HIV), bacteria, parasites (malaria), clots, and intrinsic (e.g., exosomes) and exogenous micro- and nanoparticles (NPs). The physical mechanism of the PA method is associated with thermoelastic generation of acoustic waves by laser-heated absorbing zones in target objects. According to thermal confinement, absorption of a laser pulse with a width of $t_P$ at $t_P \leq \tau_T$ ($\tau_T$, thermal relaxation time), for example by melanin or hemozoin as intrinsic PA contrast agents or by functionalized artificial PA probes (e.g., plasmonic NPs, photoswitchable NPs, or spasers), leads to a maximal temperature increase (and maximal PA effects) without the influence of heat loss due to thermal diffusion to surrounding medium. For spherical targets with radius R the thermal relaxation time may be determined using Eqn. (I), $$\tau_T = R^2/6.75k, \qquad \text{Eqn. (I)}$$

where k is thermal diffusivity. For R=10 nm, 50 nm, and 5 µm, $\tau_T$ is about 160 ps, 4 ns, and 40 µs, respectively. The pulse width $t_P$ must also satisfy acoustic confinement providing the generation of the maximum PA signal:

$$t_P \leq 2R/c_s, \qquad \text{Eqn. (II)}$$

where $c_s$ is the speed of sound. For $R_{CTC}$=12 µm (size of a whole cell) and $R_M$=0.3 µm (size of one melanosome in a melanoma cell), $t_P$ 10 ns and 400 ps, respectively. Each target object may be exposed at a laser pulse-repetition rate, $f_r \geq (V_F)/d$, where $V_F$ is blood flow velocity and d is the width of the laser beam or acoustic resolution of PAFC. In a 1-3-mm-diameter human vein, $V_F$ is ~5-15 cm/s, and for d=50-100 μm, $f_r \geq 0.5$-2 kHz. Increases in $f_r$ improve the signal-to-noise ratio (SNR). The SNR may be determined by the ratio of flash (transient) PA signals from single target objects to superposed background PA signals from red blood cells (RBCs) in the detection volume, as well as to noises of different origins (e.g., electronic, acoustic, fluctuation in RBC number, or laser energy instability).

Laser-based devices may be capable of examining a much larger volume of blood in vivo compared to conventional diagnostic techniques involving the ex vivo examination of small samples. Such devices may exploit the well-established physiological fact that almost the complete volume of blood in a human adult (i.e., 5 liters) passes through peripheral blood vessels with diameters of 2-3 mm within 0.5-1 hours. In a larger vessel, such as jugular vein or carotid artery (10-15-mm diameter), total circulation time may be on the order of 5-10 minutes or less. The examination of the entire blood volume of a subject may reduce diagnostic errors such as false positivity and false negativity for rare events. In addition, the detection limit may be significantly reduced, resulting in a threshold of sensitivity as low as 1 cell of interest (biomarkers) in 100 ml of blood (at least 100-fold more sensitive than existing assays, based on ratio of sample volume in vivo and in vitro methods) or one in 500-1000 mL.

The use of a laser-based device to conduct blood testing of the whole blood volume of a subject in vivo with greatly enhanced sensitivity may shift paradigms of the clinical role of blood tests from disease staging and/or assessment of therapy efficiency to early disease diagnosis—hypothetically before disease progression to an untreatable stage or at least to clinical symptoms. Therefore, application of a well-timed, more effective, and personalized therapy, in particular PT therapy, guided by real-time abnormal cell counting may be enabled by such a device.

I. Fractionated Photoacoustic Flow Cytometry System

The sensitivity of most optical methods may be improved by increasing laser energy, as optical signal amplitudes are often proportional to laser energy fluence (pulse mode)/intensity (continuous wave (CW) mode). An increase in laser energy on the skin is believed to be limited by the maximum permissible exposure (MPE) of skin. In the spectral range of 500-1,100 nm, for nanosecond laser pulses at a rate f 10 Hz, the MPE for skin is 20-100 mJ/cm$^2$, respectively, and the MPE is lower (0.1-1 mJ/cm$^2$) at higher pulse rates of 1-10 kHz. However, RBCs and WBCs in the NIR range (800-850 nm) have high photodamage thresholds at the level of 10-20 J/cm$^2$ and 50-100 J/cm$^2$, respectively, which is 1,000-fold higher than the MPE. Moreover, the laser safety standard was introduced on the basis of a 3.5-mm-diameter laser beam. The adverse effects at high laser pulse rates may be associated with temporal and spatial overlapping of thermal effects in the irradiated volume. Therefore, the laser beam radius may be decreased, leading to a decrease in the thermal relaxation time $\tau_T \sim R^2$ and to reduce these thermal effects.

Figure 2A:
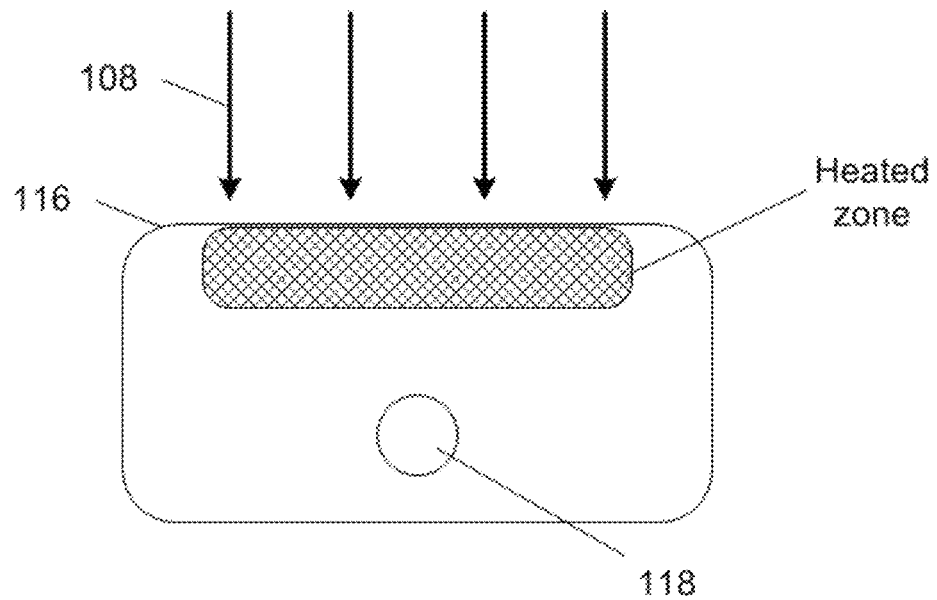
Figure 3A:
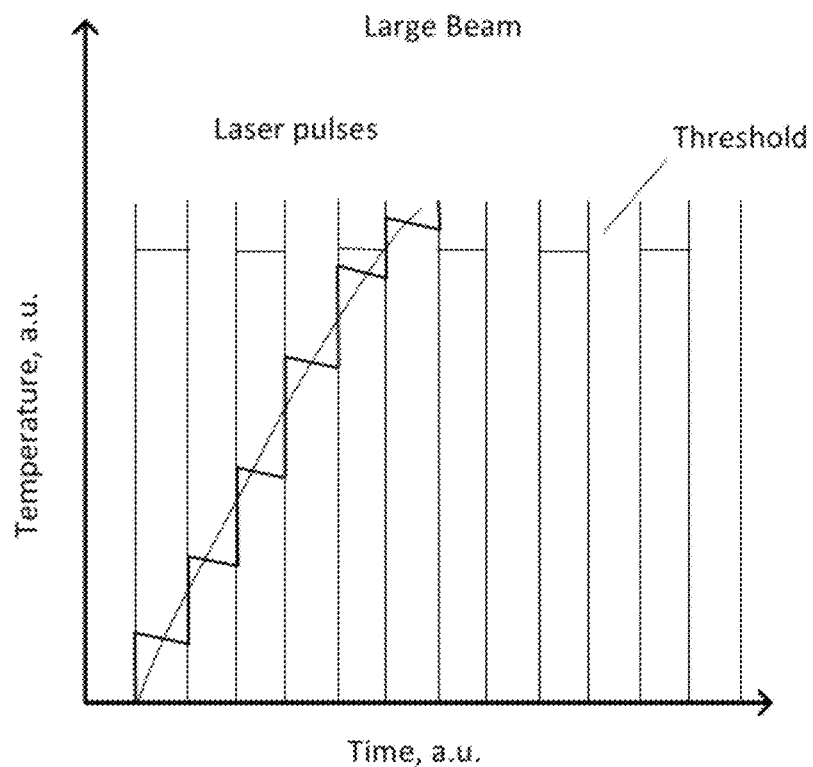
FIG. 3A shows a phenomenological model for accumulative thermal effects with a conventional broad laser beam at high laser pulse rate (frequency) and FIG. 3B shows the absence these non-desired effects in fractionated PAFC with a small diameter beam due to fast cooling of the laser-heated absorbing zones.
Figure 3B:
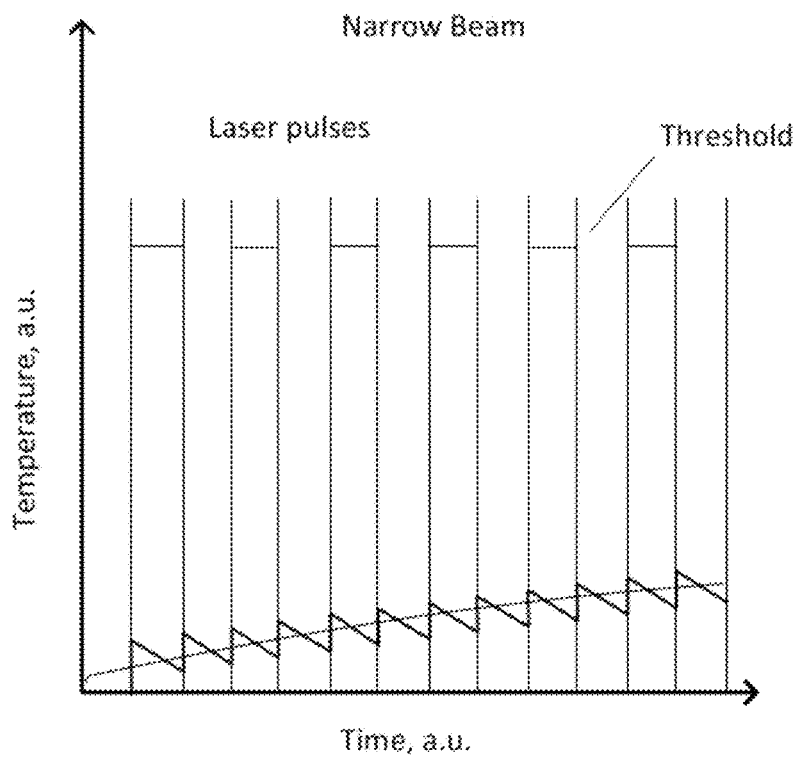
Figure 4A:
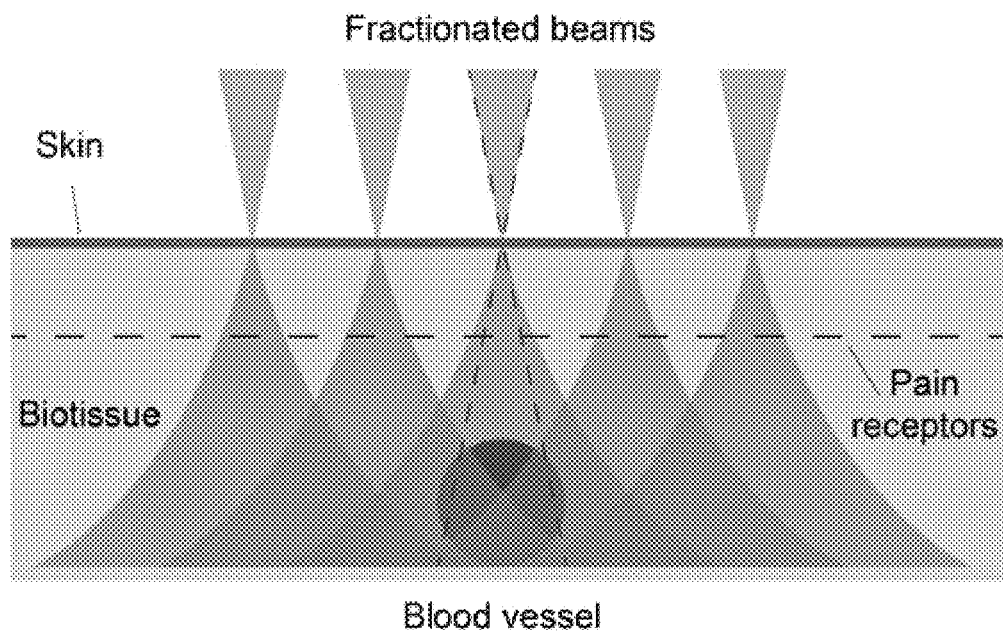
FIG. 4A and FIG. 4B show main schematics of fractionated PAFC with the fractionated laser beams allowing for dramatic improvement in delivery of high laser energy in deep tissue without skin photodamage.
Figure 4B:
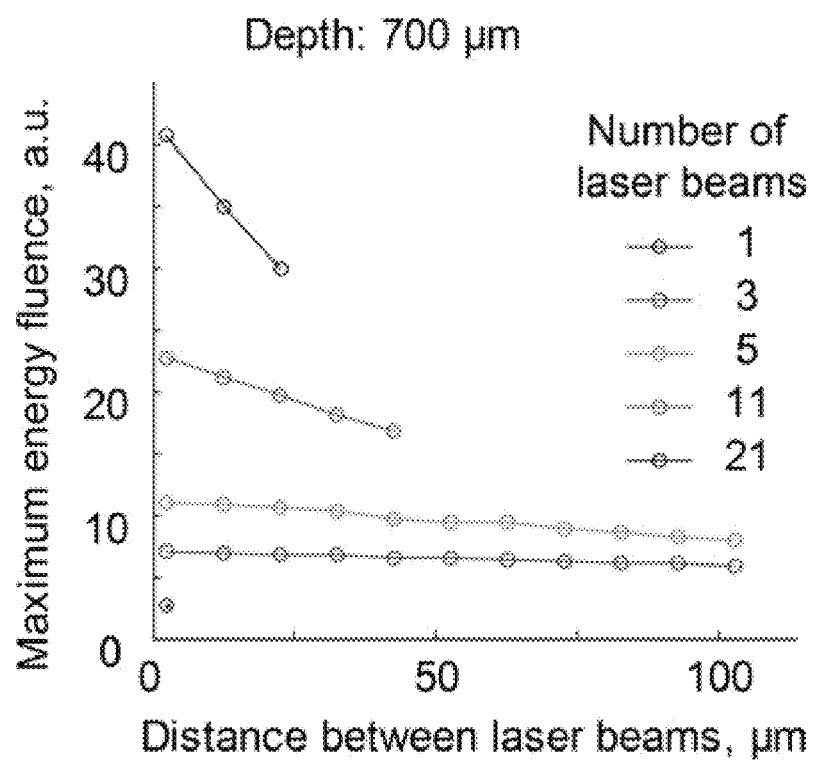

Provided herein is new concept of optical diagnosis in vivo using multiple small-diameter laser beams for the fractionated delivery of higher laser energy fluence levels (up to 100-1000 times or higher) to deep vessels without side effects and a corresponding fractionated PAFC device. In an aspect, the vessels to be imaged/monitored may be about 0.5 mm to about 50 mm deep below the skin, and even deeper with fractionated PAFC. For example, the vessels may be a vein in the hand (about 0.5-3 mm deep) or a jugular vein or carotid artery (about 15-20 mm deep). In one aspect, the vessels may be about 1 mm to about 5 mm deep. There may be no side effects because the laser energy would not be averaged and hence heat may not accumulate at a lower depth because the gaps between the individual laser beams (FIGS. 4A-4B and 7A-9) that prevent heat diffusion from one small beam to another during a short laser pulse. Thus, the gaps between beams prevent heat increase in the superficial skin layer where the first temperature, pressure, and/or pain receptors are located (FIGS. 4A-4B). In various aspects, the first pain receptors may be located at a depth below the skin of about 200 μm to about 400 μm. The shorter thermal relaxation time for a smaller-diameter laser beam allows for overcoming the limitations of relatively large laser beams with higher relaxation time. In an aspect, in fractionated PAFC, each laser pulse leads to a short temperature increase in the irradiated volume. Before the next pulse is delivered, heat dissipates and the heated volume quickly cools (because of fast thermal relaxation to about almost the initial temperature level or exceeds a little of this level by a few percent (FIG. 3B)). Thus the heat dissipation out of the laser volume after each laser pulse leads to only a non-significant average temperature increase. On the contrary, for large laser beams with longer thermal relaxation times (FIGS. 2D and 3A), accumulation of heat in irradiated zone leads to quick overheating of the surrounding zone and adverse high temperature-induced effects such as cellular protein denaturation and coagulation, skin surface burning, and the feeling of pain.

Figure 39A:
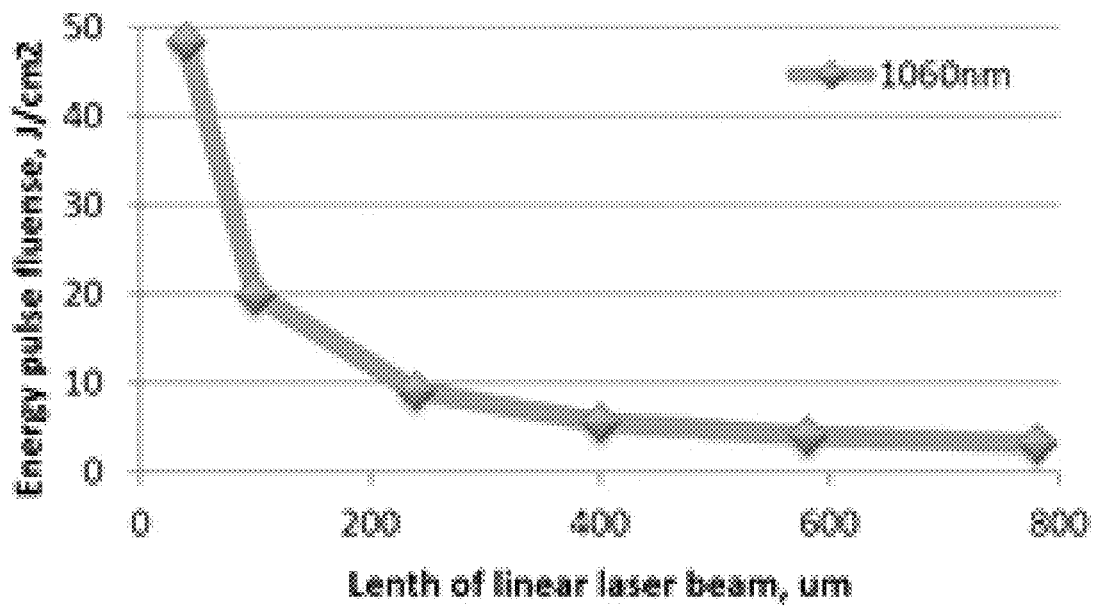
FIG. 39A illustrates a dependence of pain threshold in human hand on linear beam length at beam width of 6.5 µm at laser wavelength of 1064 nm and pulse rate of 10 kHz.
Figure 39B:
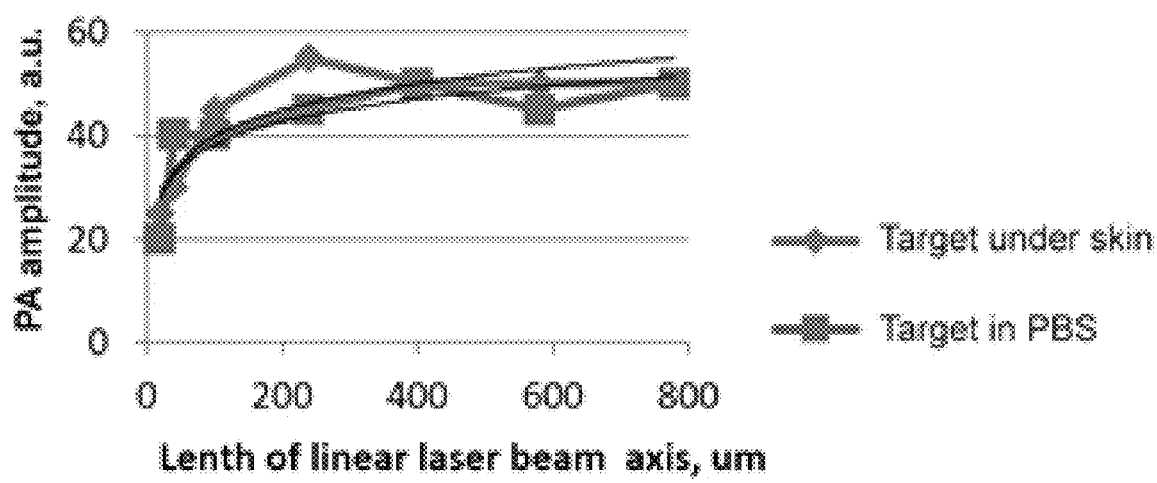
FIG. 39B illustrates a dependence of PA signals on a linear beam length from a 1 mm hand vein at depth of 1.1 mm.

The sensitivity may be increased by increasing the laser energy in deep tissue. This may be achieved not by increasing the energy in one beam but increasing the number of beams and keeping the energy of each beam below the skin damage or pain threshold. Thus, an increase in energy of only one beam would lead to increased heat in the irradiated superficial skin layer, while fractionated beams would reduce the heat in the irradiated superficial skin layer. FIG. 3A shows a phenomenological model for accumulative thermal effects with a conventional broad laser beam at high laser pulse rate (frequency) and FIG. 3B shows the absence these non-desired effects in fractionated PAFC with a small diameter beam due to fast cooling of the laser-heated absorbing zones. The significant blurring (extending) beam diameter in deep tissue due to light scattering by tissue may lead to overlapping blurred laser beams at some specific depth only (FIG. 4A), and result in an increased laser fluence within deep vessels with increasing beam number N (FIG. 4B). The overlapping of the blurred laser beams at the vessels at a specific depth may be determined by the appropriate calculation of gaps between laser beams and dependence of adverse effects (e.g., pain) and PA signal amplitude on laser beam parameters, for example on the length of a linear beam at a fixed width (FIG. 39A-39B).

Figure 5:
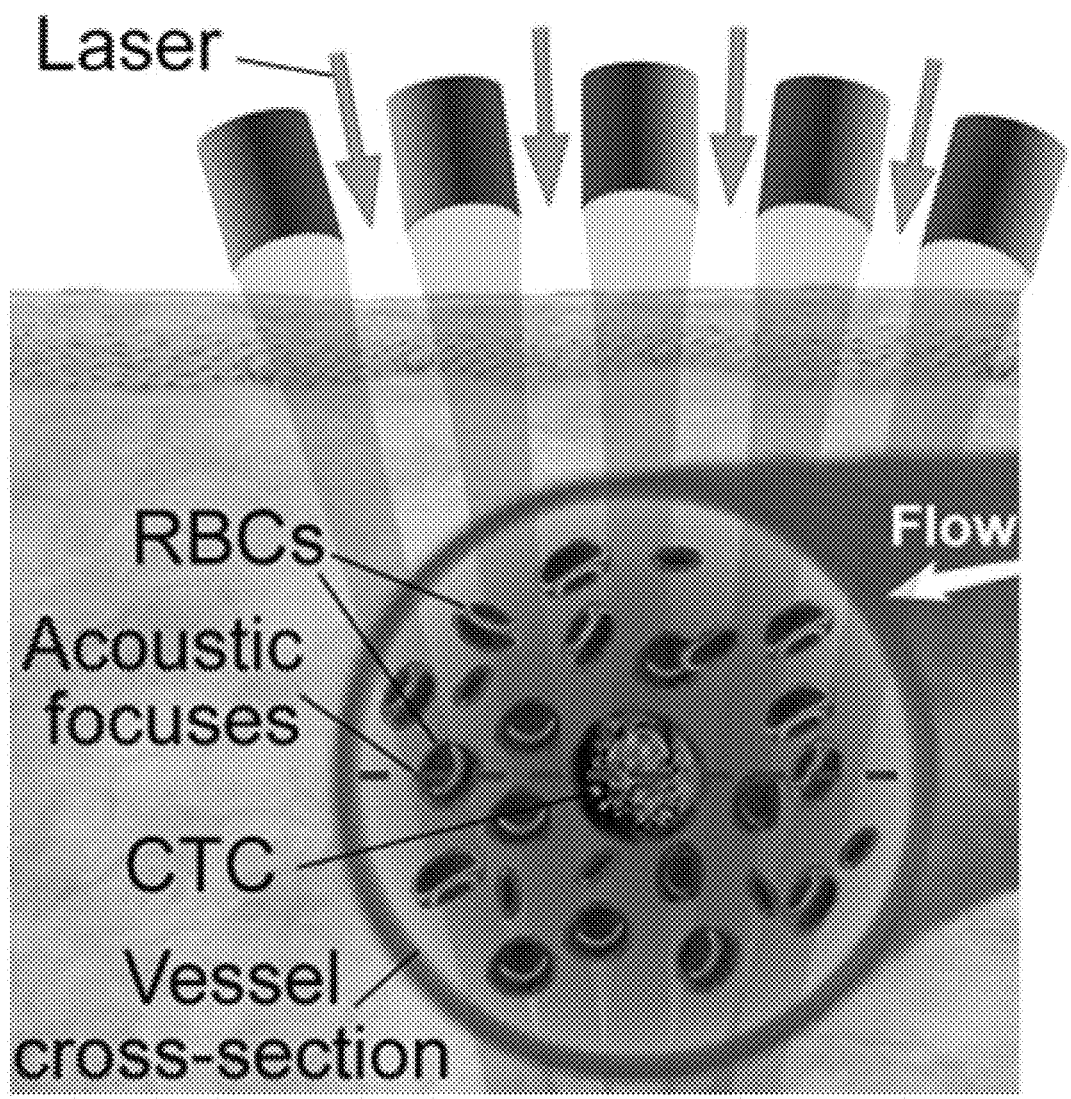
FIG. 5 illustrates a principle of a fractionated PA probe with integration of a fractionated laser beam with a fractionated acoustic detection system using multiple laser beams and focused transducers with non-overlapping focal volumes covering the whole cross-section of a vessel.
Figure 6:
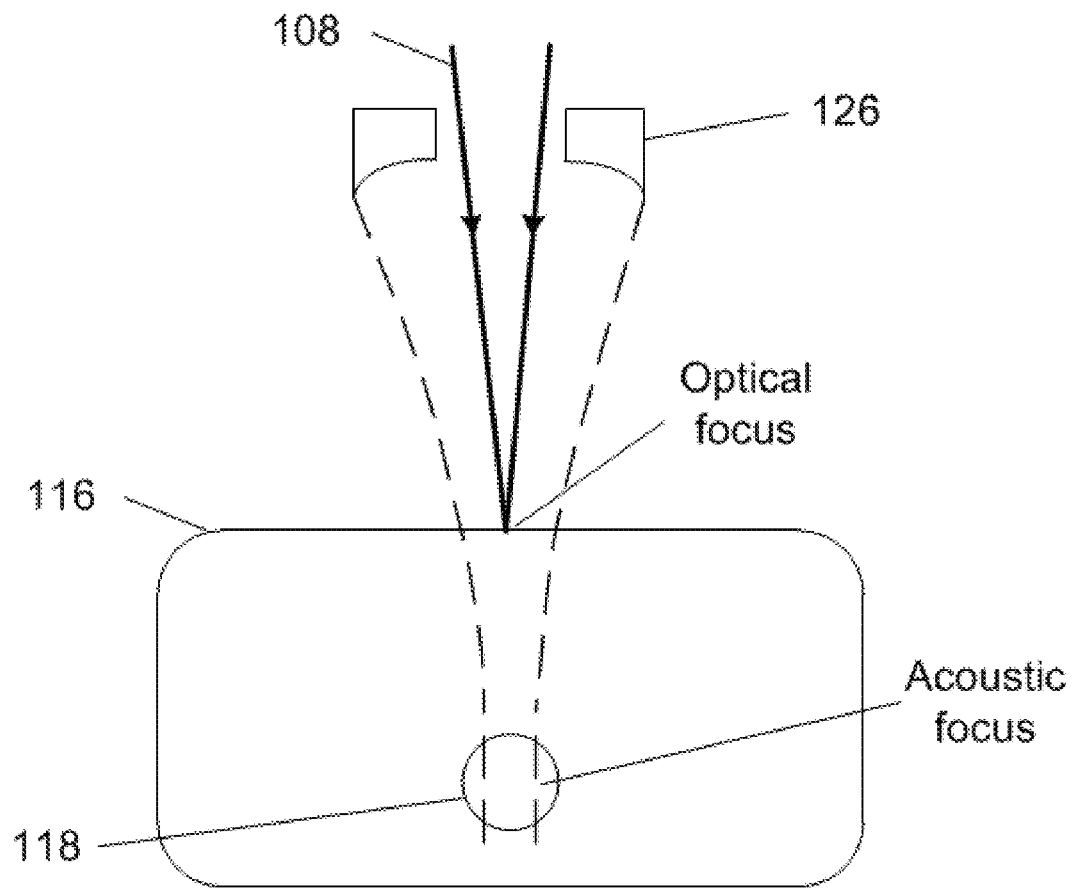
FIG. 6 illustrates a combination of a focused laser beam and focused transducers in a fractionated PAFC with non-overlapping focal volumes on the skin and into the vessel, respectively.
Figure 35A:
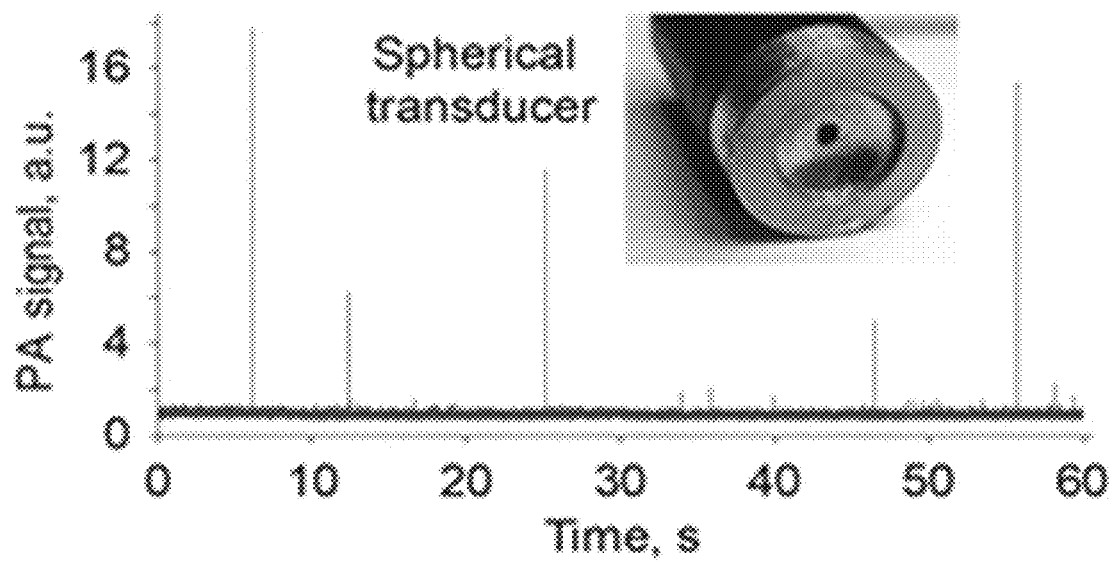
FIG. 35A is a PA signal trace from melanoma cells (C8161) in human blood with a focused spherical ultrasound transducer with a focal length of 6 mm and a lateral resolution of 45 µm.

A fractionated PAFC system may provide enhanced sensitivity for detection of target objects in deep vessels. In an aspect, the fractionated PAFC system may integrate fractionated delivery of laser energy with use of a "fractionated" single laser generating multiple beams (FIGS. 11 and 40), a laser array (i.e., several single beam lasers) with specific super-position of individual beam (e.g., FIG. 12B), and/or a fractionated optical system (FIGS. 12A-20) creating multiple beams of various spatial configurations. In some aspects, the fractionated PAFC system may further include a fractionated acoustic detection system (FIG. 5) and various combinations with a fractionated optical system (FIGS. 6, 8A-8H, 9, 10A-10B, and 28A). FIG. 5 illustrates a principle of a fractionated PA probe with integration of a fractionated laser beam with a fractionated acoustic detection system using multiple laser beams and focused transducers with non-overlapping focal volumes covering the whole cross-section of a vessel. FIG. 6 illustrates a combination of a focused laser beam and focused transducers in a fractionated PAFC with non-overlapping focal volumes on the skin and into the vessel, respectively. A fractionated acoustic detection system including a focused spherical ultrasound transducer array may provide detection of circulating target objects in a whole cross-section of large vessels with a high signal-to-noise (SNR) because there may be minimal signal background from RBCs in the smaller focal volume of each transducer (FIG. 35A). As illustrated in FIGS. 2B, 2C, 3B, 4A, and 4B, the goal of the fractionated PAFC is to enhance the laser energy fluence in deep vessels while keeping the safe level of energy in the superficial skin layer within about 200-300 µm where the temperature and pain receptors are located. Conventional flow cytometry (FC) in vitro uses linear beam shapes allowing for monitoring all the cells in the flow tube vessel. The same linear beam shape may be used with in vivo PAFC to provide detection of all cells in the blood vessel cross-section. However, increasing PAFC sensitivity by increasing laser energy in a linear beam may lead to high energy fluence in the superficial skin layers exceeding either the laser safety threshold or pain threshold. Fractionated laser beams may overcome these problems.

Figure 9:
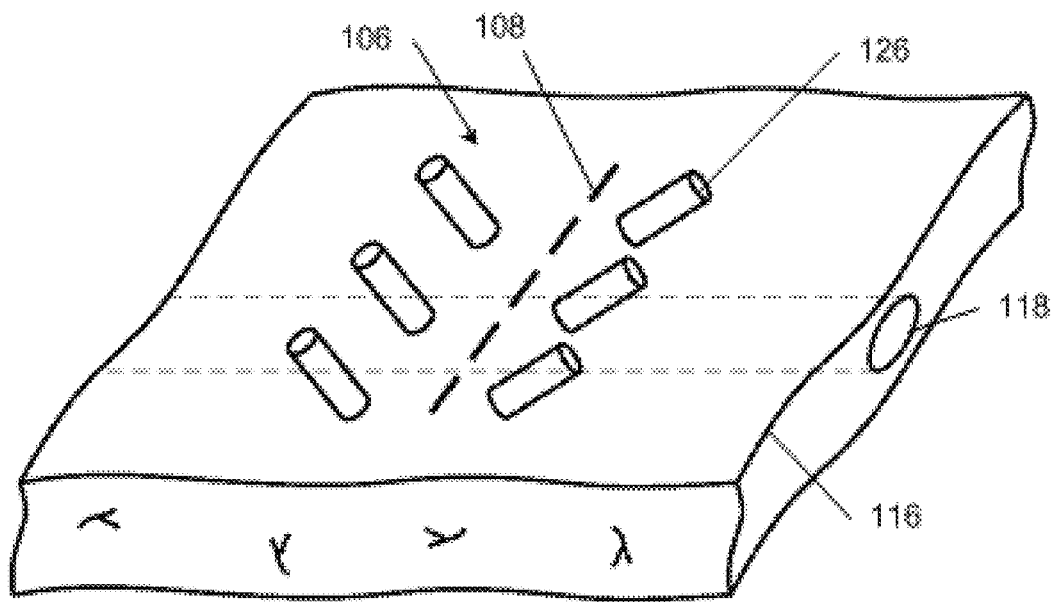
FIG. 9 illustrates an example of a dashed linear laser beam on skin and near skin surface with two linear transducer arrays (e.g., 3 transducers in each array) located from both side of linear laser beam.
Figure 10A:
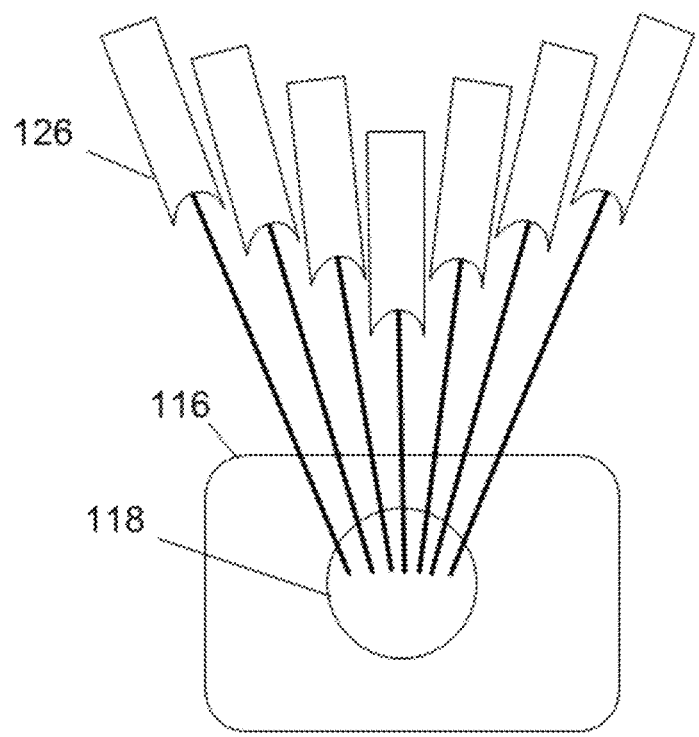
FIG. 10A and FIG. 10B illustrate a spatial configuration of ultrasound transducers in a linear array and on a spherical substrate, respectively, allowing minimizing of the array's and substrate's sizes by using the transducers of small diameters with different focal lengths, and different spatial orientation.
Figure 10B:
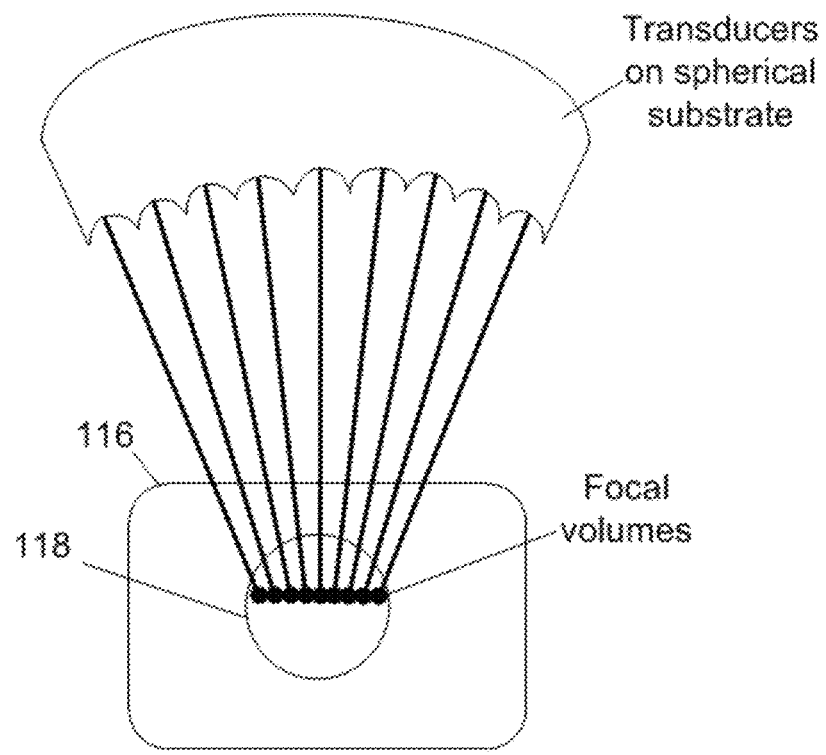

In an aspect, a fractionated PAFC system for the in vivo detection of target objects in a biofluid system or a circulatory vessel of a living organism is disclosed. In various aspects, the fractionated PAFC system may include at least one of a fractionated laser system, fractionated optical system, or fractionated acoustic system. FIG. 1 illustrates a fractionated PAFC system that includes either a fractionated laser or laser array generating multiple beams of certain spatial profiles, or/and a fractionated optical system splitting of one or several laser beams from one or several lasers into multiple beams, and a fractionated acoustic detection system using one or multiple focused ultrasound transducers arrays with individual amplifiers connecting to a recording system. As illustrated in FIG. 1, the system 100 may include a fractionated laser system 102, a fractionated optical system 104, and a fractionated acoustic system 106. The fractionated laser system 102 may include at least one pulsed laser for pulsing at least one target object 120 within the circulatory vessel 118 with at least one pulse of laser energy 124. The fractionated optical system 104 may be configured to separate the at least one pulse of laser energy 124 into more than one laser beam 108 in a spatial configuration on skin above the circulatory vessel of the living organism. As also seen in FIGS. 5, 6, 8A-8H, and 9, the fractionated acoustic system 106 may include more than one focused ultrasound transducer 126 for receiving more than one photoacoustic signal 122 emitted by the at least one target object 120 in response to the more than one laser beam 108. In one aspect, as illustrated in FIGS. 5 and 10A-10B, the fractionated acoustic system may include multiple ultrasound transducers on each side of the laser beams or on a semisphere with a central hole for delivery of the laser beams. For example, the fractionated acoustic system may include about 3-5 ultrasound transducers on each side of the laser beams as seen in FIG. 9.

Figure 23:
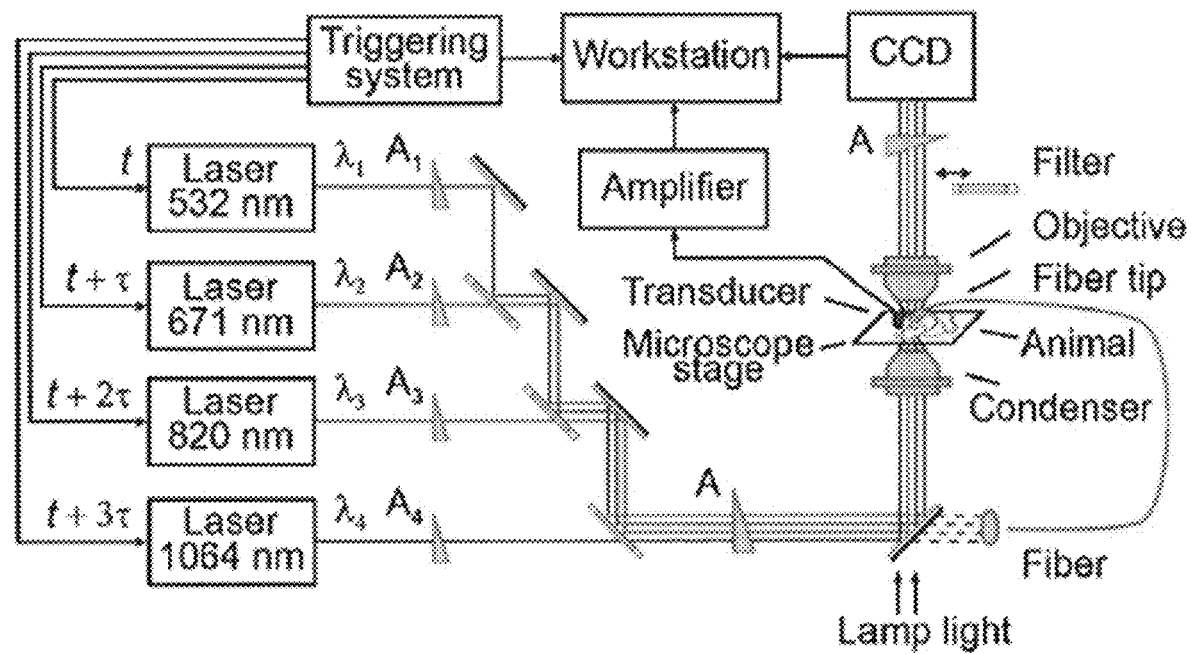
FIG. 23 illustrates fractionated multicolor PAFC schematics with time-resolved color-barcoding.

The fractionated PAFC system may further include a recording system 112 for recording the combination of photoacoustic signals emitted by the at least one target object in response to the more than one pulse of laser energy. In one aspect, the recording system 112 may be a multi-channel data acquisition board. Each focused ultrasound transducer 126 may have an independent preamplifier 110 for sending the photoacoustic signal 122 received by each focused ultrasound transducer 126 to a multichannel data acquisition board. At least one pulse of laser energy of the at least one pulsed laser 102 may have a wavelength from ultraviolet to radio wave in the range of about 200 nm to about 1 cm. The laser system 102 may include an array of more than one pulsed laser. In an aspect, each laser in the laser array may have a different wavelength for use in multicolor fractionated PAFC (FIG. 23). The system 100 may further include a triggering system 128 for controlling the more than one pulsed lasers, synchronization of the laser pulses, and/or the time-resolved recording system. In another aspect, the triggering system 128 may control the spatial scanning of the laser 102, the fractionated optical system 104, or the fractionated acoustic system 106. In various aspects, the fractionated laser system 102, fractionated optical system 104, and/or fractionated acoustic system 106 may scan independent from each other. In another aspect, the systems may be synchronized to scan together. In various aspects, the triggering system 128 may communicate with the laser system 102, the recording system 112, and combinations thereof.

Figure 7A:
FIG. 7A, FIG. 7B, FIG. 7C, and FIG. 7D illustrate multiple light beams spatial configurations in a fractionated PAFC system.
Figure 7B:
Figure 7C:
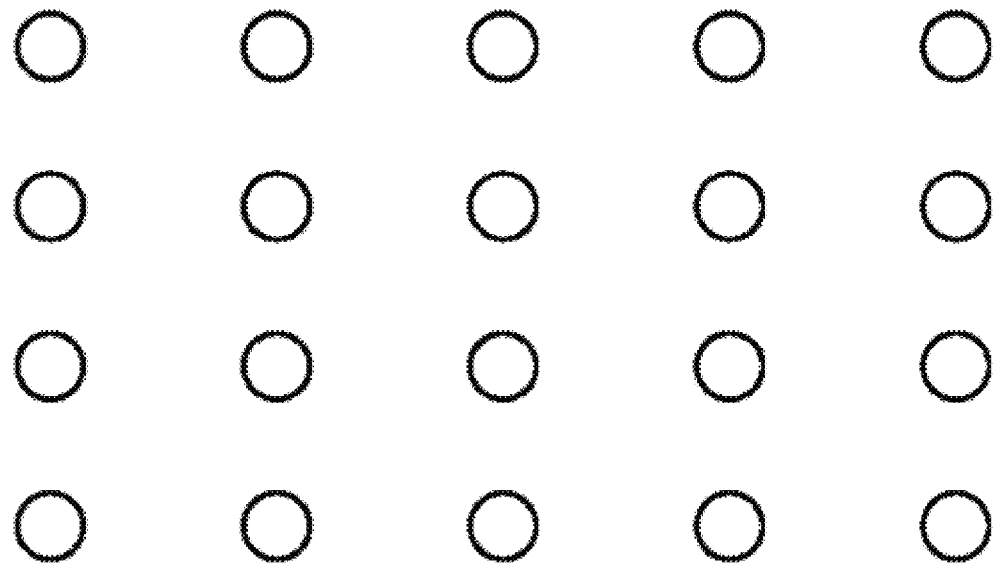
Figure 7D:
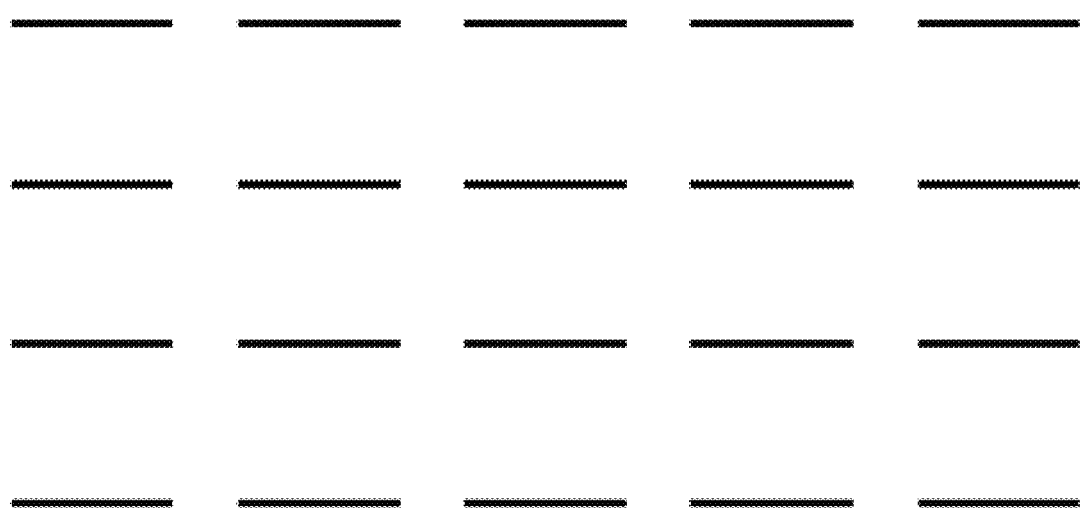
Figure 8A:
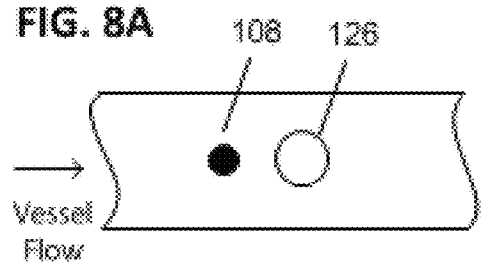
FIG. 8A, FIG. 8B, FIG. 8C, FIG. 8D, FIG. 8E, FIG. 8F, FIG. 8G, and FIG. 8H illustrate different combinations of fractionated laser beams and transducers in a fractionated PAFC system.
Figure 8B:
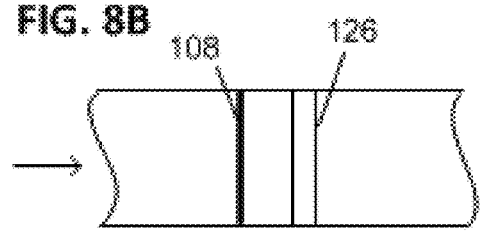
Figure 8C:
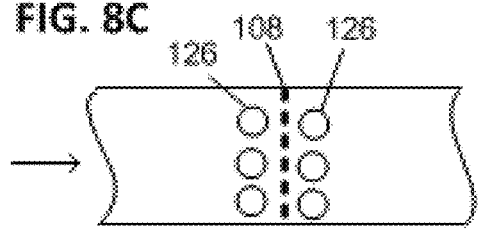
Figure 8D:
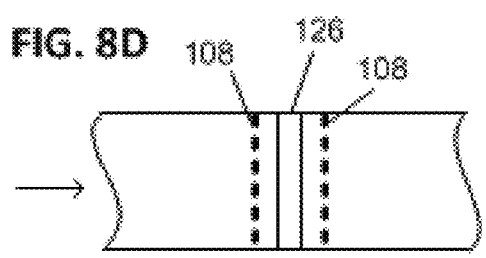
Figure 8E:
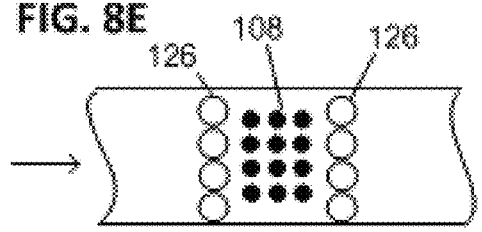
Figure 8F:
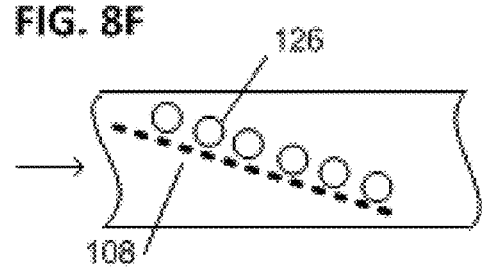
Figure 8G:
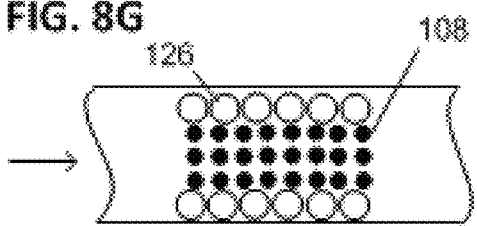
Figure 8H:
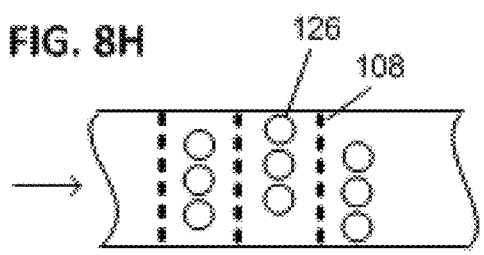

In an aspect, the more than one laser beams 108 from the fractionated optical system 104 may not overlap at a location in the living organism with the first pain receptors. The more than one laser beams 108 may spatially overlap at the circulatory vessel 118. The spatial configuration of the laser beams 108 may include gaps between the individual laser beams 108 on the skin 116 of the living organism. The gaps may be about 5 µm to about 200 µm. As illustrated in FIGS. 7A-7D and 8A-8H, the spatial configuration of the laser beams 108 may be one-dimensional (FIGS. 7A and 7B) or two-dimensional (FIGS. 7C and 7D). The fractionated optical system 104 may include an optical component for controlling the shape and number of laser beams. The optical component may be selected from a non-transparent mask, a beam splitter, an optical fiber array, a lens array, a microlens array, a mirror array, a diffraction element, a diffuser, a pinhole, and combinations thereof. The shape of the laser beams 108 may be selected from circular, linear, strip, elliptical, square, and combinations thereof. For example, FIG. 7A and FIG. 7C illustrate circular beam dimensions and FIG. 7B and FIG. 7D illustrate linear beam dimensions. The laser system, optical system, and the acoustic systems may independently be non-scanning or scanning. The fractionated optical system 104 may be configured to scan the more than one laser beams 108 across the circulatory vessel 118. Each focused ultrasound transducer 126 may have an acoustic focal volume that does not overlap or partially overlap to cover the whole blood vessel cross-section (FIG. 5). The fractionated acoustic system 106 may be configured to scan the acoustic focal volumes across the circulatory vessel. The focused ultrasound transducers 126 may be focused spherical ultrasound transducers in one aspect. Multiple beams are used in laser materials processing, optical communications, optical image processing, microelectronics, and laser treatment. However, the described multi-beam schematics have been never used in PAFC, which brings new unpredictable effects. To use multiple beams with PAFC, there is a need to increase the laser energy in deep tissue without damaging the surface layers. On the contrary, in known laser treatment with multiple beams the main goal is to damage the surface layer, which is not appropriate for safe laser diagnostics in medical fields.

In an aspect, a method for detecting a circulating target object in a circulatory vessel of a living organism may include pulsing the target object with a pulse of laser energy from a pulsed laser in a laser system at a first pulse wavelength, separating the pulse of laser energy into more than one laser beam in a fractionated optical system to form a spatial configuration on the skin above the circulatory vessel of the living organism, obtaining in a fractionated acoustic system more than one photoacoustic signal emitted by the circulating tumor cell induced by the more than one laser beams, and analyzing the photoacoustic signals to calculate the combination of photoacoustic signals emitted by the circulating target object, wherein the combination of photoacoustic signals is characteristic of the circulating target object. The method may further include pulsing the target object with a second pulse of laser energy from a second pulsed laser with a different wavelength and time delay compared to the pulse from the first laser, as seen in FIGS. 26A-26C and 48. The method may further include generating microbubbles or nanobubbles around intrinsic (e.g. melanin of hemozoin NPs) or artificial probes (e.g., plasmonic and/or photoswitchable NPs) when pulsing the circulating target object with the laser pulse with increased energy in the fractionated PAFC laser energy that leads to PA signal enhancement (FIG. 36).

Figure 2B:
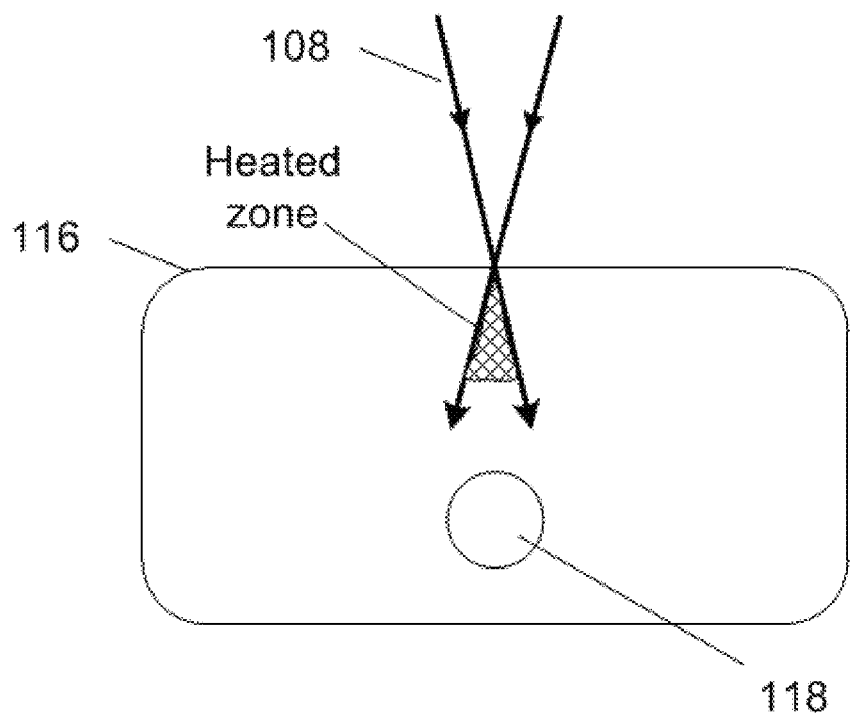
Figure 2C:
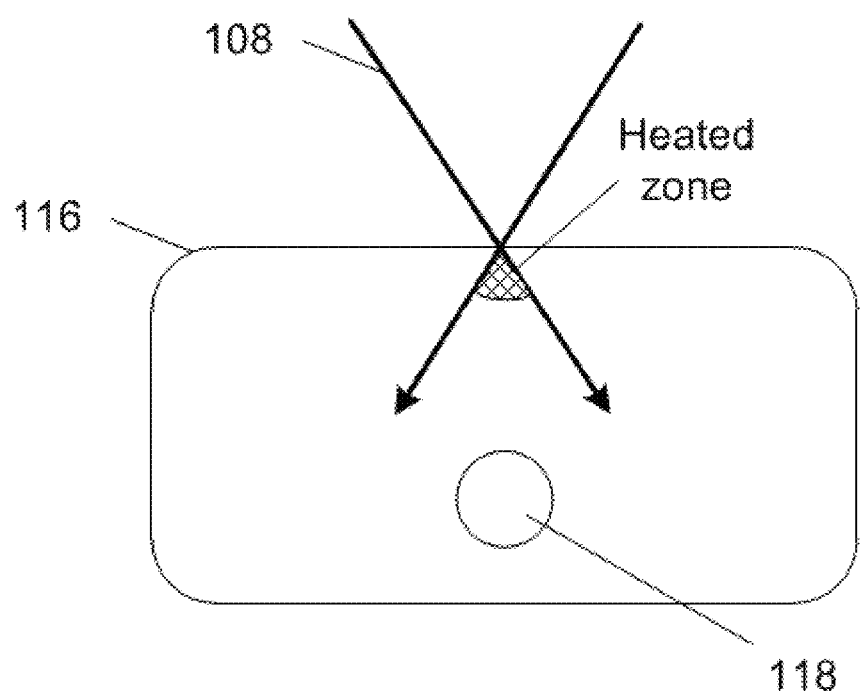

In fractionated PAFC, decreasing the laser beam diameter to a few micrometers may significantly reduce the risk of photothermal (PT)-induced superficial skin damage because of the consequent decrease in thermal relaxation time, and hence heat accumulation, especially at a high pulse rate (FIGS. 2B and 3B). In an aspect, increased PAFC sensitivity may be achieved by increasing the laser energy fluence without adverse effects by using fractionated delivery of laser energy via multiple laser beams. Various optical components may be used to create an array of laser beams. The optical components may include microlens arrays, diffusers, pinholes, and optical masks (FIGS. 12A-20). In various aspects, the laser beam array may be 1-D arrays of multiple small-diameter laser beams, with varying spacing between them and at different energy fluences in individual beams (FIGS. 7A-7D and 8A-8H).

Non-limiting examples of laser beam arrays include various numbers of laser beams, such as 1×10, 1×30, 10×10 or 20×20. The laser beams may have a cross-sectional shape of circular, linear, or elliptical. In an aspect, the diameter of the laser beams may range from about 0.25 µm to about 20 µm. Circular fractionated laser beams may have an individual diameter of about 200 nm to about 100 µm. The width of dashed linear fractionated laser beams may range from about 200 nm to about 200 µm. In various aspects, the diameter of the laser beams may range from about 0.25 µm to about 1 µm, from about 0.5 µm to about 5 µm, from about 3 µm to about 6 µm, from about 5 µm to about 10 µm, from about 7 µm to about 12 µm, from about 10 µm to about 15 µm, from about 12 µm to about 17 µm, and from about 15 µm to about 20 µm. As illustrated in FIG. 4A, the laser beams may be spaced apart at the skin such that the beams do not overlap on the skin or at the first pain receptors but do overlap at the vessel, which may be at a depth of greater than about 500 µm in one aspect. In an aspect, the optical parameters may be optimized to avoid overlapping of optical and thermal fields from each beam at the depth of the first pain receptors (200-400 µm), where laser energy is still high (maximal) before attenuation in tissue, with simultaneous spatial overlapping of attenuated light energy at the depth of the vessels (greater than about 500 µm). In an aspect, the spatial configuration of the laser beams includes gaps between the beams and the gaps may range from about 5 µm to about 1 cm. In various aspects, the gaps may range from about 5 µm to about 25 µm, from about 20 µm to about 50 µm, from about 40 µm to about 100 µm, about 75 µm to about 125 µm, about 100 µm to about 150 µm, about 125 µm to about 175 µm, and about 150 µm to about 200 µm. The fluences of the individual laser beams may be about 0.02 J/cm$^2$ to about 20 J/cm$^2$. In various aspects, the fluences may range from about 0.02 J/cm$^2$ to about 0.2 J/cm$^2$, from about 0.1 J/cm$^2$ to about 1 J/cm$^2$, from about 0.5 J/cm$^2$ to about 10 J/cm$^2$, from about 5 J/cm$^2$ to about 15 J/cm$^2$, and from about 10 J/cm$^2$ to about 20 J/cm$^2$. The total fractionated laser beam area may range from about 50 µm to about 20 mm.

The fractionated PAFC system provides for a dramatic increase (10-100-fold, if not more) laser energy level at a depth of about 1-3 mm up to about 10-15 cm without significant risk for harmful effects in the superficial skin area where the laser energy is still high before being redistributed (blurred) and attenuated in deeper tissue due to light scattering and absorption. The effects of increasing laser energy is more profound in deeper tissue due to more effective overlapping (superposition) of larger blurred beams and the possibility of using a higher number of laser beams on a relatively large skin surface area.

Figure 27A:
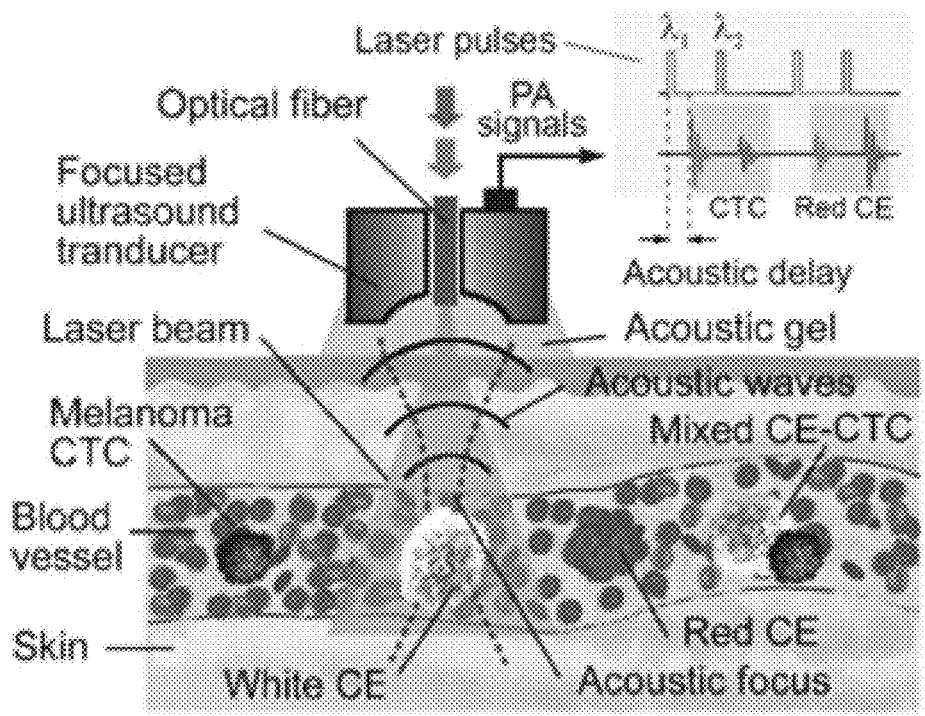
FIG. 27A illustrates PA probes of a fractionated PAFC with the focused cylindrical transducer having a central hole for lens or fiber-based delivery of a fractionated laser beam to skin.
Figure 27B:
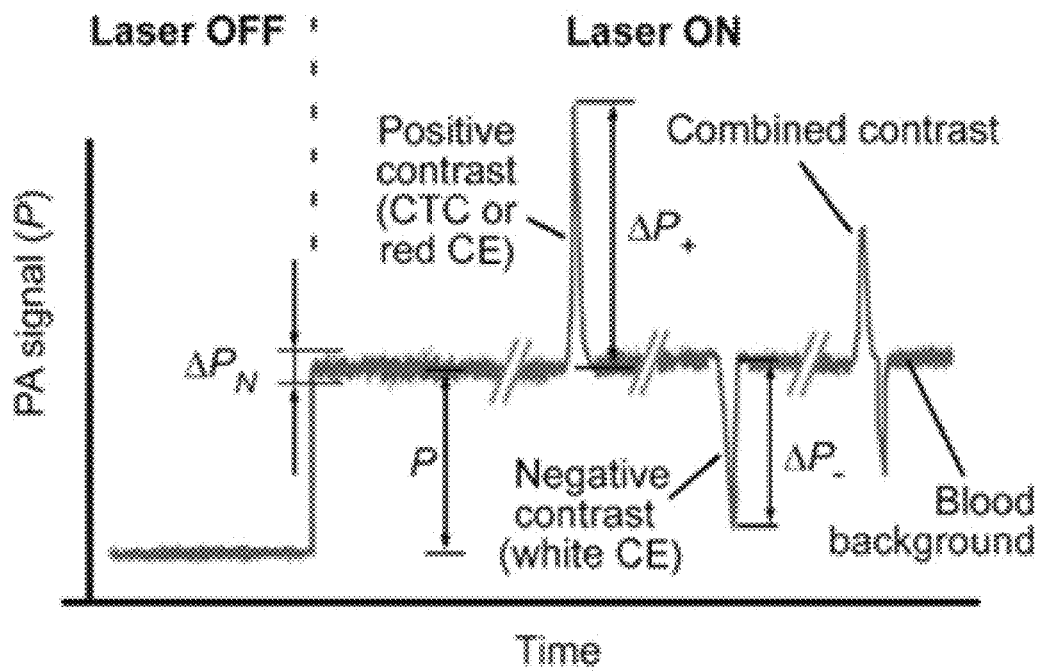
FIG. 27B shows a PA trace with positive, negative, and combined signal contrast for red circulating emboli [CE] or melanoma CTCs, white CE, and white CE-CTC aggregates, respectively.
Figure 27C:
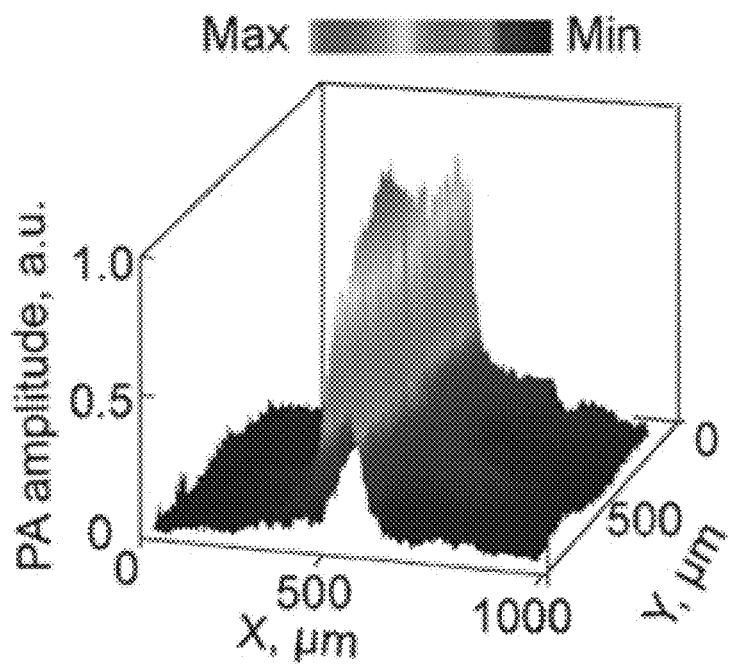
FIG. 27C shows lateral resolution (~45 µm) of the cylindrical transducer is represented as a PA signal distribution from black type during single focused small (2 um) laser beam scanning.

Fractionated PAFC can have positive and negative PA contrasts. In general, laser irradiation of blood vessels creates constant PA background signals associated with absorption by hemoglobin (Hb) in the many RBCs in the detection volume. In positive-contrast mode, when melanoma CTCs or red (Hb-rich) circulating emboli (CE) with higher absorption than the RBC background pass through the irradiated volume, localized absorption transiently increases, resulting in a sharp positive PA peak (FIG. 27B). In the negative-contrast mode, when white CE consisting of platelets, fibrin, or WBCs with lower (at least one-two orders of magnitude) absorption than the blood background (FIG. 27D) pass through the detection volume (FIG. 27A), a decrease in localized absorption results in a sharp negative PA peak (FIG. 2B). Mixed white-red CE or white CE with CTCs produce a pattern of positive and negative signals (FIG. 27B). Two-color PAFC (FIG. 27A, inset, right) can distinguish red CE and melanoma CTCs because the distinctive absorption spectra of Hb and melanin (FIG. 27D) yield specific PA signal ratios.

Negative contrast ($\Delta P^-/P$) depends on CE and blood absorption, vessel diameter ($d_V$), volume of CE ($V_{CE}$), and the detection volume ($V_D$) for a focused cylindrical transducer, $V_D \approx \Delta d \times \pi d_V^2/4$. A minimum detectable CE size ($d_{CE}$)$_{min} \sim (V_{CE})^{1/3}$ can be estimated as $(d_{CE})_{min} \approx \Delta P_N/P \times (V_D)^{1/3}$, where P and $\Delta P_N$ are PA signal amplitude and fluctuation (FIG. 27B), respectively. P is proportional to the number of RBCs (n) in the detection volume (e.g., n≈220 at $d_V$=50 µm and a hematocrit of 35-40%). In small vessels ≤20 µm, $\Delta P_N$ is determined by random changes in the number of RBCs in the detection volume, while in larger vessels $\Delta P_N$ is determined rather by instability of the laser pulse energy (typically 3-5%), electrical and acoustic noise, vibration, or physiological rhythms (e.g., heart beating or breathing). For $\Delta P_N/P \sim 0.05$, $\Delta d$=50 µm, and $d_V$=50 µm and 1 mm, $(d_{CE})_{min}$ 5-10 µm and 30-50 µm, respectively. These estimations are in line with the experimentally achieved threshold of 12-20 µm for small vessels. The duration of transient negative PA signals is short ($10^{-3}$-$10^{-4}$ s), while noise fluctuation and motion artifacts lie in the low-spectral-frequency range of <100 Hz. This may allow use of filtration and averaging to significantly (at least 5-10 fold) reduce the influence of these factors (FIGS. 24, 25A-25B, and 31A-31D) and monitor human vessel with a stable signal base over a few hours.

II. Fractionated Laser Sources

Fractionated laser beams may be created by the use of at least one laser with multiple beams and/or a laser array of more than one laser which may generate multiple laser beams having a certain spatial configuration. In an aspect, a laser system may include a single pulsed laser diode to produce fractionated laser beams. The single pulsed laser diode may have high peak power of about 200 W to about 800 W, a pulse energy up to about 5-20 µJ at 15-100 ns pulse duration, and wavelengths in broad spectral range from about 640 nm to about 1600 nm. A high power laser diode may be composed of many bars and stacks of active elements, as seen in FIG. 41A-41F, which can emit many individual beams. This figure indicates only small fragment of a laser diode, with one stack including three bars. In fractionated PAFC, many more stacks and more bars may be used (FIG. 7D). In an aspect, a laser diode used in PAFC may include up to about 3-10 stacks and up to about 5-20 bars. The beams from a pulsed laser diode, after passing through an optical system, may be directed as parallel or multiple focused beams to the skin above selected vessels. In an aspect, the optical system may include a collimator or a focusing lens.

In various aspects, the laser beams may have at least one dimension of about 0.2 µm to about 1 cm. The gaps between the laser beams may range from about 5 µm to about 1 cm. The fractionated laser beams may be one-dimensional or two-dimensional in configuration. In an aspect, the individual laser beams may have a shape selected from circular, linear, strip, elliptical, square and combinations thereof.

These fractionated beams may generate photoacoustic signals from moving target objects in deep vessels with diameters of about 0.5 to about 5 mm. Besides an increase in sensitivity, the shape of the array of laser beams may result in an appearance of consequent trains of PA signals produced by the same target objects crossing the individual strips of beams if there are not overlapped superficial microvessels with a diameter of about 10-30 µm at a depth of about 30-100 µm (e.g., in a mouse ear). Knowing the time interval between the signal trains and the distance between the strips in the focal spot, it may be possible to calculate the target object's velocity. The time interval between two consequent PA pulses may be measured and corresponds to the time of flight of the targets between two strips in the focal spots. At a depth of about 500 µm or more, light scattering leads to blurring and spatial overlapping of laser beams that does not allow for effective use of the time-of-flight technique with optical resolution (OR-PAFC). However, summing of laser energy within deep blood vessels provides the required increase in PAFC sensitivity.

III. Fractionated Optical System

Figure 12A:
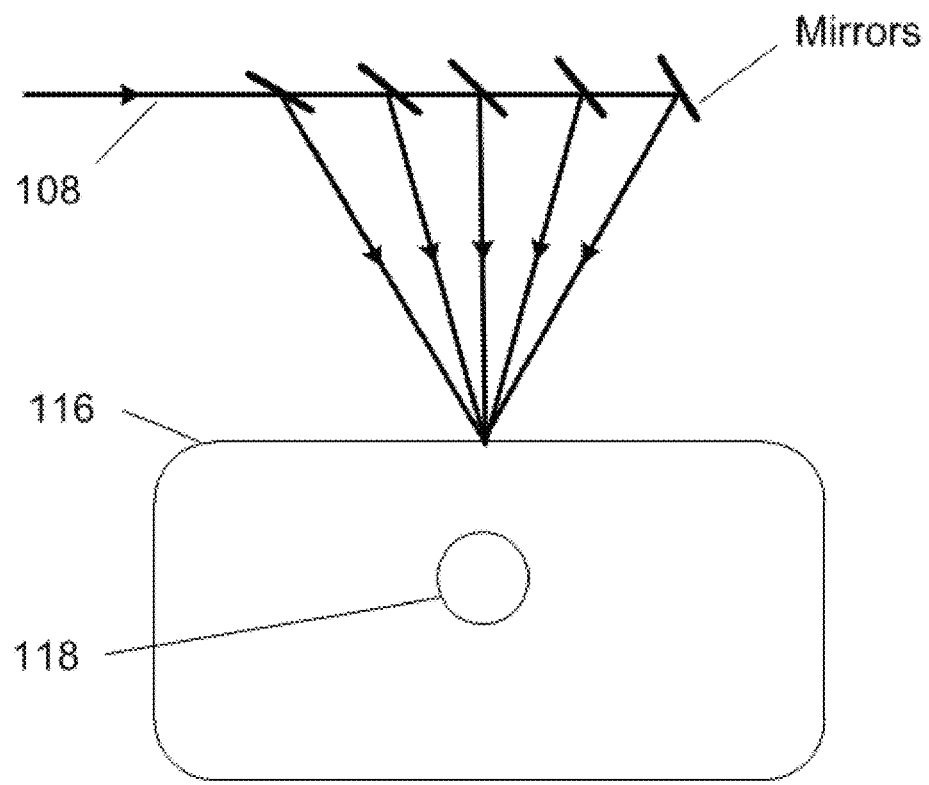
FIG. 12A and FIG. 12B illustrate the optical system with multiple mirrors providing fractionated laser beams.
Figure 12B:
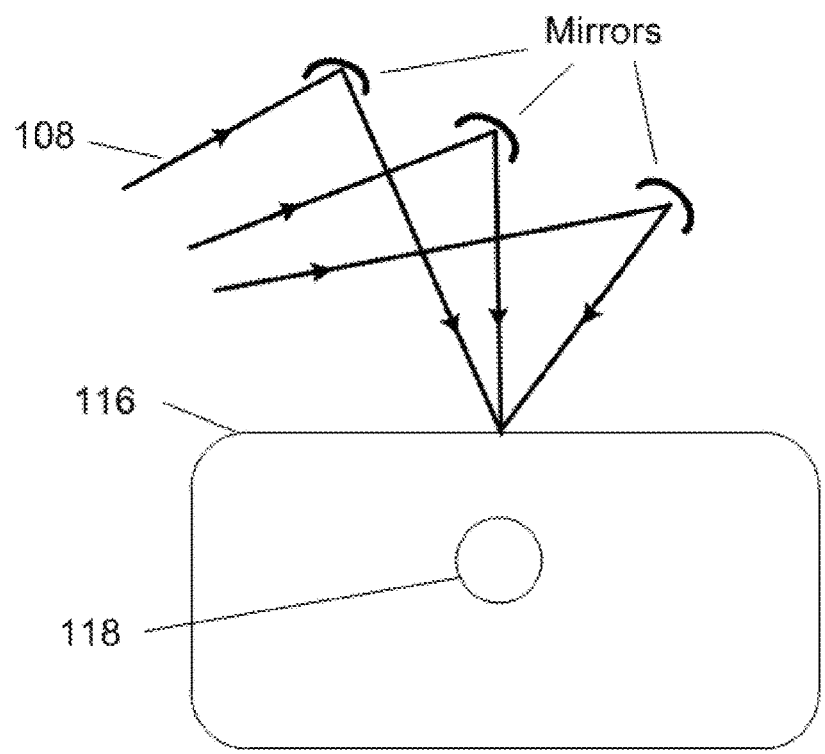
Figure 13A:
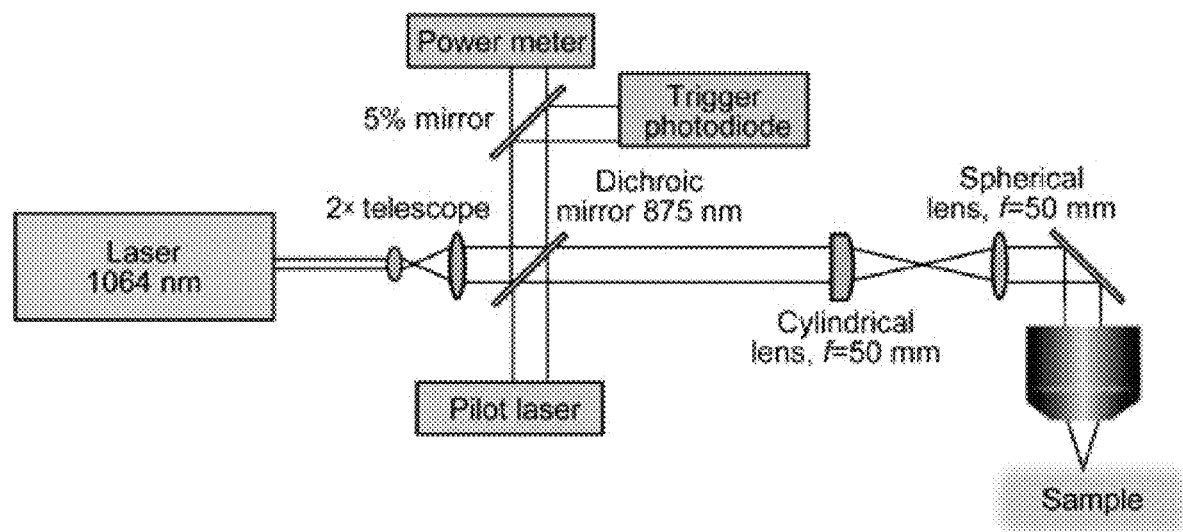
FIG. 13A is an illustration of optical system schematics for fractionated PAFC using a combination of cylindrical and spherical lenses.
Figure 13B:
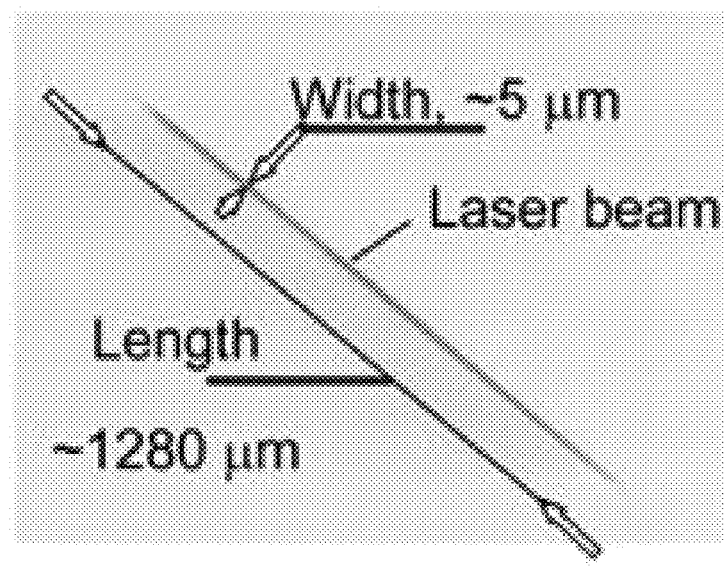
FIG. 13B shows a typical linear laser beam image and its dimension.
Figure 14A:
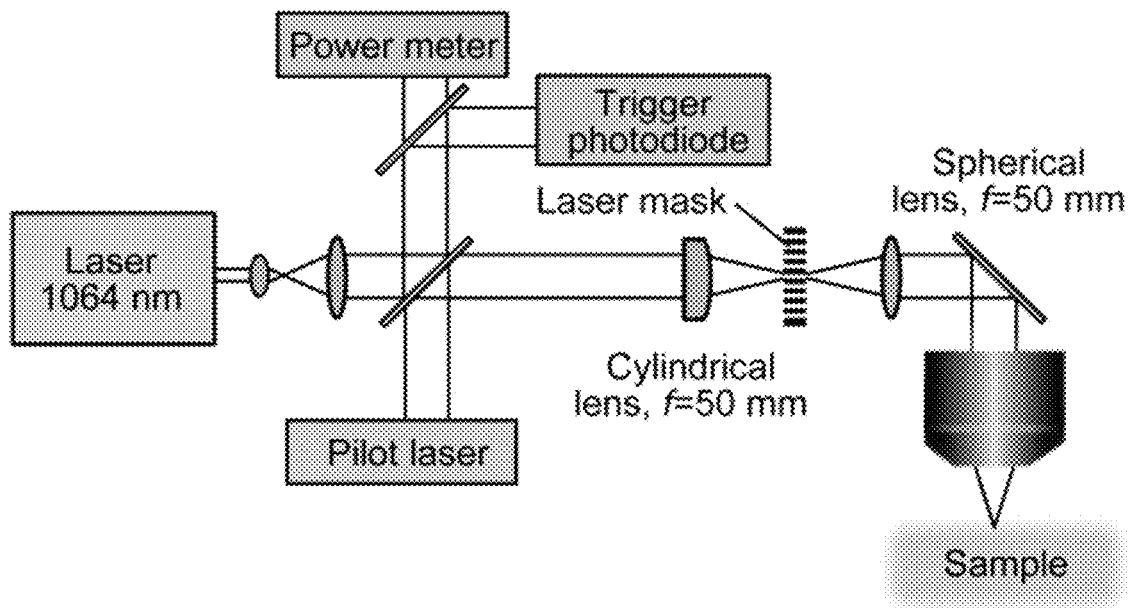
FIG. 14A is an illustration of optical system schematics for fractionated PAFC using a combination of cylindrical and spherical lenses and a non-transparent mask.
Figure 14B:
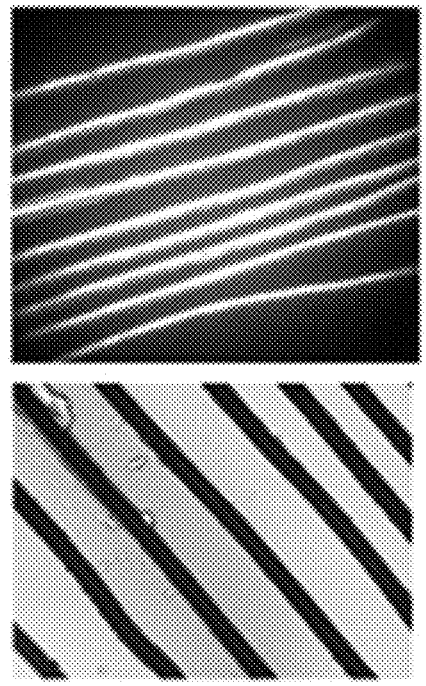
FIG. 14B is images of a laser mask for shaping a laser beam obtained with the reflected light (top) and transmission microscopy (bottom).
Figure 14C:
FIG. 14C is an example of a laser spot created with the mask.
Figure 14D:
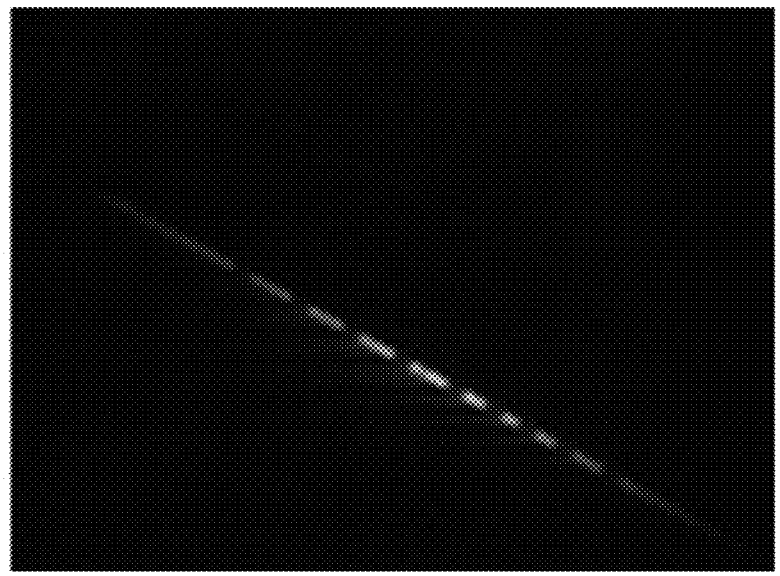
FIG. 14D is an example of a laser spot ("dashed" linear beam) created with the mask.

In an aspect, the system may include a fractionated optical system for creating multiple laser beams from a pulse of laser energy from at least one pulsed laser. The single or multiple beams may be easily separated with a mirror array of various spatial configurations (FIGS. 12A and 12B). A linear beam shape may be created by using a telescope to expand the laser beam after laser with a combination of cylindrical and spherical lenses, as illustrated in FIG. 13A. A dichroic mirror may be used to deflect a pilot beam laser for triggering data acquisition hardware and control laser energy fluctuation. The shaped laser beam may be focused into the sample using an objective. For example, a 10× objective with an NA 0.3, working distance of 16 mm, and infinity corrected may be used. The size of the laser beam spot may be measured by a custom microscope in transmission configuration by projecting the laser beam on to a microscope calibration ruler to measure exact beam dimensions, as shown in FIG. 13B.

Conversion of a linear laser beam into a line of individual laser spots may be performed using a non-transparent mask and/or an array of microlenses. In an aspect, a laser mask (nontransparent barrier on the laser beam path) may be used to create the required spatial distribution of the laser energy in the skin, as illustrated, for example, in FIG. 14A. In one aspect, the mask can be created by assembling several 40 µm steel wires into a regular pattern on a flat glass plate, as shown in the images in FIG. 14B. The mask may be placed into the focal point between cylindrical and spherical lenses of the optical system and block part of the laser light. In an aspect, the mask transmission after the objective may be around 70%. The total laser power may be required to be increase to compensate for the losses from the mask. The dash period may be measured as a combined length of bright and dark parts.

Figure 15A:
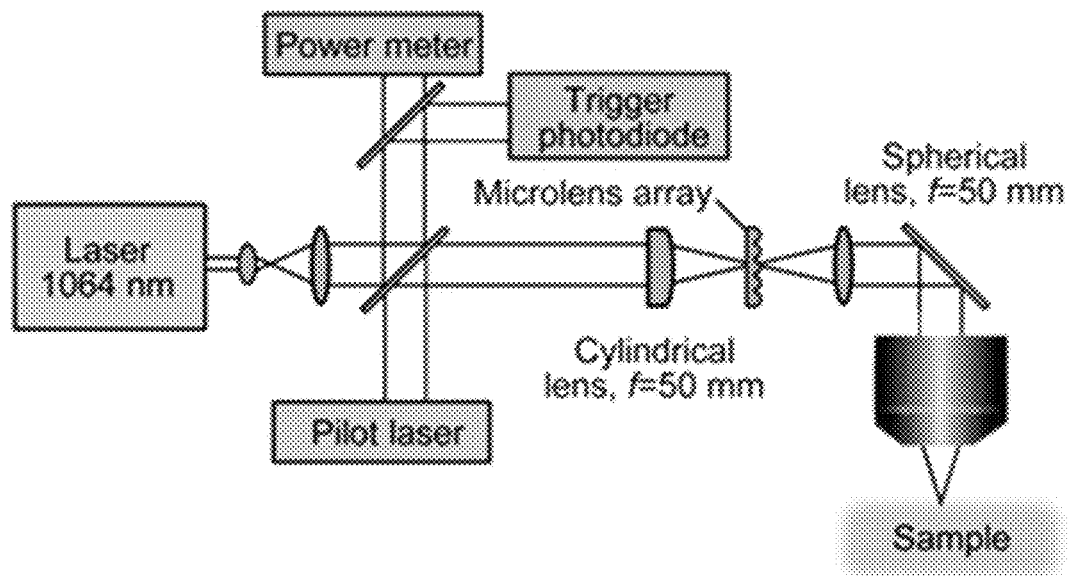
FIG. 15A illustrates optical system schematics with a microlens array for creation of 1-D light distribution in a fractionated PAFC system.
Figure 15B:
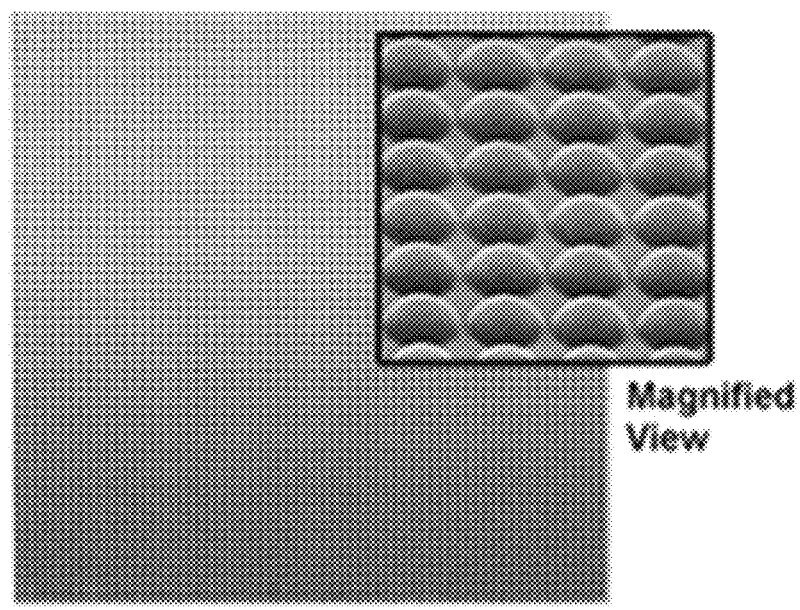
FIG. 15B is a microlens array image.
Figure 15C:
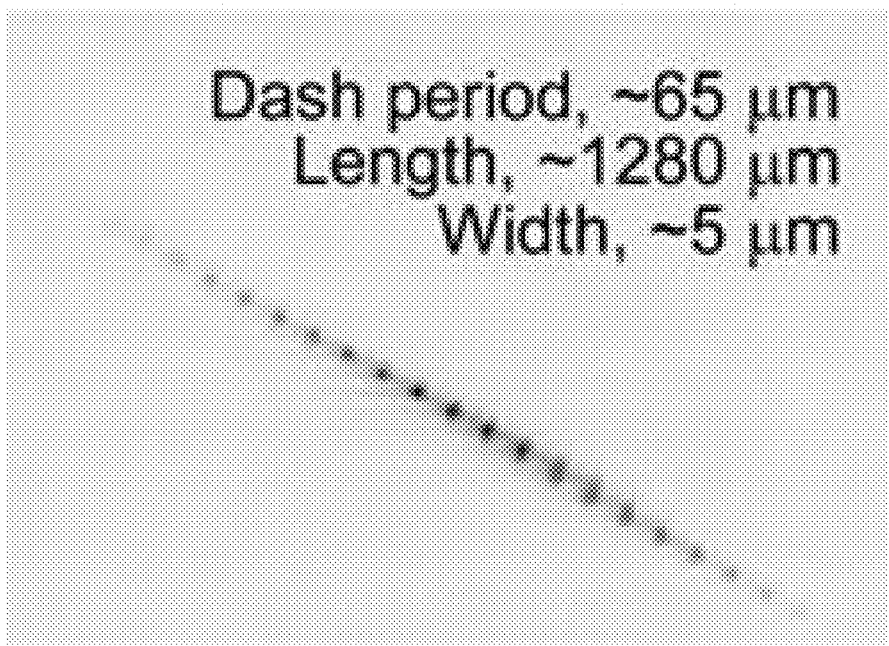
FIG. 15C is an example of laser spots ("dashed linear beam").

In an aspect, a microlens array may be used to spatially redistribute the energy of the laser beam in the fractionated optical system. A microlens array may be placed into the focal point between cylindrical and spherical lenses and interact with a linear beam shaped by a cylindrical lens, as illustrated in FIG. 15A. Thus, only one column of microlenses (FIG. 15B), may shape the beam, allowing to preserve the width of the laser beam in the sample. Laser spots in the sample may have a circular shape allowing it to concentrate laser energy in these areas compared to the regular linear beam shape (FIG. 15C). The laser beam in the sample may be sensitive toward array orientation. In various aspects, the optical system may include microlens arrays with a pitch between micro lenses of about 150 and about 300 µm. While smaller pitch means smaller dash period (higher number of laser spots along the laser line) it also may result in slightly wider line due to the fact that two or more lens columns may interact with the beam. Better results (narrower laser beam and more control over laser beam parameters) may be achieved with the use of cylindrical lens arrays having an appropriate pitch size between cylindrical lens elements.

Figure 16A:
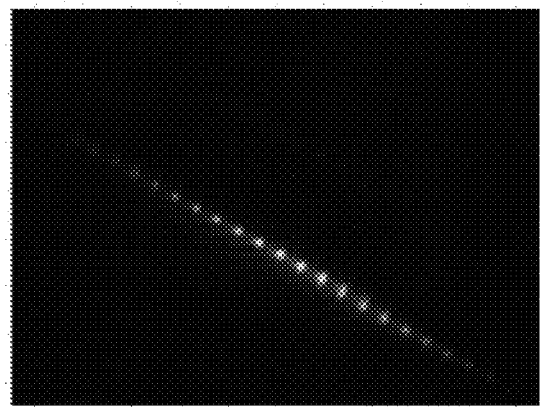
FIGS. 16A-16C illustrate the images of laser beams for a fractionated PAFC created with the microlens array in FIG. 15A.
Figure 16B:
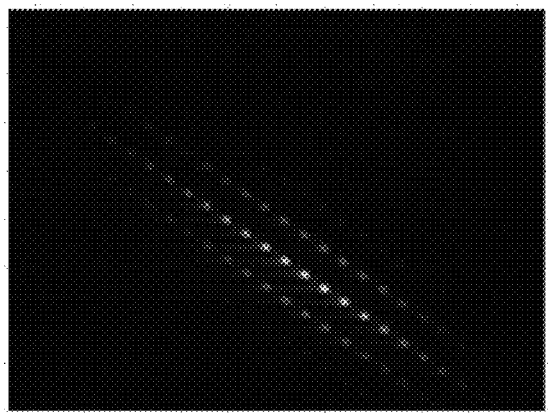
Figure 16C:
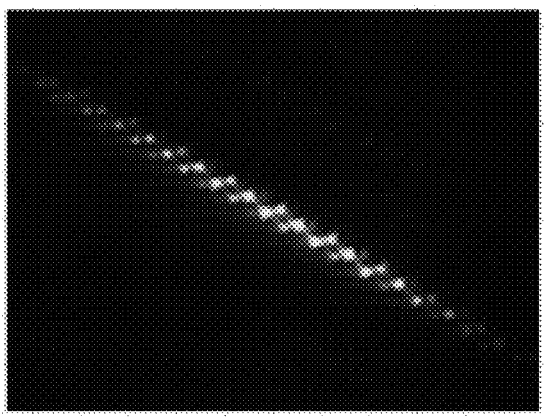

FIG. 15A illustrates optical system schematics with a microlens array for creation of 1-D light distribution and in some cases "narrow" 2-D distribution (FIGS. 16A-16C). FIG. 16A shows the light distribution on the focal plane. FIG. 16B shows the light distribution about 3 mm above the focal plane. FIG. 16C shows the light distribution in a chess-board-like light distribution after rotation of the lens array.

Figure 17A:
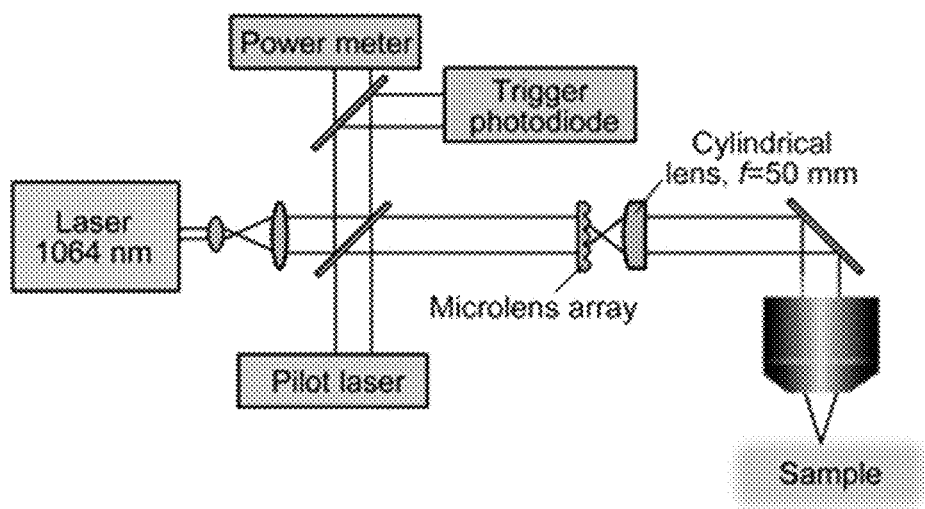
FIG. 17A illustrates optical system schematics for a fractionated PAFC system with a microlens array for creation of 2-D light distribution.
Figure 17B:
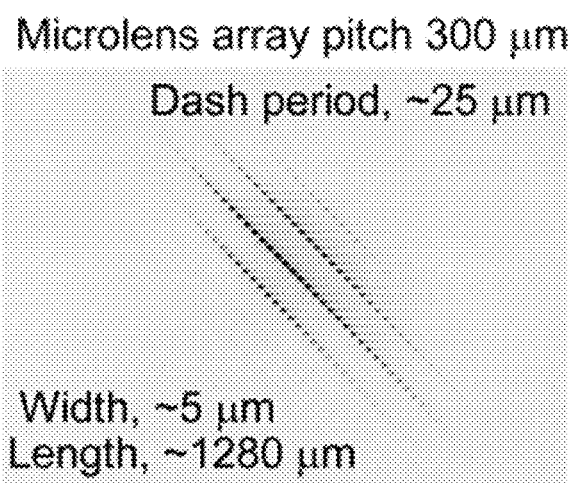
FIG. 17B and FIG. 17C show laser spots for 300 μm and 150 μm microlens arrays, respectively.
Figure 17C:
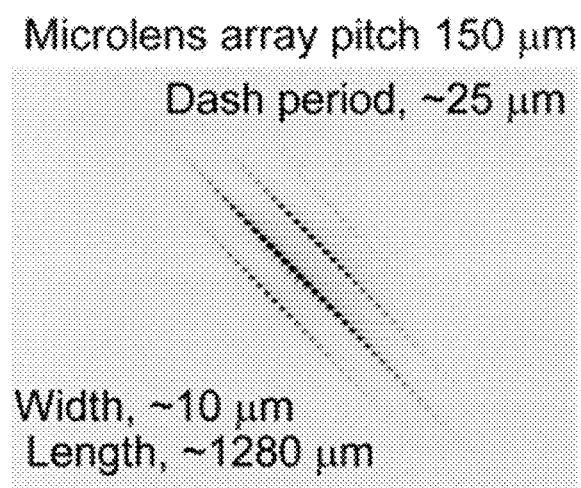
Figure 17D:
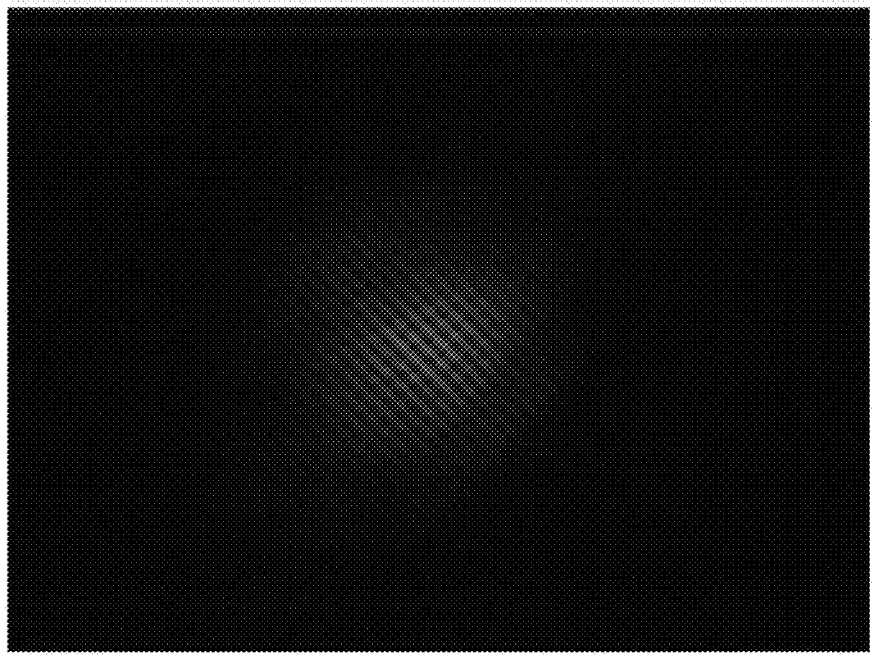
FIG. 17D shows the light distribution above the focal point (1.5 mm for 150 um pitch lens array).
Figure 17E:
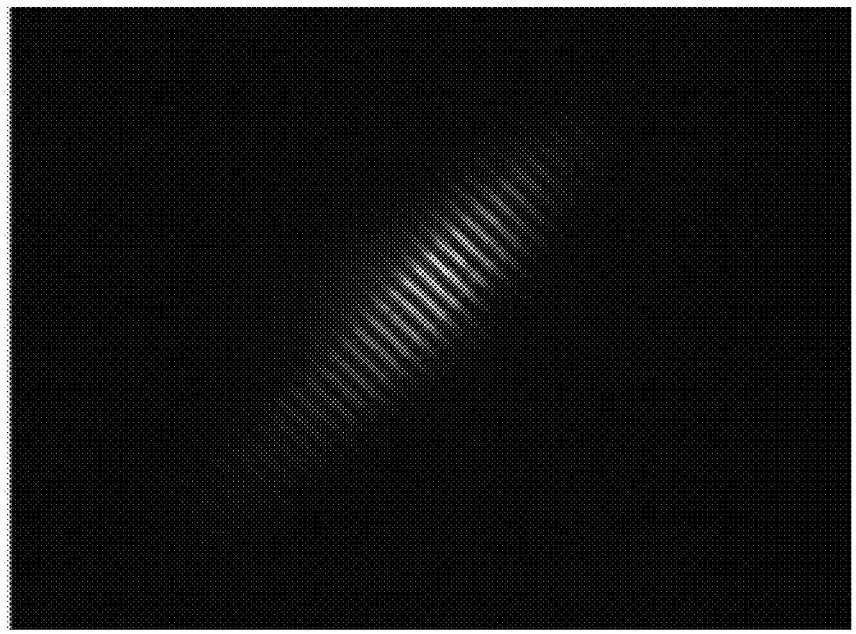
FIG. 17E shows the light distribution below the focal point (~3.0 mm for 150 um pitch lens array).

The fractionated optical system may create a 2-D light distribution of laser beams. In an aspect, the fractionated optical system may allow a microlens array to interact with a large laser beam and thus, create numerous laser spots in the sample separated by distances of only several micrometers. In this case, microlens arrays may produce an image of the pump beam into its image plane that was transferred into the sample by objective conjugated to the same image plane (FIG. 17A). The use of a cylindrical lens may allowed for the combination of multiple laser spots into a single general line accompanied by two additional lines created by the diffraction of the light. In general, 150 and 300 µm microlens arrays may create similar a distribution of the laser energy in the sample (FIG. 17B and FIG. 17C). However, the width of the laser line may be better for a 300 µm array. FIG. 17D shows the light distribution above the focal point (1.5 mm for 150 urn pitch lens array). FIG. 17E shows the light distribution below the focal point (~3.0 mm for 150 um pitch lens array).

Figure 18A:
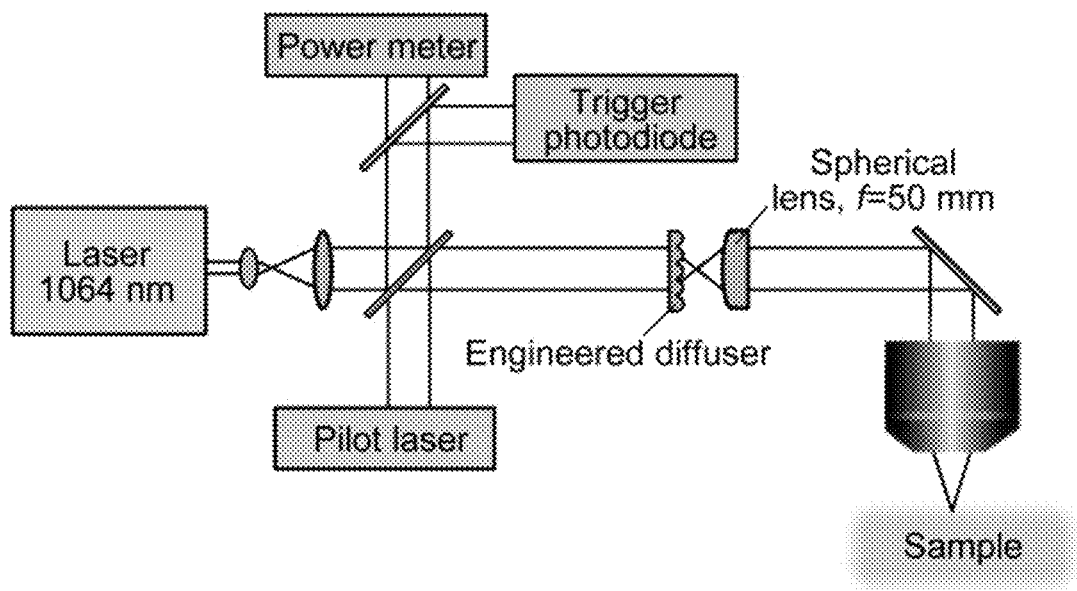
FIG. 18A illustrates an optical system schematic for a fractionated PAFC with a diffuser (MultiDots array) configuration.
Figure 18B:
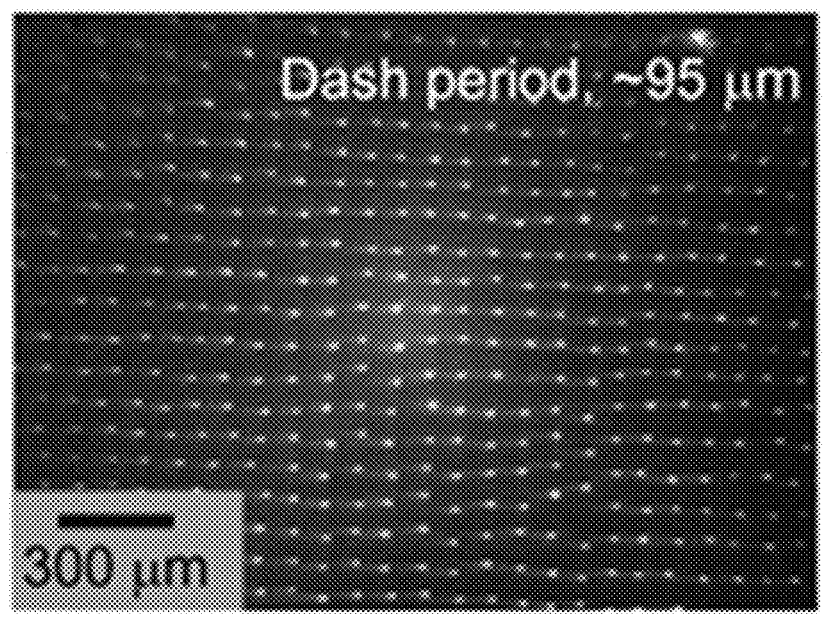
FIG. 18B shows an array of dots in the sample plane.

To dramatically increase the number of individual focal engineered laser diffusers may be used in the fractionated optical system (FIG. 18A). A laser diffuser diffuses light by producing a diffraction picture from the numerous small optical elements on its surface. Thus, compared to microlens array it can produce much higher number of focal spots as more lens-like elements interact with light. However, the diffuser has low stability in high power laser beams (usually diffusers are based on plastic materials) and may have a noisier picture due to presence of small scattering artifacts in its structure. A diffuser may be inserted into a large size laser beam expanded with two 2× and one 3× telescopes to maximize the area of contact. The light right after the diffuser may be collected by a 50 mm lens placed exactly at 50 mm after the diffuser. Thus, this lens and a 10× objective after it may create an image of the diffuser in the sample plane (FIG. 18B).

The resulting distribution of laser beams may be about 2.5 mm in diameter with spacing between dots of about 100 μm. The diameter and spacing between the dots may be controlled by translation of a spherical lens and accounting for the changes in the focal length of the system (laser focusing in the sample). In an aspect, the spherical lens may be a 50 mm spherical lens. In various aspects, the laser beams may have a range of distances from 50 to 130 μm. In one example, the energy fluence in the case of a MicroDots array may be estimated using the following approximation: beam diameter of 8 urn; number of individual identical beams, 24×24=576. All the light energy may be equally distributed only through these beams. Thus, for a 300 μJ laser pulse at 1064 nm, a laser fluence of about 0.3 J/cm$^2$ may be achieved in the center of the system.

IV. Fractionated Acoustic Detection System

In an aspect, the system may include a fractionated acoustic system. The fractionated acoustic system may include more than one focused ultrasound transducer. The more than one focused ultrasound transducer may be selected from a spherical ultrasound transducer, a cylindrical ultrasound transducer, and combinations thereof. In another aspect, the fractionated acoustic system may have a one-dimensional or two-dimensional spatial configuration.

In general, fractionated PAFC may be optical-resolution PAFC (OR-PAFC) or acoustic-resolution PAFC (AR-PAFC). In OR-PAFC, resolution is determined by optical parameters, in particular, the minimal width of a focused linear laser beam. Due to strong light scattering in tissue, the high spatial resolution at a level of about 1-10 μm can be achieved in superficial 30-50 μm in diameter vessels at a low depth of only about 0.1-0.3 mm. Thus, in fractionated PAFC with OR-PAFC, when focusing laser beams on the skin surface (FIG. 6) or a little deeper (to minimize the absorbing volume and hence the thermal relaxation time) it is important to keep individual beams separate and avoid their overlapping in the zone of first temperature and pain receptors at a depth of about 200-300 μm. In the case of detecting CTCs in superficial vessels (e.g., at high CTC concentration) the optical and acoustic focuses may be spatially coincided. In AR-PAFC, in deeper tissue with strong light scattering, the resolution in the range of 40-100 μm depends upon ultrasonic focal parameters, in particular, the transducer's frequency may be 10-50 MHz and in the same condition up to 100 MHz. In one aspect, a higher frequency may be preferred. For example, the resolution may be about 60-120-μm at a frequency of 10-60 MHz. Thus, in deeper tissue, optical resolution can be decreased to 100-500 μm at a depth of about 1-5 mm due to significant blurring of the laser beams, while high resolution of fractionated PAFC at a lever of about 60-100 μm may be achieved. Nevertheless, with further increases in frequency, the attenuation of the ultrasound waves in tissue increases. In one aspect, for a vessel deeper than 3-5 mm, the frequency may be about 50-70 MHz.

Figure 35B:
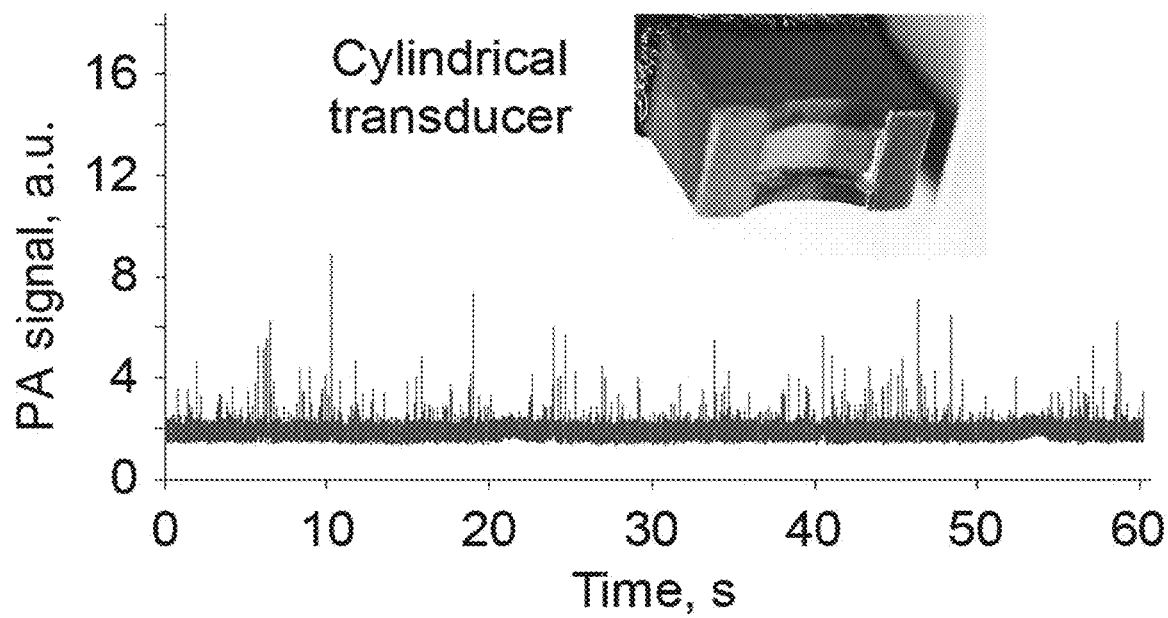
FIG. 35B is a PA signal trace from melanoma cells in human blood with a focused cylindrical ultrasound transducer with a focal length of 6 mm and a lateral resolution of 45 µm.

A focused cylindrical ultrasound transducer may be better suited for PA detection of circulating target objects because it provides a minimal detected volume due to high lateral resolution with simultaneous assessment of the entire cross section of a vessel. The spherical transducer with smaller detection volume provides higher SNR as compared to cylindrical transducers (FIGS. 35A and 35B). However, circulating target objects flowing outside the small detection volume may be missing.

In an aspect, a transducer array (fractionated acoustic detection system) may be used with close located focal volumes across a vessel, as illustrated in FIGS. 5, 9, and 10A-10B. Each transducer may provide monitoring of a small volume inside the blood vessels within its focal acoustic volume. The use several transducers with close-located focal volumes may allow for overlap of the whole blood vessel cross-section. Thus, to minimize background signal from RBCs and simultaneously enhance PAFC's ability to detect all target objects or cells throughout a vessel cross-section, the acoustic system may be fractionated to include a focused ultrasound transducer array, as shown in FIG. 9. In an aspect, the focused ultrasound transducer array may be an array of focused spherical ultrasound transducers, in which the partly overlapping focal volumes of the transducers are oriented across the vessel, thus creating a virtual focused cylindrical transducer configuration. In an aspect, each transducer may have independent preamplifiers, as illustrated in FIG. 1. The signals from the individual transducers and pre-amplifiers may be collected by a multichannel data acquisition board and presented as multiple PA signal traces. This may allow for simultaneous identification of several moving objects in the same plane but different spatial location in the vessel cross-section. The fractionated acoustic system with a focused spherical transducer array combines the advantages of conventional spherical and cylindrical transducers: high SNR with minimal background and detection of all target objects in a vessel cross-section, respectively.

Figure 20:
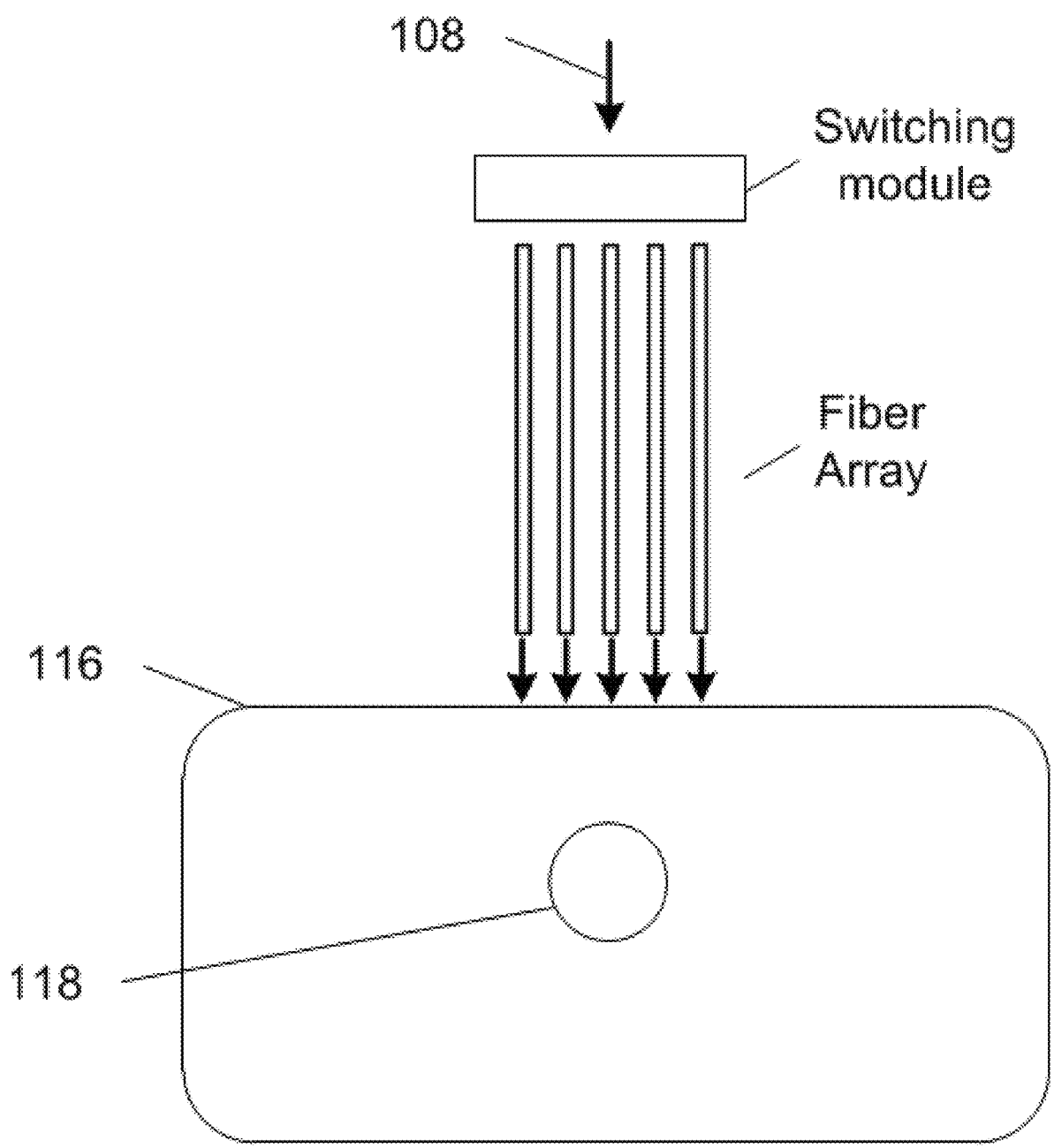
FIG. 20 illustrates an optical system for a fractionated PAFC system using a fiber array for delivery of multiple laser beams with fast spatial switching.
Figure 21:
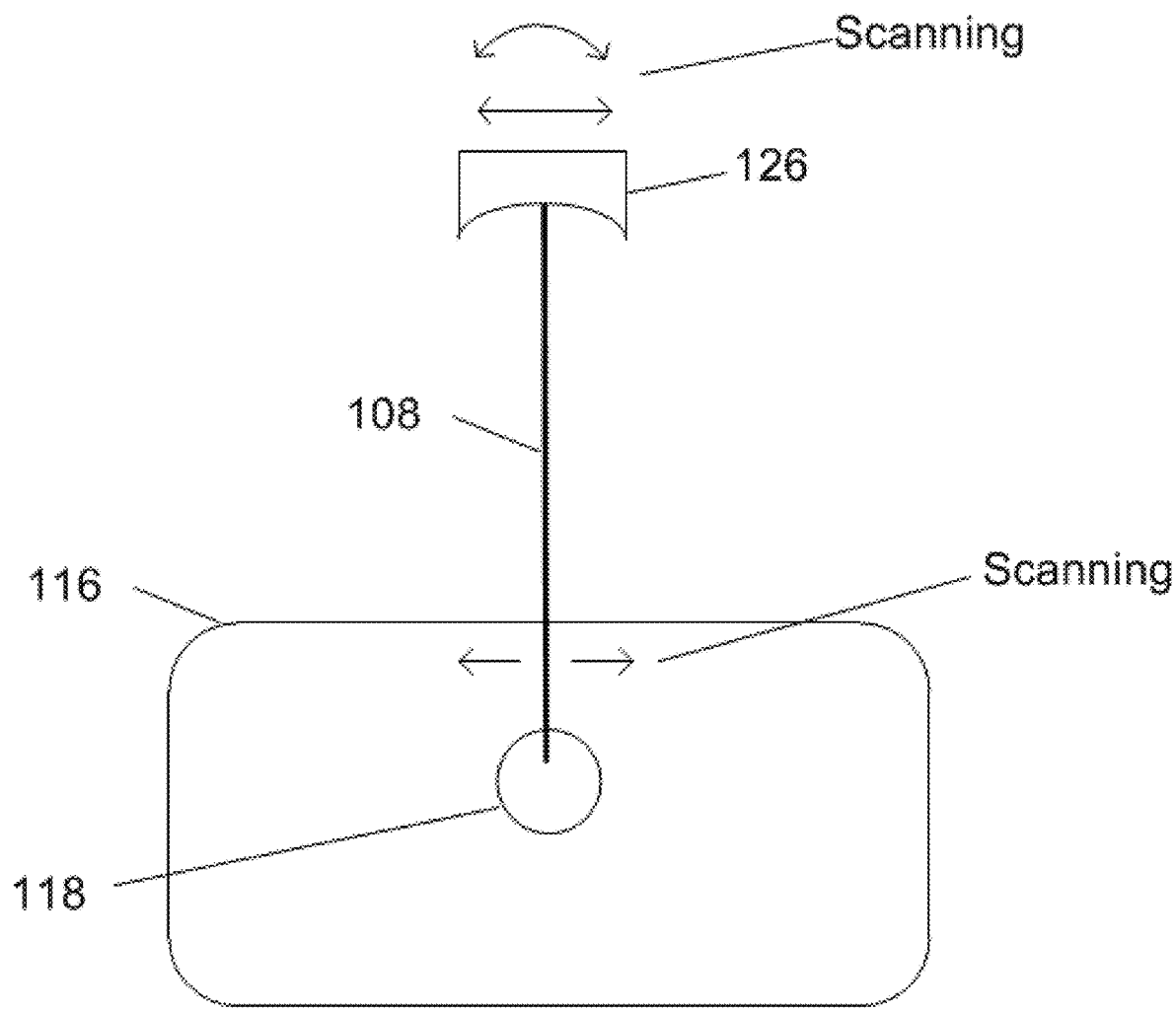
FIG. 21 illustrates an acoustic system for a fractionated PAFC using a fast spatial scanning of ultrasound transducers across a vessel.
Figure 22A:
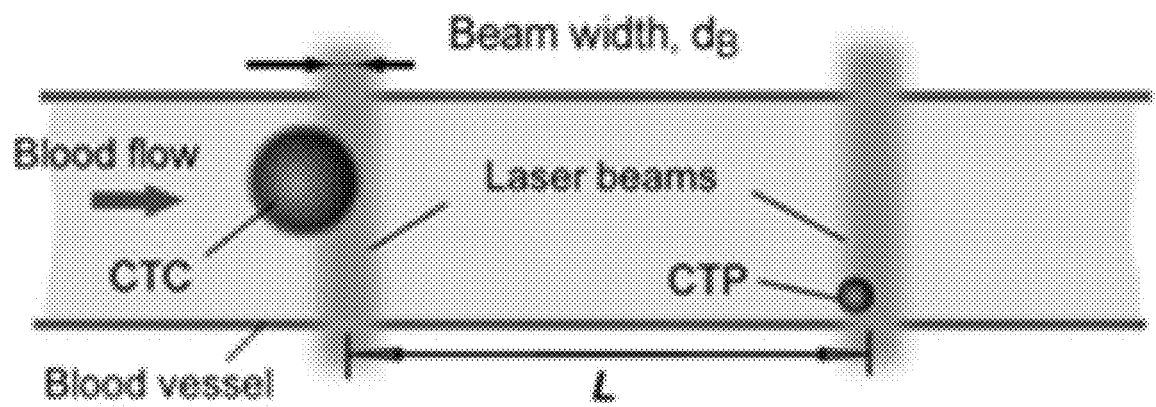
FIG. 22A and FIG. 22B illustrate a principle of a fractionated PAFC with two-beam time-of-flight mode.
Figure 22B:
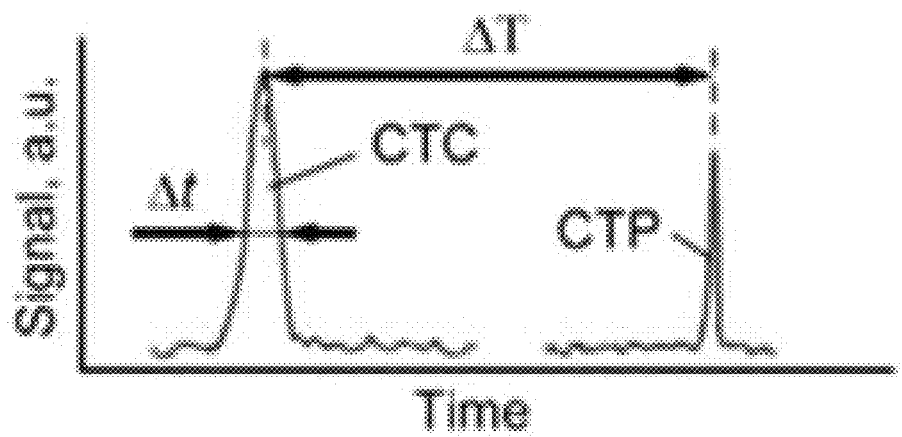

To minimize background signal from RBCs and simultaneously enhance PAFC's ability to detect all target objects or cells throughout a vessel cross-section, ultrasound transducers with fast spatial (either mechanical and/or acoustic) scanning of the focal volume across vessels may also be used (FIG. 20). In an aspect, the spatial scanning may be at a rate of about 1 kHz to about 30 kHz. In various aspects, the spatial scanning may range from about 1 kHz to about 10 kHz, from about 5 kHz to about 15 kHz, from about 10 kHz to about 20 kHz, from about 15 kHz to about 25 kHz, and from about 20 kHz to about 30 kHz. The high acoustic resolution of fractionated PAFC (AR-PAFC) with focused ultrasound transducers may increase the SNR by decreasing background signals from RBCs in a small detection volume. Spherical focused transducers may provide maximal SNR, but target objects flowing outside of the acoustic focal detection volume may be skipped. Therefore, the combination of a cylindrical transducer with a linear focal detection volume and a linear laser beam may allow for detection of all target objects in a blood vessel cross-section; however, background signals from RBCs may be increased due to the larger detection volume than that obtained with a spherical transducer. To overcome these limitations, the fractionated acoustic system may include fast spatial scanning (about 1-30 kHz) of at least one spherical transducer, which may provide scanning of the focal acoustic volume across the vessel using standard mechanical or acoustic scanners. For example, the scanners may be piezoelectric or galvano-based scanners. In various aspects, the fractionated acoustic system may include more than one spherical transducer. In this aspect, lasers with high pulse repetition rates up to about 30-100 kHz and even 500 kHz may be required to collect many signals from moving target objects during one transducer scan. In an aspect, at relatively low blurring laser beam up to about 50-100 um at a depth of about 0.5-1 mm, scanning circular or short length linear beams in combination with not scanning a focused cylindrical transducer achieve similar positive effects as with scanning a spherical focused transducer. These effects include minimal background noise due to high spatial resolution (OR-PAFC) at a level of about 50-100 µm and detection of all moving target objects in a whole blood cross-section because of fast spatial scanning across the vessel.

V. Fractionated PAFC with Multicolor Ultrasharp Spectral Resonances for Bio-Barcoding of Multiple Markers Most diseases may be difficult to diagnose by detecting a single marker, due to decreasing marker expression during disease progression or absence of a particular marker in some patients. The spectral selectivity to identify markers using the conventional PAFC platform is limited by the wide near-infrared (NIR) spectral band (80-150 nm) of most PA contrast agents (e.g., chromophores, dyes, or NPs) in linear laser mode, which typically enables effectively the use of only two PAFC colors. Fractionated PAFC with enhanced laser energy fluence in tissue overcomes this problem by exploiting the spectrally narrow (ultrasharp) PA resonances near the center of the absorption band, where the relationship between laser energy and PA signal amplitude may show strong nonlinearity, as seen in FIG. 26A.

Figure 11:
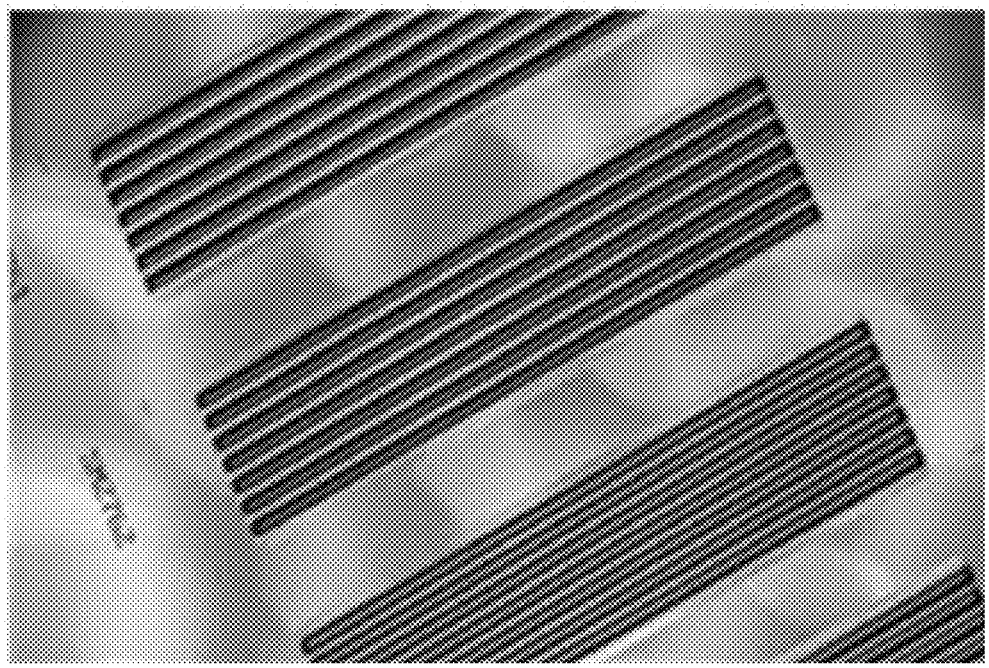
FIG. 11 illustrates one fractionated laser for fractionated PAFC as a high-power laser diode with an active element including multiple stacked bars.
Figure 26A:
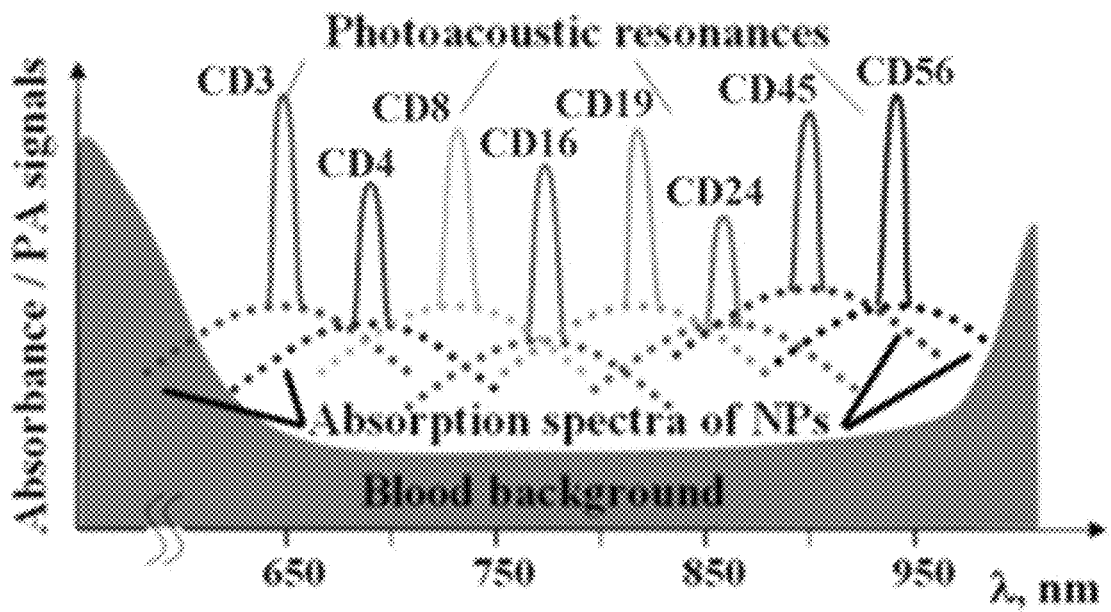
FIGS. 26A, 26B, and 26C illustrate multiplex targeting/detection of biomarkers related to immune disorders.
Figure 26B:
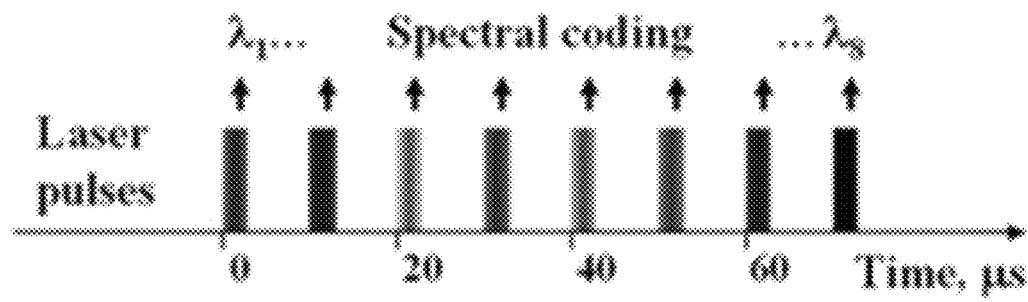
Figure 26C:
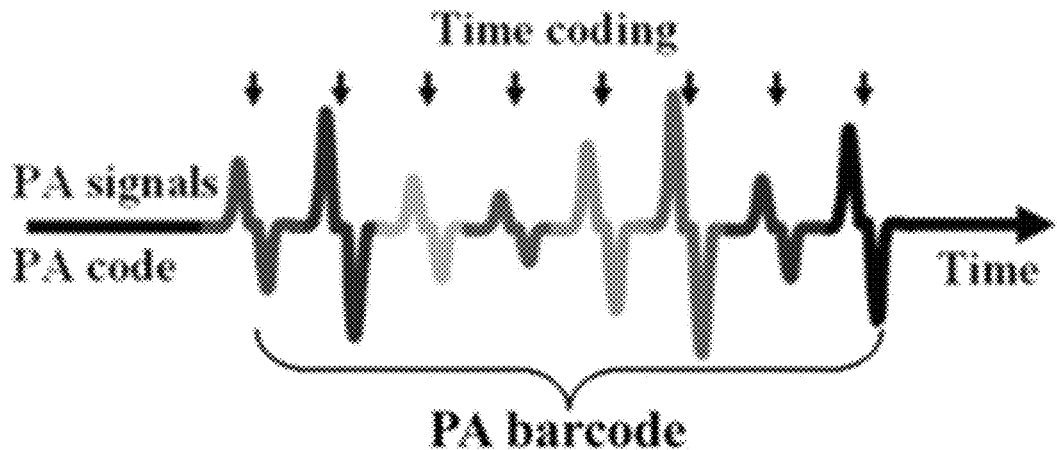

The simultaneous targeting of several markers may be realized in three interrelated steps: multicolor encoding using the time delays between laser pulses with different wavelengths (FIG. 26B), nonlinear signal amplification leading to narrowing of PA spectra (FIG. 26A), and multicolor decoding though time-resolved spectral reading of color-coded PA signals (FIG. 26C). Thus, fractionated PAFC using spatial laser beam coding (FIG. 7A-D) for every single laser pulse, may provide a unique opportunity for simultaneous temporal color coding using laser pulses with different wavelengths (FIGS. 23, 24, 25A-25B, 26A-26C). This may be performed by using a laser array, in which each laser with different wavelength (FIGS. 23 and 26A) provides the same fractionated laser beam, as for example, in a laser diode (FIG. 11). This may be performed with a laser array, in which each laser generates a pulse with different wavelengths and delay (FIG. 26B). In an aspect, each laser may have a single non-fractionated beam, which may be split further by the optical system 104 (FIG. 1) into fractionated beams (spatial coding for each laser providing already temporal color coding). This may be also performed by using one laser generating radiation in the broad spectral range including white color radiation with mixed wavelength from UV to red. In this aspect, temporal color coding (FIG. 26B) and spatial beam coding (FIG. 7A-7D) may be performed in one optical system (e.g., interferometer, spectral prism or diffraction grating), or several optical systems responsible for color coding (e.g., standard modules with optical fiber array introducing the time delay between pulses with different wavelengths) and beam fractionating (spatial coding), respectively.

Thus, each disease-associated marker may be identified in the fractionated PAFC by a bio-barcoding process as a sequence of PA signals with spectral-temporal encoding, as illustrated in FIGS. 26A-C.

VI. Multicolor Fractionated PAFC

Provided herein is a system for the in vivo detection of target objects in a circulatory vessel of a living organism. The system may include an in vivo fractionated PAFC, a triggering system for controlling more than one laser pulse with different wavelengths from a fractionated laser system, a fractionated laser system and/or optical system for delivery of multiple laser beams, and a fractionated acoustic system for detecting the combination of photoacoustic signals emitted by the at least one target object in response to the more than one pulse of laser energy. The in vivo fractionated PAFC system may include a laser array including more than one pulsed lasers with different wavelengths for pulsing at least one target object within the circulatory vessel with more than one pulse of laser energy, and a ultrasound transducers for receiving more than one photoacoustic signal emitted by the at least one target object in response to the more than one pulse of laser energy.

As seen in FIG. 23, a multicolor fractionated PAFC system with one multispectral pulse laser or a multicolor laser array may be used for biobarcoded detection of target objects or cells with multiple markers. This system may be used with particular commercially available laser diodes having the necessary parameter set, including wavelengths in the NIR range, an adjustable picosecond and nanosecond pulse width, a high-pulse-repetition rate, and sufficient pulse energy for in vivo applications. In an aspect, the multispectral pulse laser may be an array of pulse lasers. In an aspect, the laser pulses may have a specific fractionated (i.e, multibeam) shape. The time delays between laser pulses with different wavelengths may be selected to provide time-resolved detection of multiple PA signals from the same fast moving cells using a fractionated laser beam.

In various aspects, the wavelengths of the lasers may range from about 650 nm to about 1200 nm, from about 650 nm to about 760 nm, from about 760 nm to about 830 nm, from about 830 nm to about 904 nm, about 904 nm to about 1060 nm, and about 1060 nm to about 1200 nm. In one aspect, a system may include an array of lasers, each having a wavelength of about 760 nm, about 830 nm, about 904 nm, and about 1060 nm, respectively. In an aspect, the lasers may have a pulse width ranging from about 3 ps to about 1 ns, from about 1 ns to about 1 ms, from about 100 ps to about 500 ps, from about 250 ps to about 750 ps, from about 500 ps to about 1 ns, from about 1 ns to about 100 ps, from about 50 ns to about 500 ns, from about 1000 ns to about 0.1 ms, and from about 0.5 ms to about 1 ms. The pulse-repetition rate of the lasers may range from about 1 Hz to about 100 kHz, from about 100 kHz to about 1 MHz, from about 1 MHz to about 10 MHz, from about 10 MHz to about 100 MHz, from about 1 kHz to about 40 kHz, from about 10 kHz to about 30 kHz, from about 20 kHz to about 60 kHz, from about 40 kHz to about 80 kHz, and from about 60 kHz to about 100 kHz. The pulse energy of the lasers may be up to about 1 µJ to about 10 mJ. In various aspects, the pulse energy of the lasers may range from about 1 µJ to about 100 µJ, from about 100 µJ to about 500 µJ, from about 500 µJ to about 1 mJ, and from about 1 mJ to about 10 mJ. In an aspect, a beam may be split into fractionated beams in which each spatially separated beam has a smaller energy from a few nJ to a few pJ. For example, in laser diodes with multiple bars and stacks, laser energy may be up to about 100 μJ to about 2 mJ. In an aspect, the laser pulses may provide an energy fluence up to about 0.001 J/cm$^2$ to about 100 J/cm$^2$. The time delays between laser pulses with different wavelengths may range from about 5 ps to about 20 ps, from about 5 ps to about 15 ps, and from about 10 ps to about 1050 ps, depending on the laser pulse rate. For example, the laser pulse rate may range from about 1 kHz to about 100 kHz.

The multispectral laser array may include at least two pulsed lasers, at least four pulsed lasers, at least 8 pulsed lasers, or any number of pulsed lasers capable of pulsing the target object with a pulse of energy at a wavelength different from the other lasers within the array. In one aspect, the laser array is on a microchip. The beam of the pulsed lasers at the same wavelength may be separated in the array such that the laser beams from each of the more than one beams in the laser beam array are separated by a distance of about 5 μm to about 1 cm, about 5 μm to about 200 μm, and about 200 μm to about 1 cm. The spacing of the laser beams may allow for laser beam from each of the more than one lasers beams at the same wavelength to not overlap at a location in the living organism with pain receptors, however, the laser beams may spatially overlap at the circulatory vessel. Simultaneously, laser beams with different wavelengths may spatially overlap, partially overlap, or not overlap.

In an aspect, the fractionated optical system passing laser pulses with different wavelengths may include an optical component. The optical component may include, but is not limited to, an optical fiber, a lens, a microlens array, a diffuser, a pinhole, an optical mask, diffraction elements, and combinations thereof. The fractionated acoustic system may include a focused spherical ultrasound transducer, a focused cylindrical ultrasound transducer, or combinations thereof. As illustrated in FIG. 27A, the ultrasound transducers may also include a central hole for delivery of a fractionated laser beam in one aspect. In an aspect, the focused spherical ultrasound transducer may have an acoustical spatial scanning rate ranging from about 1 kHz to about 30 kHz. In one aspect, the fractionated acoustic system may include an array of ultrasound transducers.

To make the system more adaptable to monitoring fast moving target objects such as circulating tumor cells (CTCs), virus, bacteria, parasites (e.g., malaria) and clots, high-pulse-repetition-rate lasers with different wavelengths may be used. In an aspect, the fast moving target objects may be moving at a rate of about 5-10 cm/s in 1-2 mm blood vessels. The lifetime of CTCs in the detection volume is short, in the range of 0.1-2 ms, which makes it extremely difficult for spectral identification of fast moving CTCs. To address this problem, fractionated PAFC systems and methods may include (a) a fast spectrum scanning laser; (b) multiplex spectral detection by simultaneous irradiation of moving objects with several laser beams at different wavelengths, modulated at different acoustic frequencies, and; (c) fast switching between two laser wavelengths (i.e., laser discrete frequency modulation).

Figure 19:
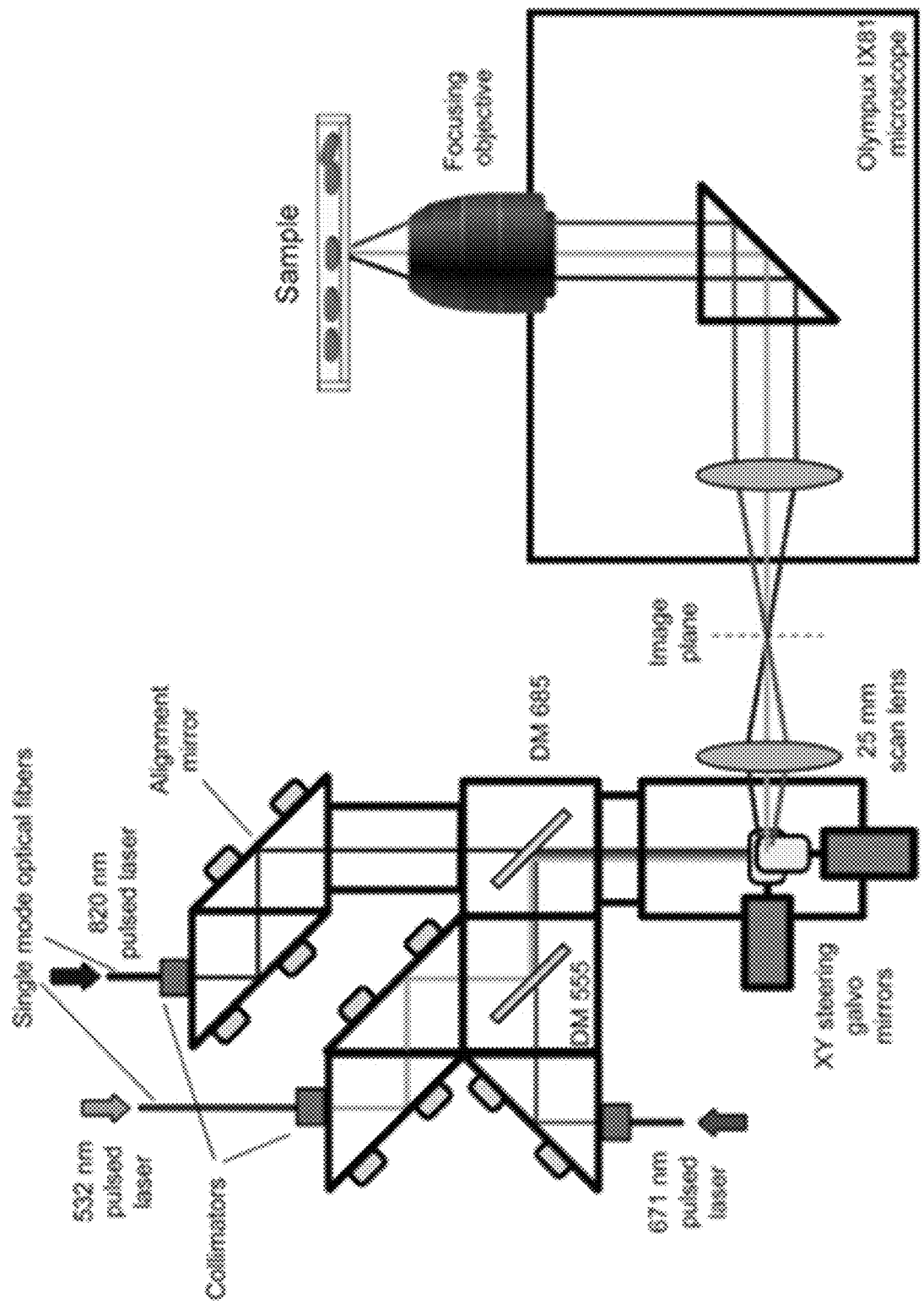
FIG. 19 illustrates an optical system for a fractionated PAFC using fast scanning of a fractionated linear beam across a vessel.
Figure 47:
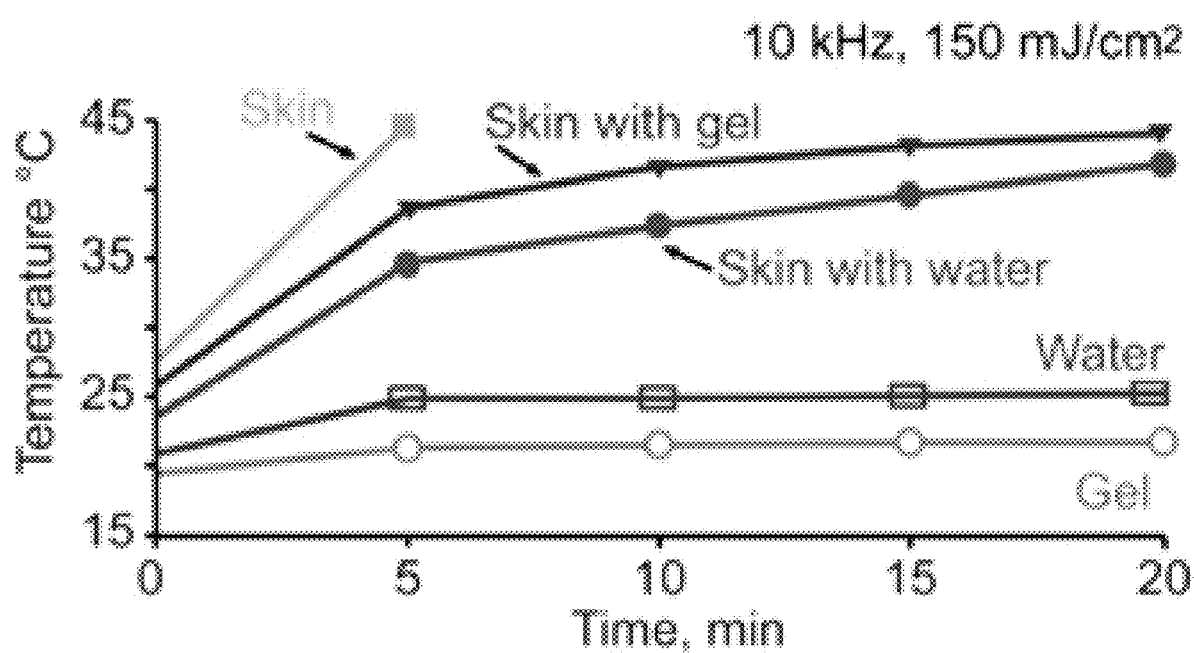
FIG. 47 illustrates cooling effects with gel and water between transducers and mouse skin at 1060 nm, pulse rate of 10 kHz and energy fluence of 100 mJ/cm$^2$ during 20 min of laser exposure with laser beam size of 6.5 µm×790 µm.
Figure 48:
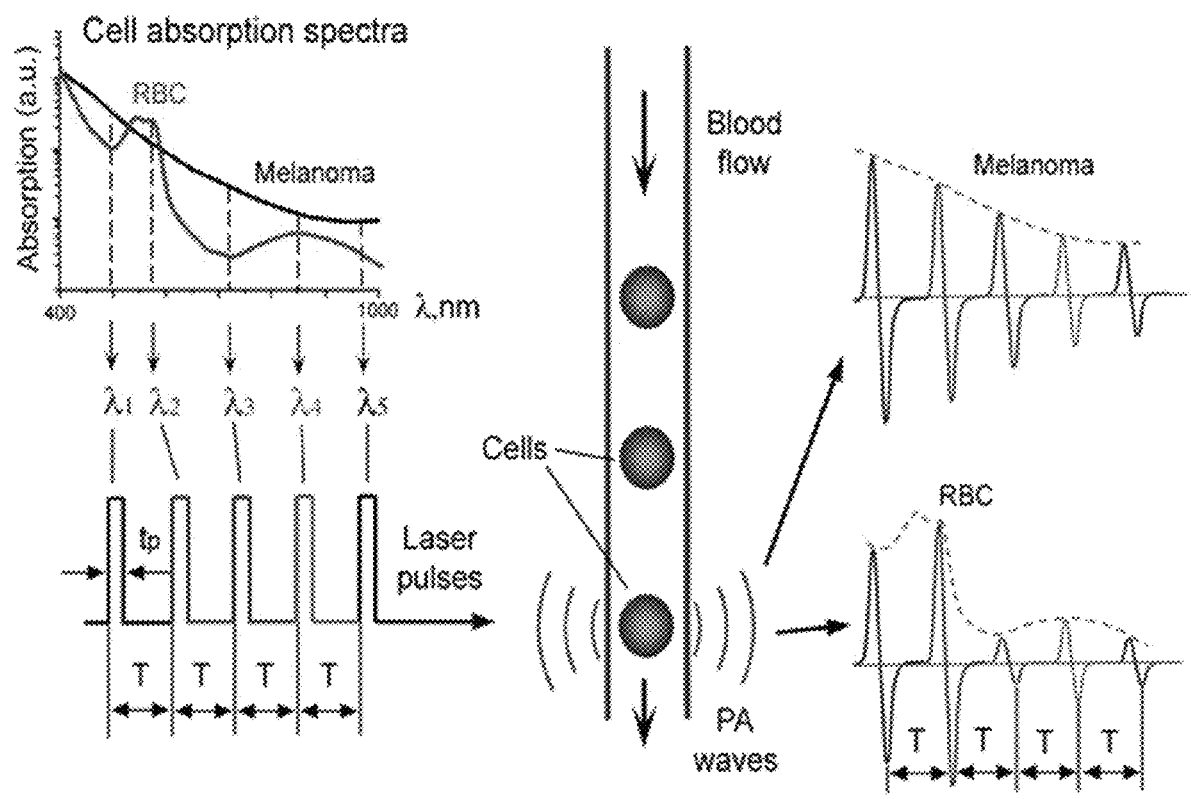
FIG. 48 illustrates color-coding in multicolor fractionated PAFC using laser pulses with high rates and different wavelengths and the time delays between corresponding laser pulses for fast spectral identification of circulating melanoma cells in blood background.

In another aspect, real-time multicolor fractionated PAFC may be conducted at discrete wavelengths with laser pulses at different wavelengths and time pulse delays, in combination with time-resolved detection of PA signals (FIG. 48). A pulse-repetition rate of about 2-30 kHz may be selected for all lasers and a delay between laser pulses in the range of about 5-20 ps, depending on wavelength number used. Laser pulses may be triggered by a digital delay/pulse generator for time and color coding. Each laser may be driven by an independent triggering channel at the selected pulse rate, with delays between consecutive channels. Thus, the time delay between laser pulses with different wavelengths may provide time-color coding for time-resolved detection of different "color" PA signals, even using a single ultrasound transducer, such as a focused cylindrical transducer. However, a fractionated acoustic detection system with a focused spherical transducer array may provide more sensitive detection (up to 10-20 fold) of all objects in any blood vessel cross-section because of lower background from RBCs in a smaller focal volume and many focal volumes covering the whole vessel cross-section, respectively. Linear parallel laser beams (3-10 μm×0.1-2 mm) of different wavelengths can be either overlapped at the sample plane or separated by adjustable gaps using different optical modules and optical components including prisms, mirrors, lenses, and fibers, for example as illustrated in FIGS. 19 and 20. The PA signals may be recorded with a high-speed analog-to-digital converter boards and after acquisition and averaging (FIGS. 24 and 25A-25B), may be presented as signal traces in which amplitudes, widths for each of the peaks, and coincidence at different traces may be analyzed with customized software. In an aspect, as seen in FIG. 31A-31D, 10-50 PA signals from each target object, such as a CTC, may be averaged. The method in an aspect may allow for "in real-time" the ability to analyze PA signals from the same target object at different laser wavelengths.

Nevertheless, spectral capability of PAFC may be limited to wide NIR spectral bands (50-200 nm in width) of chromophores and NPs, especially plasmonic NPs. Recently, it was unexpectedly discovered that nanobubble-induced ultrasharp nonlinear PA resonances in various absorbing structures may be used for enhancement of multicolor fractionated PAFC capability through dramatic sharpening of spectral bands to 1-5 nm width. The mechanism of these resonances is associated with laser-induced nonlinear amplification (10-100-fold) of PA signals near the center of the absorption bands only. A tuning of the laser wavelength toward the absorption center may lead to increased absorbed energy, raising the temperature above the nanobubble-formation threshold, accompanied by significant nonlinear signal amplification. As a result, spectrally dependent signal amplification may lead to the sharpening of PA resonances near the center of the absorption peaks at an optimal laser energy. The fractionated PAFC is an ideal tool for ultrasharp resonances because the energy necessary for such resonances for nonlinear PA effects may be created in deep vessels due to the increased laser energy fluence in the vessel. For example, these effects may amplify the PA signals even from small absorption peaks of melanin in melanoma CTCs in the NIR range, carotid in *S. aureus* at about 760 nm, hemozoin in malaria affected RBCs (FIG. 44B) near 650-665 nm, or exosomes (FIG. 38A-38E).

These phenomena are relatively universal and applicable to various absorbing nanostructures. In particular, dynamic spectral sharpening may occur in different single and clustered nanoparticles (NPs) and dyes: gold nanospheres (GNSs), gold nanorods (GNRs), carbon nanotubes (CNTs), golden nanotubes (GNTs), magnetic nanoparticles (MNPs), golden magnetic NP hybrid, quantum dots (QDs), cellular chromophores (e.g., melanin, hemoglobin, cytochromes, carotinoids, and hemozoin) and dyes (e.g., FITC and ICG), photoswitchable proteins and NPs and their nanoclusters. More profound sharpening (up to 0.8-1 nm in width) may be observed in plasmonic NPs (GNRs and GNTs), compared to typical widths of PA resonances for other objects in the range of 2-10 nm. Nonlinear, ultrasharp PA spectral resonances may be accompanied by significant amplification of PA signals that lead to dramatic increases in both the specificity and sensitivity of fractionated PAFC and enhanced efficiency of photothermal (PT)-based theranostics using laser-induced nanobubbles around overheated targets for target destruction either thermally, mechanically or with both mechanisms.

VII. Time-Resolved Spectral Reading of Barcodes

To provide time-resolved multicolor probing of biobarcoded markers (FIGS. 26A and 48), fast-flowing cells may be irradiated with high-repetition-rate nanosecond and picosecond pulses from compact laser arrays at different wavelengths and time delays. In an aspect, the repetition-rate may range from about 1 kHz to about 500 kHz. In another aspect, the time delays between laser pulses may be about 1 ps, about 5 ps, about 10 ps, about 20 ps, or about 30 ps. In one aspect, the laser array may be on a microchip. Time-resolved detection of PA signals from rare abnormal cells in multi-file blood cell flow may be enabled using a focused ultrasound transducer. Nanosecond and picosecond pulses are ideally matched to the characteristically short thermal and acoustic relaxation times of small target objects such as intrinsic melanin and hemozoin NPs or artificial or NPs. In an aspect, the thermal and acoustic relaxation times may range from about 20 ps to about 1000 ps. In various aspects, the target objects or NPs may range in size from about 3 nm to about 500 nm, from about 3 nm to about 10 nm, from about 10 nm to about 100 nm, and from about 100 nm to about 500 nm.

VIII. Nonlinear Fractionated Blood Test with Multiple Laser Beams

PA detection of single cells in vivo using the fractionated PAFC system may be limited by the blood absorption background determined by the number of RBCs in the detected volume. The fractionated acoustic system may provide 10-20-fold reduction of blood background due to the small detection volume of each focused spherical transducer. In addition, fractionated PAFC with enhanced laser fluence/intensity in targeted objects provides various other approaches to reduce the influence of the absorption background, including: 1) generation of second harmonic PA signals from saturated absorption in targeted absorbing agents only (e.g., melanin, hemozoin, or NPs) in the presence of a linear background from hemoglobin in RBCs; 2) multiphoton absorption in targeted absorbing agents that only selectively increase absorbed energy and hence PA signals from these targets; 3) two beam excitation with different wavelengths and/or modulation frequencies, and detection of PA signals at different frequencies; 4) discrimination of targets with different temperature-dependent absorption and relaxation times; and 5) changes in blood oxygenation, osmolarity, and hematocrit within physiologic norms.

Disclosed herein is a method for detecting a circulating target objects with fractionated laser beams, including CTCs, in flowing blood. The method may include pulsing the circulating target object with a first pulse of laser energy from a first laser in a laser array at a first pulse wavelength, obtaining a first photoacoustic signal emitted by the circulating target object induced by the first pulse of laser energy, pulsing the circulating target object with at least one additional pulse of laser energy from a second laser in the laser array at a second pulse wavelength, obtaining a second photoacoustic signal emitted by the circulating target object induced by the at least one additional pulse of laser energy, and analyzing the photoacoustic signals to calculate the combination of photoacoustic signals emitted by the circulating target object. The combination of photoacoustic signals may be characteristic of the circulating target object. Analyzing the combination of photoacoustic signals may include averaging consecutive photoacoustic signals to help reduce noise or increase the SNR.

In various aspects, a method of PA detection of single cells in vivo makes use of laser generation of nanobubbles as significant (5-fold to 50-fold), PA signal amplifiers and PT therapy enhancers in strongly absorbing, spatially localized targets in a relatively homogenous absorption background. This approach may be used to enhance PA contrast of melanoma cells, NPs and their nanoclusters in blood and histological, cancer-related samples with simultaneous spectral burning of the absorption background with dominant absorption at specific laser wavelengths coinciding with the maximum absorption of target objects or background.

Taking into account that laser-induced nanobubbles and microbubbles may enhance PA signals and simultaneously destroy mechanically CTCs, this approach may be applied for theranostics of individual CTCs. The thresholds of nanobubble generation demonstrate high sensitivity to melanin or NP clustering (e.g., larger nanocluster corresponds to a lower nanobubble threshold) that was used to control the clustering of NPs in tumor cells. A nanobubble-associated, nonlinear PAFC was detonated initially for label-free detection of single melanoma cells (B16F10) in blood background in vitro and in vivo. Specifically, at low laser energy, the PA signal from a single low pigmented melanoma cell was below blood background as the super-position of PA signals from individual RBCs in the detection volume. At higher energy, nonlinearly-amplified PA signals from overheated melanin nanoclusters in melanoma cells became detectable above the linear blood background. In particular, the detailed measuring of PA signals from melanoma cells with different pigmentations was performed in blood as a function of laser fluences.

Figure 36A:
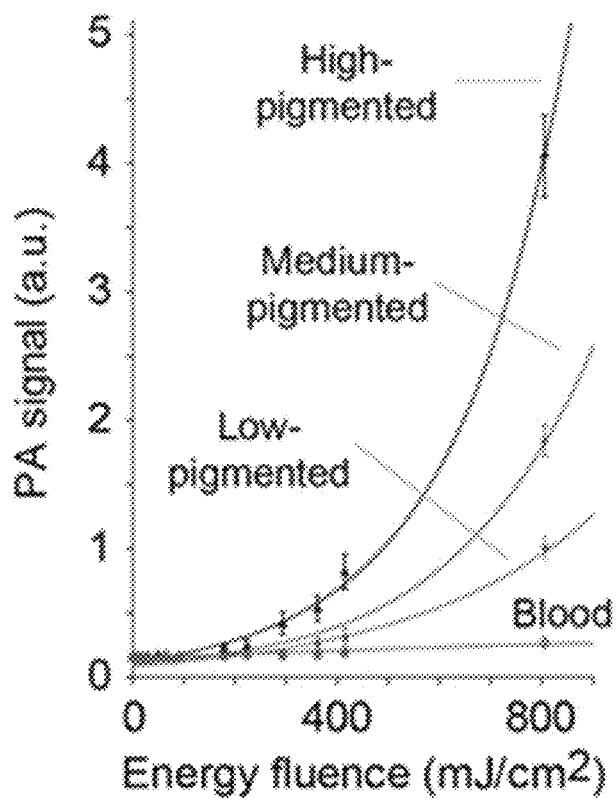
FIG. 36A illustrates nonlinear PA signal amplification at 820 nm in melanoma cells (SK-MEL-1) with different pigmentation in static conditions as a function of laser energy fluence.
Figure 36B:
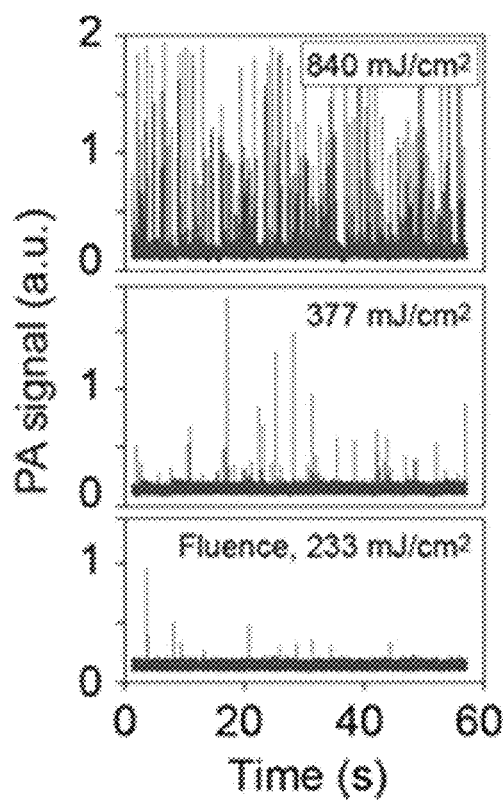
FIG. 36B illustrates nonlinear PA signal amplification at 820 nm in melanoma cells (SK-MEL-1) with different pigmentation in flow conditions as a function of laser energy fluence.
Figure 37A:
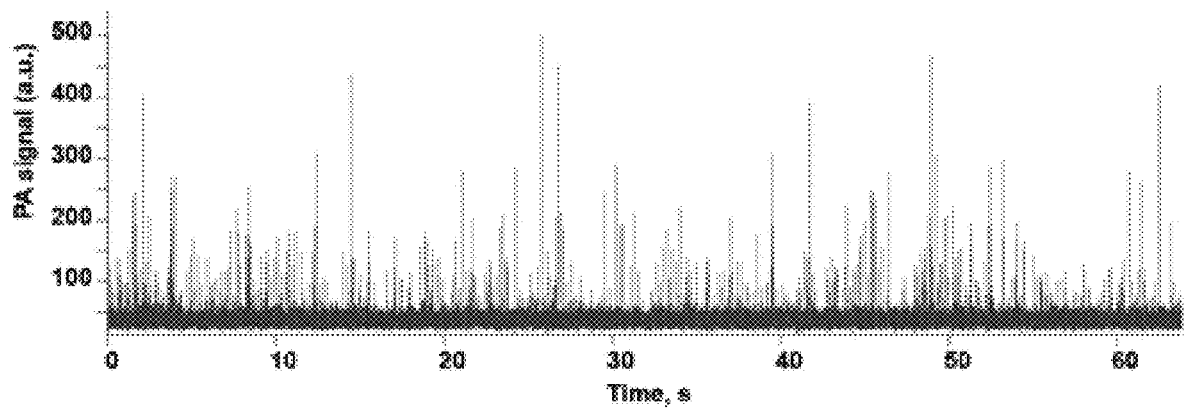
FIGS. 37A-37B illustrate examples of PA traces from moving melanoma cells (B16F01) in mouse blood in 0.9 mm capillary tube at flow velocity of 10 cm/s at laser fluence of 904 mJ/cm$^2$ (FIG. 37A) and 33 mJ/cm$^2$ (FIG. 37B) as modeling of fractionated and not fractionated PAFC at a laser wavelength of 1060 nm, respectively.
Figure 38A:
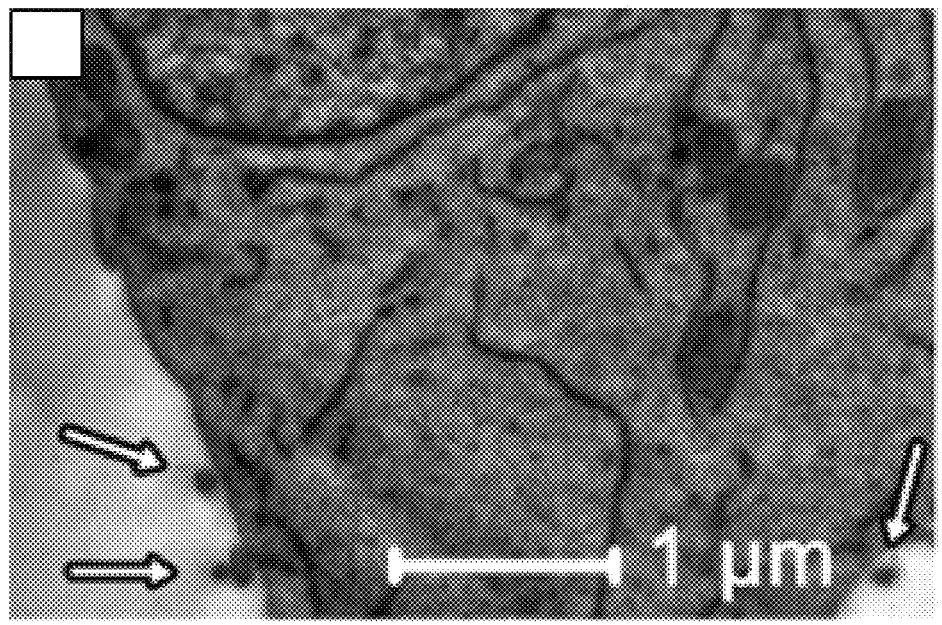
FIG. 38A illustrates a TEM image of melanoma cell (B16F10) with exosomes (arrows).
Figure 38B:
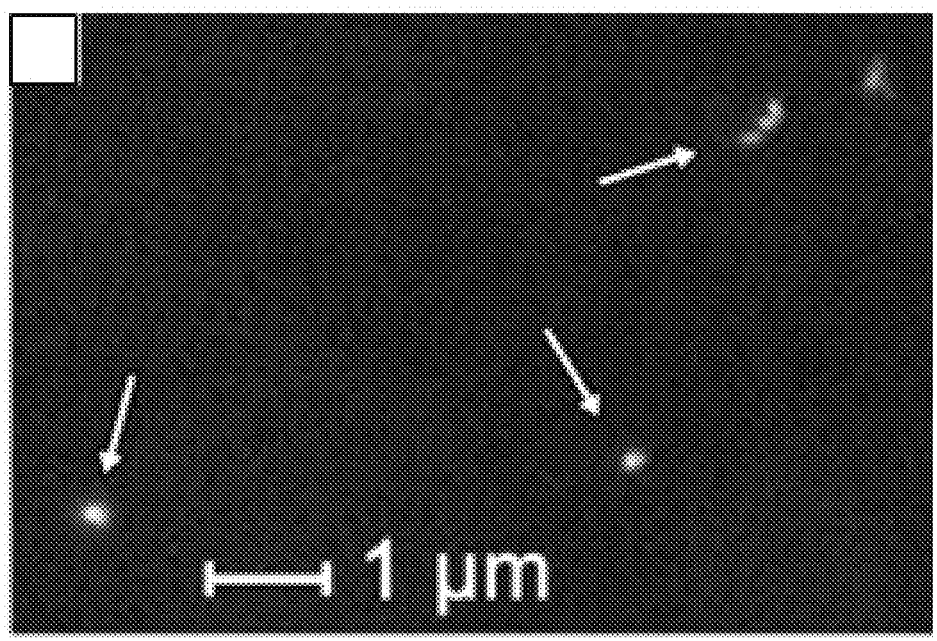
FIG. 38B illustrates a dark field image of melanoma cell (B16F10) with exosomes (arrows).

Significant (5-fold to 15-fold) signal amplification from these cells were observed as compared to linear effects from RBCs with relatively spatially homogenous Hb distribution (FIG. 36A) that led to the detection of more CTC-associated PA peaks at higher fluences (FIGS. 36B and 38A). As a result of laser-induced nanobubbles acting as nonlinear PA signal amplifiers, significant PA signal amplification was observed at specific laser fluences (FIGS. 36A and 37A) from melanoma cells with heterogeneous melanin distribution in human blood. These cells exhibited linear signals only because of the relatively homogeneous spatial distribution of Hb in RBCs without highly localized absorbing zones as in melanoma cells. As a result, significantly a larger number of melanoma-associated PA peaks (40-fold) can be detected at higher fluences (FIGS. 36A and 36B).

However, weakly pigmented cells may require a high laser pulse energy (up to 0.05-1 $J/cm^2$) that exceeds the laser safety standards of 100 $mJ/cm^2$ at 1064 nm and a pulse rate below 10 Hz, and of up to 0.1-1 $mJ/cm^2$ at higher pulse rates of 1-10 kHz. In view of an earlier finding that RBCs and WBCs have high photodamage thresholds in the NIR range (800-850 nm) at the level of 10-20 $J/cm^2$ and 50-100 $J/cm^2$, respectively, and the laser safety standard for a 3.5-mm-diameter laser beam for procedures involving human subjects, studies were performed on healthy volunteers using smaller-diameter laser beams. In these studies, the subjects reported only a warming sensation with no pain or observable changes in skin properties when laser fluence levels reached approximately 5 $J/cm^2$ and 250 $mJ/cm^2$ (pulse-repetition rate, 10 kHz; linear beam sizes, 6×660 μm and 20×1500 μm, respectively). Moreover, with a single circular laser beam with a diameter of approximately 4 μm, a warming sensation was reported by subjects at a fluence of 25 J/cm², a fluence in excess of the laser safety standard for a 3.5 µm beam by more than $10^4$-fold.

Theoretical modeling indicated that the adverse effects of laser pulses reported by the subjects are primarily associated with thermal effects and temporal overlapping (accumulation) of these thermal effects at high laser pulse-repetition rates (FIG. 23). Additional data indicated that the shorter thermal relaxation time for a smaller-diameter laser beam enabled the use of higher laser fluences, especially in the near-infrared (NIR) range. The warming sensation is thought to be associated with the thermal response of pain receptors located approximately 200-300 µm deep in the skin, while PA signals from absorbing cells (e.g., melanoma) are proportional to averaged laser energy at a depth of 1-2 mm, as illustrated in FIG. 4A. Taken together, a novel method for fractionated PA diagnosis may make use of multiple small-diameter laser beams for fractionated delivery of laser energy that enable the delivery of higher laser energy to deep vessels (up to $10^3$-fold higher laser fluence) without adverse side effects because laser energy would not be averaged and hence heat would not accumulate at a lower depth than that of the temperature, pressure, and pain receptors.

In various aspects, fractionated PAFC technology with enhanced sensitivity for detection of weakly absorbing cells may integrate the principle of nonlinear PAFC, fractionated delivery of laser energy, nanosecond and picosecond lasers, and a focused spherical ultrasound transducer array. Most absorbing targets (e.g., Hb, nanoparticle clusters) have sizes on the order of about 30 nm to about 100 nm. According to known acoustic confinement principles, effective generation of PA signals from such small particles may require a laser pulse width from about 20 ps to about 100 ps. In these various aspects, the fractionated PAFC device may include picosecond lasers with a wavelength of 650-1200 nm, pulse energies up to few mJ, high-pulse-repetition rates of up to about 1-500 kHz, as well as fiber and/or lens-based delivery of laser radiation. In one aspect, lens-based delivery of laser may be used to reduce the risk of possible fiber photodamage at laser fluences in excess of 250-400 mJ/cm².

The use of fractional PAFC may decrease the laser beam diameter pulses to a few micrometers, thereby reducing the risk of photothermal (PT)-induced superficial skin damage because of the consequent decrease in thermal relaxation time, and hence heat accumulation, especially at a high pulse rates. Fractional PAFC laser pulse delivery may increase PAFC sensitivity by increasing the laser energy fluence without adverse effects using delivery of laser energy via multiple laser beams. Different optical schemes (e.g., microlens arrays, diffusers, pinholes, and optical masks) may be used to create 1-D arrays (e.g., from 1×10 to 1×30 beams) and 2-D arrays (e.g., 10×10 or 20×20 beams) of multiple small-diameter (3-6 µm) laser beams, with varying spacing (5-200 µm) between them and at different energy fluences in individual beams (0.01-25 J/cm²). The optical parameters must be optimized to avoid overlapping of optical and thermal fields from each beam at the depth of the first pain receptors (200-300 µm), where laser energy is still high (maximal) before attenuation in tissue, with simultaneous spatial overlapping of attenuated light energy at the depth of the vessels (2-3 mm).

This design in various aspects enables a key advantage of laser energy-dependent PA diagnosis: a dramatic increase (at least $10-10^2$-fold) in laser energy level for 2-4 mm-diameter vessels without significant risk for harmful effects in superficial skin area where the laser energy is still high before being redistributed and attenuated in deeper tissue due to light scattering and absorption. Fractionated delivery of nanosecond or picosecond laser radiation will enhance non-linear PA signals in small absorbing targets which will be detected with a focused ultrasound transducer array that minimizes background signal from blood.

IX. Target Objects

Figure 27D:
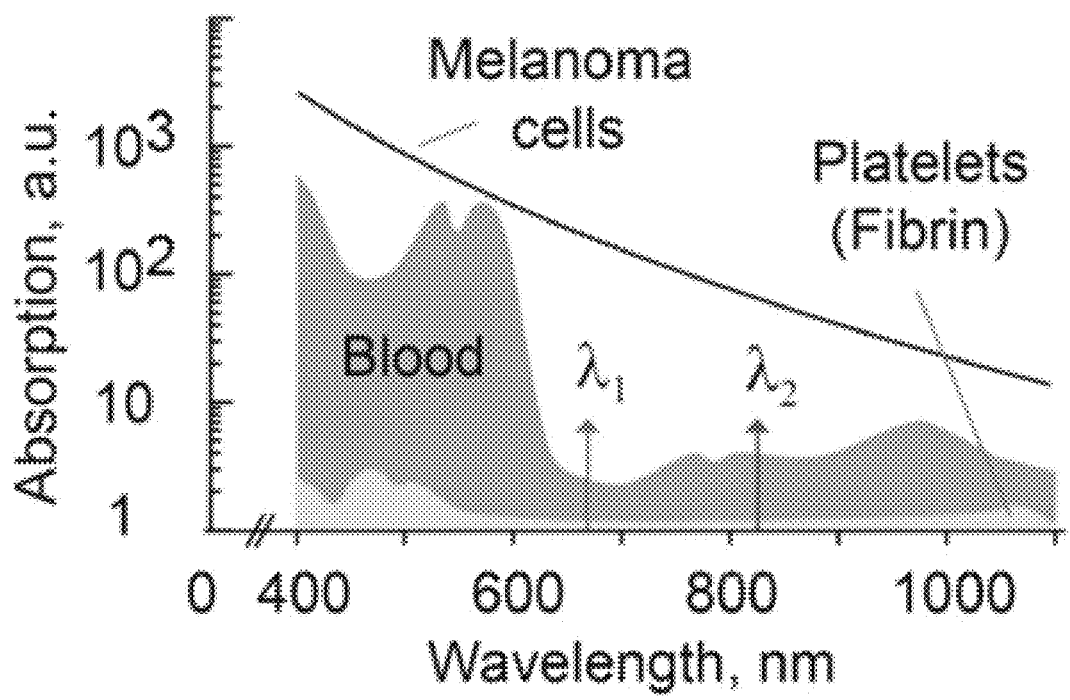
FIG. 27D illustrates absorption spectra of RBCs, melanoma, and platelets.
Figure 28A:
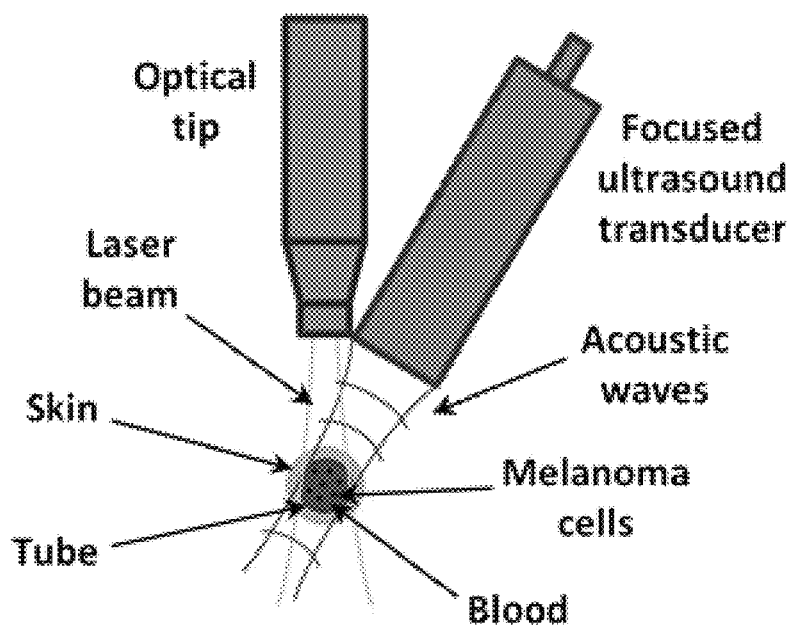
FIG. 28A illustrates a PA probes for a fractionated PAFC with integrated optical and acoustic resolution using a focused cylindrical transducer and cylindrical focusing fiber-based optics.
Figure 28B:
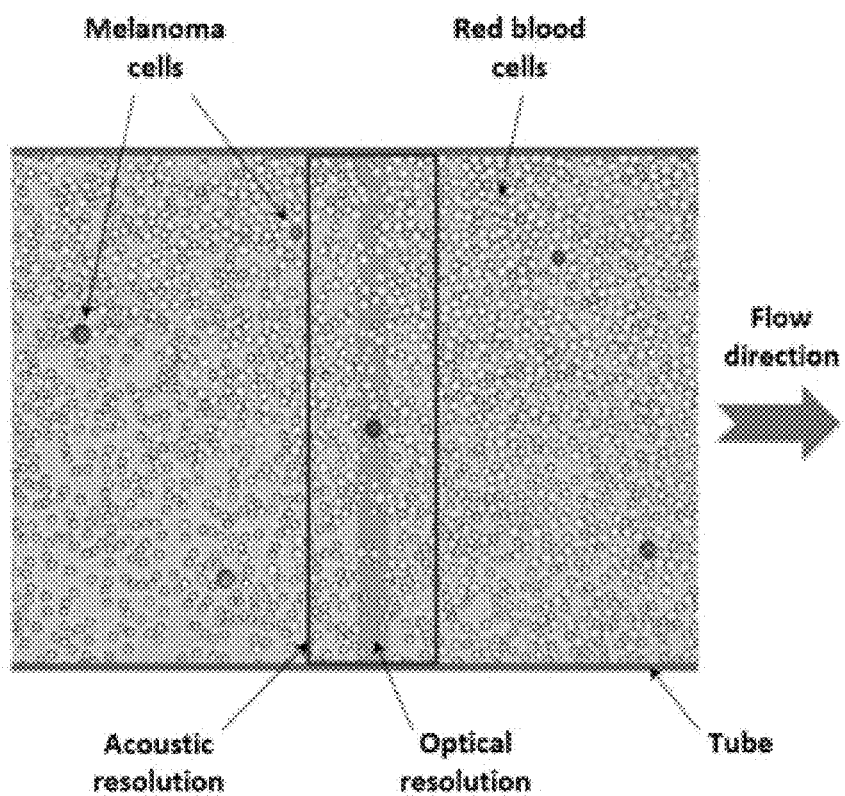
FIG. 28B shows a position of cylindrical optical and acoustic focus in blood sample with melanoma cells.

In an aspect, the target objects may be detected with fractionated PAFC within circulatory vessels at a depth ranging from about 1 mm to about 5 cm below the surface of the skin. Non-limiting examples of circulatory vessels include capillaries, arterioles, venules, arteries, veins, and lymphatic vessels. The diameters of the circulatory vessels may range between about 10 µm and about 2 cm. The diameter of the circulatory vessel may be selected in order to enhance the negative contrast of the clots relative to the surrounding blood flow. Leukocytes and the plasma layer within the blood flow may also produce significantly lower PA signals compared to surrounding RBCs, resulting in negative contrast signals that confound the analysis techniques used to detect clots (FIGS. 27B and 27D). Within small circulatory vessels such as capillaries, the confounding negative contrast from leukocytes, platelets, fibrin, and plasma is more pronounced; this confounding negative contrast is attenuated in larger-diameter circulatory vessels. In an aspect, the circulatory vessels in which target objects are detected may have a mean diameter of at least about 25 µm.

The circulatory vessels targeted with fractionated PAFC may be located in various organs and tissues, including, but not limited to skin, lips, eyelid, interdigital membrane, retina, ear, nail pad, scrotum, brain, breast, prostate, lung, colon, spleen, liver, kidney, pancreas, heart, testicles, ovaries, lungs, uterus, skeletal muscle, smooth muscle, and bladder. Target objects may be detected with fractionated PAFC in the circulatory vessels of any organism that possesses cells circulating in vessels or sinuses chosen from the group of organisms including mammals, reptiles, birds, amphibians, fish, mollusks, insects, arachnids, annelids, arthropods, roundworms, and flatworms.

The target objects detected in various aspects may include but are not limited to unlabeled biological cells, biological cell products, unbound contrast agents, biological cells labeled using contrast agents, clots, aggregations of cells, platelet-rich white clots, red blood cell-rich clots, heterogeneous clots comprising platelets and one or more other target object types, and any combination thereof. The target objects may be unlabeled endogenous or exogenous biological cells or cell products including but not limited to normal, apoptotic and necrotic red blood cells and white blood cells; aggregated RBCs or clots; infected cells (e.g., RBCs infected with malaria parasites); inflamed cells; stem cells; dendritic cells; platelets; metastatic cancer cells resulting from melanoma, leukemia, breast cancer, prostate cancer, ovarian cancer, and testicular cancer; bacteria (e.g., *S. aureus*); viruses; parasites (e.g. malaria); fungal cells; protozoa; microorganisms; pathogens; animal cells; plant cells; and leukocytes activated by various antigens during an inflammatory reaction and combinations thereof.

The target objects detected by fractionated PAFC may also be biological cell products, including but not limited to products resulting from cell metabolism or apoptosis, cytokines or chemokines associated with the response of immune system cells to infection, exotoxins and endotoxins produced during infections, specific gene markers of cells such as tyrosinase mRNA and p97 associated with cancer cells, MelanA/Mart1 produced by melanoma cells, PSA produced by prostate cancer, and cytokeratins produced by breast carcinoma.

The target objects detected by fractionated PAFC may also be contrast agents chosen from the group including indocyanine green dye, melanin, fluoroscein isothiocyanate (FITC) dye, Evans blue dye, Lymphazurin dye, trypan blue dye, methylene blue dye, propidium iodide, Annexin, Oregon Green, C3, Cy5, Cy7, Neutral Red dye, phenol red dye, AlexaFluor dye, Texas red dye, photoswitchable proteins and NPs, gold nanospheres, gold nanoshells, gold nanorods, gold cages, carbon nanoparticles, prefluorocarbon nanoparticles, carbon nanotubes, carbon nanohorns, magnetic nanoparticles, quantum dots, binary gold-carbon nanotube nanoparticles, multilayer nanoparticles, clustered nanoparticles, liposomes, liposomes loaded with contrast dyes, liposomes loaded with nanoparticles, micelles, micelles loaded with contrast dyes, micelles loaded with nanoparticles, microbubbles, microbubbles loaded with contrast dyes, microbubbles loaded with nanoparticles, dendrimers, aquasomes, lipopolyplexes, nanoemulsions, polymeric nanoparticles, and combinations thereof.

The target objects detected by fractional PAFC may also be labeled cells, clots, platelets, or other target objects listed herein above, marked with molecular markers and tags comprised of contrast agents listed herein above. The molecular markers or tags may be attached to the cells without modification, or the contrast agents may be functionalized for binding to the cells using molecules including, but not limited to: antibodies, proteins, folates, ligands for specific cell receptors, receptors, peptides, vitamins, wheat germ agglutinin, and combinations thereof. Non-limiting examples of suitable ligands include: ligands specific to folate, epithelial cell adhesion molecule (Ep-CAM), Hep-2, PAR, CD44, epidermal growth factor receptor (EGFR), as well as receptors of cancer cells, stem cells receptors, protein A and lipoprotein receptors of *Staphylococcus aureus*, chitin receptors of yeasts, ligands specific to blood or lymphatic cell endothelial markers, as well as polysaccharide and siderophore receptors of bacteria.

Exogenous target objects such as unbound contrast agents and exogenous unlabeled biological cells may be introduced into the circulatory vessels of the organism parenterally, orally, intradermally, subcutaneously, or by intravenous or intraperitoneal administration.

X. PA Switchable Probes

Photoswitchable fluorescent proteins (PFPs) that change their emission color in response to light has led to breakthroughs in studying static cells. However, use of PFPs for dynamic tracking of cells in vivo is challenging. Moreover, conventional photoswitching methods are not readily applicable to weakly fluorescent proteins. As an alternative, PA techniques, and in particular fractionated PAFC has tremendous potential for the study of nonfluorescent structures in the visible and NIR ranges. However, little progress has been made in the combination of fractionated PAFC and photoswitchable PA probes with controllable spectral shifts in absorption. In an aspect, switchable PA probes may be used for in vivo fractionated PAFC. By way of non-limiting example, reversible magnetic—PT switching of conventional and gold-coated magnetic NPs and PT-based photoswitching of plasmonic resonances in gold NPs, in particular GNR, may be used to track circulating target objects in vivo. These photoswitchable probes may enable the dynamic tracking of CTCs and other circulating cells to provide insight on metastasis development and other cell-mediated phenomena.

Knowledge is limited as to how CTCs or infections disseminate through the body and cause primary and secondary metastases as conceptualized by existing theories such as the cascade metastases model. For example, CTCs or bacteria from a primary tumor or an initial metastatic site or site of first infection invasion may seed metastasis in other sites (i.e., new seeding or re-seeding, respectively) and/or in the primary tumor (self-seeding). To date, the cascade metastasis model is supported preferentially by indirect clinical and basic observations because current detection and imaging techniques using conventional labeling are not suitable for identifying the origin of CTCs, bacteria, parasites, or viruses (i.e., from primary tumor and/or from metastases) because all seeding cells (new seeds, re-seeds, and self-seeds) are identically labeled. Therefore, it is important to develop an imaging/detection approach that can label and track individual cells throughout the body. This will not only enhance the study of metastasis progression, but also elucidate the mechanisms of in vivo cell biology related to behavior, long-term fate, and pathways of dissemination, and recirculation of individual normal and abnormal cells.

The development of photoswitchable (also termed photoconvertible) fluorescent proteins (PFPs) (e.g., Dendra2, mEos2) that can control the light/dark states or spectral shifts in emission in response to light has led to breakthroughs in the tracking of intracellular proteins, organelles, and cells. Use of these techniques in vivo, however, is challenging because of the phototoxicity of high intensity UV—violet light used with low penetration into tissue 500 µm), toxicity and photobleaching of labels, and lack of PFPs for the near-infrared (NIR) window of biotissue transparency (750-1100 nm). In addition, these studies were conducted on static cells, using relatively long (0.5-10 sec) photoconversion times, which are too slow to study dynamic biological processes or fast-moving cells in blood flow that are in the irradiated volume for only 1-10 MS.

PAFC, and particularly fractionated PAFC, using various NPs offer promising alternatives to these limitations. However, despite progress in PAFC and NP development, integration of photoswitchable NPs (SNPs) and fractionated PAFC have not yet been utilized for in vivo applications. In one aspect, a platform is provided for engineering SNPs that can provide a new class of multicolor PA contrast agents undergoing ultrafast (nanosecond scale) spectral shifts (up to 50-200 nm) in NIR absorption spectra in response to short laser pulses, suitable for single cell tracking with fractionated PAFC within the vascular system using ultrafast photolabeling of single cells in circulation. This approach may provide an innovative research tool to gain insights into the in vivo behavior of circulating normal and abnormal cells. In particular, it can provide insights into metastases progression through real-time dynamic monitoring of the release of CTCs from a primary tumor or metastasis and study self-seeding and reseeding processes at the single-cell level with focus on multiplex identification and tracking of metastatically aggressive CTC population.

In an aspect, a method of targeting and tracking circulating cells using SNPs with ultrafast ($10^{-8}$ sec) controllable laser switching of SNP color directly in the bloodstream is provided. Spectral selectivity for the identification of multiple markers is limited by the wide NIR spectral band (80-150 nm) of most NPs which allows effective use of only two non-overlapping colors, at most. To target multiple markers, photoswitchable multicolor SNPs with ultrasharp nonlinear PA resonances in plasmonic NPs with spectral width up to 1 nm may be used to label individual circulating cells. According to Rayleigh criteria, up to about 40 distinct colors, each color corresponding to a distinguishable PA response in response to a particular wavelength of light pulse, may be simultaneously distinguished in the NIR window of tissue transparency. In an aspect, 6-8 colors of switchable multicolor SNPs may be used to label circulating cells for PAFC detection in vivo. With 8 SNP colors, 10 signal levels, and 3 switchable selected colors, these "ultrasharp rainbow" SNPs may enable bio-barcoding characterized by an enormous number of color-code combinations (theoretically up to about $10^7$ combinations) in the NIR range at low NP toxicity and low laser energy levels.

In general, the fractionated PAFC platform in which enhanced laser energy fluence in deep vessels will facilitate photoswitching in deep tissues and as a result, till provide a better understanding of poorly known mechanisms of early metastatic disease with focus on tracking of single bulk of cancer stem cells. In general, single-cell photolabeling can uniquely track the fate of any circulating group of cells of interest in different animal models to discover physiological and pathological mechanisms related to health and diseases, including sepsis, clotting, immune system dysfunction (through tracing of white blood cell [WBC] sub-population such as neutrophils, lymphocytes, or monocytes), and identification of abnormal red blood cells [RBC] such as sickle cells).

XI. SNP Switchable Nanoparticles

Provided herein is a method for monitoring a photoswitchable target object in a circulatory vessel in a living organism. The method may include pulsing the photoswitchable target object having a first color within the circulatory vessel with a first pulse of laser energy at a first pulse wavelength from a multicolor fractionated PAFC, obtaining a first photoacoustic signal emitted by the photoswitchable target object induced by the first pulse of laser energy, pulsing the photoswitchable target object with a second pulse of laser energy at a second pulse wavelength to switch the color of the photoswitchable target object to a second color, pulsing the photoswitchable target object within the circulatory vessel with at least one additional pulse of laser energy at a third pulse wavelength, obtaining a second photoacoustic signal emitted by the photoswitchable target object induced by the at least one additional pulse of laser energy; and analyzing the photoacoustic signals to calculate the combination of photoacoustic signals emitted by the photoswitchable target object. The combination of photoacoustic signals may be characteristic of the photoswitchable target object within the circulatory vessel.

The method may further include monitoring at least a second photoswitchable target object. In an aspect, up to about 8 colors from the photoswitchable target object may be detected. The photoswitchable target object may be associated with a circulating cell in the circulatory vessel. In one aspect, the circulating cell may be a circulating tumor cell. The pulse of laser energy may have a pulse width of about 0.1 ps to about 20 ns to switch the color of the photoswitchable target object. The photoswitchable target object may include, but is not limited to, a photoswitchable plasmonic gold nanocluster and a gold nanorod. In an aspect, pulsing the photoswitchable target object with a second pulse of laser energy at a second pulse wavelength causes a red shift in absorption of the photoswitchable target object.

Figure 45:
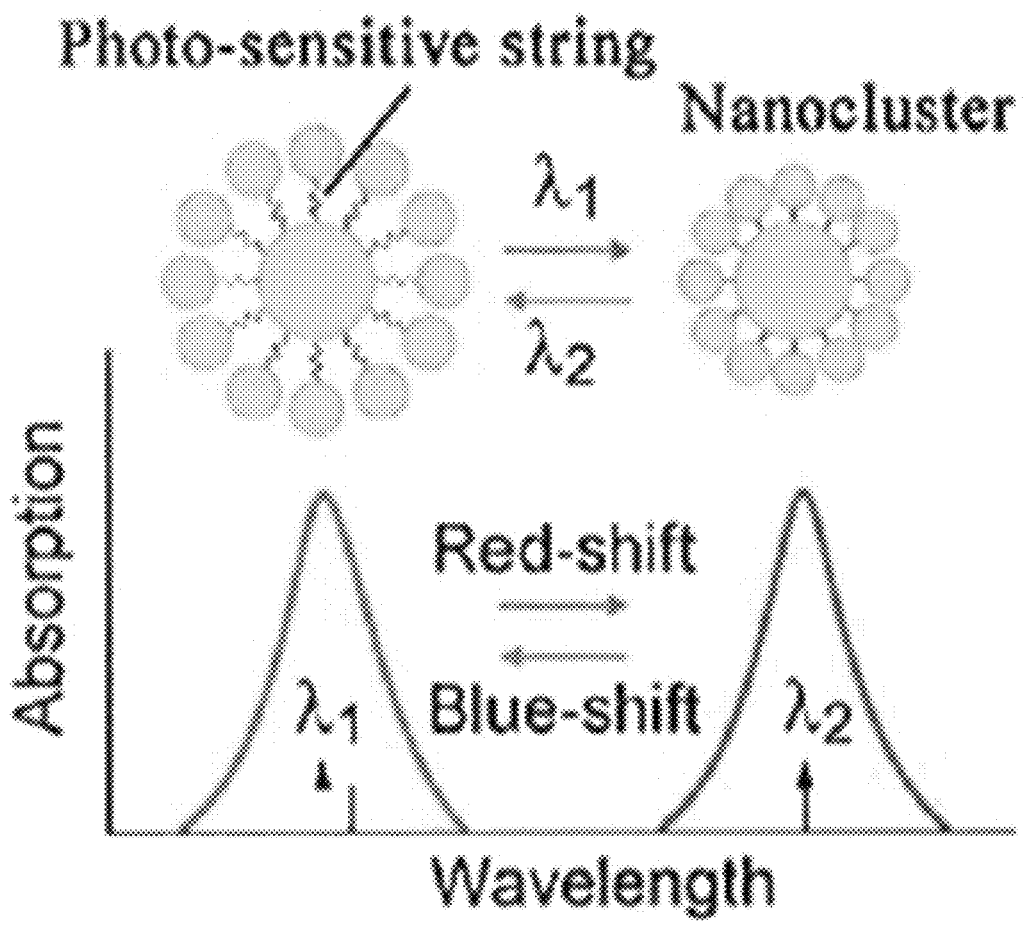
FIG. 45 illustrates photoswitchable plasmonic gold nanoclusters with light-sensitive links between individual nanoparticles.
Figure 46A:
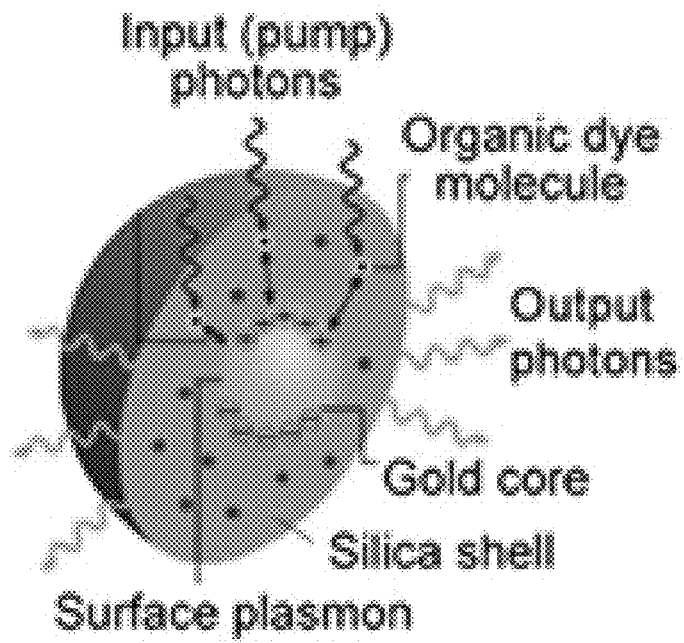
FIG. 46A is a spaser schematic.
Figure 46B:
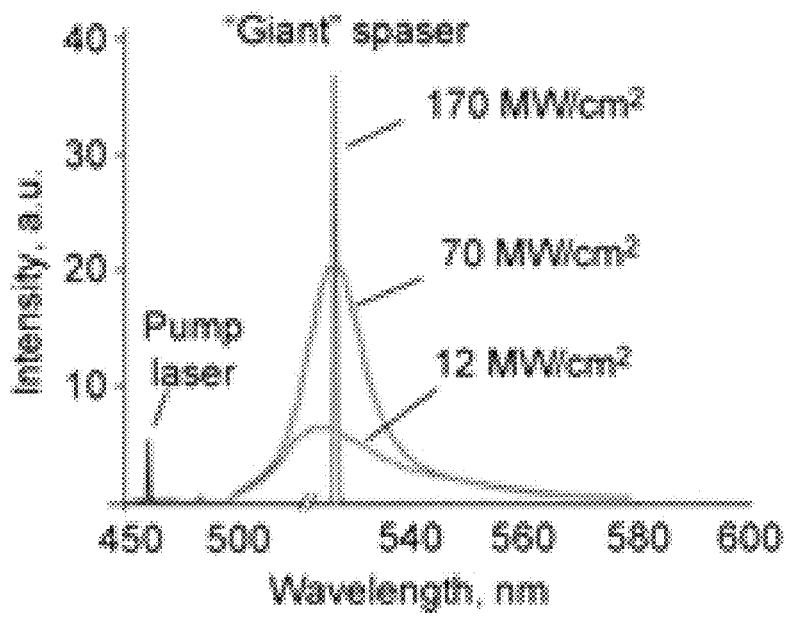
FIG. 46B shows spaser emission at 528 nm at different pump intensities at 488 nm.
Figure 46C:
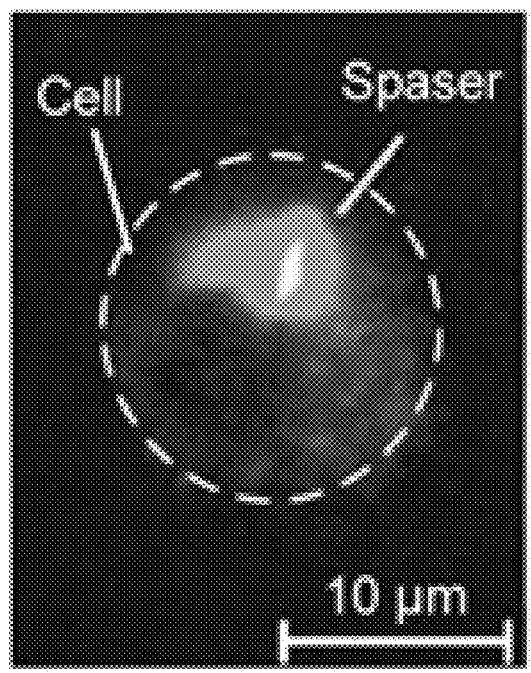
FIG. 46C is an image of a cancer cell with a spaser obtained with a lamp (cell background) and a focused pump beam (bright sport).
Figure 46D:
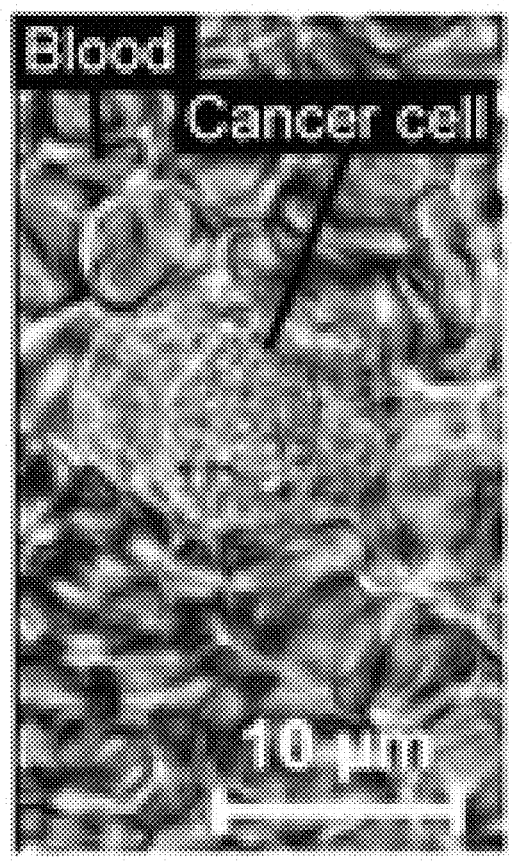
FIG. 46D is an image of a cancer cell in blood.
Figure 46E:
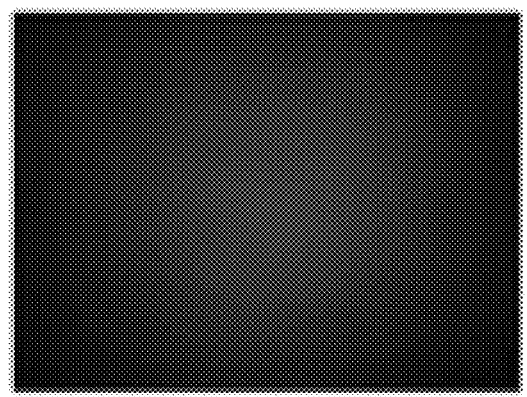
FIG. 46E is a fluorescence image below the spaser threshold (6 MW/cm$^2$) through 1.5 mm blood.
Figure 46F:
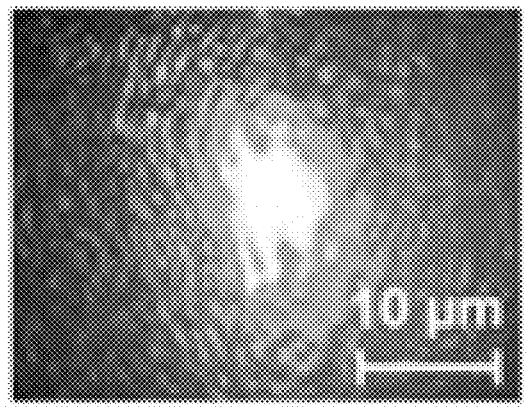
FIG. 46F is a fluorescence image above the spaser threshold (6 MW/cm$^2$) through 1.5 mm blood.

In various aspects, plasmonic reversible-cascade phenomena may be used to enable the switching mechanism of the switchable nanoparticles (SNPs). In these aspects, different plasmon modes may be coupled for NPs with different shapes (rods, spheres, triangles, prisms, wires, etc.), sizes, compositions (e.g., Au, Fe, and polymer) and spatial (1-, 2-, 3-D) structures (e.g., chains or multilayers). By way of non-limiting example, in SNP clusters, the individual NPs may be connected by light-sensitive materials (e.g., DNA, protein and polymer) that may act as photo-activated light-sensitive materials. Laser-induced localized thermal-dependent or photochemical-dependent (e.g., photoisomerization) reversible changes in the distances between individual NPs, clustered together, may be accompanied by blue and red shifts in the collective plasmon resonances as interparticle distances increase and decrease, respectively, using different wavelength for switching, as illustrated in FIG. 45.

In various other aspects, photochromism may be used to provide a switching mechanism. In these other aspects, porous silica NPs, loaded with $TiO_2$ and Ag matrix with absorption in the visible and far-red ranges, may be exposed to a first laser pulse in this absorption range to create photogenerated electrons in the $TiO_2$. The photogenerated electrons may lead to the formation of Ag NP clusters with red-shifted absorption in the NIR range. A second laser pulse in the NIR range may be used to disintegrate the Ag NP clusters into individual Ag NPs, returning the color of SNP back to the visible (or far-red) range. Any other known photochromic materials may be used without limitation.

In various additional aspects, laser-induced modifications of gold NP size and shape may be used as a switching mechanism in fractionated PAFC. More specifically, laser-induced temperature-dependent changes in the shape of gold nanorods (GNRs) from cylindrical to ellipsoidal are accompanied by a blue shift in longitudinal plasmon resonance. Red and blue shifts may also be induced in gold nanoshells (GNSs) due to laser-induced decreases or increases in the thickness of the gold shell around the silica core. These highly localized effects may be enhanced in clusters of different NP types (e.g., GNRs, GNSs) or synthesized by golden carbon nanotubes (GNTs) under a low pulse energy fluence (1-20 $mJ/cm^2$) that is safe for living cells. In an aspect, the number of switchable colors may be increased up to 6-8 in the range of 700-1100 nm using ultrasharp nonlinear PA resonances.

By way of non-limiting example, FIG. 23 illustrates a 4-color PAFC system mounted on an Olympus 1X71 microscope or with fiber delivery of multicolor laser radiation to the skin may be used to dynamically monitor circulating cells using the fast-switching phenomena. Both the available high-pulse laser arrays with fixed wavelengths of 532/671/820/1064 nm and time color coding may be used, as schematically illustrated in FIG. 26A, along with new, tunable, high-pulse rate lasers (spectral range, about 680-950 nm; pulse width, about 0.6-1 ns; pulse rate, 10 kHz; pulse energy, up to 300 µJ) providing spectral optimization of PT-based photoswitching phenomena. In one aspect, this system may be used for detecting SNPs at low laser energy and for fast (nanosecond scale) PT switching of SNPs produced by increasing the pulse energy within a short time period. This system in various aspects may provide measurements of ultrasharp PA resonances and may further enable the capability to switch the SNPs in both static and flowing conditions.

The SNPs in various aspects may be used as PA contrast agents with the capability for fast (10-20 ns) PT switching of the linear and nonlinear (ultrasharp) plasmonic resonances in NIR range. With optimized SNPs and laser parameters, spectral switching may be achieved in the range of 10-100 nm and a fractionated PAFC sensitivity threshold of 5-10 SNPs in the sample volume. Ultrasharp nonlinear PT and PA spectral resonance in plasmonic SNPs with widths up to 1-5 nm may enable control of small spectral shifts in the broad absorption spectra of conventional NPs (50-100 nm); this capability may enable additional colors up to about 10-12 colors for the SNPs in the NIR range. SNPs may be used for both PA detection and tracking of targeted and "switched" in vivo CTCs that have the potential to provide insights on metastasis cascades. SNPs may enable molecular targeting, and PT switching in the targeted cells. By way of non-limiting example, CTCs may be molecularly targeted with conjugated gold-based NPs directly in the bloodstream in vivo. Moreover, gold nanorods (GNRs) and spasers in single cells may be spectrally switched by nanosecond laser pulses that allow them to be tracked in vivo within the complex blood network.

The SNPs in various aspects may be used with in vivo multicolor fractionated PAFC to offer real-time detection, molecular identification, and enumeration of CTCs with different profiles (e.g., bulk and stem) in blood circulation. The SNPs in these aspects may enable 7-8 colors of marker, and the PAFC may male use of negative contrast to further enhance sensitivity. PT switching in vivo directly in the blood flow may be enabled with optimized SNPs in an aspect. Using this approach, the understanding of metastatic progression may be enhanced by elucidating: 1) dynamic changes in the origin of CTCs during metastasis progression; 2) pathways of metastasis growth by processes of self-seeding and re-seeding with aggressive variants of CTCs; and 3) ability of micrometastases to produce CTCs. Seeding cells may be detected in metastatic lesions (likely in the lungs) with localization near the blood vessels, which may provide an indication of their potential aggressiveness. PT switching for SNPs with small spectral shifts and broad absorption spectra may be enabled using ultrasharp nonlinear PA resonances in vivo for selected SNPs.

XII. PA Signal Processing

Figure 24:
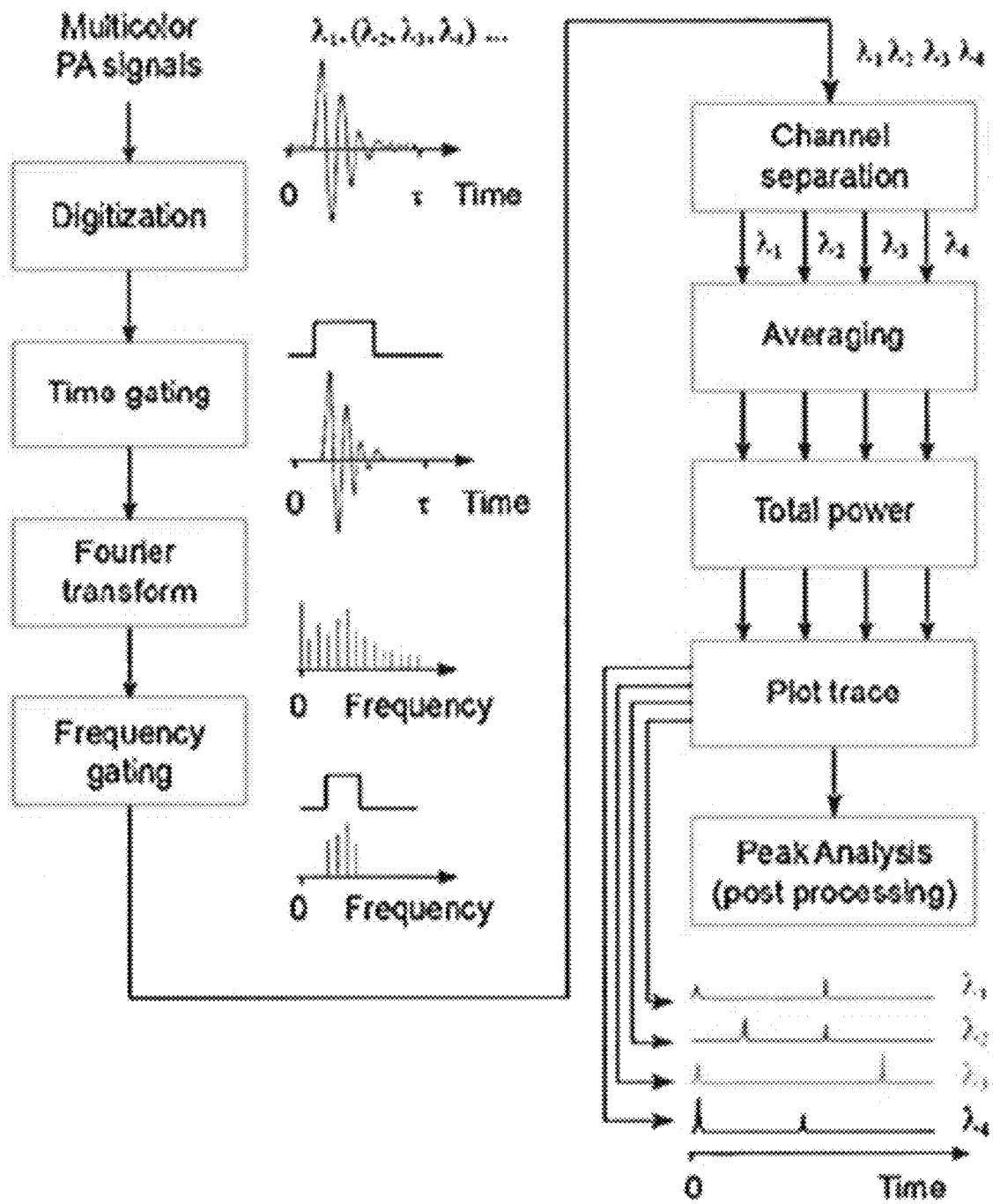
FIG. 24 illustrates a signal-processing schematic diagram for a four-color fractionated PAFC system. Blocks on the left-hand side are implemented by the digitizer in real-time, and the resulting spectral data are saved. The remaining steps for acquiring PA traces are performed by a workstation either in real-time or as post-processing. Peak analysis is performed on the full PA trace after the data acquisition is completed.

A schematic diagram of the signal processing scheme of the multicolor fractionated PAFC system in one aspect is illustrated in FIGS. 24 and 25A-25B. PA signals measured within the fractionated PAFC system in this aspect may be characterized as wideband signals. Depending on the transducer used, high sampling rates (f) for digitization may be required (at least twice the maximum frequency, per Nyquist criteria) to enable sufficient data for analysis. In this aspect, analog-to-digital conversion may be accomplished at 500 MHz. Since there is a certain delay between the laser delivery and PA signal arrival, the location of the PA peak may relatively stable. Thus, it is possible to define a region of interest (ROI), as illustrated by blue rectangular highlighting in FIG. 25A and FIG. 25B, and sample only this ROI. ROI selection enables the reduction of the acquired data size, and the required computing time in subsequent steps. It also helps reduce the noise related with laser electronics and scattered light. In the next step of signal processing as illustrated in FIG. 25A, N consecutive PA signals are ensemble averaged. Averaging is performed on the FPGA firmware of the digitizer, and resulting PA signals are transferred to the computer memory. By selecting N=1, no averaging is performed. While increasing SNR, averaging also reduces the throughput by a factor of N.

In this aspect, data throughput may be calculated by Eqn. (III):

$$\text{Throughput}=f[Hz]*f[Hz]*\text{ROI length}[S]*\text{sample length}[byte]/N \qquad \text{Eqn. (III)}$$

By way of non-limiting example, for a 500 MHz sampling rate, 2 bytes sample length, 10 kHz pulse rate, an ROI length of 4, and no averaging (N=1), the throughput is 40 MB/s. In this case, a 1 hour long record would produce 144 GB of data.

Further real-time processing of the PA signals may be executed on the computer CPU in various aspects. Incoming PA signals may be filtered and their peak-to-peak amplitudes may be traced as illustrated in FIG. 25A. Thus, the PA trace consists of f/N points per second. A high f/N ratio is desirable as it provides better time resolution in the PA trace. Raw PA signals and the resulting PA trace are optionally streamed to a hard disk drive in an aspect. At the same time, the PA trace and a subset of the acquired PA signals may be visualized in real time. Visualization in real time may enable the user to monitor system status and to intervene if necessary (e.g., loss of focus due to subject movement can be observed by change in PA background). Peak detection routines using known methods may also be performed in real-time in an aspect. More detailed peak detection and statistical analysis of the results may be performed during post-processing. All acquisition process steps after averaging may be repeated with different parameters using recorded raw data in one aspect. In this aspect, N is limited by $N_{new}=k*N_{old}$, where k is an integer.

The availability of raw PA signals may enable further analysis of any detected PA peaks in a PA trace. PA signals may contain important information about the size and location of the cell. The PA signals may also facilitate the identification of any random electromagnetic noise or the artifacts introduced in post processing, by analyzing the signal shape. In demanding applications such as CTC detection in vivo where only a few cells are detected, it is essential to go back to the raw data and closely examine the raw PA signal shapes to eliminate any false positivity. On the other hand, for a repeatable application in which thousands of PA peaks are detected, false positivity may not be as critical, hence the analysis of raw PA signals.

Performance characteristics for the fractionated PAFC system may be selected according to the application in various aspects. Most in vivo applications involve continuous monitoring of more than an hour. Thus one major characteristic is that the fractionated PAFC system should function in real-time. Otherwise, higher performance may be enabled by bursts of acquisition until a limited size memory on the acquisition board is filled. Therefore, one performance criteria is to maximize f/N ratio in one aspect, while recording raw data and performing real-time visualization of the data to enable user intervention. Almost all parameters have a direct effect on the performance (e.g., f, fROI length, filter type, etc.). Thus, any extreme parameters or complex algorithms that may introduce a time lag in data processing may be implemented in post-processing in various aspects.

XIII. PA Peak Analysis

In various aspects, recorded PA traces may be analyzed in post-processing to identify events and perform statistical analysis of the data. Any object entering or leaving the detection volume transiently changes amplitude of the signal, i.e., appears as a narrow peak in PA traces. It is a challenge to detect these peaks in a noisy PA trace, especially for in vivo experiments, where the background signals are relatively strong and fluctuating due to physiological effects, etc.

In an aspect, a PAFC peak analyzer is provided that performs at least one or more of several steps to enable peak detection. The PAFC peak analyzer may perform high-pass filtering (fc=10 Hz) to eliminate any low frequency fluctuations in background level. The filtered trace may be split into short segments. Within each segment, the average value (m)

and standard deviation (s) may be calculated, and the peak threshold, th=m+cxs may be determined (c is a coefficient determined as the largest value that does not produce any false positive signals in control experiments). All peaks above the threshold may be identified; a peak may be defined as any data point that is larger than both of its neighboring data points. The edges of the peaks may be determined as the zero-crossing points closest to the peak. As identified in this aspect, a peak includes a part of the PA trace that consists of at least three points. Any overlapping peaks may be aggregated and represented as a single peak, and various parameters including, but not limited to amplitude, normalized amplitude, width, time stamp, area, etc. may be calculated for each peak.

A multicolor fractionated PAFC device used to obtain PA traces in an aspect may be equipped with four high-pulse-repetition rate nanosecond lasers with the following parameters: 1) wavelength, 532 nm; pulse energy, 116 µJ; pulse width, 5.3 ns; and repetitions rate, up to 100 kHz (model: LUCE 532, Bright Solutions, Cura Carpignano, Italy); 2) 671 nm, 36 µJ, 25 ns, and 100 kHz (model: QL671-500, CrystaLaser, Reno, Nev., USA); 3) adjustable spectral range, 690-890 nm (820 nm used in this study); 76 µJ, 8 ns, and 30 kHz (model: LUCE 820, Bright Solutions); and 4) 1,064 nm, 350 µJ, 10 ns, and 750 kHz (model: MOPA-M-10, Multiwave Photonics, Portugal). A pulse-repetition rate of 10 kHz was selected for all lasers, and the delay between laser pulses was 25 ps. Laser pulses were triggered by a digital delay/pulse generator (DG645, Stanford Research Systems, Sunnyvale, Calif.) for time-color coding. PA signals from the ultrasound transducers (see above) were recorded, digitized (14-bit resolution, 125 mega-samples per second; model: custom AD484; 4DSP Inc., Reno, Nev.), and analyzed with custom-written software on the workstation (Precision T7500, Dell, Round Rock, Tex.).

The acquired PA signals may have a bipolar shape transformed into a pulse train because of reflection and resonance effects in transducer holder. To address this potentially confounding factor, the spectral power in a small frequency band may be monitored as illustrated in FIG. 9, where increased power indicates a PA event. Because a significant reduction in data occurs at the beginning of the process and before averaging, it is possible to continuously record raw data from all triggered events for later reprocessing with different parameters (averaging, spectral region) and hence avoid the loss of temporal details. Using these spectral analysis methods, may enable the detection of PA events with a higher SNR compared to waveform (time-domain) analysis methods.

In various aspects, spectral analysis methods may be used to analyze the PA traces obtained by the fractionated PAFC system as illustrated in FIG. 24. PA signals may be collected through one or multiple transducer(s) and then digitized. The digitizer may perform a fast Fourier transform (FFT) on each triggered event, using its custom field-programmable gate array (FPGA) firmware. A user can define several parameters for this operation: sampling frequency, ($f_s$=8; 80 or 120 MHz), FFT length (1,024 or 512 points), wait time before acquisition after a trigger (0-10 ps), and frequency region of interest (fROI) (1-1,024 points) to be returned to the host program for further real-time and post-processing routines. The digitizer may be controlled with software custom-written in C++ for fast acquisition and recording of the raw spectral data. Other real-time and post-processing operations may be implemented in MATLAB.

The delay between a laser pulse and the resulting PA signal may depend on the distance between the laser focal point and the transducer. Setting a wait time for acquisition is essentially a time-resolved gating that enables accurate selection of PA signals and removal of any noise between the trigger and the start of the PA signal, such as the electromagnetic noise originating from the laser hardware. Fourier coefficients in the specified frequency band (fROI) may be calculated from the gated time signals. Selection of fROI may plays two roles in this method: 1) data compression (approximately 50×) by discarding any irrelevant frequency components and 2) SNR improvement by focusing on the most significant frequencies discriminating PA signals from noise.

For each trigger event, complex Fourier coefficients may be combined with a trigger counter and a laser flag, constituting a frame. A laser flag may be extracted from a second channel on the digitizer, which may function as a trigger signal for one of the four lasers. The data may then be returned to the workstation and saved to hard-disk drive. For the typical settings of $f_s$=80 MHz, FFT length=1,024 points, fROI=1.6-3.28 MHz ($20^{th}$ to $41^{st}$ coefficients), and 4f=40 kHz, the data rate was 440 MB/min.

The PA signals resulting from multicolor lasers may be acquired from the same transducer. Hence, each series of frames may be separated into abstract channels and associated with a laser using a flag or other index. Within each channel, coherent spectral averaging may be applied to N frames in order to reduce variance and increase SNR by a factor of $N^{1/2}$. N consecutive frames may be selected with 50% or no overlapping. As a result, the number of frames was reduced by a factor of N/2 or N, respectively.

At this point, two types of PAFC traces may be created: 1) by calculating the total spectral power in each frame (PA spectral power trace) and 2) by taking the inverse FFT of each frame and finding the maximum peak-to-peak voltage in the reconstructed time-domain signal (PA amplitude trace). In this way, each triggered event may be translated into a number and traced similarly to conventional fluorescence cytometry, in which each point in the trace represents a direct reading of light intensity. Peaks in this trace correspond to PA events in various aspects.

The digitizer may enable up to a 75-kHz and a 150-kHz trigger rate for 1,024- and 512-point FFT, respectively. The performance of the software may depend on the selected process parameter values. For a typical case of four lasers operating at 4f=40 kHz, the digitizer may run in real-time for N≥10. However, because the raw data for all triggered events may be recorded, it may be possible to recreate PA traces for different parameters requiring heavier computation.

Recorded traces for each laser may be analyzed for PA event detection and statistics. The custom written peak analyzer in one aspect may finds a baseline in the trace, set the threshold level based on the mean and a multiple of the standard deviation, detect any peaks above this threshold, and perform statistical analysis by acquiring time stamps, amplitudes, and widths of the detected peaks.

IV. Photochemically Induced Blood Flow Manipulation with Fractionated PAFC

Photorheological fluids have rheological properties, such as viscosity, that may be dramatically (up to $10^4$-fold) altered by illumination with light in a reversible manner. Existing photorheological fluids are typically based on specialized organic molecules, such as photoresponsive surfactants, photoresponsive polymers, or wormlike micelles filled with a photochromic chemical compound. For example, a photoisomerization from trans- to cis-forms alters molecular packing at the micellar interface, resulting in transformation of the long micelles into much shorter entities and, in turn, a decrease in the solution's viscosity. However, the use of existing techniques in vivo in blood may be challenging due to the phototoxicity of high-intensity UV—violet light used to enable a photorheological change, the shallow penetration of UV light into tissue (500 µm), the toxicity of the chemicals used, the lengthy photoconversion time for dynamic study, and the lack of chemicals for the NIR window of biotissue transparency (650-1100 nm).

Provided herein is a method for manipulating the viscosity of blood using fractionated PAFC including administering a light sensitive material to the blood and pulsing the light sensitive material with a pulse of laser energy at a pulse wavelength and a pulse width. The pulse of laser energy may cause a photoconversion of the light sensitive material such that the viscosity of the blood is reduced. In various aspects, adding light-sensitive biocompatible materials to blood may allow manipulation of flow parameters (e.g., viscosity) with fast ($10^{-3}$-$10^{-5}$ sec) photoconversion of light sensitive materials to appropriate forms at low toxicity and low laser energy levels. In an aspect, the pulse width of the laser pulse may range from about 10 ps to about 1 ms. The wavelength of the laser pulse may range from about 200 nm to about 2500 nm. In one aspect, the light-sensitive biocompatible materials may respond to laser pulses in the NIR range from about 650 nm to about 1400 nm. In various aspects, this method may be used to reduce blood viscosity and inhibit blood flow to a full stop.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

EXAMPLES

The following examples illustrate the invention.

Example 1: Basic PAFC Technical Platform

The PAFC setup was equipped with a tunable optical parametric oscillator (OPO; spectral range, 420-2,200 nm; pulse width, 5-8 ns; pulse-repetition rate, 10 and 100 Hz; pulse energy, 2 mJ) and four (only one was proposed in the original application) high-pulse-repetition-rate lasers with the following parameters: wavelengths, 532, 671, 820, and 1,064 nm; pulse width, 5-10 ns; pulse rate, 1-100 kHz; pulse energy, 50-100 µJ. Ultrasound transducers for detecting PA signals included the following: 1) unfocused: frequency, 3.5 MHz; diameter, 5.5 mm (model 6528101; (masonic); 2) focused cylindrical: frequency, 20 MHz; focal length, 12.5 mm (model V316-SM; Panametrics); 3) customized cylindrical without and with a hole to accommodate an optical fiber or free beam 30-40 MHz; focal length, 4-8 mm; lateral resolution, 55-70 µm; and 4) customized miniature spherical transducers: 50 MHz, external diameter, 3.2 mm; focal length, 4 mm. Individual PA signals with a typical bipolar shape (waveform) or more complex temporal structures due to resonance effects in transducers or transducer holder (FIGS. 8A-8H, 9, 41C) and a duration of 0.1-0.3 µs were then amplified (amplifier model 5662: bandwidth, 50 kHz-5 MHz; gain, 54 dB; and model 5678: bandwidth, 40 MHz; gain, 60 dB; both from Olympus Panametrics-NDT). To collect PA signals, the setup was equipped with a high-speed analog-to-digital converter board and LabVIEW and MAT-LAB software. After digitation and averaging (e.g., 10-50 PA signals from each CTC), PAFC data were represented as signal traces, in which amplitude and width of each resulting peak exceeding the established background level were analyzed with customized software. For the animal studies, this setup was built on the platform of an inverted Olympus IX-81 microscope integrated with transmission, fluorescence, and PT modules Example 2: Preclinical Studies in Animals PAFC's diagnostic value in vitro and in vivo was evaluated in healthy nude mice after melanoma cells were injected intravenously (i.v) in the tail vein, and in tumor-bearing nude mice that naturally produce CTCs. By measuring the PA spectra, the optimal near-infrared (NIR) spectral ranges were determined (e.g., 690-740 nm, 840-950 nm and 1,030-1,070 nm) with the maximal PA spectral contrast of melanoma cells in blood and background tissue. CTCs were monitored in blood vessels of ear and abdominal skin and in carotid arteries (at a depth of 2-3 mm) with diameters of 30-70 µm, 100-300 µm, and 0.8-1 mm, respectively. CTC rates in these vessels at week 3 of tumor inoculation were 0.05, 2.7, and 91 CTCs/min, respectively, that underscoring the higher probability of detecting CTCs in larger vessels with high flow rates. Daily monitoring of B16F10 tumor-bearing mice revealed the capability of PAFC to detect CTCs during the first week of tumor development with no sign of metastasis by conventional assays. Intravenous injection of red and white blood cells (RBCs and WBCs) labeled with ICG (approved for use in humans), and of melanoma cells in different functional states revealed their different clearance rates: 1-2 min for necrotic cells, 5-15 min for apoptotic cells, 30-60 min for highly metastatic B16F10 cells, 1-2 h for tumor cells with lower metastatic activity (e.g., SK-MEL-1), and 3-5 days and 1-3 days, respectively, for normal RBCs and WBCs; these findings are in line with published data. As verified in multiple studies using an in vivo mouse model and ex vivo human blood spiked with melanoma cells (e.g., B16F10, HTB-65, C8161, SK-MEL-1), PAFC with NIR lasers can detect single melanoma CTCs in the presence of 500-800 RBCs because of the higher coefficient of absorption of melanin than hemoglobin (Hb) in NIR range. By i.v. injection of trypan blue as a high PA contrast agent at 5-10-fold lower concentrations than those used for cell viability tests in vitro, at 671 nm rare PA signals associated with cells in necrotic or late-apoptotic stages were observed taking up dye directly in the bloodstream. This is important for identifying viable CTCs, the putative drivers of metastasis, and for monitoring of the response to therapies that produce apoptosis and necrosis of CTCs. It was also shown that melanoma CTCs can be molecularly targeted by magnetic nanoparticles (MNPs) as PA contrast agents conjugated with monoclonal antihuman melanoma-associated chondroitin sulfate proteoglycan (MCSP) antibodies (Abs) directly in the mouse bloodstream.

Example 3: Schematics of One Color Fractionated Photoacoustic (PA) Flow Cytometry (PAFC)

Figure 29:
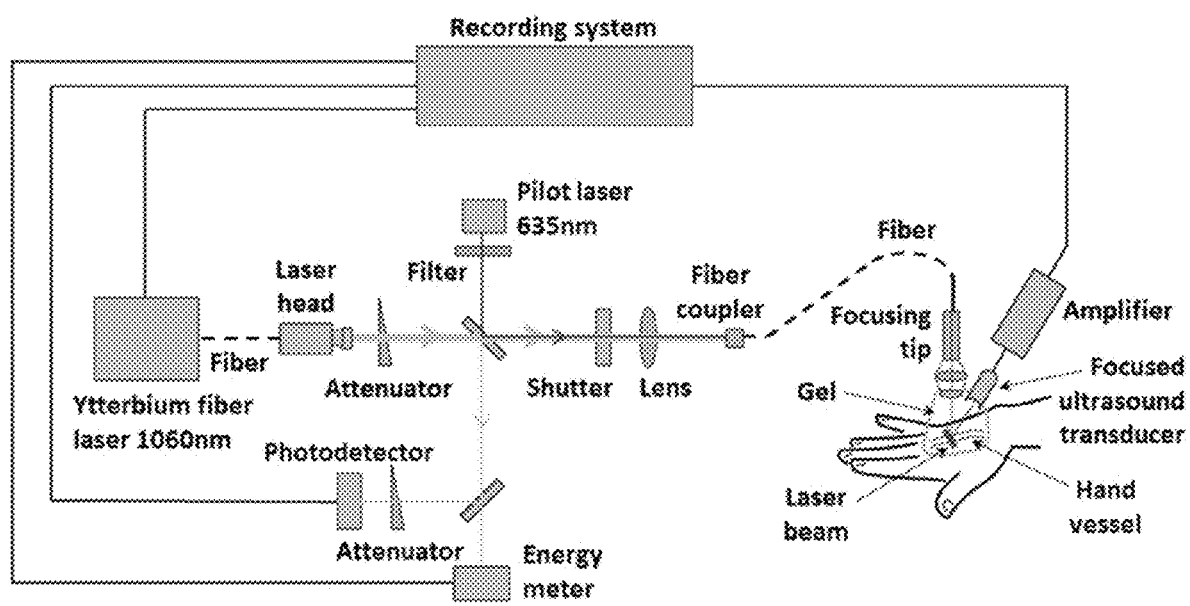
FIG. 29 shows schematics of a fractionated PAFC system for clinical applications.

A fractionated PAFC experimental setup was built on the base of Yb-fiber laser YLPM-0.3-A1-60-18 (IPG Photonics Corp.) having 1060 nm wavelength, pulse repetition rate of 10-600 kHz, and pulse duration of 0.6-0.8 ns, 5 ns, and 10 ns (FIG. 29). A "red" 635 nm pilot laser CPS180 (Thorlabs, Inc.) was introduced through 757 nm dichroic mirror (Semrock, Inc). Laser radiation was focused into the sample by an assembly of aspheric (C560TME-C) and cylindrical (LJ1310-L1-C) lenses (Thorlabs Inc.) resulting in a tight focal standard beam shape, e.g., single circular with diameter from 3 um to 20 um or linear dimensions 3.5×790 µm or 6.5×1200 µm. To create the fractionated beams, additional changeable optical components were used (FIGS. 13A-20). Laser power was controlled in real time by power meter PM100USB with S302C head (Thorlabs, Inc.). A mechanical chopper MC2000 (Thorlabs, Inc.) was introduced into the system to allow single pulse picking and PAFC at pulse repetition rates below 10 kHz, in particular 1, 2 and 5 kHz. 1060 nm laser provided pulse energy of 240 µJ/pulse after focusing optics. Fast photodetector PDA10A (Thorlabs, Inc.) with 150 MHz bandwidth was used to trigger data acquisition hardware. Dimensions of the laser spot were controlled using Xli DX-2M camera (Brunel Microscopes, Ltd, UK).

Laser-induced acoustic waves were detected using various transducers (Example 1 and schematics in FIGS. 5, 27A-27D, and 28A) including a single a custom-made cylindrical 28-µm polyvinylidene fluoride (PVDF) ultrasound cylindrical focused transducer with broadband frequency response, 0.2-32 MHz. The transducer was mounted on an independent XYZ-stage to allow micrometer-precision adjustment of its position. Cylindrical geometry of the transducer surface was custom designed to provide PA signal acquisition across the capillary from a minimal blood volume (acoustic resolution PAFC). At focal distance of 8 mm its acoustic resolution was 45×1100 µm along the short and long axes, respectively. The transducer signals were pre-amplified using 20 dB amplifier (0.05-100 MHz bandwidth, AH-2010-100, Onda Corp.) attached to the transducer and amplified by a second amplifier (40 dB, 0.2-40 MHz, 5678, Olympus-NDT Corp.). The signals were recorded using a fast digitizer ATS9350, 12 bit, 500 MS/s digitizer with 128 MB dual-port memory (Alazar Technologies, Inc.) on a Precision T3500 workstation (Dell, Inc.) under control of a custom MatLab (MathWorks, Inc.) based software.

Each measurement in studies and procedure (below) was performed three times, and the average for all three experiments was used in the paper. Counted data (M counts) were presented as MatLab 2012 was used for all the statistical calculations.

Example 4: Clinical Studies

Figure 30A:
FIG. 30A shows a clinical PAFC prototype.
Figure 30B:
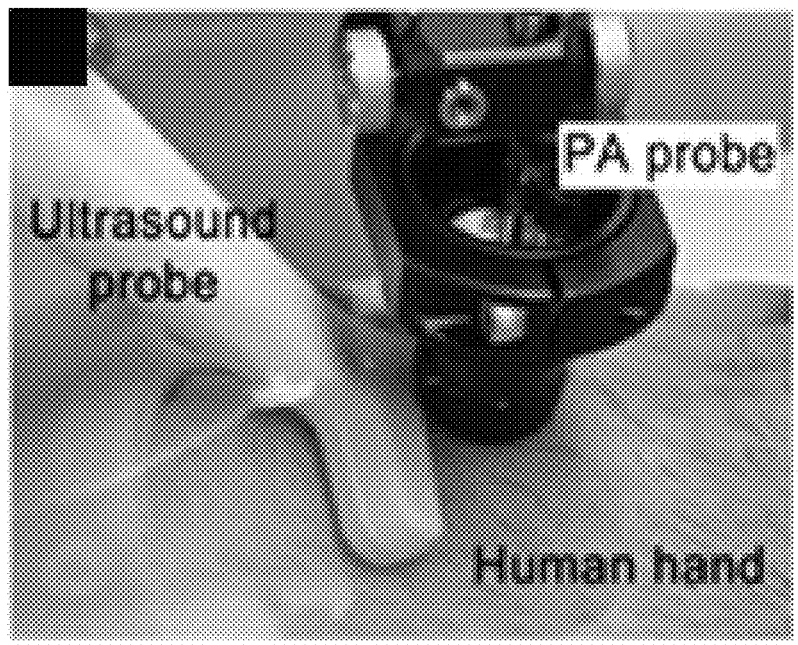
FIG. 30B shows a PA probe with a cylindrical transducer (right) and a conventional ultrasound probe (left).

An IRB-approved PAFC prototype was developed on a moveable cart (protocol 133965) (FIG. 30A). The prototype uses a picosecond-nanosecond (600 ps, 5 ns, and 10 ns) width, high-pulse-repetition rate (1-10 kHz) ytterbium fiber laser (model YLP-R-0.3-A1-60-18; IPG Photonics) at a wavelength of 1,060 nm, and includes in preliminary study a portable PA probe (FIG. 30B) with a customized cylindrical ultrasound transducer (frequency, 32 MHz; focal length, 8 mm; lateral resolution, 60 µm) and optics to form fractionated laser beams. Initial clinical trials were performed with a linear laser beam shape of 20×1,800 µm, than 3.5×800 um and then with dash linear beams (short 50-100 µm linear beams) with the 30-50 um gaps between them. The acquisition system consists of a fast digital board (ATS9350: 12 bit, 500 MS/s, 128-MB dual-port memory; AlazarTech, Inc.), and a workstation (Dell Precision T3500) using customized MatLab software (MathWorks).

Figure 30C:
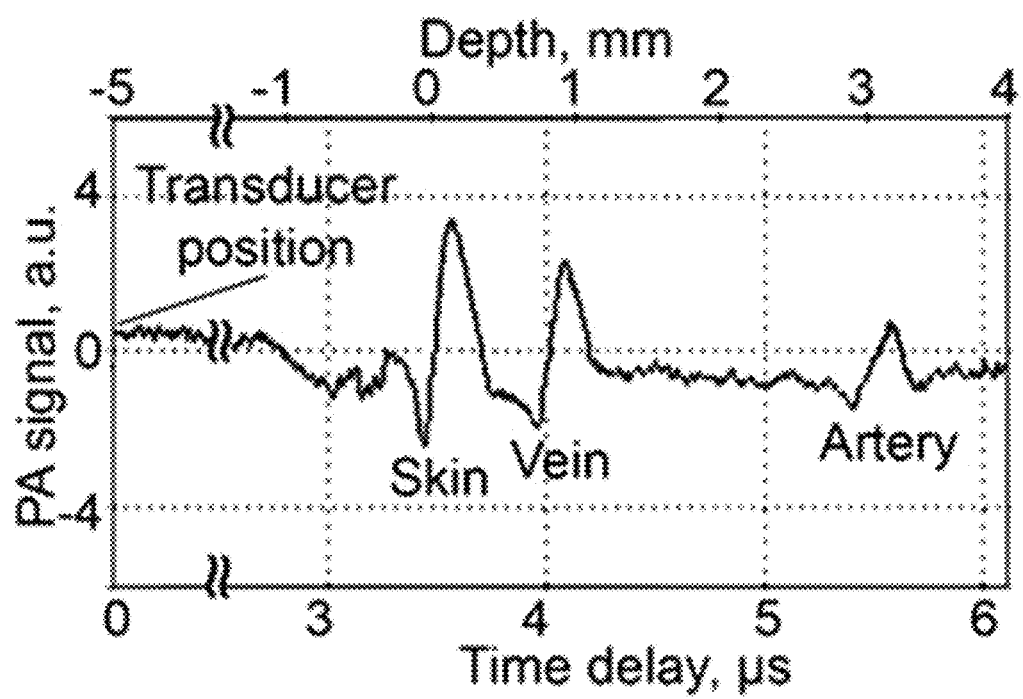
FIG. 30C demonstrates a time-resolved detection of PA signals from a human vein in the dorsum of the hand against PA signal from skin.
Figure 30D:
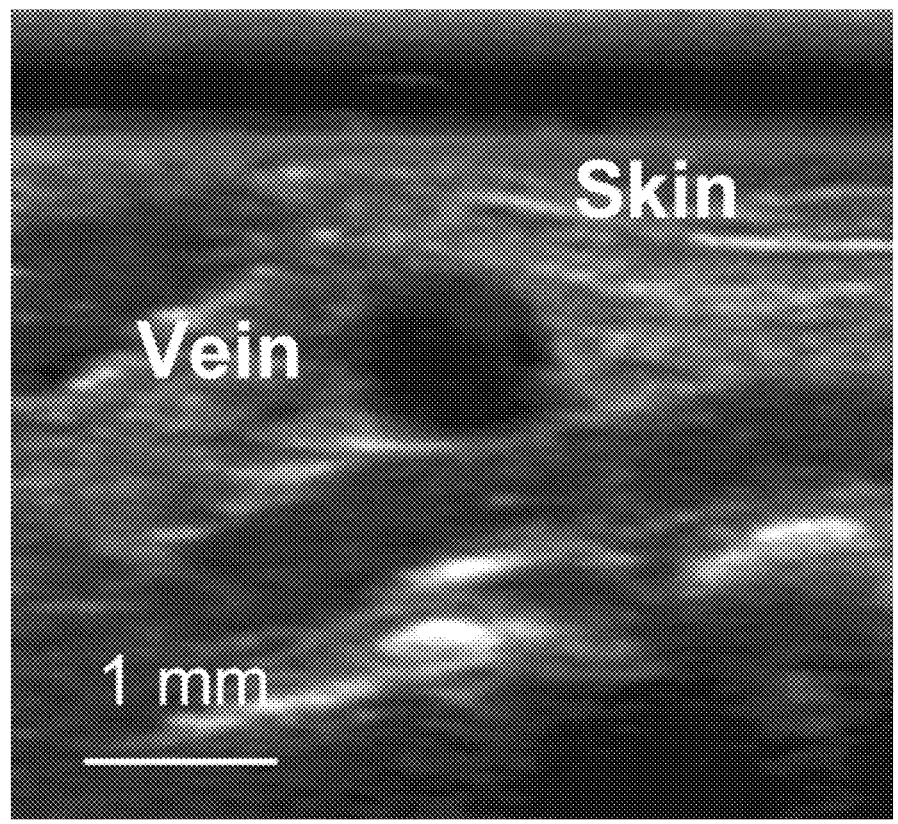
FIG. 30D illustrates a typical ultrasound image of examined vein in FIG. 30C.
Figure 30E:
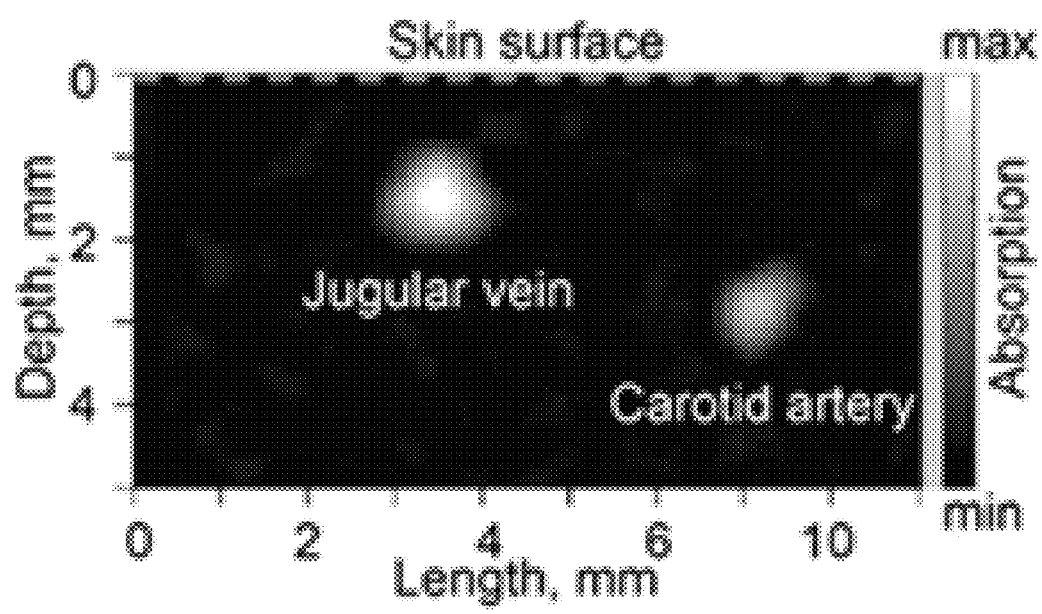
FIG. 30E illustrates PA imaging of blood vessels.

The human subjects were seated in a chair, and the examined hand was gently fixed in a customized holder with flexible Velcro strips (FIG. 30A). Standard ultrasound gel provided acoustic coupling between the transducer and the skin. The position of the selected vessel (0.9-2-mm-diameter vein with a flow velocity of 5-10 cm/s at a depth of 1-1.5 mm) in the dorsum of the hand was controlled by conventional ultrasound imaging (M7; Mindray DS USA, Inc.) (FIG. 30D) and by time-resolved monitoring of pulsed PA signals with a width of 0.1-0.2 ps coming from these vessels with a well-resolved delay (0.5-2 ps) compared to signals from the pigmented skin layer (FIG. 30C). In preclinical studies, PA imaging by spatial scanning of a PA probe near the mouse's neck area was tested (FIG. 30E). To obtain maximal PA signals from selected vessels, the positions of the laser beam and the acoustic focus were adjusted by means of a customized miniature 3D translation stage controlled by joystick or computer. The PAFC setup was initially tested in 10 healthy volunteers (7 white and 3 African American) with different PAFC parameters and a monitoring time of ~1 h. At a wavelength of 1,060 nm, PA contrast from blood vessels was 2-5-fold higher than the background signal of surrounding skin in white subjects (FIG. 30A, left) and 1.3-2 fold higher in African American subjects (i.e., pigmented skin produces higher background signal). At a pulse rate of 10 kHz the white volunteers indicated a warming feeling at fluences of 200-300 mJ/cm2, while volunteers with skin pigmentation indicated similar effects at fluences 2-3 times lower. At a pulse rate of 1 kHz the white volunteers indicated a warming feeling at fluences of 8-10 J/cm$^2$ (i.e., at least 104 compared to established "conventional" laser safety threshold that confirms the advantages of fractionated PAFC) at linear beam size of 6.5×1300 µm. For further study, a fluence of 3 J/cm$^2$ was used.

No CTC-associated PA peaks were observed in the healthy volunteers. 18 white patients with stage III-IV melanoma (i.e., with diagnosed metastases) were then tested. In most (94%) of the white patients with stage III-IV melanoma (i.e., with diagnosed metastases), it was observed that 1) positive PA peaks with different amplitudes (due to varied melanin pigmentation) above the blood background associated with CTCs; 2) in 9 patients (50%), negative PA peaks associated with white platelet-rich clots; and 3) combined positive and negative PA peaks associated with CTC-platelet-WBC aggregates (emboli). The positive PA peaks with complex shapes and larger widths (2-5 ms) than the average width from single CTCs (0.6-0.8 ms) indicated the presence of CTC-CTC aggregates and/or emboli, while shorter peaks (0.1-2 ms) were associated with CTPs (FIGS. 31A-31D).

Figure 31A:
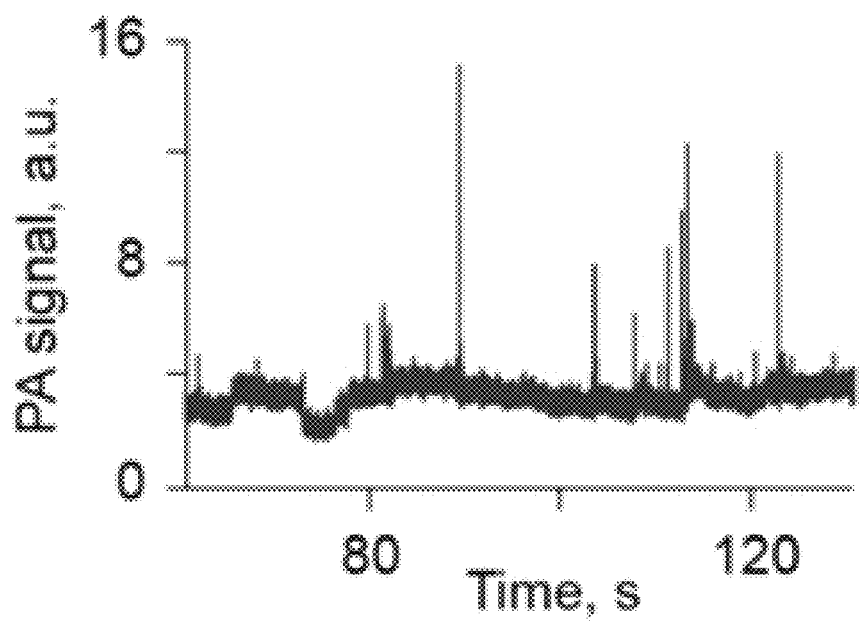
FIG. 31A presents typical PA traces from melanoma CTCs with positive contrasts in a cancer patient before signal filtration.
Figure 31B:
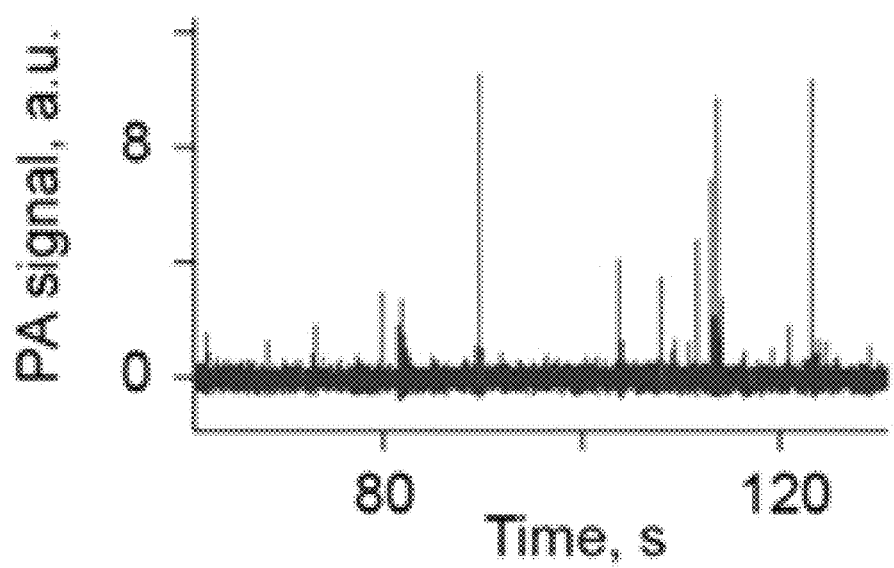
FIG. 31B presents typical PA traces from melanoma CTCs with positive contrasts in a cancer patient after signal filtration.
Figure 31C:
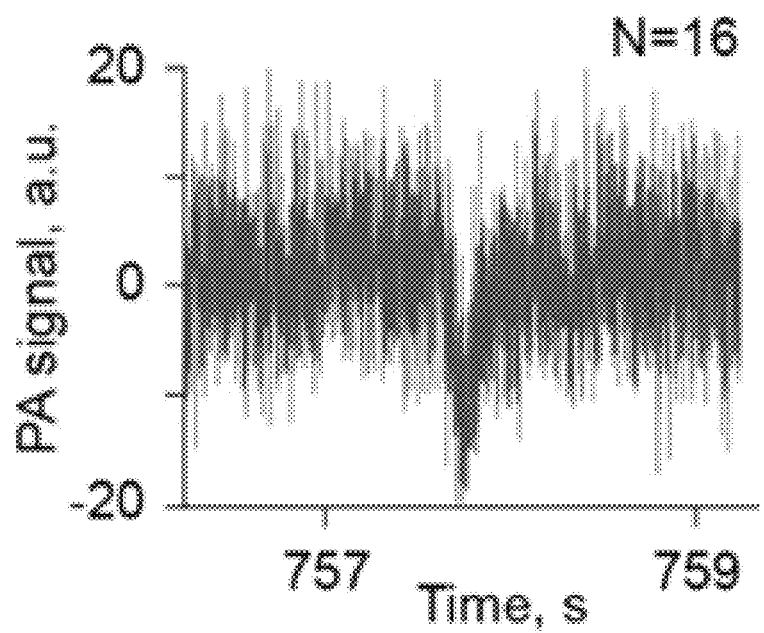
FIG. 31C presents typical PA traces from circulating emboli CE or clots before optimal signal averaging.
Figure 31D:
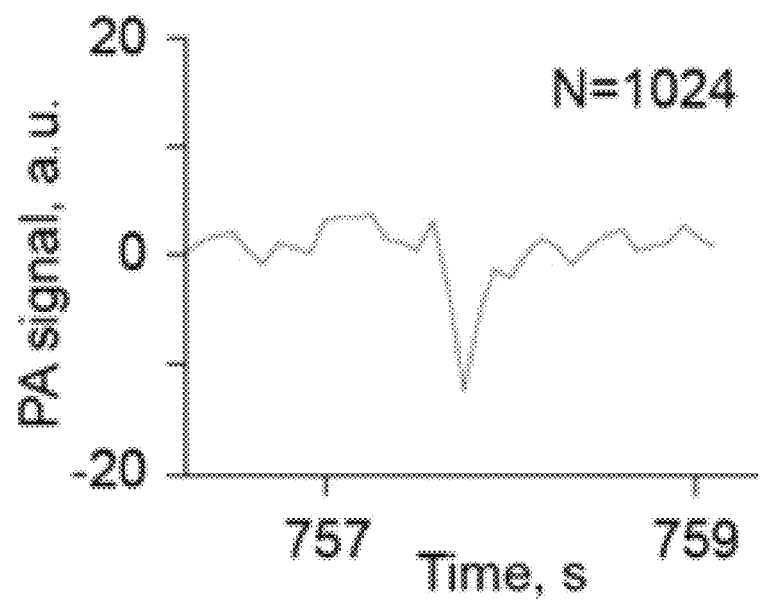
FIG. 31D presents typical PA traces from circulating emboli CE or clots after optimal signal averaging.

Hand movements caused some instability of the baseline PA signal traces (FIG. 31A). Because the duration of PA peaks from CTCs was shorter (0.1-1 ms) than that from various physiological artifacts 0 ms), spectral filtration of the signal allowed to reduce the influence of these factors (FIG. 31B). Negative-signal averaging led to significant noise reduction (FIG. 31 C,D).

Figure 32A:
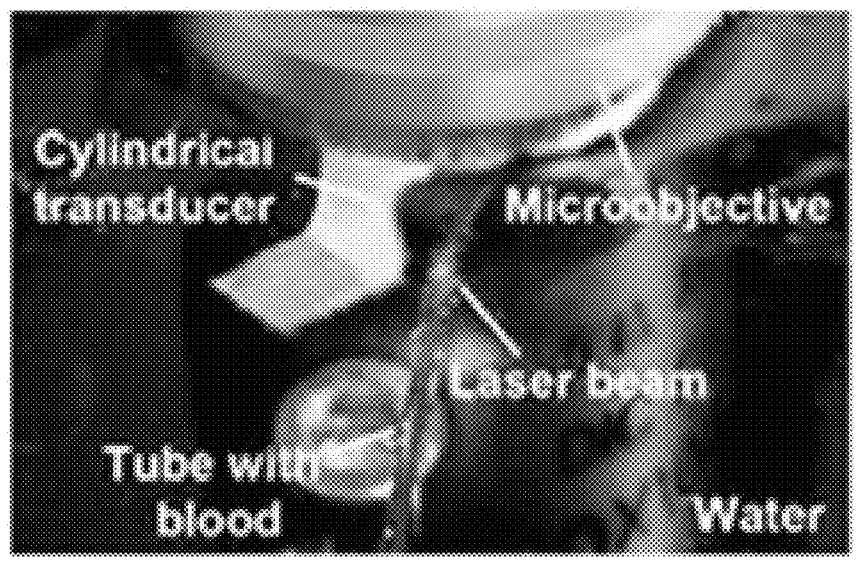
FIG. 32A presents a schematic of PAFC in vitro.
Figure 32B:
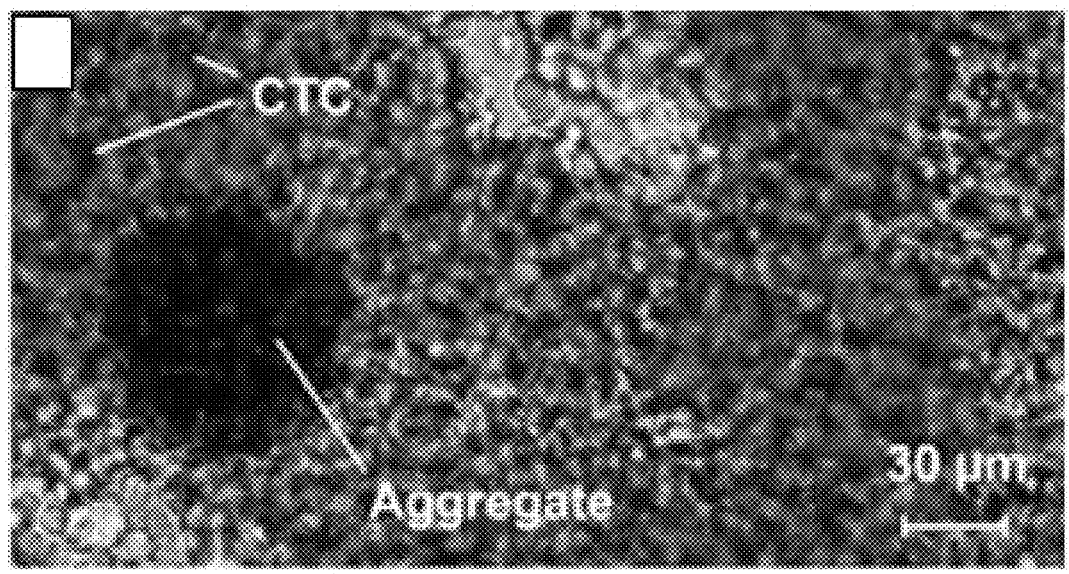
FIG. 32B demonstrates blood sample from melanoma patient with unusual high concentration of CTCs, with fragments and large melanin aggregates in the blood plasma.
Figure 32C:
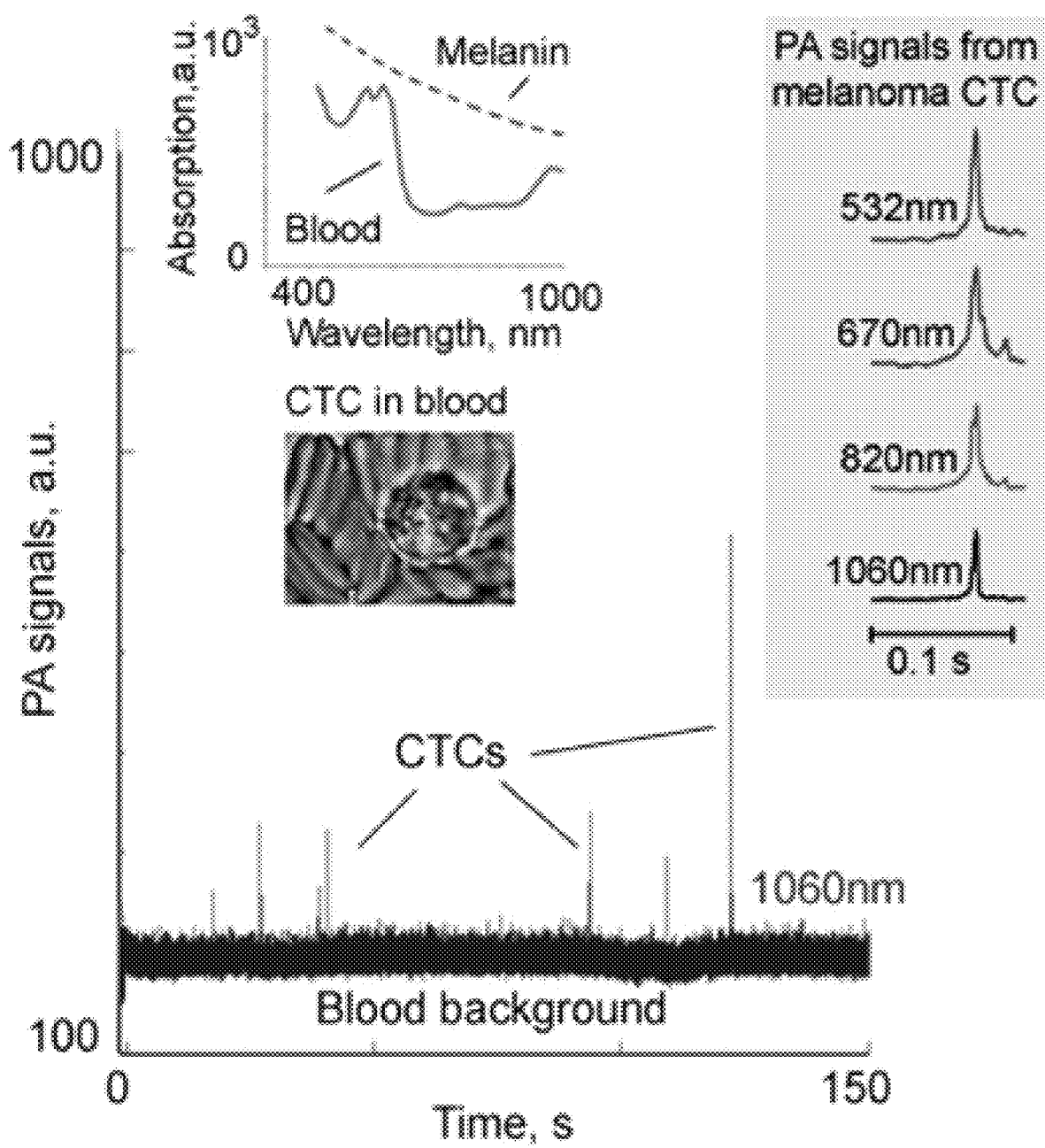
FIG. 32C illustrates a PA signal trace from melanoma CTCs in a whole blood in vitro. Inset, left: absorption spectra of melanin and blood. Inset, right: simultaneous 4-color detection of single CTC.
Figure 32D:
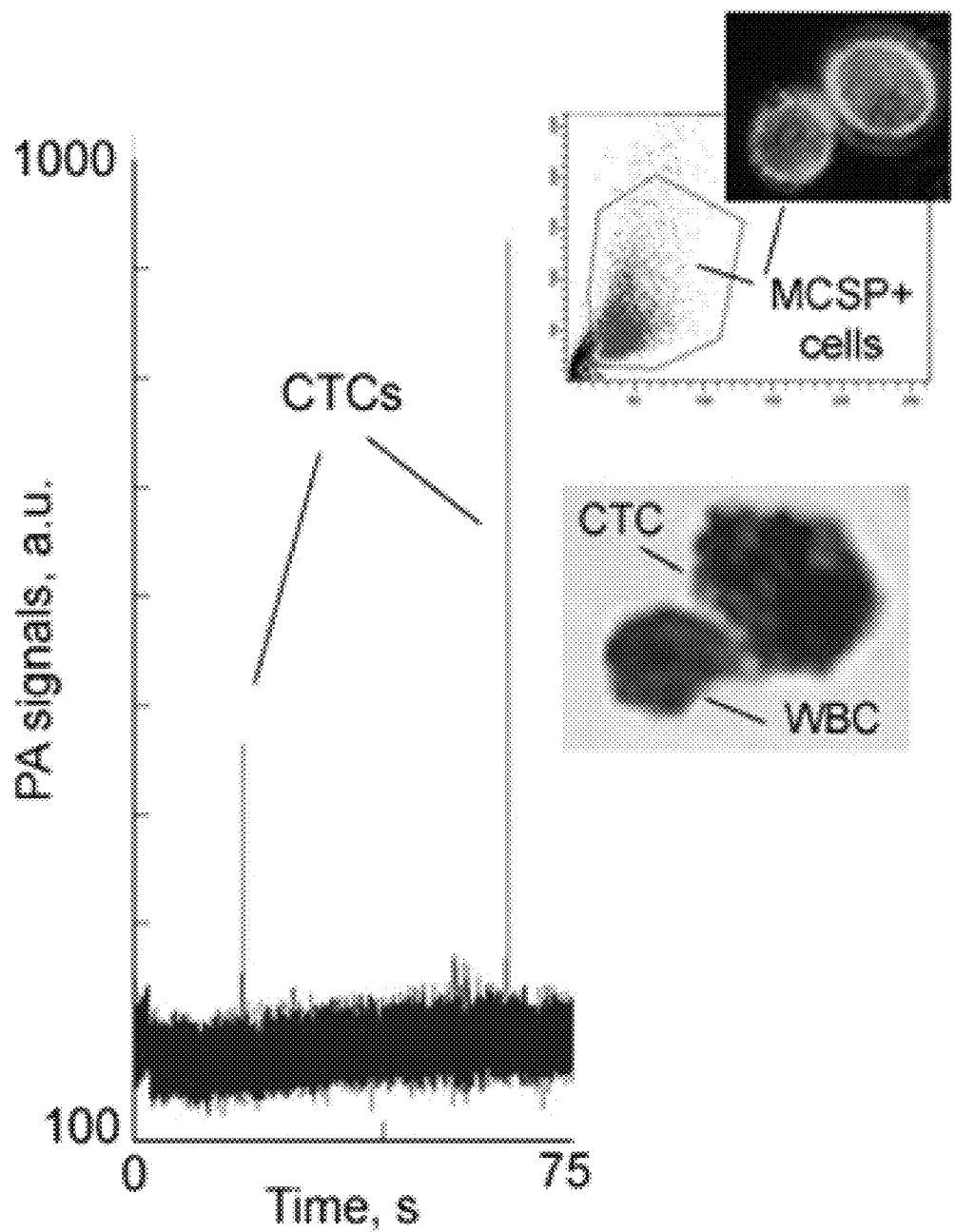
FIG. 32D illustrates a PA signal from melanoma CTCs. Inset, right top: conventional flow cytometry data and image of MCSP+ cells labeled by Abs-PE. Inset, right bottom: image of melanoma CTC and WBC after immune-staining.

The presence of high concentrations of CTCs (>1 CTC/mL) found in ~30% of patients was independently confirmed by many ex vivo assays: 1) magnetic-activated cell sorting (MACS) using MCSP as a melanoma marker; 2) conventional fluorescence flow cytometry (FFC) using label-Ab conjugates to target the melanoma markers CD146 and MCSP and the WBC marker CD45; 3) in vitro four-color (532, 671, 820, and 1,060 nm) PAFC using a 0.8-mm-diameter glass tube with a flow rate of 0.3 mL/min and a cylindrical transducer (32 MHz; focal length, 6 mm) located in a water bolus around the tube (FIG. 32A); 4) RT-PCR with seven melanoma markers, ABCB5, MAGEA3, MCAM, MLANA, PAX3, TGFB2, and TYR, together with the housekeeping gene GAPDH; and 5) immmunocytochemical staining using the HiDef Detection system (Cell Marque Corp.) and the Pan Melanoma Ab cocktail (HMB45, MART-1, tyrosinase; CBLPath, Inc.). WBCs were distinguished from CTCs by labeling them with anti-CD45 antibody and by immunohistochemical staining (FIG. 32D, inset). The presence of CTCs was also microscopically confirmed by their larger size, averaging 12-16 µm compared to 5-8 µm for WBCs and RBCs (FIG. 32C). In a few blood samples, unusually high concentrations of CTCs and free melanin aggregates were observed (FIG. 32B). Label-free PAFC monitoring ex vivo of whole blood samples for just 5-10 min (MACS requires 6-8 h) revealed a larger (2-3-fold) number of CTCs (FIG. 32C) than in samples in which RBCs were removed, confirming an ~2-fold loss of CTCs during blood processing (FIG. 32D) (a loss of up to 60-80% of CTCs with MACS). In vitro multicolor PAFC showed that the distribution of PA signal amplitudes at 532, 671, 820, and 1,060 nm (FIG. 32C, inset, right) correlated more with the absorption spectrum of melanin than with that of Hb in RBCs (FIG. 32C, insets, left). Testing large blood samples (up to 40 mL) revealed that PAFC in vitro is faster (100-fold) and more sensitive (3-10-fold 1CTC/10-20 mL) than CTC assays in vitro that allows to use in vitro PAFC to verify PA data in vivo at high CTC counts (>1 CTC/mL).

PAFC in vivo revealed CTC counts in melanoma patients in the range of 5-1,000 CTCs/100 mL with a threshold of ~1 CTC/300 mL; this result represents a ~100-fold improvement over the detection limit of existing assays. The low counts (<1 CTC/mL) found by us in most patients (~70%) may explain the failure of conventional low-sensitivity assays to detect CTCs in 30-60% of patients with metastatic cancer.

Example 5: Fractionated Laser Delivery

To demonstrate fractionated delivery of laser radiation to deep tissue, the following experiment was performed using smaller-diameter laser beams. The volunteers reported only a warming sensation with no pain or observable changes in skin properties when laser fluence levels reached ~2 J/cm$^2$ and 300 mJ/cm$^2$ (pulse-repetition rate, 10 kHz; linear beam sizes, 6×660 µm and 20×1,800 µm, respectively). Moreover, with a single circular ~4-µm-diameter laser beam, a warming sensation occurred at 25 J/cm$^2$ only for 10 Hz, which exceeds the MPE 104-fold. Thus, the shorter thermal relaxation time for a smaller-diameter laser beam enables overcoming the above limitations. These energy fluences are still lower than those employed in many FDA-approved laser pulsed therapeutic systems that have been broadly used to treat blood vessel abnormalities (e.g., port-wine stains) and especially skin resurfacing and hair removal using NIR nanosecond laser pulses with fluence up to 10 J/cm$^2$ with no evidence of significant risk. In particular, procedures with skin resurfacing and especially hair removal are frequently accompanied by local pain and red spots healed within few days. However, use of a single small laser beam even at a higher fluence reduces the laser energy delivered to deep vessels. In addition, the warming sensation is associated with the thermal response of pain receptors located ~200-300 µm deep in the skin, while PA signals from CTCs are proportional to averaged laser energy at a depth of 2-3 mm. This problem may be solved by the proposed fractionated laser diagnosis with multiple small beams: each beam has relatively low energy, but superposition energy from many beams in local and large surface areas (up to almost whole body) allows to dramatically increase energy in deep tissue (up to 10-15 cm) in local and especially large areas, in particular in neck, legs, breast, head, lung, liver and other organs with extensive circulation with large blood vessels. Fractionated diagnosis can be performed using multiple modules (with laser and optical system) to cover a large skin area.

Example 6: Fractionated PAFC System

Figure 40:
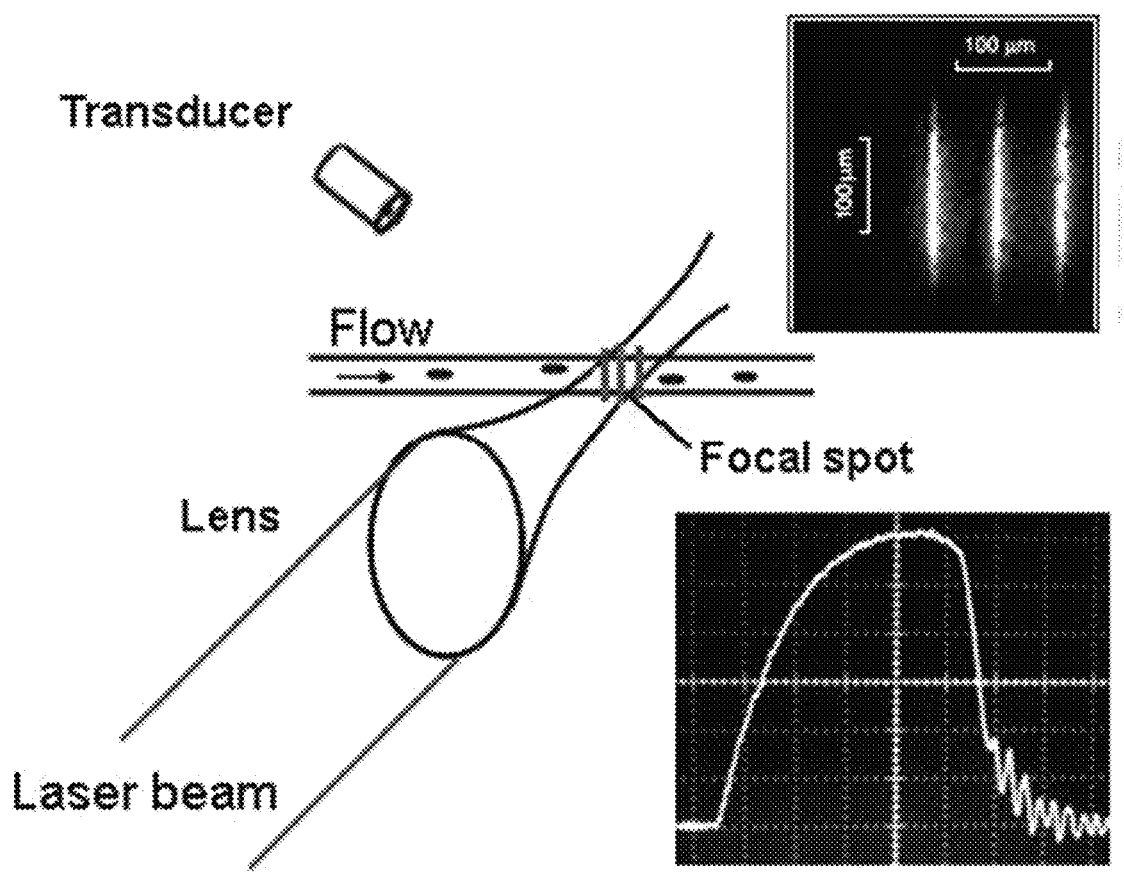
FIG. 40 is a PAFC schematic with a laser diode showing a fragment of three fractionated beams (total 3 stacks in each 3 shown bars) and a temporal laser pulse shape with a width of 45 ns.

As illustrated in FIG. 40, a fractionated PA flow cytometry (PAFC) system using a laser diode was built on the platform of an Olympus BX51 microscope (Olympus America, Inc.). A laser diode, model 905D3S3J08X (Power Technology, Inc.) operating at a 905 nm wavelength provided a peak optical output power of 328W when driven with a peak current of 30 Å. The duty cycle was 0.1%, allowing it to be driven at repetition rate of up to 100 kHz when driven with pulse durations of 100 ns. A compact driver (Model IL30C, Power Technology, Inc.) was used with the diode allowing the pulse duration to be continuously varied from 15 ns to 120 ns. While using the laser diode with the PAFC system, the laser beam passed through an aspheric collimating lens with focal length of 11 mm (Model C220 TM-B, Thorlab), and with a mirror was directed through a condenser (Model U-AC2, Olympus America, Inc.) into a sample. FIG. 40 shows one 3-linear fragment of a fractionated laser beam, while the total was 9 with 3 stacks. PA signals from an ultrasonic transducer (model 6528A101, (masonic SA) attached to the samples (e.g., microscopic slide, animal tissue, or human skin) and amplifier (Model 5660B, Panametrics) were recorded with a PV with customized software.

Example 7: Detection of Circulating Melanoma Cells in Mouse Abdominal Blood Microvessels Circulating melanoma cells injected intravenously were detected in mouse abdominal blood microvessels (300 µm) using fractionated PAFC. The measurement in vitro was performed in capillary with a flow (3-5 mm/s) of melanin particles (300 nm) in PBS or melanoma cells (B16F10) in mouse blood. Concentration of melanin was low (~2 µg/ml) to provide separate melanin particles moving along the capillary. The measurement in vivo was performed with nude mice. The diode was composed of 3 stacks of 3 active elements with the size of each strip of 12×140 nm separated by an interval of 67 nm. The maximal laser pulse energy measured was 13.5 µJ at pulse width of 86 ns and pulse rate of 3 kHz. This energy corresponds to the laser fluence of 270 mJ/cm$^2$. In this study the potential for the use of pulsed laser diodes with fractionated beams for PA detection of melanin particles and melanoma cells in blood flow phantom in vitro as well as in vivo in a mouse model was demonstrated.

Figure 37B:
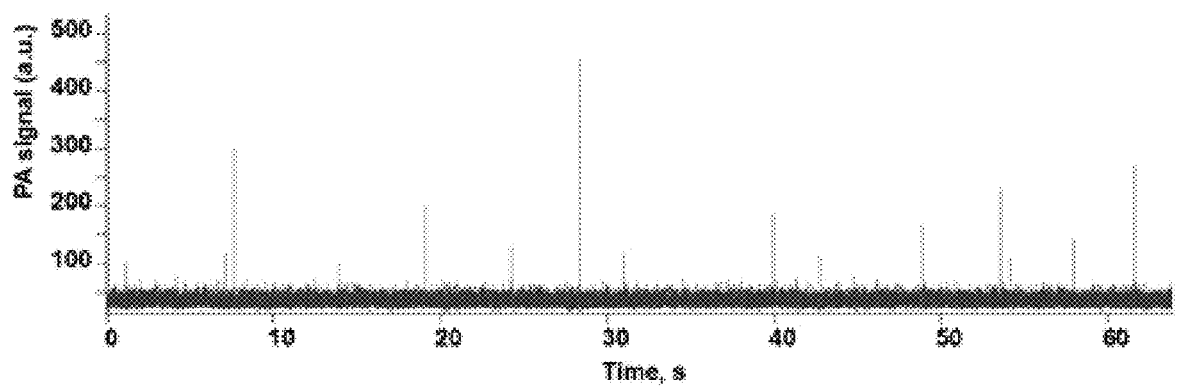
Figure 41A:
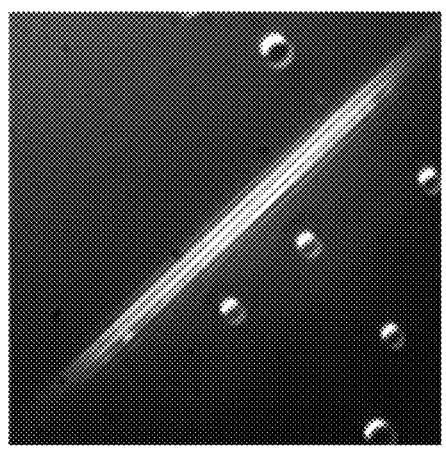
FIG. 41A is an image of a laser diode fractionated beam including three strips.
Figure 41B:
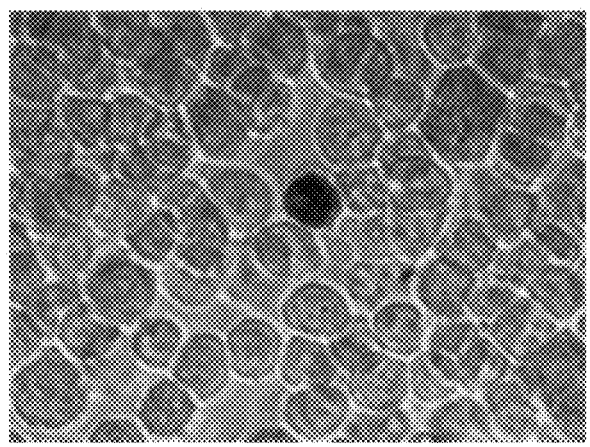
FIG. 41B is an image of a single melanoma cell (B16F10, dark spot) among mouse red blood cells in capillary with diameter of 100 um.
Figure 41C:
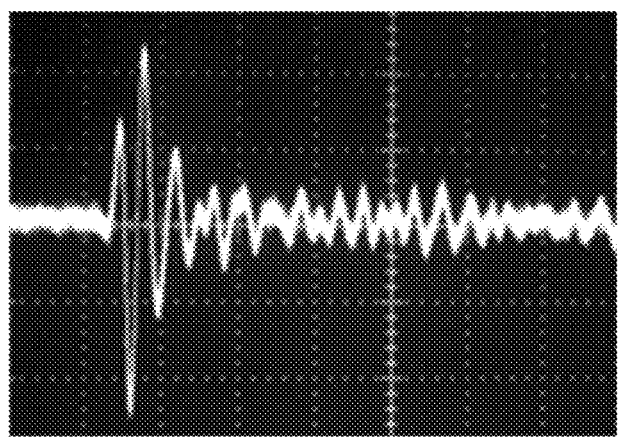
FIG. 41C is a typical PA signal from a single melanoma cell.
Figure 41D:
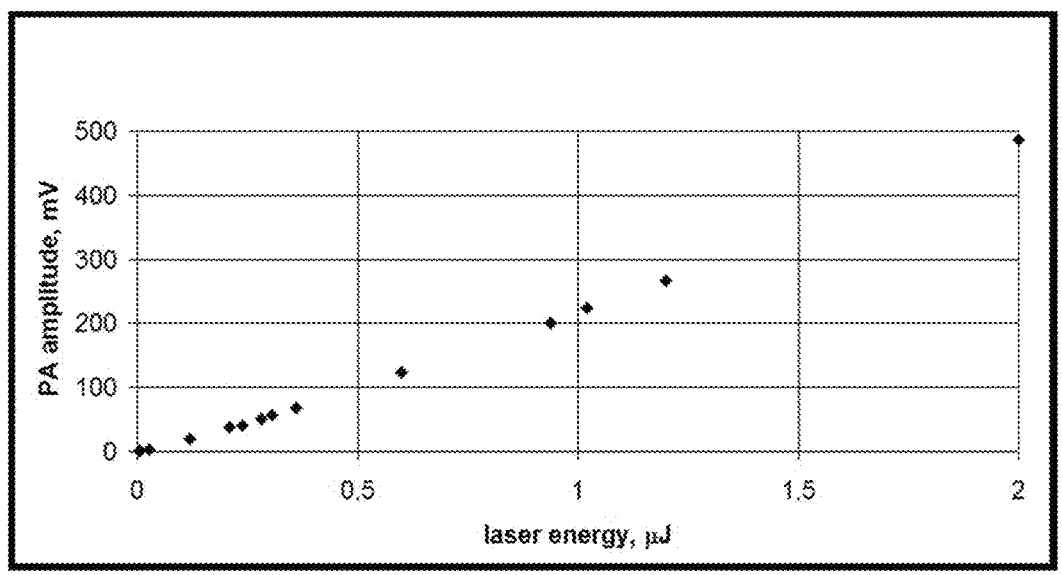
FIG. 41D is a graph showing the dependence of PA signal amplitude from a melanoma cell on laser diode pulse energy in vitro.
Figure 41E:
FIG. 41E is a photo of a mouse with an ultrasound transducer.
Figure 41F:
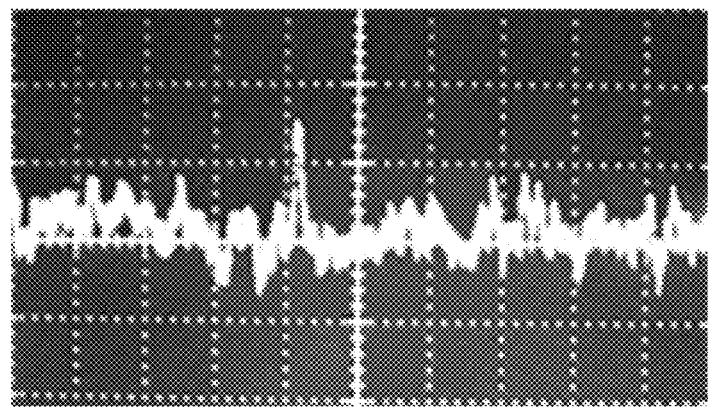
FIG. 41F is a PA signal showing detection of a single circulating melanoma cell in mouse abdominal blood microvessels.
Figure 42A:
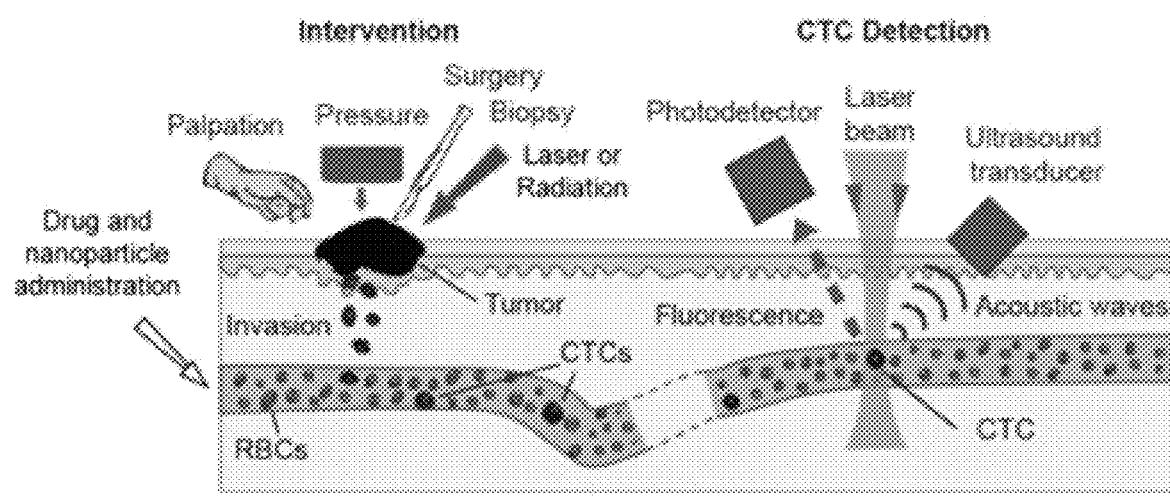
FIG. 42A demonstrates schematics of integrated fluorescence flow cytometry (FFC) and PAFC for controlled CTC release during medical procedures.
Figure 42B:
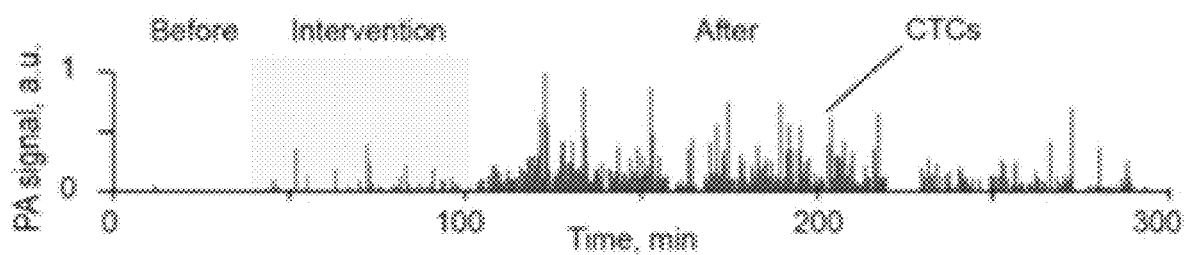
FIG. 42B shows a PA signal trace at pressure (~120 g) impact on a 5-mm skin melanoma tumor (B16F10-GFP).

FIG. 41A is an image of a fragment of a laser diode fractionated beam including three strips (total 3 stacks with 3 strips/bars). FIG. 41B is an image of a single melanoma cell (B16F10, dark spot) among mouse red blood cells in capillary with diameter of 100 um. FIG. 41C is a typical PA signal from a single melanoma cell. FIG. 41D is a graph showing the dependence of PA signal amplitude from a melanoma cell on laser diode pulse energy in vitro. FIG. 41E is a photo of mouse with ultrasound transducers. FIG. 41F is a PA signal showing detection of circulating melanoma cells in mouse abdominal blood microvessels. Other examples of PA traces demonstrating time-resolved CTC detection, identification of large CTC aggregates, emboli and circulating tumor-associated particles (CTPs), as well as the influence of energy fluence on PA signal amplitudes are shown in FIGS. 11 and 37A-37B.

Example 8: The PAFC Sensitivity Increase by Increasing Laser Energy Through Laser-Induced Nanobubbles as PA Signal Amplifiers Exploiting the role of laser-induced nanobubbles a nonlinear PA signal amplifiers, it was observed at specific laser fluences (FIG. 36A) that significant (5-15-fold) PA signal amplification from melanoma cells in vitro with heterogeneous melanin distribution in human blood. These cells exhibited linear signals only because of the relatively homogeneous spatial distribution of Hb in RBCs without highly localized absorbing zones as in melanoma cells. As a result, significantly a larger number of melanoma-associated PA peaks (40-fold) can be detected at higher fluences (FIG. 36B).

Example 9: Comparison of Focused Cylindrical and Spherical Transducers

PAFC assessment of flowing blood spiked with melanoma cells in a 0.8-mm-diameter tube revealed that a spherical transducer provides a 2-4-fold higher signal-to-noise-ratio (SNR) but fewer PA peaks (FIG. 35A) than a cylindrical transducer (FIG. 35B). This difference is related to the smaller detection volume of a spherical transducer and thus the presence of fewer RBCs producing background signal; however, CTCs flowing outside the detection volume of a single transducer would be missed. This result indicates potential to use a fractionated acoustic detection system with a focused spherical ultrasound transducer array to provide simultaneously low blood background and detection of CTCs in a whole blood vessel cross-section.

Example 10: PAFC with Optical Clearance

Figure 33A:
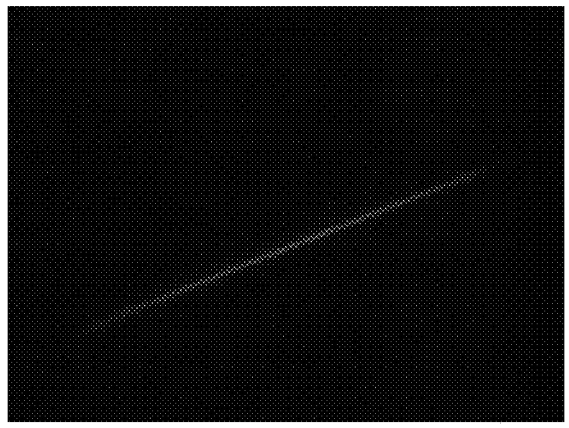
FIG. 33A shows the image of linear laser beam in air (laser wavelength, 1060 nm) with sizes of 8 µm×1280 µm.
Figure 33B:
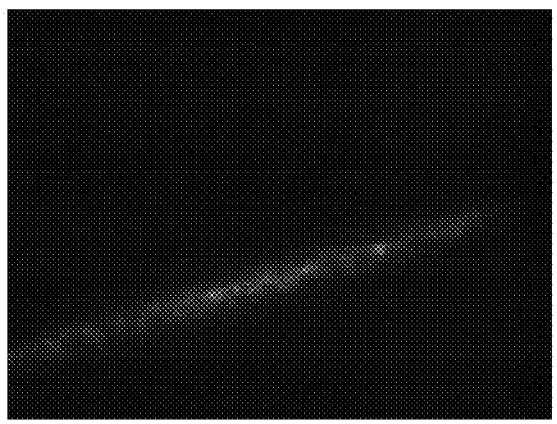
FIG. 33B shows an image of the same beam blurred to size of 72 µm×1298 µm after propagation through fresh mouse skin with thickness of 750 µm (transmission, 42.8%).
Figure 33C:
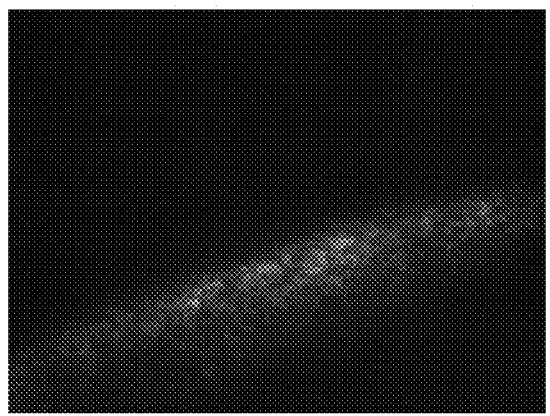
FIG. 33C shows an image of the same beam blurred to a size of 290 µm×1320 µm after propagation through double layer of fresh mouse skin with thickness of 1600 µm (transmission, 29.2%).
Figure 33D:
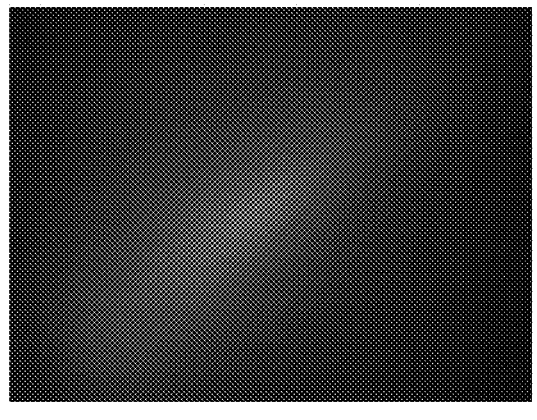
FIG. 33D shows an image of the same beam after propagation through fresh mouse blood with thickness of 1800 µm): (transmission, 9.2%).
Figure 33E:
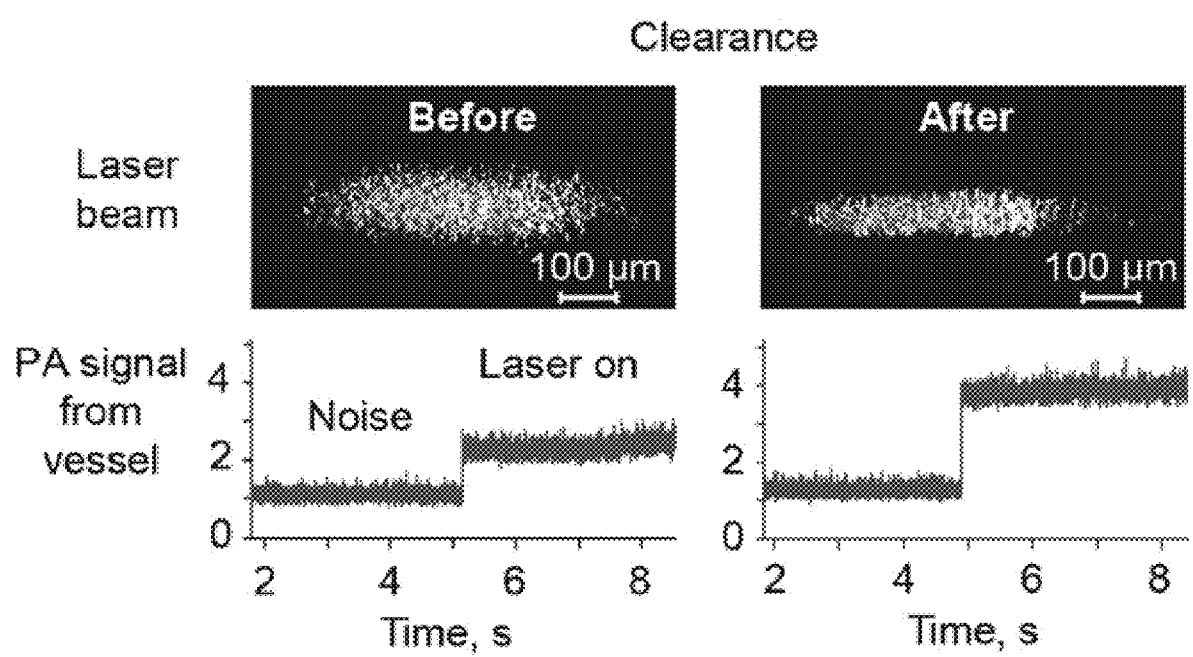
FIG. 33E illustrates a laser beam after 0.9 mm mouse skin (top) and signals from human 1-mm vein at depth of 1.3 mm (bottom) before (left) and after (right) optical clearing.
Figure 34:
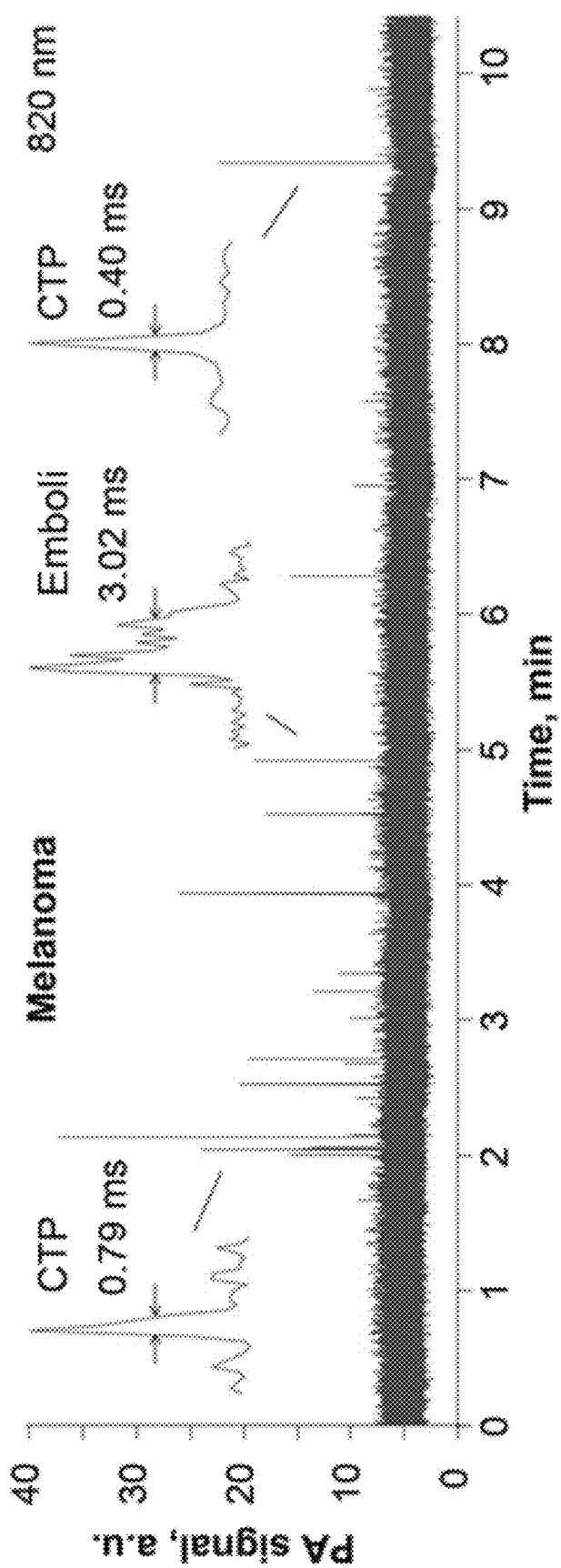
FIG. 34 is a graph summarizing an example PA trace with different shapes from single and clusters of melanoma CTCs as well as emboli.

Optical clearance (OC) PAFC may enhance the fractionated PAFC's capability to assess deep vessels by decreasing beam blurring due to light scattering in skin. FIGS. 33B, 33C and 33D show the examples of a laser beam's blurring after passing one (FIG. 33B) and two (FIG. 33C) layers of 750 um mouse skin as well as blood phantom (FIG. 33D) compared to a laser beam in air (FIG. 33A). FIG. 33E shows laser beams after passing through fresh 0.9-mm-thick mouse skin (top) and PA signals from a 1-mm-diameter human vein at depth of 1.3 mm (bottom) before (left) and after (right) optical clearance.

Studies were performed using glycerol in combination with dermal ablation and then sonophoresis that allowed for achieving clearance for 10-20 min compared to 1-1.5 h for glycerol alone. A 6×600-μm linear laser beam propagated through a fresh 0.9-mm-thick layer of mouse skin was attenuated about 3-fold and blurred into an ellipsoidal shape with a width of 70-90 μm. Topical administration of glycerol and the combined dermal treatment for 10 min partly reduced the influence of scattering light, resulting in an about 2-fold decrease in blurring of the laser beam (i.e., 2-fold increase in lateral resolution) (FIG. 33A-33E). Application of this procedure to a human subject's hand eventually resulted in a 2.1-fold increase in PA signal from a 1-mm deep blood vessel. These results suggest that fractionated PAFC's detection capability can be improved by optical clearing.

Example 11: Effects of Waveform Averaging

In the presence of noise and the background signals from blood, improved signal detection may enhance the detection of rare circulating blood cells such as CTCs. Signal detection may be improved by averaging consecutive PA signals, which reduces the random noise, and increases SNR. However, in dynamic applications such as PAFC, the target objects may appear only for a short time of life, $t_L$. In this case, N cannot exceed $t_L*f$ where f is the pulse repetition frequency of the laser. If $N > t_L*f$, then the PA signals from the target may be averaged with the PA signals from background, which results in loss of PA peaks in the trace or reduced SNR.

In addition to waveform averaging, other types of filters may be applied to PA waveforms and/or PA traces. For comparison, 3 minute-long in vivo PAFC recordings from a melanoma patient were re-analyzed with different parameters. When N=2 and no additional filters used, analysis took 10 s, and 20 CTCs were detected in the peak analysis. When N was increased to 10, analysis took 8 s, but only 4 CTCs were detected. When N was 2 and a wavelet filter applied to all waveforms, analysis took 40 minutes, and 40 CTCs were detected. SNRs of the traces were 33, 51, and 76 respectively. SNR was calculated as the ratio of peak amplitude (largest peak was taken as reference) to the standard deviation of the trace (5 second segment that does not contain a peak). It should be noted that SNR gain between described measurements were not correlated with the detected CTCs, as it is more related with tr. Comparison of signals, on the other hand, may be more realistic since N was constant. In this comparison, SNR gain of 2.3 resulted in 2-fold CTC count. Although the wavelet approach provided the best results, currently the method is prohibitively expensive in terms of the processing time (13 times the record duration).

Example 12: Dependence of SNR on the Selection of N and Frequency Region of Interest (fROI)

To estimate SNRs at different laser energy and acquisition parameters (i.e., N, fROI), PA signals were traced from human blood in a slide after exposure to a 532-nm-wavelength laser. Each measurement lasted about 1 min on the same spot, with no visible damage to the sample. Between measurements, the beam was blocked, the laser energy level was changed, and the sample was moved with the microscope stage to avoid cumulative effects. The baselines in the traces were noise, when there was no laser radiation. The whole procedure was repeated twice for each energy level. The recorded data were then post-processed for different N and fROI values. SNRs were calculated as the ratio of the mean signal amplitude to the standard deviation of the baseline. For comparison, PA waveform amplitudes were also recorded for each measurement with the oscilloscope.

The mean amplitude remained the same in the PA spectral power traces for different N values; however, reduced variance as the value of N increased resulted in significant SNR improvement. The relation between peak amplitudes in the PA spectral power trace and the PA waveform amplitude is nonlinear. This is the result of nonlinearity in the spectral power calculation and is apparent as nonlinear curves and as increased deviation for higher signals. PA amplitude traces were obtained through inverse FFT. Although this conversion is lossy because of discarding of spectral bands, the SNR for this amplitude trace showed excellent agreement with the SNR of the PA waveform measurements taken from the oscilloscope (N=512). SNR values were lower than those of the spectral power traces; however, they were linear.

SNR dependence on the selection of fROI was analyzed by changing the size and location of fROI. SNR did not change significantly as the size of fROI changed, as long as a specific region fell in the selection. However, when the size of fROI was kept constant but its location changed, the change in SNR was more significant, suggesting the importance of the selection of fROI.

Example 13: In Vivo 8-Color FC Integrating 4-Color PA and 4-Color Fluorescence Detection Methods (PAFFC)

Figure 43:
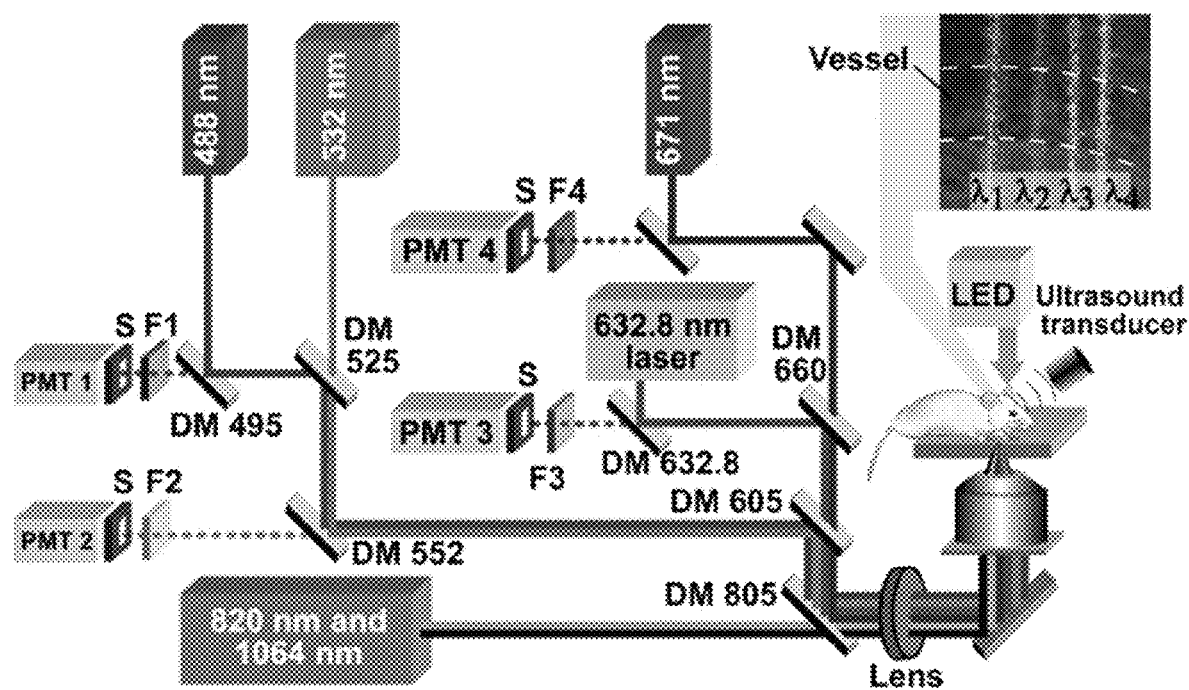
FIG. 43 illustrates schematics in vivo of an 8-color flow cytometer integrating 4-color fluorescence flow cytometry (FFC) and 4-color PAFC. DM, dichroic mirror; PMT, photomultiplier tube; F, filter; S, slit. Inset: 4 linear beams.

A single detection color limits the range of markers that can be employed. An 8-color integrated PAFFC platform (e.g., as a research tool using animal models of human disease) was developed integrating PAFC and fluorescence flow cytometry (FFC) modules (FIG. 43). Multicolor fractionated PAFC is based on the irradiation of selected vessels with short laser pulses at different wavelengths, followed by detection of laser-induced acoustic waves (referred to as PA signals) with an ultrasound transducer attached to the skin. The PAFC platform incorporates an Olympus inverted IX81 microscope equipped with 4 high-pulse-repetition-rate lasers: 1) wavelength, 532 nm; pulse energy, 100 µJ; pulse width, 5 ns; and repetition rate, up to 100 kHz; 2) 671 nm, 35 µJ, 25 ns, and 100 kHz; 3) 820 nm, 75 µJ, 8 ns, and 30 kHz; and 4) 1064 nm, 100 µJ, 10 ns, and 10-500 kHz. Parallel linear laser beams of different wavelengths either overlap in the sample plane or are separated by narrow gaps (FIG. 43) to provide time-of-flight mode (below). PA waves are detected by ultrasound transducers (e.g., unfocused: model 6528101; 0.5 MHz; diameter 5.5 mm; (masonic; and focused: model V316-SM; 20 MHz; focal length 12.5 mm; Panametrics) and then amplified (amplifier model 5662: bandwidth 50 kHz-5 MHz; and model 5678: 40 MHz). In FFC, 3 continuous-wave (CW) lasers are used with wavelengths of 488, 540, and 632.8 nm and 4 photomultiplier tubes (FIG. 43). To collect PA and 3 fluorescent signals, the setup is equipped with a high-speed analog-to-digital converter board and LabVIEW and MATLAB software. In particular, PA signals are sampled at 80 or 120 megasamples per second (MSPS) with 14-bit resolution. The delay time (25 ps) between laser pulses with different wavelengths, for the first time, allows time-color encoding for time-resolved detection of PA signals from the same fast moving single cells with the use of one ultrasound transducer. Signals from the 4 PMTs are continuously sampled at a rate of 4 MHz and down-sampled to a 10-kHz rate with 400 points on average. Both signals are presented as signal traces in which amplitudes, locations, and widths of peaks are analyzed with customized software. In general, PAFFC can detect 4 PA signals at 4 different laser wavelengths (532, 671, 820, and 1064 nm) and 4 fluorescent signals (emission/color near 510, 590, 630, and 720 nm).

Example 14: Multiplex Detection of Breast CTCs in Tumor-Bearing Mice

CTCs were labeled in the bloodstream by intravenous (i.v.) injection in the mouse tail vein of functionalized PA and fluorescent labels such as dyes, quantum dots (QDs) gold nanospheres (GNSs), and gold nanorods (GNRs) with different emission and absorption spectra. Markers were selected that were highly expressed in targeted cells (e.g., CTCs) but almost absent in normal blood cells and vice versa, for example, EpCAM and folate receptors (MDA-MB-231-GFP), CD45 (WBCs), and CD62P (activated platelets). To target selected cells, the following labels were used conjugated with antibodies (Abs) to specific markers: EpCAM-GNR671, CD45-GNR820, CD24-GNR1060, folate-GNS532, folate-QD590, CD62P-QD630, and CD44-PerCP-Cy5.5720.

The new PAFC platform was verified with a focus on label-free (i.e., via intrinsic melanin) and NP-targeted detection, safe laser energy parameters, NP toxicity, labeling efficiency of cells of interest with functionalized NPs directly in the bloodstream, clearance rates of labels alone and of labeled cells, identification of nonspecific binding, false-positivity and false-negativity, and the influence of partly overlapping absorption spectra of multicolor NPs and emission spectra of fluorescent labels. Dyes provide detectable fluorescent signals typically at concentrations of 30-100 µg/cell, which produce PA signals (because abortions and partly nonradiative relaxation of absorbed energy) below those of the absorption background of blood. Labeling efficiency, typically in the range of 80-95%, was initially estimated in vitro with cells alone or spiked with fresh blood under static and flow conditions by means of conventional FC, fluorescence microscopy, PAFC (with a flow module), and photothermal (PT) cytometry-microscopy. Then, to estimate labeling efficiency in vivo, cells (e.g., mimic CTCs) alone were injected into mouse models with subsequent injection of labels. Depending on the cell marker and NP properties, the labeling procedure in the mouse models took from 10 to 30 min. Surprisingly, the labeling time with NPs (e.g., GNRs) was shorter than with dye probes (e.g., 25 min and 120 min, respectively, to target WBCs using CD45 receptor), which is an issue for investigation in the proposed project. Likely, high labeling efficiency is associated with frequent NP-cell collisions in partly turbulent blood flow. In accordance with modeling, injection into a mouse's blood circulation of $10^{10}$ NPs in an ~2-mL volume provides, on average, 103 collisions/min with expected differences in the velocities of NPs and CTCs of mm/s, while their absolute velocities may be 5-10 mm/s. This allows the capture of Abs by cell-surface markers, and the capturing efficiency does not decrease at relative differences in the velocities of labels and cells of 1-1.5 mm/s or a shear stress ≤0.5 dyn/cm². PA signals from NP-targeted cells, typically with 100-300 NPs/cell and more, are much higher than the PA background signals from red blood cells (RBCs), unbound NPs (which typically number of 4-8 in the detection volume), or NPs nonspecifically bound to normal blood cells (e.g., macrophages). Nonspecific NPs, ranging from 3% to 8% of the total injected, were verified through the coincidence of PA signals from CTCs targeted by NPs and fluorescent signals from the same CTCs with GFPs. NP clustering around naturally densely packed cancer markers led to a highly localized NP absorption, increasing PA signals at least 5-10-fold in linear mode and 50-100-fold in nonlinear mode because even a relatively low energy fluence within the laser safety standard in the NIR range (e.g., 70-100 mJ/cm² at wavelengths of 800-1100 nm) induced the formation of nanobubbles as PA signal amplifiers (i.e., dynamic nanobubbles serve as super-contrast PA signals). In most studies, the number of injected NPs were optimized in the range of $10^9$-$10^{10}$ NPs per mouse. These NPs did not produce notable signals immediately after injection, but later gradual increases in PA signal amplitude and rate indicated a successful labeling process. Occasionally, strong PA signals were observed immediately after injection of NPs, which were associated with NP aggregates that were then quickly (typically within a few minutes) disappeared/cleared from the circulation. To minimize this effect, NP clusters were disaggregated by ultrasound or/and filtered. Gold NPs were used with a polyethylene glycol (PEG) coating and were injected at concentrations of $10^9$-$10^{11}$ per mouse. It should be noted that the targeting of CTCs directly in blood requires much lower (50-100-fold) concentrations of NPs than are required to target tumors by delivery NPs through blood vessel walls.

The optimized probe cocktails were injected into orthotropic xenograft mouse models of breast cancer, and monitoring of multicolor PA and fluorescent signals in ~50-μm-diameter ear vessels followed. PAFFC demonstrated the molecular targeting of naturally shed CTCs from the parent tumor with different phenotypes and various signal traces (FIG. 44A-44E). The coincidence of these signals at different wavelengths in the PA and fluorescent channels made it possible to identify cell types. Cells with an $EpCAM^+$/$CD45^-$ or $folate^+$/$CD45^-$ phenotype, ¬or both, were defined as bulk CTCs, while cells with an $EpCAM^+$/$CD44^+$/$CD24^{-/low}$ profile were considered as breast cancer stem cells. CD45 was used as a known marker of WBCs to distinguish CTCs (CD45−) from WBCs (CD45+), which may nonspecifically take up GNRs. The fluorescence module was used to count the number of bulk CTC-GFPs (green channel; excitation/emission: 488 nm/505-515 nm), which also enabled us to control the efficiency of NP targeting by the coincidence of PA and fluorescent signals at a specific wavelength. In particular, the counting of PA signals after the injection of folate-GNS520 and $EpCAM$-$GNR_{670}$ probes separately showed a labeling efficiency of 79±5.6% and 21±3.7%, respectively, while injection of a cocktail of $EpCAM$-$GNR_{670}$ and folate-$GNR_{670}$ increased the labeling efficiency of CTCs to 92±6.9%. Signals in the 671-nm PA channel and in the green-fluorescence channel, combined with the absence of PA signals at 1024 nm and 820 nm, were associated with $EpCAM^+$/$GFP^+$/$CD24^-$/$CD45^-$CTCs that are related to stem CTCs. The $GFP^+$/$CD44+$/$EpCAM^+$/$CD62P+$/$CD24^-$/$CD45^-$ combination was associated with stem CTC-platelet aggregates, $GFP^+$/$folate^+$/CD45− with bulk CTCs, CD45+ with WBCs, and CD62P+ with platelets. At week 1 of tumor development, 44±10 signals/30 min were counted and associated with $EpCAM^+$/$CD24^-$/$CD45^-$ CTCs; and at weeks 2, 53±7 signals/30 min were detected. At week 2, mice with a higher number of stem CTCs showed the presence of micrometastases in lung. In contrast, mice with a low number of stem CTCs showed no metastases, suggesting a significant role for stem CTCs in metastasis progression.

Example 15: Multicolor Detection of Malaria

Figure 44A:
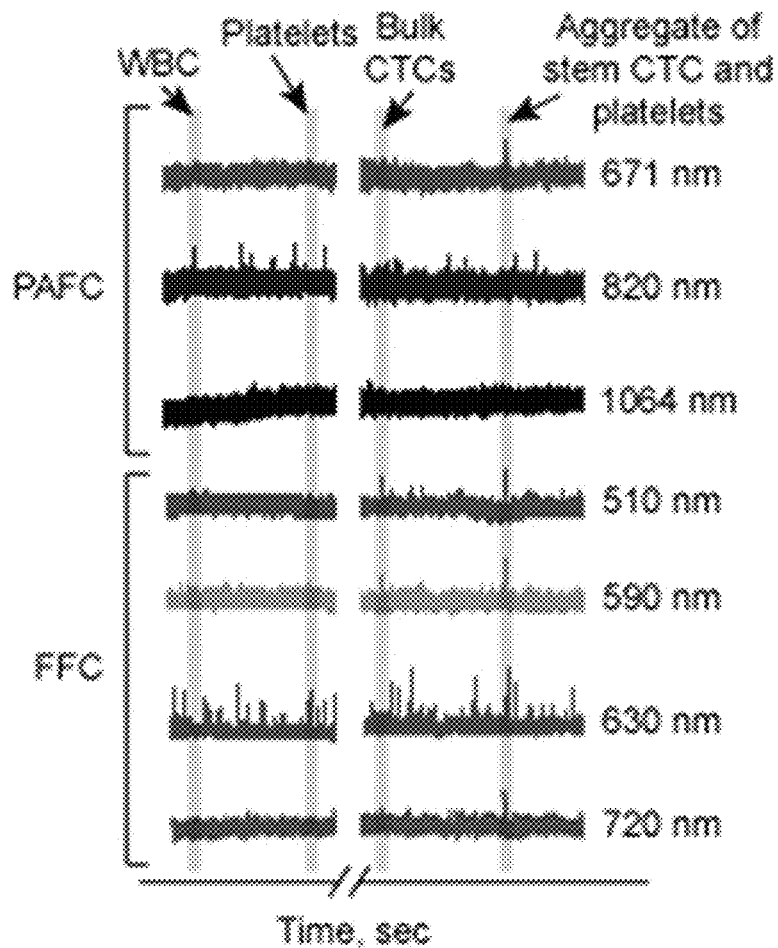
FIG. 44A shows results of monitoring circulating bulk and stem CTCs, WBCs and platelets, as well as stem CTC-clot aggregates in ear vessels of a tumor bearing mouse using in vivo multicolor integrated flow cytometry (FFC and PAFC) platform after IV injection of a PA and fluorescent labeling cocktail.
Figure 44B:
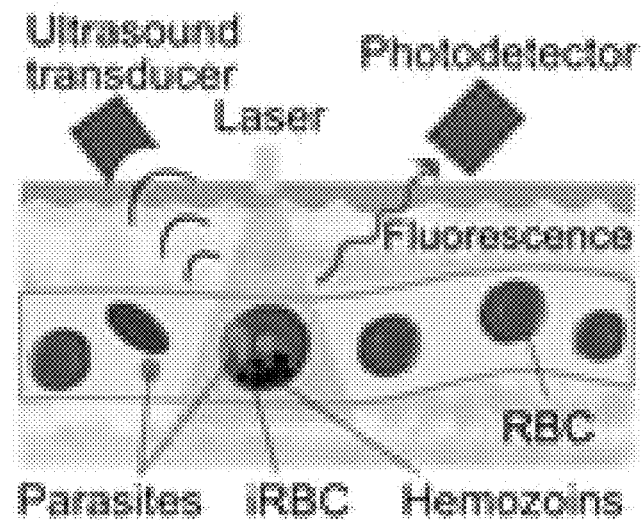
FIGS. 44B-E shows results of monitoring a vessel infected with malaria parasites RBCs with three color PAFC at 532 nm, 671 nm, and 802 nm.
Figure 44C:
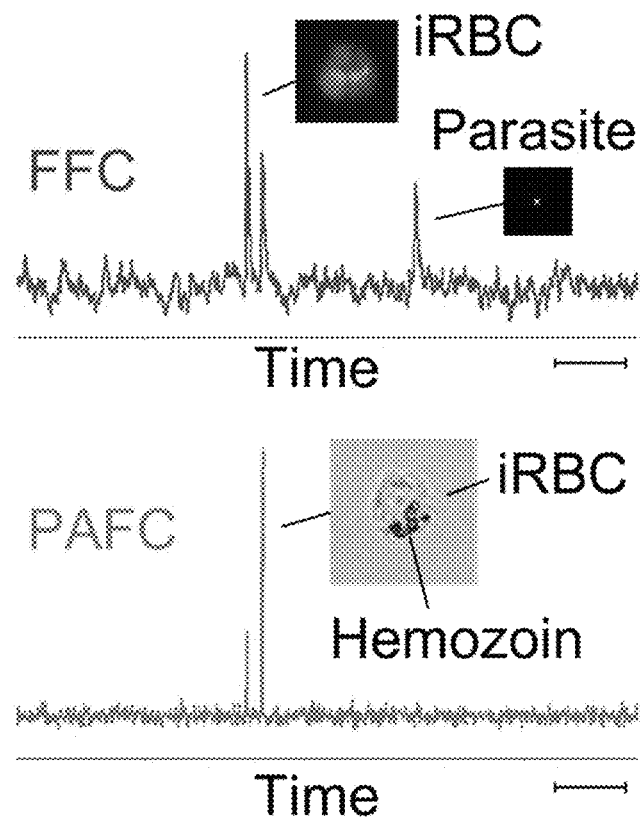
Figure 44D:
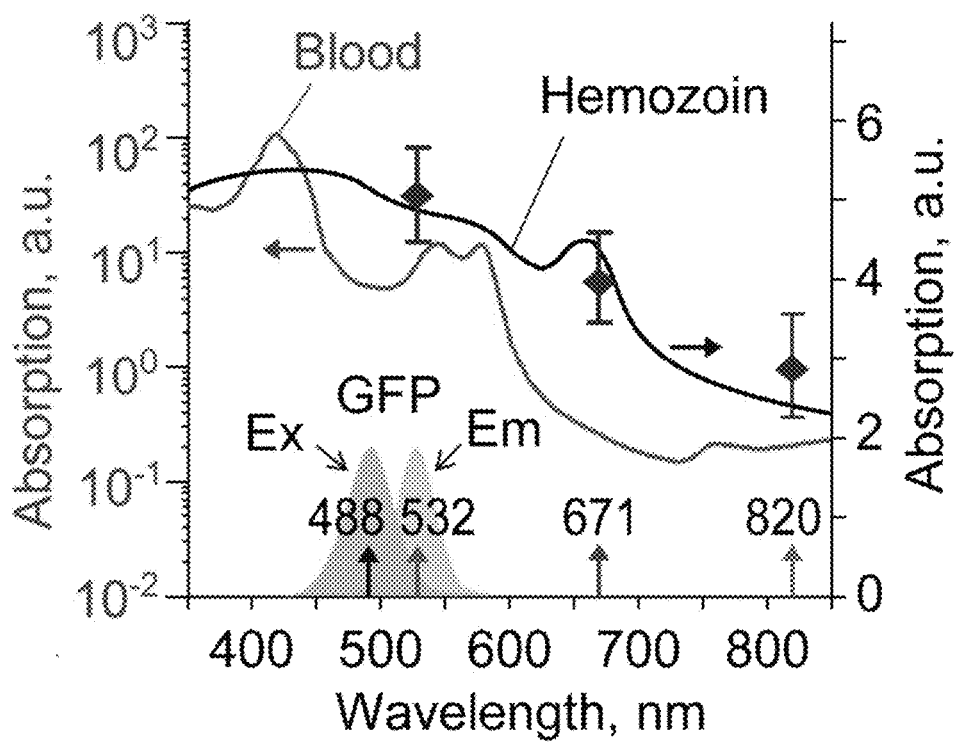
Figure 44E:
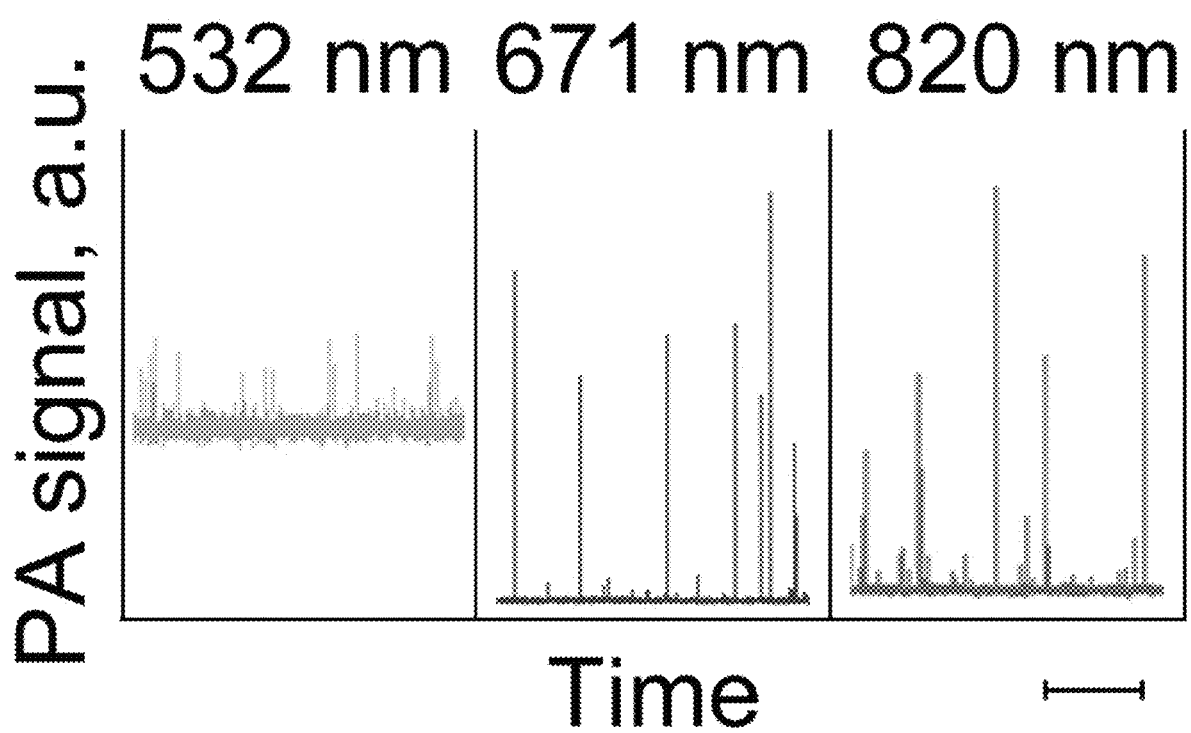

In vivo flow cytometry has demonstrated a great potential for detection of extremely rare abnormal circulating cells in whole blood volume. However, this powerful method has not yet been applied for diagnosis of malaria despite its medical significance. The existing malaria tests using blood smears can detect the disease when 0.001-0.1% of blood cells are infected that is already accompanied by clinical symptoms such as a fever and nausea. FIG. 44B illustrates in vivo fractionated PAFC which provides label-free early detection of malaria prior to clinical symptoms at an extremely low level of parasitemia of 0.00000001%, which is at least ~$10^4$ times better than the existing tests. Multicolor PAFC with high pulse repetition rate lasers at 532 nm, 671 nm, and 820 nm provided rapid spectral identification of circulating infected red blood cells (iRBCs) carrying parasite-produced hemozoin as a high contrast PA agent (FIGS. 44C and 44E). Integration of PAFC with fluorescence flow cytometry (FIG. 44B) provided simultaneous detection of iRBCs and parasites expressing green fluorescence proteins (GFP), respectively in vitro in flow conditions and in blood circulation in vivo at single RBC and parasite levels (FIG. 44B). High sensitivity fractionated PAFC provides detection of infected RBCs even in linear mode with or without manifestation of laser-induced nanobubbles around overheated hemozoins as an additional PA signal amplifier and cell killer. Fractionated PAFC may be used to control laser therapy efficiency by counting infected RBCs before, during and after laser treatment. The PAFC-FFC and fractionated PAFC platforms represent a powerful tool to provide insight on malaria progression both in vitro and in vivo in animals and humans.

Example 16: Multicolor Detection of CTC Release During Medical Procedures as a Result of Surgery, Drug, or Radiotherapy PAFC was integrated with FFC (FIGS. 42A and 42B) to form a universal FC platform (Example 13). The PAFC-FFC system provides for simultaneous detection of melanoma CTCs expressing GFP with PAFC at 1,064 nm (or 820 nm) using melanin as intrinsic PA agent and GFP as a fluorescent agent with a continuous-wave (CW) laser (excitation at 488 nm and emission detection at 515 nm). Using PAFC, the fractionated schematics (e.g., linear beam, increased energy fluence, etc.), and melanoma-bearing mice, it was demonstrated that palpation, biopsy, and surgery might either initiate release of CTCs into the bloodstream where they were not previously present, or dramatically increase (10-60-fold) CTC counts above their previous levels. For example, the pressure of a 120-g weight (imitation of palpation or pressure used in breast cancer screening) notably increased the CTC count (FIG. 42B), which eventually led to the appearance of lung metastases 3 weeks after tumor implantation; in contrast, without the application of pressure or palpation, metastases were absent at this time. Further, resection of a primary melanoma tumor with a positive margin led to quick (within a few hours) disappearance of previously observed CTCs. In tumor-bearing mice with GFP-expressing cancer cells (4T1), it was discovered during FFC monitoring of 50-μm-diameter ear vessels that the CTC level significantly increased after irradiation (20 Gy, 2 min) In addition, i.v. injection of tumor necrosis factor (TNF) at typical doses also led to notable increases in CTCs. Possible explanations of these poorly known phenomena may be associated with a suction effect during surgery or drug- or radiation-induced vascular permeability changes. Fractionated PAFC with enhanced sensitivity is an ideal tool to explore these and similar phenomena.

Example 17: Detection of Circulating Tumor-Associated Nano- and Microparticles (CTPs)

Figure 38C:
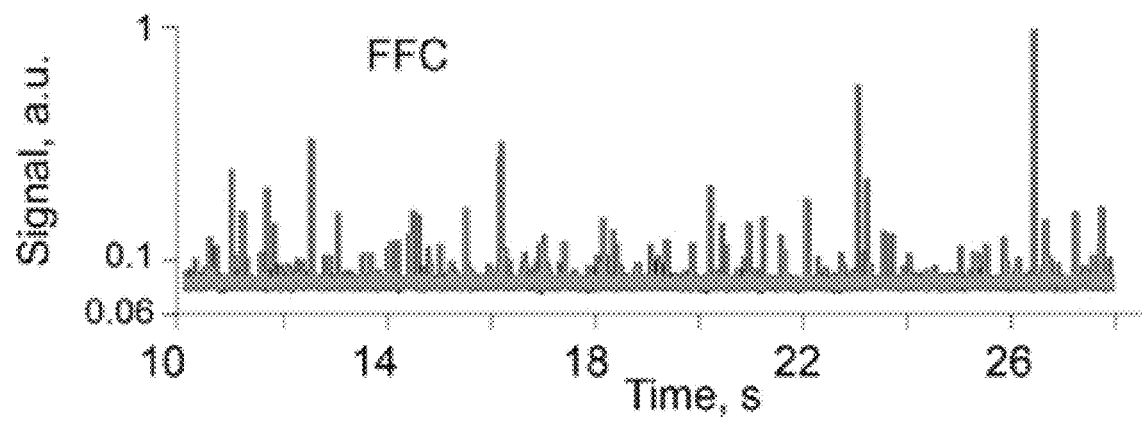
FIG. 38C shows fluorescence traces in 50-µm capillary tube with stained by PKH67 dye exosomes.
Figure 38D:
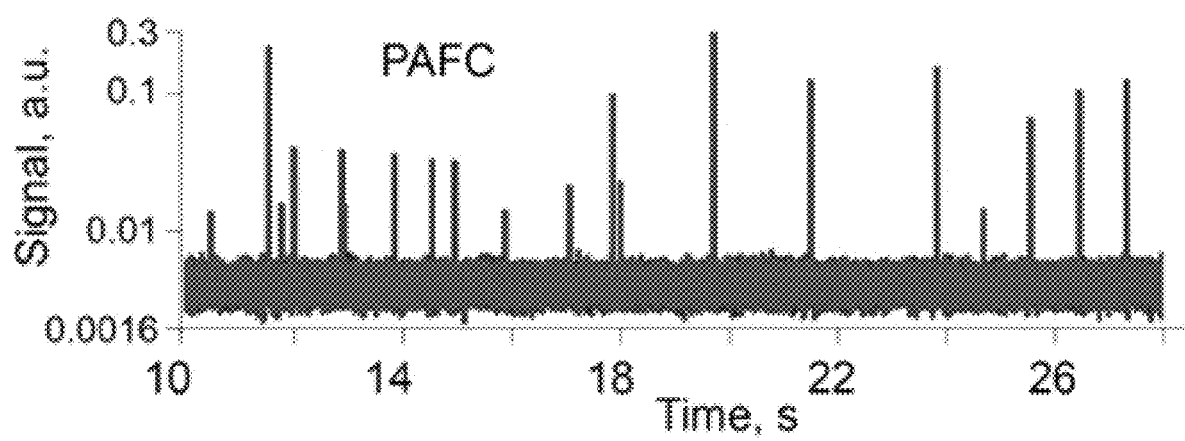
FIG. 38D shows PA traces in 50-µm capillary tube with stained by PKH67 dye exosomes.
Figure 38E:
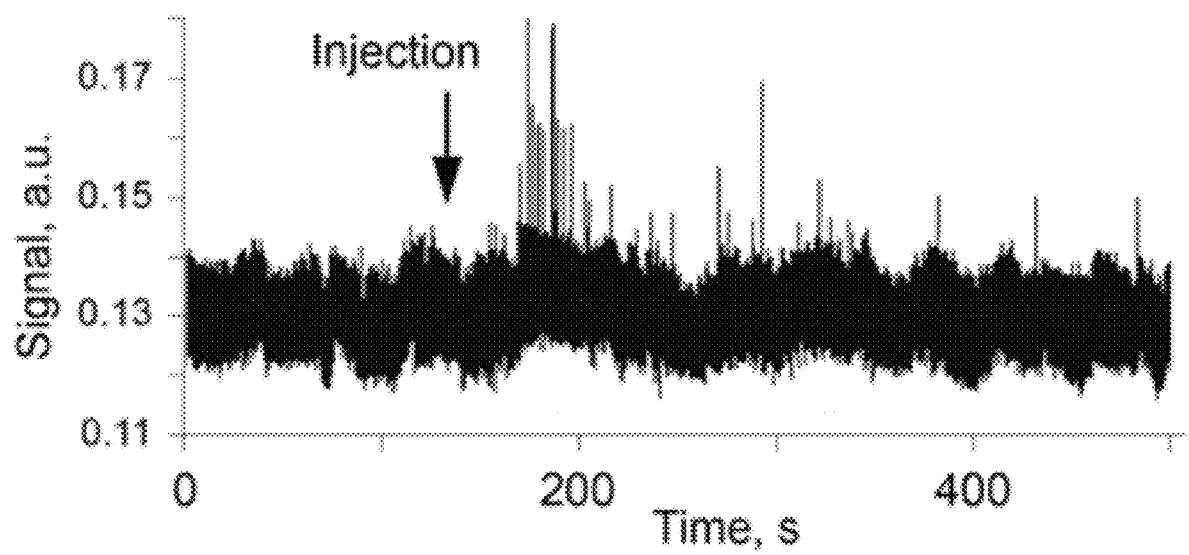
FIG. 38E demonstrates a PA trace from 50-µm vessels in mouse ear after IV injection of melanoma exosomes in a mouse tail.

To verify the capability of PAFFC to detect CTPs, exosomes were isolated from melanoma cells (B16F10) by well-established procedures (e.g., ultracentrifugation). TEM, light transmission, and dark field imaging (FIGS. 38A and 38B) revealed many exosomes with sizes in the range of 100-300 nm and some portion of exosomes (around 36%) were relatively dark suggesting the presence of melanin. Also rare larger clusters were observed with sizes up to ~1-2 μm. The study of these samples with PAFFC in vitro in a 50-μm capillary flow tube confirmed these findings: unstained sample produced many PA peaks, and staining with the bright membrane fluorescence dye (PKH67) produced coinciding fluorescence and PA peaks (FIGS. 38C and 38D). Thus, CTPs secreted from melanoma cells can be detected with PAFC in label-free mode. Intravenous (i.v) injection of exosomes isolated from melanoma cells followed by monitoring of mouse ear microvessels with PAFFC led also to appearance of PA peaks (FIG. 38E), although the number of these peaks in the presence of absorption and fluorescence background from skin and blood was notably lower compared to ideal optical condition in vivo (FIG. 38D). The clearance rate (life time) of these intentionally introduced CTPs was around 10-15 min. Injection of tumor cells led the appearance of peaks with larger amplitude and wider peak that allowed us to differentiate CTP and CTCs.

The sensitivity of the fractionated PAFFC can be further increased, an advanced picosecond laser that is more optimal for effective generation of PA signals from small absorbing targets like CTPs and spaser as new supercontrast agents (below).

Example 18: Spaser as New Super Contrast Multimodal Agents for Fractionated PAFC Surface plasmon amplification by stimulated emission of radiation (spaser) represents a new optical probe that may overcome the limitations of conventional probes labels such as weak signal intensity masked by the strong autofluorescent background of blood and limited multimodal capability with only PA or/and fluorescent contrast at least in a research tools using animal models of humans diseases. Many modifications of spasers, also called plasmonic nanolasers, have been developed; however, investigation of their biomedical applications has been lacking. Spasers were synthesized consisting of 10±2-nm-diameter spherical gold NPs surrounded by a 12±4-nm-thick silica shell doped with uranium (FIG. 46A), a low-toxicity, water-soluble form of disodium fluorescein that is widely used in the medical field. Irradiation of spasers in solution in a thin (~1 μm) slide with a focused 1.1-μm-diameter pump beam (488 nm) produced the highest ratio of stimulated emission intensity to spontaneous emission background of $1.3\times10^4$ ("giant spasing") and the narrowest emission peak of 0.8 nm (FIG. 46B); these findings are 300-fold and 30-fold, respectively, better than those for quantum dots (QDs), which are one of the best conventional fluorescent probes. Because of strong absorption by gold NPs in their cores, spasers also exhibited tremendous potential also as PA probes in the fractionated PAFC, in which the enhanced laser energy in deep tissue will allow to detect there small targets such as spaser-based functionalized probes. After incubation of spasers with MDA-MB-231breast cancer cells, stimulated emission from individual cells alone were monitored (FIG. 46C) through a 1.5-mm-thick layer of human blood in vitro (FIG. 46 D-46F), and in the tissue of live mice in vivo. The image contrast that was obtained revealed the potential of spasers for detecting labeled single cells at depths of up to 0.5-1 cm in tissue, which is impossible with conventional QDs (light penetration of only ~100 μm). Finally, no toxic effects were found in a broad range of spaser concentrations, which is consistent with the low toxicity of gold and uranium. The pump fluence levels used were close to the laser safety standard for humans. Photobleaching of spasers was negligible at the pump intensity level used, which yielded much brighter emissions than are possible with a dye alone because of the stimulated nature of the emission. Thus, spasers as the smallest biocompatible lasers (10-20 nm) with superbright, monochromatic (1-2 nm), and plasmonic properties can dramatically improve sensitivity ($10^2$-$10^3$-fold) and spectral specificity (up to 10-15 colors). These unique advantages may enhance both fluorescence and PA signals from small targeted objects including CTPs.

Example 19

In other examples, gel and water between skin and transducers may provide effective cooling skin allowing to delivery more laser energy in skin ever with single beam (FIG. 47). Furthermore, increasing the length of linear beams leads to an increase in the skin sensitivity and related pain (FIG. 39A) and PA signals from 1-mm human vein at depth of 1 mm. Results show the potential to use different cooling devices to further increase laser energy without temperature increase in skin (e.g., standard devices used previously in laser therapy only including transparent optical plates or plates with central hole for light delivery and channels with running water or thermoelectrical effects). Results further show an increase laser energy in deep tissue with increased linear beam length that allows for determining the optimal "dashed" geometry (FIGS. 7B and 7D), including the length of individual linear beam fragments (100-200 um) and the gaps between these fragments (20-100 um).

It should be understood from the foregoing that, while particular aspects have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A fractionated photoacoustic flow cytometry system for the in vivo detection of at least one target object in a biofluid system of a living organism, comprising:
   a laser system comprising at least one laser comprising at least one wavelength for providing at least one laser beam having an energy;
   a fractionated optical system configured to separate the at least one laser beam into a fractionated dashed and/or dot laser beam comprising a plurality of beam fragments separated by gaps to spatially redistribute the energy of the at least one laser beam, wherein the dashed and/or dot laser beam has a spatial configuration on the skin above the biofluid system of the living organism, and wherein each beam fragment is absorbed by at least one target object within a cross-section of the biofluid system; and
   an acoustic system comprising an array of focused ultrasound transducers forming non-overlapped acoustic focal volumes together covering the whole cross-section of the biofluid system, the focused ultrasound transducers being operable for receiving a photoacoustic signal emitted by the at least one target object in response to the beam fragments.

2. The system of claim 1, wherein each transducer is selected from the group consisting of a spherical ultrasound transducer, a cylindrical ultrasound transducer, and combinations thereof.

3. The system of claim 2, wherein each focused ultrasound transducer has an independent amplifier for sending the photoacoustic signal received by each focused ultrasound transducer to a multichannel data acquisition board to create traces of signals from the at least one target object passing the non-overlapped acoustic focal volumes together covering the whole cross-section of the biofluid system.

4. The system of claim 2, wherein the acoustic system is configured to scan the acoustic focal volumes of the ultrasound transducers across the biofluid system.

5. The system of claim 1, wherein the fractionated optical system comprises an optical component selected from the group consisting of a non-transparent mask, a beam splitter, an optical fiber array, a lens array, a microlens array, a mirror array, a diffraction element, a diffuser, a pinhole, and combinations thereof.

6. The system of claim 1, wherein the plurality of beam fragments from the fractionated optical system do not overlap at a location in the living organism with first temperature, pressure, or pain receptors and wherein the beam fragments spatially overlap at the biofluid system.

7. The system of claim 1, wherein the gaps are about 5 μm to about 1 cm between the beam fragments on the skin of the living organism.

8. The system of claim 1, wherein the spatial configuration of the beam fragments is one-dimensional or two-dimensional, and wherein the beam fragments have a shape selected from the group consisting of circular, linear, strip, elliptical, square, and combinations thereof.

9. The system of claim 1, wherein the fractionated optical system is configured to scan the at least one laser beams across the biofluid system.

10. The system of claim 1, wherein the laser system comprises more than one laser assembled into a laser array comprising independent lasers or a microchip with individual emitters, and wherein the fractionated photoacoustic flow cytometry system further comprises a triggering system for controlling the more than one laser.

11. The system of claim 10, wherein each laser has a different wavelength and the triggering system provides a time delay between the laser beams with different wavelengths.

12. A fractionated photoacoustic flow cytometry system for the in vivo detection of at least one target object in a biofluid system of a living organism, comprising:
a fractionated laser system comprising an array of more than one laser for providing more than one focused dash and/or dot laser beam, each comprising a plurality of beam fragments separated by gaps;
an optical system configured to deliver the more than one focused dash and/or dot laser beams in a spatial configuration on the skin above a cross-section of the biofluid system of the living organism; and
an acoustic system comprising an array of focused ultrasound transducers forming non-overlapped acoustic focal volumes together covering the whole cross-section of the biofluid system, the focused ultrasound transducers being operable for receiving a photoacoustic signal emitted by the at least one target object in response to the beam fragments.

13. The system of claim 12, wherein each focused ultrasound transducer in the focused ultrasound transducer array is selected from the group consisting of a spherical ultrasound transducer, a cylindrical ultrasound transducer, and combinations thereof, and wherein each focused ultrasound transducer is a non-scanning or scanning ultrasound transducer.

14. The system of claim 12, wherein the more than one laser provides laser pulses with different wavelengths, wherein the fractionated photoacoustic flow cytometry system further comprises a triggering system for providing time delays between the laser pulses with different wavelengths to provide time-resolved detection of multiple photoacoustic signals.

15. A fractionated photoacoustic flow cytometry method for detecting circulating target objects in a biofluid system of a living organism in vivo, the method comprising:
providing a laser beam from a laser in a laser system at a first wavelength;
separating the laser beam into a fractionated dashed and/or dot laser beam in a fractionated optical system to form a plurality of beam fragments separated by gaps having a spatial configuration on the skin above a cross-section of the biofluid system of the living organism;
obtaining, in a fractionated acoustic system comprising an array of focused ultrasound transducers forming non-overlapped acoustic focal volumes together covering the whole cross-section of the biofluid system, more than one photoacoustic signal emitted by the circulating target objects induced by the fractionated dashed and/or dot laser beam; and
analyzing the photoacoustic signals to calculate a combination of photoacoustic signals emitted by the circulating target objects, wherein the combination of photoacoustic signals is characteristic of each circulating target object.

16. The method of claim 15, further comprising:
color-coding the target objects by providing the target objects with a second laser beam from a second laser in the laser system at a second wavelength;
introducing time delays from a triggering system between laser beams with different wavelengths; and
color decoding by time-resolved detection of a color-coded photoacoustic signal.

17. The method of claim 15, further comprising generating microbubbles or nanobubbles by the fractionated dashed laser beams to detect the circulating target objects with intrinsic photoacoustic contrast or the circulating target objects labeled with a non-photoswitchable or photoswitchable photoacoustic probe.

18. The method of claim 15, further comprising cooling the skin by placing clearing or cooling agents on the skin.

* * * * *